US012582609B2

(12) United States Patent
Valiante et al.

(10) Patent No.: US 12,582,609 B2
(45) Date of Patent: Mar. 24, 2026

(54) CANCER VACCINES

(71) Applicant: ModernaTX, Inc., Cambridge, MA (US)

(72) Inventors: Nicholas Valiante, Cambridge, MA (US); Tal Zaks, Newton, MA (US); Eric Yi-Chun Huang, Boston, MA (US)

(73) Assignee: ModernaTX, Inc., Cambridge, MA (US)

( * ) Notice: Subject to any disclaimer, the term of this patent is extended or adjusted under 35 U.S.C. 154(b) by 1239 days.

(21) Appl. No.: 15/769,710

(22) PCT Filed: Oct. 21, 2016

(86) PCT No.: PCT/US2016/058317

§ 371 (c)(1),
(2) Date: Apr. 19, 2018

(87) PCT Pub. No.: WO2017/070618

PCT Pub. Date: Apr. 27, 2017

(65) Prior Publication Data

US 2018/0318409 A1 Nov. 8, 2018

Related U.S. Application Data

(60) Provisional application No. 62/368,810, filed on Jul. 29, 2016, provisional application No. 62/247,472, filed on Oct. 28, 2015, provisional application No. 62/247,317, filed on Oct. 28, 2015, provisional application No. 62/245,129, filed on Oct. 22, 2015, provisional application No. 62/245,031, filed on Oct. 22, 2015.

(51) Int. Cl.

| | |
|---|---|
| ***A61K 9/51*** | (2006.01) |
| ***A61K 9/10*** | (2006.01) |
| ***A61K 39/00*** | (2006.01) |
| ***A61P 35/00*** | (2006.01) |

(52) U.S. Cl.

CPC .............. *A61K 9/5123* (2013.01); *A61K 9/10* (2013.01); *A61K 39/0011* (2013.01); *A61K 39/001114* (2018.08); *A61P 35/00* (2018.01); *A61K 2039/53* (2013.01); *A61K 2039/545* (2013.01); *A61K 2039/55588* (2013.01)

(58) Field of Classification Search

CPC ............ A61K 39/0011; A61K 2039/53; A61K 39/001114; A61K 9/10; A61K 9/5123; A61K 2039/545; A61K 2039/55588; A61P 35/00

See application file for complete search history.

(56) References Cited

U.S. PATENT DOCUMENTS

| | | | |
|---|---|---|---|
| 6,589,940 | B1 | 7/2003 | Raz et al. |
| 6,610,661 | B1 | 8/2003 | Carson et al. |
| 7,763,253 | B2 | 7/2010 | Hedlund et al. |
| 8,158,601 | B2 | 4/2012 | Chen et al. |
| 8,217,016 | B2 | 7/2012 | Hoerr et al. |
| 8,569,256 | B2 | 10/2013 | Heyes et al. |
| 8,603,499 | B2 | 12/2013 | Zale et al. |
| 8,603,500 | B2 | 12/2013 | Zale et al. |
| 8,603,501 | B2 | 12/2013 | Zale et al. |
| 8,691,966 | B2 | 4/2014 | Kariko et al. |
| 8,710,200 | B2 | 4/2014 | Schrum et al. |
| 8,734,853 | B2 | 5/2014 | Sood et al. |
| 8,754,062 | B2 | 6/2014 | De Fougerolles et al. |
| 8,822,663 | B2 | 9/2014 | Schrum et al. |
| 8,853,179 | B2 | 10/2014 | Mauro et al. |
| 8,999,380 | B2 | 4/2015 | Bancel et al. |
| 9,221,891 | B2 | 12/2015 | Bancel et al. |
| 9,283,287 | B2 | 3/2016 | Bancel et al. |
| 9,303,079 | B2 | 4/2016 | Bancel et al. |
| 9,464,124 | B2 | 10/2016 | Bancel et al. |
| 9,512,456 | B2 | 12/2016 | Wang et al. |
| 9,533,047 | B2 | 1/2017 | de Fougerolles et al. |
| 9,572,896 | B2 | 2/2017 | Bancel et al. |
| 9,597,380 | B2 | 3/2017 | Chakraborty et al. |
| 9,669,089 | B2 | 6/2017 | Thess et al. |
| 9,764,026 | B2 | 9/2017 | Sampson et al. |
| 9,803,199 | B2 | 10/2017 | Koizumi et al. |
| 9,868,691 | B2 | 1/2018 | Benenato et al. |
| 9,872,900 | B2 | 1/2018 | Ciaramella et al. |
| 10,064,934 | B2 | 9/2018 | Ciaramella et al. |
| 10,064,935 | B2 | 9/2018 | Ciaramella et al. |
| 10,124,055 | B2 | 11/2018 | Ciaramella et al. |
| 10,155,031 | B2 | 12/2018 | Sahin et al. |
| 10,207,010 | B2 | 2/2019 | Besin et al. |
| 10,232,055 | B2 | 3/2019 | Kariko et al. |

(Continued)

FOREIGN PATENT DOCUMENTS

| | | | |
|---|---|---|---|
| AU | 652831 | B2 | 9/1994 |
| AU | 2015210364 | A1 | 3/2017 |

(Continued)

OTHER PUBLICATIONS

Peters et al.; Examining the independent binding assumption for binding of peptide epitopes to MHC-I molecules; Bioinformatics; vol. 19, No. 14, pp. 1765-1772, Sep. 22, 2003 (Year: 2003).*

(Continued)

*Primary Examiner* — Abigail Vanhorn

(74) *Attorney, Agent, or Firm* — Foley & Lardner LLP

(57) ABSTRACT

The disclosure relates to cancer ribonucleic acid (RNA) vaccines, as well as methods of using the vaccines and compositions comprising the vaccines.

36 Claims, 19 Drawing Sheets

Specification includes a Sequence Listing.

(56) References Cited

U.S. PATENT DOCUMENTS 10,273,269 B2 4/2019 Ciaramella
10,286,086 B2 5/2019 Roy et al.
10,323,076 B2 6/2019 Ellsworth et al.
10,385,088 B2 8/2019 Fraley et al.
10,449,244 B2 10/2019 Ciaramella et al.
10,465,190 B1 11/2019 Chen et al.
10,493,143 B2 12/2019 Ciaramella et al.
10,526,629 B2 1/2020 Rabideau et al.
10,653,712 B2 5/2020 Hoge
10,653,767 B2 5/2020 Ciaramella et al.
10,695,419 B2 6/2020 Ciaramella et al.
10,751,386 B2 8/2020 Bancel et al.
10,857,105 B2 12/2020 Benenato et al.
10,925,958 B2 2/2021 Ciaramella
11,045,540 B2 6/2021 Ciaramella
11,103,578 B2 8/2021 Ciaramella et al.
11,248,264 B2 2/2022 Sahin et al.
11,285,222 B2 3/2022 Besin et al.
11,351,242 B1 6/2022 Lori et al.
11,384,352 B2 7/2022 Miracco
11,406,703 B2 8/2022 Kramarczyk et al.
11,464,848 B2 10/2022 Ciaramella et al.
11,485,960 B2 11/2022 Dousis et al.
11,497,807 B2 11/2022 Ciaramella et al.
11,564,893 B2 1/2023 Smith
11,576,961 B2 2/2023 Ciaramella et al.
11,643,441 B1 5/2023 Ciaramella et al.
11,696,946 B2 7/2023 Ciaramella
11,752,206 B2 9/2023 Ciaramella et al.
11,767,548 B2 9/2023 Rabideau et al.
11,786,607 B2 10/2023 Hoge et al.
11,851,694 B1 12/2023 Mauger et al.
11,866,696 B2 1/2024 Issa et al.
11,872,278 B2 1/2024 Ciaramella et al.
11,905,525 B2 2/2024 Brito et al.
11,911,453 B2 2/2024 Ciaramella et al.
11,912,982 B2 2/2024 Issa et al.
12,150,980 B2 11/2024 Ciaramella et al.
12,151,029 B2 11/2024 Hennessy et al.
12,233,084 B2 2/2025 Hoge et al.
12,246,029 B2 3/2025 Hoge et al.
2004/0132683 A1 7/2004 Felgner et al.
2005/0032730 A1 2/2005 Von Der Mulbe et al.
2005/0059624 A1 3/2005 Hoerr et al.
2005/0112141 A1 5/2005 Terman
2005/0250723 A1 11/2005 Hoerr et al.
2007/0117185 A1 5/2007 Kopetzki
2008/0025944 A1 1/2008 Hoerr et al.
2008/0171711 A1 7/2008 Hoerr et al.
2009/0093433 A1 4/2009 Woolf et al.
2010/0047261 A1 2/2010 Hoerr et al.
2010/0129877 A1 5/2010 Sahin et al.
2010/0130588 A1 5/2010 Yaworski et al.
2010/0189729 A1 7/2010 Hoerr et al.
2010/0239608 A1 9/2010 Von Der Mulbe et al.
2010/0291156 A1 11/2010 Barner et al.
2010/0305196 A1 12/2010 Probst et al.
2011/0269950 A1 11/2011 Von Der Mulbe et al.
2011/0311472 A1 12/2011 Hoerr et al.
2012/0009221 A1 1/2012 Hoerr et al.
2012/0101148 A1 4/2012 Aking et al.
2012/0213818 A1 8/2012 Hoerr et al.
2013/0102034 A1 4/2013 Schrum et al.
2013/0156849 A1 6/2013 De Fougerolles et al.
2013/0195867 A1 8/2013 Hoerr et al.
2013/0195967 A1 8/2013 Guild et al.
2013/0202645 A1 8/2013 Barner et al.
2013/0236974 A1 9/2013 De Fougerolles
2013/0245103 A1 9/2013 de Fougerolles et al.
2013/0245105 A1* 9/2013 de Fougerolles .. A61K 48/0066
514/44 R
2013/0259923 A1 10/2013 Bancel et al.
2013/0266640 A1 10/2013 De Fougerolles et al.
2013/0336998 A1 12/2013 Kallen et al.
2014/0037660 A1 2/2014 Folin-Mleczek et al.
2014/0065228 A1 3/2014 Yaworski et al.
2014/0079774 A1 3/2014 Brinker et al.
2014/0127301 A1 5/2014 Alexis et al.
2014/0134201 A1 5/2014 Tureci et al.
2014/0147432 A1 5/2014 Bancel et al.
2014/0148502 A1 5/2014 Bancel et al.
2014/0178438 A1* 6/2014 Sahin .................... G16B 40/00
424/277.1
2014/0193482 A1 7/2014 Bancel et al.
2014/0206752 A1 7/2014 Afeyan et al.
2014/0255472 A1 9/2014 Geall et al.
2014/0275229 A1 9/2014 Bancel et al.
2014/0308304 A1 10/2014 Manoharan et al.
2014/0378538 A1 12/2014 Bancel
2015/0051268 A1 2/2015 Bancel et al.
2015/0056253 A1 2/2015 Bancel et al.
2015/0086614 A1 3/2015 Bancel et al.
2015/0111248 A1 4/2015 Bancel et al.
2015/0141499 A1 5/2015 Bancel et al.
2015/0246139 A1 9/2015 Bancel et al.
2015/0307542 A1 10/2015 Roy et al.
2015/0315541 A1 11/2015 Bancel et al.
2016/0022580 A1 1/2016 Ramsay et al.
2016/0024140 A1 1/2016 Issa et al.
2016/0024141 A1 1/2016 Issa et al.
2016/0032273 A1 2/2016 Shahrokh et al.
2016/0038612 A1 2/2016 Hoge et al.
2016/0151474 A1 6/2016 Kallen et al.
2016/0194368 A1 7/2016 Hoge et al.
2016/0194625 A1 7/2016 Hoge et al.
2016/0243221 A1 8/2016 Hoge et al.
2016/0317647 A1 11/2016 Ciaramella et al.
2016/0331844 A1 11/2016 Fotin-Mleczek et al.
2016/0361411 A1 12/2016 Gindy et al.
2016/0367638 A1 12/2016 Byers et al.
2016/0367651 A1 12/2016 Shiku et al.
2017/0043037 A1 2/2017 Kariko et al.
2017/0130255 A1 5/2017 Wang et al.
2017/0173128 A1 6/2017 Hoge et al.
2017/0202979 A1 7/2017 Chakraborty et al.
2017/0204152 A1 7/2017 Nelson et al.
2017/0210697 A1 7/2017 Benenato et al.
2018/0000953 A1 1/2018 Almarsson et al.
2018/0002393 A1 1/2018 Bancel et al.
2018/0078634 A1 3/2018 Ogembo et al.
2018/0237849 A1 8/2018 Thompson
2018/0243225 A1 8/2018 Ciaramella
2018/0243230 A1 8/2018 Smith
2018/0256628 A1 9/2018 Hoge et al.
2018/0271795 A1 9/2018 Martini et al.
2018/0271970 A1 9/2018 Ciaramella et al.
2018/0273977 A1 9/2018 Mousavi et al.
2018/0274009 A1 9/2018 Marquardt et al.
2018/0296663 A1 10/2018 Hipp et al.
2018/0303929 A1 10/2018 Ciaramella et al.
2018/0311336 A1 11/2018 Ciaramella et al.
2018/0311343 A1 11/2018 Huang et al.
2018/0318409 A1 11/2018 Valiante et al.
2018/0363019 A1 12/2018 Hoge
2018/0369374 A1 12/2018 Frederick et al.
2018/0371047 A1 12/2018 Ticho et al.
2019/0002890 A1 1/2019 Martini et al.
2019/0008887 A1 1/2019 Mousavi et al.
2019/0008938 A1 1/2019 Ciaramella et al.
2019/0008948 A1 1/2019 Ciaramella et al.
2019/0015501 A1 1/2019 Ciaramella et al.
2019/0085368 A1 3/2019 Bancel et al.
2019/0099481 A1 4/2019 Ciaramella et al.
2019/0161728 A1 5/2019 Zagury et al.
2019/0175517 A1 6/2019 Martini et al.
2019/0175727 A1 6/2019 Huang et al.
2019/0192646 A1 6/2019 Cohen et al.
2019/0192653 A1 6/2019 Hoge et al.
2019/0211065 A1 7/2019 Ciaramella
2019/0241633 A1 8/2019 Fotin-Mleczek et al.
2019/0274968 A1 9/2019 Weissman et al.
2019/0275170 A1 9/2019 Benenato et al.
2019/0298657 A1 10/2019 Martini et al.
2019/0298658 A1 10/2019 Benenato

(56) References Cited

U.S. PATENT DOCUMENTS

| | | | |
|---|---|---|---|
| 2019/0300906 | A1 | 10/2019 | Martini et al. |
| 2019/0314292 | A1 | 10/2019 | Benenato et al. |
| 2019/0314493 | A1 | 10/2019 | Ciaramella et al. |
| 2019/0336452 | A1 | 11/2019 | Brader |
| 2019/0336595 | A1 | 11/2019 | Ciaramella |
| 2019/0351040 | A1 | 11/2019 | Valiante et al. |
| 2019/0382774 | A1 | 12/2019 | Hoge et al. |
| 2019/0390181 | A1 | 12/2019 | Benenato et al. |
| 2020/0030432 | A1 | 1/2020 | Ciaramella et al. |
| 2020/0032274 | A1 | 1/2020 | Mauger et al. |
| 2020/0038499 | A1 | 2/2020 | Narayanan et al. |
| 2020/0054737 | A1 | 2/2020 | Ciaramella et al. |
| 2020/0069599 | A1 | 3/2020 | Smith et al. |
| 2020/0069793 | A1 | 3/2020 | Ciaramella |
| 2020/0069794 | A1 | 3/2020 | Ciaramella et al. |
| 2020/0071689 | A1 | 3/2020 | Miracco |
| 2020/0085916 | A1 | 3/2020 | Martini et al. |
| 2020/0109420 | A1 | 4/2020 | Brito et al. |
| 2020/0129445 | A1 | 4/2020 | Patel et al. |
| 2020/0129608 | A1 | 4/2020 | Ciaramella et al. |
| 2020/0129615 | A1 | 4/2020 | Ciaramella et al. |
| 2020/0163878 | A1 | 5/2020 | Baumhof et al. |
| 2020/0239869 | A1 | 7/2020 | Issa et al. |
| 2020/0254086 | A1 | 8/2020 | Hoge et al. |
| 2020/0282047 | A1 | 9/2020 | Ciaramella et al. |
| 2021/0023199 | A1 | 1/2021 | Kallen et al. |
| 2021/0030866 | A1 | 2/2021 | Kallen et al. |
| 2021/0046173 | A1 | 2/2021 | Ciaramella et al. |
| 2021/0060175 | A1 | 3/2021 | Baumhof et al. |
| 2021/0087135 | A1 | 3/2021 | Benenato et al. |
| 2021/0163919 | A1 | 6/2021 | Issa et al. |
| 2021/0187097 | A1 | 6/2021 | Ciaramella et al. |
| 2021/0217484 | A1 | 7/2021 | Giessel et al. |
| 2021/0228707 | A1 | 7/2021 | Mektar et al. |
| 2021/0268086 | A1 | 9/2021 | Zhong et al. |
| 2021/0309976 | A1 | 10/2021 | Dousis et al. |
| 2022/0031631 | A1 | 2/2022 | Almarsson et al. |
| 2022/0047518 | A1 | 2/2022 | Hennessy et al. |
| 2022/0054653 | A1 | 2/2022 | Martini et al. |
| 2022/0062408 | A1 | 3/2022 | Kramarczyk et al. |
| 2022/0125899 | A1 | 4/2022 | Ashburn et al. |
| 2022/0145381 | A1 | 5/2022 | Elich et al. |
| 2022/0152178 | A1 | 5/2022 | Ciaramella et al. |
| 2022/0236253 | A1 | 7/2022 | Hopson |
| 2022/0241399 | A1 | 8/2022 | Lusso et al. |
| 2022/0265857 | A1 | 8/2022 | Besin et al. |
| 2022/0323572 | A1 | 10/2022 | Metkar et al. |
| 2022/0347292 | A1 | 11/2022 | Panther et al. |
| 2022/0348900 | A1 | 11/2022 | Shamashkin et al. |
| 2022/0349006 | A1 | 11/2022 | Amato et al. |
| 2023/0000970 | A1 | 1/2023 | Nachbagauer et al. |
| 2023/0142529 | A1 | 5/2023 | White et al. |
| 2023/0181481 | A1 | 6/2023 | White et al. |
| 2023/0190761 | A1 | 6/2023 | Brader et al. |
| 2023/0212645 | A1 | 7/2023 | Marquardt et al. |
| 2023/0287437 | A1 | 9/2023 | Smith et al. |
| 2023/0338506 | A1 | 10/2023 | Shaw et al. |
| 2023/0346914 | A1 | 11/2023 | Stewart-Jones et al. |
| 2023/0355743 | A1 | 11/2023 | Stewart-Jones et al. |

FOREIGN PATENT DOCUMENTS

| | | | | | |
|---|---|---|---|---|---|
| CN | 1360025 | A | | 7/2002 | |
| CN | 107847572 | A | | 3/2018 | |
| CN | 110974954 | A | | 4/2020 | |
| EP | 1905844 | A2 | | 2/2008 | |
| EP | 2 569 633 | B1 | | 2/2016 | |
| EP | 3292873 | A1 | | 3/2018 | |
| EP | 3452101 | A2 | | 3/2019 | |
| EP | 3 608 308 | A | | 2/2020 | |
| WO | WO 1991/007425 | A1 | | 5/1991 | |
| WO | WO 1992/019752 | A1 | | 11/1992 | |
| WO | WO 1995/027069 | A1 | | 3/1995 | |
| WO | WO 1999/034015 | A2 | | 7/1999 | |
| WO | WO 1999/052503 | A2 | | 10/1999 | |
| WO | WO-02/061113 | A2 | | 8/2002 | |
| WO | WO-2005040356 | A2 | * | 5/2005 | ......... C07K 14/4746 |
| WO | WO 2006/008154 | A1 | | 1/2006 | |
| WO | WO 2006/020071 | A2 | | 2/2006 | |
| WO | WO 2006/110585 | A1 | | 10/2006 | |
| WO | WO 2007/000668 | A2 | | 1/2007 | |
| WO | WO 2007/094854 | A2 | | 8/2007 | |
| WO | WO 2007/101227 | A2 | | 9/2007 | |
| WO | WO-2008/083949 | A2 | | 7/2008 | |
| WO | WO 2008/103276 | A2 | | 8/2008 | |
| WO | WO 2009/046738 | A1 | | 4/2009 | |
| WO | WO 2009/046739 | A1 | | 4/2009 | |
| WO | WO 2009/046974 | A2 | | 4/2009 | |
| WO | WO 2009/046975 | A1 | | 4/2009 | |
| WO | WO-2009/127060 | A1 | | 10/2009 | |
| WO | WO 2009/127230 | A1 | | 10/2009 | |
| WO | WO 2010/037539 | A1 | | 4/2010 | |
| WO | WO-2010/054406 | A1 | | 5/2010 | |
| WO | WO-2010/088537 | A2 | | 8/2010 | |
| WO | WO-2010/088537 | A3 | | 8/2010 | |
| WO | WO-2011/000107 | A1 | | 1/2011 | |
| WO | WO-2011/025566 | A1 | | 3/2011 | |
| WO | WO-2011/076807 | A2 | | 6/2011 | |
| WO | WO 2011/140627 | A1 | | 11/2011 | |
| WO | WO 2011/143656 | A2 | | 11/2011 | |
| WO | WO-2012/000104 | A1 | | 1/2012 | |
| WO | WO-2012/006377 | A2 | | 1/2012 | |
| WO | WO-2012/006378 | A1 | | 1/2012 | |
| WO | WO 2012/065164 | A2 | | 5/2012 | |
| WO | WO 2012/140130 | A1 | | 10/2012 | |
| WO | WO-2012/158643 | A1 | | 11/2012 | |
| WO | WO 2012/159643 | A1 | | 11/2012 | |
| WO | WO 2012/159754 | A1 | | 11/2012 | |
| WO | WO 2013/006837 | A1 | | 1/2013 | |
| WO | WO 2013/024865 | A1 | | 2/2013 | |
| WO | WO 2013/086373 | A1 | | 6/2013 | |
| WO | WO 2013/090648 | A1 | | 6/2013 | |
| WO | WO-2013/113326 | A1 | | 8/2013 | |
| WO | WO-2013/113501 | A1 | | 8/2013 | |
| WO | WO-2013/113502 | A1 | | 8/2013 | |
| WO | WO-2013/113736 | A1 | | 8/2013 | |
| WO | WO-2013/120500 | A1 | | 8/2013 | |
| WO | WO-2013/120627 | A1 | | 8/2013 | |
| WO | WO 2013/143555 | A1 | | 10/2013 | |
| WO | WO 2013/143683 | A1 | | 10/2013 | |
| WO | WO 2013/151666 | A2 | | 10/2013 | |
| WO | WO 2013/151672 | A2 | | 10/2013 | |
| WO | WO-2013/151771 | A1 | | 10/2013 | |
| WO | WO-2013151736 | A2 | * | 10/2013 | ......... A61K 31/7088 |
| WO | WO-2013/174409 | A1 | | 11/2013 | |
| WO | WO-2014/071219 | A1 | | 5/2014 | |
| WO | WO 2014/082729 | A1 | | 6/2014 | |
| WO | WO 2014/089239 | A1 | | 6/2014 | |
| WO | WO-2014/127917 | A1 | | 8/2014 | |
| WO | WO 2014/136086 | A1 | | 9/2014 | |
| WO | WO 2014/144196 | A1 | | 9/2014 | |
| WO | WO 2014/145038 | A1 | | 9/2014 | |
| WO | WO 2014/159813 | A1 | | 10/2014 | |
| WO | WO 2014/168874 | A1 | | 10/2014 | |
| WO | WO-2014/180569 | A1 | | 11/2014 | |
| WO | WO 2015/005253 | A1 | | 1/2015 | |
| WO | WO 2015/034928 | A1 | | 3/2015 | |
| WO | WO 2015/050158 | A1 | | 4/2015 | |
| WO | WO 2015/061467 | A1 | | 4/2015 | |
| WO | WO 2015/095346 | A1 | | 6/2015 | |
| WO | WO-2015/095811 | A2 | | 6/2015 | |
| WO | WO 2015/130584 | A2 | | 9/2015 | |
| WO | WO-2015199952 | A1 | * | 12/2015 | ......... A61K 38/4846 |
| WO | WO-2016/011226 | A1 | | 1/2016 | |
| WO | WO 2016/091391 | A1 | | 6/2016 | |
| WO | WO-2016/128060 | A1 | | 8/2016 | |
| WO | WO 2016/128376 | A1 | | 8/2016 | |
| WO | WO 2016/164762 | A1 | | 10/2016 | |
| WO | WO-2016/170176 | A1 | | 10/2016 | |
| WO | WO 2016/172346 | A1 | | 10/2016 | |
| WO | WO 2016/176761 | A1 | | 11/2016 | |
| WO | WO-2016/184822 | A1 | | 11/2016 | |
| WO | WO-2016/193206 | A1 | | 12/2016 | |
| WO | WO 2016/201377 | A1 | | 12/2016 | |

(56) References Cited

FOREIGN PATENT DOCUMENTS

| | | | | |
|---|---|---|---|---|
| WO | WO-2016/203025 A1 | 12/2016 | | |
| WO | WO 2017/011773 A2 | 1/2017 | | |
| WO | WO 2017/015457 A1 | 1/2017 | | |
| WO | WO 2017/020026 A1 | 2/2017 | | |
| WO | WO 2017/066789 A1 | 4/2017 | | |
| WO | WO 2017/070601 A1 | 4/2017 | | |
| WO | WO 2017/070618 A1 | 4/2017 | | |
| WO | WO 2017/075531 A1 | 5/2017 | | |
| WO | WO-2017/081082 A1 | 5/2017 | | |
| WO | WO-2017/106638 A1 | 6/2017 | | |
| WO | WO 2017/112865 A1 | 6/2017 | | |
| WO | WO 2017/127750 A1 | 7/2017 | | |
| WO | WO 2017/191274 A2 | 11/2017 | | |
| WO | WO 2017/201333 A1 | 11/2017 | | |
| WO | WO-2018/033254 A2 | 2/2018 | | |
| WO | WO-2018/078053 A1 | 5/2018 | | |
| WO | WO 2018/081459 A1 | 5/2018 | | |
| WO | WO-2018/081638 A1 | 5/2018 | | |
| WO | WO 2018/144082 A1 | 8/2018 | | |
| WO | WO 2018/157009 A1 | 8/2018 | | |
| WO | WO 2018/170245 A1 | 9/2018 | | |
| WO | WO 2018/170256 A1 | 9/2018 | | |
| WO | WO 2018/170260 A1 | 9/2018 | | |
| WO | WO 2018/140826 A9 | 10/2018 | | |
| WO | WO 2018/187590 A2 | 10/2018 | | |
| WO | WO-2018/195357 A1 | 10/2018 | | |
| WO | WO-2018/220553 A1 | 12/2018 | | |
| WO | WO-2018/224405 A1 | 12/2018 | | |
| WO | WO 2018/232355 A1 | 12/2018 | | |
| WO | WO 2018/232357 A1 | 12/2018 | | |
| WO | WO 2019/018765 A1 | 1/2019 | | |
| WO | WO 2019/036670 A1 | 2/2019 | | |
| WO | WO 2019/036683 A1 | 2/2019 | | |
| WO | WO 2019/036685 A1 | 2/2019 | | |
| WO | WO 2019/103993 A1 | 5/2019 | | |
| WO | WO 2019/148101 A1 | 8/2019 | | |
| WO | WO 2019/169120 A1 | 9/2019 | | |
| WO | WO-2019/175356 A1 | 9/2019 | | |
| WO | WO-2019/227106 A1 | 11/2019 | | |
| WO | WO 2020/006242 A1 | 1/2020 | | |
| WO | WO-2020/020444 A1 | 1/2020 | | |
| WO | WO-2020/020894 A1 | 1/2020 | | |
| WO | WO-2020/022897 A1 | 1/2020 | | |
| WO | WO-2020/022898 A2 | 1/2020 | | |
| WO | WO-2020/037102 A1 | 2/2020 | | |
| WO | WO 2020/056370 A1 | 3/2020 | | |
| WO | WO 2020/061284 A1 | 3/2020 | | |
| WO | WO 2020/061295 A1 | 3/2020 | | |
| WO | WO 2020/061367 A1 | 3/2020 | | |
| WO | WO 2020/097291 A1 | 5/2020 | | |
| WO | WO-2020/132586 A1 | 6/2020 | | |
| WO | WO 2020/146814 A1 | 7/2020 | | |
| WO | WO-2020/150152 A1 | 7/2020 | | |
| WO | WO 2020/172239 A1 | 8/2020 | | |
| WO | WO 2020/185811 A1 | 9/2020 | | |
| WO | WO 2020/190750 A1 | 9/2020 | | |
| WO | WO 2020/243561 A1 | 12/2020 | | |
| WO | WO 2021/016430 A1 | 1/2021 | | |
| WO | WO 2021/030533 A1 | 2/2021 | | |
| WO | WO 2021/050864 A1 | 3/2021 | | |
| WO | WO 2021/055811 A1 | 3/2021 | | |
| WO | WO 2021/138447 A1 | 7/2021 | | |
| WO | WO-2021/155149 A1 | 8/2021 | | |
| WO | WO 2021/155243 A1 | 8/2021 | | |
| WO | WO 2021/155274 A1 | 8/2021 | | |
| WO | WO 2021/159040 A2 | 8/2021 | | |
| WO | WO 2021/159130 A2 | 8/2021 | | |
| WO | WO-2021163339 A1 * | 8/2021 | ................ | A61P 1/16 |
| WO | WO 2021/211343 A1 | 10/2021 | | |
| WO | WO 2021/222304 A1 | 11/2021 | | |
| WO | WO 2021/231929 A1 | 11/2021 | | |
| WO | WO 2021/231963 A1 | 11/2021 | | |
| WO | WO 2021/237084 A1 | 11/2021 | | |
| WO | WO 2021/247817 A1 | 12/2021 | | |
| WO | WO 2022/032154 A2 | 2/2022 | | |
| WO | WO 2022/067010 A1 | 3/2022 | | |
| WO | WO 2022/150717 A1 | 7/2022 | | |
| WO | WO 2022/155524 A1 | 7/2022 | | |
| WO | WO 2022/155530 A1 | 7/2022 | | |
| WO | WO 2022/187698 A1 | 9/2022 | | |
| WO | WO 2022/197624 A1 | 9/2022 | | |
| WO | WO 2022/204491 A1 | 9/2022 | | |
| WO | WO 2022/212191 A1 | 10/2022 | | |
| WO | WO 2022/212442 A1 | 10/2022 | | |
| WO | WO 2022/212711 A1 | 10/2022 | | |
| WO | WO 2022/221335 A1 | 10/2022 | | |
| WO | WO 2022/221336 A1 | 10/2022 | | |
| WO | WO 2022/221359 A1 | 10/2022 | | |
| WO | WO 2022/221440 A1 | 10/2022 | | |
| WO | WO 2022/226277 A1 | 10/2022 | | |
| WO | WO 2022/226318 A1 | 10/2022 | | |
| WO | WO 2022/232585 A1 | 11/2022 | | |
| WO | WO 2022/241103 A1 | 11/2022 | | |
| WO | WO 2022/245888 A1 | 11/2022 | | |
| WO | WO 2022/266010 A1 | 12/2022 | | |
| WO | WO 2022/266012 A1 | 12/2022 | | |
| WO | WO 2022/266389 A1 | 12/2022 | | |
| WO | WO 2023/283642 A1 | 1/2023 | | |
| WO | WO 2023/283645 A1 | 1/2023 | | |
| WO | WO 2023/283651 A1 | 1/2023 | | |
| WO | WO 2023/014649 A1 | 2/2023 | | |
| WO | WO 2023/018773 A1 | 2/2023 | | |
| WO | WO 2023/018923 A1 | 2/2023 | | |
| WO | WO 2023/019181 A1 | 2/2023 | | |
| WO | WO 2023/056401 A1 | 4/2023 | | |
| WO | WO 2023/069625 A1 | 4/2023 | | |
| WO | WO 2023/069895 A1 | 4/2023 | | |
| WO | WO 2023/069900 A1 | 4/2023 | | |
| WO | WO 2023/076658 A1 | 5/2023 | | |
| WO | WO 2023/081311 A1 | 5/2023 | | |
| WO | WO 2023/092069 A1 | 5/2023 | | |
| WO | WO 2023/107999 A2 | 6/2023 | | |
| WO | WO 2023/114307 A1 | 6/2023 | | |
| WO | WO 2023/132885 A1 | 7/2023 | | |
| WO | WO 2023/137149 A1 | 7/2023 | | |
| WO | WO 2023/150256 A1 | 8/2023 | | |
| WO | WO 2023/154818 A1 | 8/2023 | | |
| WO | WO 2023/196914 A1 | 10/2023 | | |
| WO | WO 2023/201204 A1 | 10/2023 | | |
| WO | WO 2023/201294 A1 | 10/2023 | | |
| WO | WO 2023/201296 A1 | 10/2023 | | |
| WO | WO 2023/212696 A1 | 11/2023 | | |
| WO | WO 2023/225524 A1 | 11/2023 | | |
| WO | WO 2023/250119 A1 | 12/2023 | | |
| WO | WO 2024/010993 A1 | 1/2024 | | |
| WO | WO 2024/015890 A1 | 1/2024 | | |
| WO | WO 2024/026005 A1 | 2/2024 | | |
| WO | WO 2024/030369 A1 | 2/2024 | | |

OTHER PUBLICATIONS

Boegel et al. "A catalog of HLA type, HLA expression, and neo-epitope candidates in human cancer cell lines" OncoImmunology (2014) 3(8):1-13. (Year: 2014).*

Coomber "Generation of Anti-p53 Fab Fragments from Individuals with Colorectal Cancer Using Phage Display". J Immunol Aug. 15, 1999; 163 (4): 2276-2283 (Year: 1999).*

Heyes, James, et al. "Cationic lipid saturation influences intracellular delivery of encapsulated nucleic acids." Journal of controlled release 107.2 (2005): 276-287. (Year: 2005).*

U.S. Appl. No. 16/036,318, filed Jul. 16, 2018, Ciaramella et al.

U.S. Appl. No. 16/144,394, filed Sep. 27, 2018, Ciaramella et al.

U.S. Appl. No. 17/683,171, filed Feb. 28, 2022, Ciaramella et al.

U.S. Appl. No. 15/748,773, filed Jan. 30, 2018, Ciaramella et al.

U.S. Appl. No. 17/554,182, filed Dec. 17, 2021, Ciaramella et al.

U.S. Appl. No. 15/753,293, filed Feb. 17, 2018, Smith.

U.S. Appl. No. 15/767,587, filed Apr. 11, 2018, Ciaramella.

U.S. Appl. No. 16/833,409, filed Mar. 27, 2020, Ciaramella.

U.S. Appl. No. 15/767,600, filed Apr. 11, 2018, Ciaramella et al.

U.S. Appl. No. 15/767,609, filed Apr. 11, 2018, Ciaramella et al.

U.S. Appl. No. 15/767,613, filed Apr. 11, 2018, Ciaramella et al.

(56) References Cited

OTHER PUBLICATIONS

U.S. Appl. No. 15/767,618, filed Apr. 11, 2018, Ciaramella et al.
U.S. Appl. No. 17/590,479, filed Feb. 1, 2022, Ciaramella et al.
U.S. Appl. No. 16/897,859, filed Jun. 10, 2020, Ciaramella et al.
U.S. Appl. No. 17/737,532, filed May 5, 2022, Ciaramella et al.
U.S. Appl. No. 17/583,674, filed Jan. 25, 2022, Besin et al.
U.S. Appl. No. 17/523,034, filed Nov. 10, 2021, Hoge et al.
U.S. Appl. No. 17/523,060, filed Nov. 10, 2021, Hoge et al.
U.S. Appl. No. 17/548,172, filed Dec. 10, 2021, Ciaramella et al.
U.S. Appl. No. 17/839,401, filed Jun. 13, 2022, Ciaramella et al.
U.S. Appl. No. 16/897,734, filed Jun. 10, 2020, Ciaramella et al.
U.S. Appl. No. 17/830,742, filed Jun. 2, 2022, Miracco.
U.S. Appl. No. 16/001,765, filed Jun. 6, 2018, Marquardt et al.
U.S. Appl. No. 17/852,974, filed Jun. 29, 2022, Marquardt et al.
U.S. Appl. No. 17/127,949, filed Dec. 18, 2020, Ciaramella.
U.S. Appl. No. 17/385,655, filed Jul. 26, 2021, Ciaramella et al.
U.S. Appl. No. 16/603,111, filed Oct. 4, 2019, Brito et al.
U.S. Appl. No. 16/482,844, filed Aug. 1, 2019, Valiante et al.
U.S. Appl. No. 16/496,135, filed Sep. 20, 2019, Narayanan et al.
U.S. Appl. No. 16/483,012, filed Aug. 1, 2019, Mauger et al.
U.S. Appl. No. 17/350,662, filed Jun. 17, 2021, Rabideau et al.
U.S. Appl. No. 16/362,366, filed Mar. 22, 2019, Ciaramella.
U.S. Appl. No. 16/493,986, filed Sep. 13, 2019, Ciaramella et al.
U.S. Appl. No. 16/494,130, filed Sep. 13, 2019, Ciaramella et al.
U.S. Appl. No. 16/494,103, filed Sep. 13, 2019, Ciaramella et al.
U.S. Appl. No. 17/245,973, filed Apr. 30, 2021, Ciaramella.
U.S. Appl. No. 16/494,988, filed Sep. 17, 2019, Ciaramella et al.
U.S. Appl. No. 17/155,592, filed Jan. 22, 2021, Ciaramella et al.
U.S. Appl. No. 16/639,265, filed Feb. 14, 2020, Issa et al.
U.S. Appl. No. 16/639,305, filed Feb. 14, 2020, Issa et al.
U.S. Appl. No. 16/765,285, filed May 19, 2020, Ciaramella et al.
U.S. Appl. No. 16/302,607, filed Nov. 16, 2018, Benenato et al.
U.S. Appl. No. 16/623,069, filed Dec. 16, 2019, Hoge et al.
U.S. Appl. No. 16/639,403, filed Feb. 14, 2020, Hoge et al.
U.S. Appl. No. 17/531,211, filed Nov. 19, 2021, Ciaramella et al.
U.S. Appl. No. 16/965,589, filed Jul. 28, 2020, Ciaramella et al.
U.S. Appl. No. 17/255,949, filed Dec. 23, 2020, Zhong et al.
U.S. Appl. No. 17/277,423, filed Mar. 18, 2021, Almarsson et al.
U.S. Appl. No. 17/277,452, filed Mar. 18, 2021, Hennessy et al.
U.S. Appl. No. 17/276,112, filed Mar. 12, 2021, Martini et al.
U.S. Appl. No. 17/438,049, filed Sep. 10, 2021, Elich et al.
U.S. Appl. No. 17/634,939, filed Feb. 11, 2022, Shamashkin et al.
U.S. Appl. No. 17/291,947, filed May 6, 2021, Ashburn et al.
U.S. Appl. No. 17/439,198, filed Sep. 14, 2021, Lusso et al.
U.S. Appl. No. 17/325,883, filed May 20, 2021, Dousis et al.
U.S. Appl. No. 17/816,696, filed Aug. 1, 2022, Dousis et al.
U.S. Appl. No. 17/737,581, filed May 5, 2022, Panther et al.
U.S. Appl. No. 16/794,318, filed Feb. 19, 2020, Mauger et al.
U.S. Appl. No. 17/761,420, filed Mar. 17, 2022, Amato et al.
U.S. Appl. No. 17/145,164, filed Jan. 8, 2021, Giessel et al.
U.S. Appl. No. 17/615,202, filed Nov. 30, 2021, Hopson.
U.S. Appl. No. 17/641,967, filed Mar. 10, 2022, John et al.
U.S. Appl. No. 17/840,478, filed Jun. 14, 2022, Kramarczyk et al.
U.S. Appl. No. 17/796,401, filed Jul. 29, 2022, Shaw et al.
U.S. Appl. No. 17/518,542, filed Nov. 3, 2021, Metkar et al.
U.S. Appl. No. 17/796,208, filed Jul. 28, 2022, Stewart-Jones et al.
U.S. Appl. No. 17/797,784, U.S. Appl. No. 17/797,784, Stewart-Jones et al.
U.S. Appl. No. 17/572,465, filed Jan. 10, 2022, Nachbagauer et al.
U.S. Appl. No. 17/726,971, filed Apr. 22, 2022, Hennessy.
PCT/US2016/058317, Feb. 22, 2017, International Search Report and Written Opinion.
[No Author Listed], Clinical First-in-human Dose Escalation Study Evaluating the Safety and Tolerability of Intravenous Administration of a Tetravalent RNA-lipoplex Cancer Vaccine Targeting the Tumor-associated Antigens NY-ESO-1, Tyrosinase, MAGE-A3, and TPTE in Patients With Advanced Melanoma. Dialog. Published Apr. 22, 2015. Retrieved via Internet Jan. 16, 2023. 4 pages.
[No Author Listed], Moderna and Merck Announce mRNA-4157/V940, an Investigational Personalized mRNA Cancer Vaccine, in Combination with KEYTRUDA(R) (pembrolizumab), Met Primary Efficacy Endpoint in Phase 2b KEYNOTE-942 Trial. Press Release. Dec. 13, 2022. 24 pages.
Akinc et al., A combinatorial library of lipid-like materials for delivery of RNAi therapeutics. Nat Biotechnol. May 2008;26(5):561-9. doi: 10.1038/nbt1402. Epub Apr. 27, 2008.
Almeida, "STINGing" Liposomal Delivery for Cancer Immunotherapy. Advance Science News. Jan. 24, 2017. 2 Pages.
Bei et al., TAA polyepitope DNA-based vaccines: a potential tool for cancer therapy. J Biomed Biotechnol. 2010;2010:102758. doi: 10.1155/2010/102758. Epub Jun. 17, 2010.
Buckwalter et al., "It is the antigen(s), stupid" and other lessons from over a decade of vaccitherapy of human cancer. Semin Immunol. Oct. 2008;20(5):296-300. doi: 10.1016/j.smim.2008.07.003. Epub Aug. 20, 2008.
Buschmann et al, Nanomaterial Delivery Systems for mRNA Vaccines. Vaccines (Basel). Jan. 19, 2021;9(1):65. doi: 10.3390/vaccines9010065.
Corrales et al., Molecular Pathways: Targeting the Stimulator of Interferon Genes (STING) in the Immunotherapy of Cancer. Clin Cancer Res. Nov. 1, 2015;21(21):4774-9. doi: 10.1158/1078-0432.CCR-15-1362. Epub Sep. 15, 2015.
Danaei et al., Impact of Particle Size and Polydispersity Index on the Clinical Applications of Lipidic Nanocarrier Systems. Pharmaceutics. May 18, 2018;10(2):57. doi: 10.3390/pharmaceutics 10020057.
Ding et al., Analysis of next-generation genomic data in cancer: accomplishments and challenges. Hum Mol Genet. Oct. 15, 2010;19(R2):R188-96. doi: 10.1093/hmg/ddq391. Epub Sep. 15, 2010.
Garcia-Manyes et al., Nanomechanics of lipid bilayers: heads or tails? J Am Chem Soc. Sep. 22, 2010;132(37):12874-86. doi: 10.1021/ja1002185.
Geall et al., RNA: the new revolution in nucleic acid vaccines. Semin Immunol. Apr. 2013;25(2):152-9. doi: 10.1016/j.smim.2013.05.001. Epub Jun. 2, 2013.
Gjetting et al.,A simple protocol for preparation of a liposomal vesicle with encapsulated plasmid DNA that mediate high accumulation and reporter gene activity in tumor tissue. Results Pharma Sci. Sep. 3, 2011;1(1):49-56. doi: 10.1016/j.rinphs.2011.08.001. eCollection May 2011.
Guevara et al., Advances in Lipid Nanoparticles for mRNA-Based Cancer Immunotherapy. Front Chem. 2020; 8: 589959.
Guimaraes et al., Ionizable lipid nanoparticles encapsulating barcoded mRNA for accelerated in vivo delivery screening. J Control Release. Dec. 28, 2019;316:404-417. doi: 10.1016/j.jconrel.2019.10.028. Epub Oct. 31, 2019.
Hoarau et al., Novel long-circulating lipid nanocapsules. Pharm Res. Oct. 2004;21(10):1783-9. doi: 10.1023/b:pham.0000045229.87844.21.
Hörr, RNA vaccine for the induction of specific cytotoxic T lymphocytes (CTL) and antibodies. Eberhard Karls University of Tübingen. Dissertation. English-Language Translation. 1999. 138 Pages.
Hou et al., Lipid nanoparticles for mRNA delivery. Nature Reviews Materials vol. 6, pp. 1078-1094 (2021).
Iden et al., In vitro and in vivo comparison of immunoliposomes made by conventional coupling techniques with those made by a new post-insertion approach. Biochim Biophys Acta. Aug. 6, 2001;1513(2):207-16. doi: 10.1016/s0005-2736(01)00357-1.
Ishida et al., A combinatorial approach to producing sterically stabilized (Stealth) immunoliposomal drugs. FEBS Lett. Oct. 22, 1999;460(1):129-33. doi: 10.1016/s0014-5793(99)01320-4.
Kramps et al., Messenger RNA-based vaccines: progress, challenges, applications. Wiley Interdiscip Rev RNA. Nov.-Dec. 2013;4(6):737-49. doi: 10.1002/wrna.1189. Epub Jul. 25, 2013.
Leung et al., Lipid Nanoparticles Containing siRNA Synthesized by Microfluidic Mixing Exhibit an Electron-Dense Nanostructured Core. J Phys Chem C Nanomater Interfaces. Aug. 30, 2012;116(34):18440-18450. doi: 10.1021/jp303267y. Epub Jul. 18, 2012.
Li et al., Effects of local structural transformation of lipid-like compounds on delivery of messenger RNA. Sci Rep. Feb. 26, 2016;6:22137. doi: 10.1038/srep22137.

(56) References Cited

OTHER PUBLICATIONS

Li et al., Lipid-based nanoparticles for nucleic acid delivery. Pharm Res. Mar. 2007;24(3):438-49. doi: 10.1007/s11095-006-9180-5.
Li et al., Targeted delivery of antisense oligodeoxynucleotide and small interference RNA into lung cancer cells. Mol Pharm. Sep.-Oct. 2006;3(5):579-88. doi: 10.1021/mp060039w.
Maclachlan, Chapter 9 Liposomal Formulations for Nucleic Acid Delivery. Retrieved from the Internet on Aug. 10, 2020 from http://arbutusbio.com/docs/Liposome_Formulations_Proof_for_Distribution.pdf; originally published 2007, pp. 237-270.
Navin et al., Tumour evolution inferred by single-cell sequencing. Nature. Apr. 7, 2011;472(7341):90-4. doi: 10.1038/nature09807. Epub Mar. 13, 2011.
Rammensee et al., Towards patient-specific tumor antigen selection for vaccination. Immunol Rev. Oct. 2002;188:164-76. doi: 10.1034/j.1600-065x.2002.18815.x.
Rodriguez-Gascon et al., Development of nucleic acid vaccines: use of self-amplifying RNA in lipid nanoparticles. Int J Nanomedicine. 2014; 9: 1833-1843.
Santos et al., Design of peptide-targeted liposomes containing nucleic acids. Biochim Biophys Acta. Mar. 2010;1798(3):433-41. doi: 10.1016/j.bbamem.2009.12.001. Epub Dec. 11, 2009.
Segal et al., Epitope landscape in breast and colorectal cancer. Cancer Res. Feb. 1, 2008;68(3):889-92. doi: 10.1158/0008-5472.CAN-07-3095.
Srivastava et al., Modeling the repertoire of true tumor-specific MHC I epitopes in a human tumor. PLoS One. Jul. 10, 2009;4(7):e6094. doi: 10.1371/journal.pone.0006094.
Sugiyama et al., Change in the character of liposomes as a drug carrier by modifying various polyethyleneglycol-lipids. Biol Pharm Bull. 2013;36(6):900-6. doi: 10.1248/bpb.b13-00084.
Tam et al., Advances in Lipid Nanoparticles for siRNA Delivery. Pharmaceutics. Sep. 18, 2013;5(3):498-507. doi: 10.3390/pharmaceutics5030498.
To et al., An overview of rational design of mRNA-based therapeutics and vaccines. Expert Opin Drug Discov. Nov. 2021;16(11):1307-1317. doi: 10.1080/17460441.2021.1935859. Epub Jul. 19, 2021.
Ulmer et al., RNA-based vaccines. Vaccine. Jun. 22, 2012;30(30):4414-8. doi: 10.1016/j.vaccine.2012.04.060. Epub Apr. 28, 2012.
Zhang et al., Delivery of mRNA vaccine with a lipid-like material potentiates antitumor efficacy through Toll-like receptor 4 signaling. Proc Natl Acad Sci U S A. Feb. 9, 2021;118(6):e2005191118. doi: 10.1073/pnas.2005191118.
Zhao et al., MHC-Peptide binding prediction for epitope based vaccine design. Int. J. Integr. Biol. 2007;1(2):127-140.
International Search Report and Written Opinion for Application No. PCT/US2016/058317, mailed Feb. 22, 2017.
[No Author Listed] Programme of the 1st International mRNA Health Conference, Germany; Oct. 2013. 32 pages.
[No Author Listed], Clinical Trial NCT03382405. "Safety, Reactogenicity, and Immunogenicity of Cytomegalovirus Vaccines mRNA-1647 and mRNA-1443 in Healthy Adults." First posted Dec. 22, 2017. Retrieved online Nov. 13, 2020 from www.clinicaltrials.gov/ct2/show/study/NCT03382405?term=modernatx&draw=3&rank=14.
[No Author Listed], Clinical Trial NCT04283461. "Safety and Immunogenicity Study of 2019-nCoV Vaccine (mRNA-1273) for Prophylaxis of SARS-CoV-2 Infection (COVID-19)." First posted: Feb. 25, 2020. Retrieved online Aug. 26, 2021 from clinicaltrials.gov/ct2/show/NCT04283461.
Ajbani et al., Immunogenicity of Semliki Forest Virus Based Self-Amplifying RNA Expressing Indian HIV-1C Genes in Mice. Int J Biol Macromol. Nov. 2015;81:794-802. doi: 10.1016/j.ijbiomac.2015.09.010. Epub Sep. 8, 2015.
Araujo et al., Before It Gets Started: Regulating Translation at the 5 UTR. Hindawi Publishing Corporation Comparative and Functional Genomics vol. 2012, Article ID 475731, 8 pages, doi:10.1155/2012/475731.
Ashley, D.M. et al., Bone marrow-generated dendritic cells pulsed with tumor extracts or tumor RNA induce antitumor immunity against central nervous system tumors. J Exp Med. Oct. 6, 1997; 186(7): 1177-82.
Awasthi et al., Nucleoside-modified mRNA encoding HSV-2 glycoproteins C, D, and E prevents clinical and subclinical genital herpes. Sci Immunol. Sep. 20, 2019;4(39): eaaw7083.
Boczkowski, D. et al., Induction of tumor immunity and cytotoxic T lymphocyte responses using dendritic cells transfected with messenger RNA amplified from tumor cells. Cancer Res. Feb. 15, 2000;60(4):1028-34.
Boisguerin et al., Translation of genomics-guided RNA-based personalised cancer vaccines: towards the beside. British Journal of Cancer. Oct. 14, 2014;111(8):1469-75. doi: 10.1038/bjc.2013.820.
Bolhassani A., et al. , Improvement of Different Vaccine Delivery Systems For Cancer Therapy, Molecular Cancer, Biomed Central, London, GB, 2011, vol. 10, No. 3, pp. 1-20.
Bonehill, A., et al., Single-step antigen loading and activation of dendritic cells by mRNA electroporation for the purpose of therapeutic vaccination in melanoma patients. Clin Cancer Res. May 2009; 15(10): 3366-3375.
Brito et al., Self-amplifying mRNA vaccines. Adv Genet. 2015;89:179-233. doi: 10.1016/bs.adgen.2014.10.005. Epub Dec. 4, 2014.
Carralot, J.P. et al., Production and characterization of amplified tumor-derived cRNA libraries to be used as vaccines against metastatic melanomas. Genet Vaccines Ther. Aug. 22, 2005;3:6.
Cesano et al., Bringing the next Generation of Immuno-Oncology Biomarkers to the Clinic. Biomedicines. Feb. 2, 2018;6(1):14. doi: 10.3390/biomedicines6010014.
Chudley et al., Harmonisation of short-term in vitro culture for the expansion of antigen-specific CD8(+) T cells with detection by ELISPOT and HLA-multimer staining. Cancer Immunol Immunother. 2014;63(11):1199-1211.
Clinical trial NCT04528719: A Dose Escalation Study to Evaluate Safety, Reactogenicity, and Immunogenicity of mRNA-1345 in Healthy Adults and in Children Who Are Respiratory Syncytial Virus Seropositive (ModernaTX, Inc.) First Posted Aug. 27, 2020. Retrieved online on Mar. 15, 2021 at www.clinicaltrials.gov/ct2/show/NCT04528719?term=NCT04528719&draw=2&rank=1.
Conry, R.M. et al., Characterization of a messenger RNA polynucleotide vaccine vector. Cancer Res. Apr. 1, 1995 ;55 (7):1397-1400.
Cross, Without these lipid shells, there would be no mRNA vaccines for COVID-19. Chem Eng News. Mar. 6, 2021; 99(8). 4 pages.
Cullis et al., Lipid Nanoparticle Systems for Enabling Gene Therapies. Mol Ther. Jul. 5, 2017;25(7):1467-1475. doi: 10.1016/j.ymthe.2017.03.013. Epub Apr. 13, 2017.
Davidsen et al., Deep generative models for T cell receptor protein sequences. Elife. Sep. 5, 2019;8:e46935. doi: 10.7554/eLife.46935.
De Carvalho, Biologic properties of human leukemic and tumoral RNA. IV. Leukemia and neoplasms induced in mice with human leukemic RNA carried in tissue culture. J Lab Clin Med. May 1960;55:706-14.
Diken et al., Current Developments in Actively Personalized Cancer Vaccination with a Focus on RNA as the Drug Format. Prog Tumor Res. 2015;42:44-54. doi: 10.1159/000437184. Epub Sep. 4, 2015. Review.
Diken et al., mRNA: A Versatile Molecule for Cancer Vaccines. Curr Issues Mol Biol. 2017;22:113-128. doi: 10.21775/cimb.022.113. Epub Nov. 1, 2016.
Durbin et al., RNAs Containing Modified Nucleotides Fail To Trigger RIG-I Conformational Changes for Innate Immune Signaling. mBio. Sep. 20, 2016;7(5):e00833-16. doi: 10.1128/mBio.00833-16.
Egan et al., An HSV-2 nucleoside-modified mRNA genital herpes vaccine containing glycoproteins gC, gD, and gE protects mice against HSV-1 genital lesions and latent infection. PLoS Pathog. Jul. 27, 2020;16(7):e1008795.
Elayadi et al., Application of PNA and LNA oligomers to chemotherapy. Curr Opin Investig Drugs. Apr. 2001;2(4):558-61.
Freyn et al., A Multi-Targeting, Nucleoside-Modified mRNA Influenza Virus Vaccine Provides Broad Protection in Mice. Mol Ther. Jul. 8, 2020;28(7):1569-1584. doi: 10.1016/j.ymthe.2020.04.018. Epub Apr. 19, 2020.

(56) References Cited

OTHER PUBLICATIONS

Furuichi et al., Viral and cellular mRNA capping: past and prospects. Adv Virus Res. 2000;55:135-84. doi: 10.1016/s0065-3527(00)55003-9.
Furuichi, Caps on Eukaryotic mRNAs. eLS. John Wiley & Sons. Jul. 2014. 1-12.
Genini et al., Serum Antibody Response to the gH/gL/pUL128-131 Five-Protein Complex of Human Cytomegalovirus (HCMV) in Primary and Reactivated HCMV Infections. J Clin Virol. Oct. 2011;52(2):113-8. doi: 10.1016/j.jcv.2011.06.018. Epub Aug. 4, 2011.
Gilboa, E. et al., Cancer immunotherapy with mRNA-transfected dendritic cells. Immunol Rev. Jun. 2004;199:251-63.
Grabbe et al., Translating nanoparticulate-personalized cancer vaccines into clinical applications: case study with RNA-lipoplexes for the treatment of melanoma. Nanomedicine (Lond). Oct. 2016;11(20):2723-2734.
Hadinoto et al., Lipid-polymer Hybrid Nanoparticles as a New Generation Therapeutic Delivery Platform: A Review. Eur J Pharm Biopharm. Nov. 2013;85(3 Pt A):427-43. doi: 10.1016/j.ejpb.2013.07.002. Epub Jul. 17, 2013.
Hartmaier et al., Genomic analysis of 63,220 tumors reveals insights into tumor uniqueness and targeted cancer immunotherapy strategies. Genome Med. Feb. 24, 2017;9(1):16. doi: 10.1186/s13073-017-0408-2.
Hartmann et al., Handbook of RNA Biochemistry, Second Edition, “Part I RNA Synthesis and Detection.” 2014. p. 1-27.
Hassett et al., Optimization of Lipid Nanoparticles for Intramuscular Administration of mRNA Vaccines. Mol Ther Nucleic Acids. Apr. 15, 2019;15:1-11. Epub Feb. 7, 2019.
Heesch et al., Abstract CT020: MERIT: introducing individualized cancer vaccines for the treatment of TNBC—a phase I trial, [abstract]. In: Proceedings of the 107th Annual Meeting of the American Association for Cancer Research; Apr. 16-20, 2016; New Orleans, LA. Philadelphia (PA): AACR; Cancer Res 2016; 76 (14 Suppl).
Heesch, S. et al. “The Mutanome Engineered RNA Immuno-Therapy (MERIT) project”, American Association for Cancer Research Annual Meeting, 2015, Presentation Abstract CT201, Presented Apr. 20, 2015 from 8am-12pm. Retrieved online: www.abstractsonline.com/Plan/ViewAbstract.aspx?sKey=9d07e19c-3e4b-44d9-9b40-c8c9373541de&cKey=fae745eb-1173-4f15-899a-43aaf8fe377d&mKey=%7b19573A54-AE8F-4E00-9C23-BD6D62268424%7d. Abstract. Last accessed Nov. 1, 2016.
Heidenreich et al., A novel RNA-based adjuvant combines strong immunostimulatory capacities with a favorable safety profile. Int J Cancer. Jul. 15, 2015;137(2):372-84. doi: 10.1002/ijc.29402. Epub Jan. 8, 2015.
Heiser, A. et al., Induction of polyclonal prostate cancer-specific CTL using dendritic cells transfected with amplified tumor Rna. J Immunol. Mar. 1, 2001; 166(5):2953-60.
Hess et al., Vaccination with mRNAs encoding tumor-associated antigens and granulocyte-macrophage colony-stimulating factor efficiently primes CTL responses, but is insufficient to overcome tolerance to a model tumor/self antigen. Cancer Immunol Immunother. Jun. 2006;55(6):672-83. Epub Aug. 20, 2005.
Hoerr, I. et al., In vivo application of RNA leads to induction of specific cytotoxic T lymphocytes and antibodies. Eur J Immunol. Jan. 2000;30(1):1-7.
Hoerr, More than a messenger: A new class of drugs-mRNA-based therapeutics. Genetic Engineering & Biotechnology News. Jun. 18, 2013. www.genengnews.com/gen-articles/more-than-a-messenger-a-new-class-of-drugs-mrna-based-therapeutics/4916/ [last accessed Mar. 25, 2016].
Hori et al., Antitumor Activity of Cationic Liposome-Mediated Bax mRNA Transfer in HOSM-1 Mandibular Osteoosarcoma Cells: A Comparative Study of Local Administration and Systemic Administration. Journal of Oral and Maxillofacial Surgery, 2014, vol. 72, No. 9, Suppl. 1, p. e107, Abstract No. 98.
John et al., Multi-antigenic human cytomegalovirus mRNA vaccines that elicit potent humoral and cell-mediated immunity. Vaccine. Mar. 14, 2018;36(12):1689-1699. doi:10.1016/j.vaccine.2018.01.029. Epub Feb. 15, 2018.
Kallen et al., A development that may evolve into a revolution in medicine: mRNA as the basis for novel, nucleotide-based vaccines and drugs. Ther Adv Vaccines. Jan. 2014;2(1):10-31. doi: 10.1177/2051013613508729.
Kallen et al., A novel, disruptive vaccination technology: self-adjuvanted RNActive(®) vaccines. Hum Vaccin Immunother. Oct. 2013;9(10):2263-76. doi: 10.4161/hv.25181. Epub Jun. 4, 2013. Review.
Karlsson et al., Comparison of the ELISPOT and cytokine flow cytometry assays for the enumeration of antigen-specific T cells. J Immunol Methods. 2003;283(1-2):141-153.
Kauffman et al., Materials for non-viral intracellular delivery of messenger RNA therapeutics. J Control Release. Oct. 28, 2016;240:227-234. doi: 10.1016/j.jconrel.2015.12.032. Epub Dec. 21, 2015.
Kloke, B. et al. “IVAC Mutanome: Individualized vaccines for the treatment of cancer”, American Association for Cancer Research Annual Meeting, 2015, Presentation Abstract CT202, Presented Apr. 20, 2015 from 8am-12pm. Retrieved online: www.abstractsonline.com/Plan/ViewAbstract.aspx?sKey=9d07e19c-3e4b-44d9-9b40-c8c9373541de&cKey=98132924-513a-4ab9-affa-ef01b3514ef4&mKey=%7b19573A54-AE8F-4E00-9C23-BD6D62268424%7d. Abstract. Last accessed Nov. 1, 2016.
Koido, S. et al., Induction of antitumor immunity by vaccination of dendritic cells transfected with MUC1 RNA. J Immunol. Nov. 15, 2000;165(10):5713-9.
Kowalski et al., Delivering the Messenger: Advances in Technologies for Therapeutic mRNA Delivery. Molecular Therapy vol. 27 No. 4 Apr. 2019.
Koyama et al., Analysis on GENIE reveals novel recurrent variants that affect molecular diagnosis of sizable number of cancer patients. BMC Cancer. Feb. 1, 2019;19(1):114. doi: 10.1186/s12885-019-5313-1.
Kreiter et al, Mutant MHC class II epitopes drive therapeutic immune responses to cancer. Nature. Apr. 30, 2015;520(7549):692-6. doi: 10.1038/nature14426. Epub Apr. 22, 2015. Erratum in: Nature. Jul. 16, 2015;523(7560):370.
Kreiter, S., et al., Intranodal vaccination with naked antigen-encoding RNA elicits potent prophylactic and therapeutic antitumoral immunity. Cancer Res. 2010; 70: 9031-9040.
Kreiter, S., et al., Tumor vaccination using messenger RNA: prospects of a future therapy. Curr Opinion in Immun. Jun. 2011; 23(3): 399-406.
Kumar et al., Shielding of Lipid Nanoparticles for siRNA Delivery: Impact on Physicochemical Properties, Cytokine Induction, and Efficacy. Mol Ther Nucleic Acids. Nov. 18, 2014;3(11):e210. doi: 10.1038/mtna.2014.61.
Kurimoto et al., PEG-OligoRNA Hybridization of mRNA for Developing Sterically Stable Lipid Nanoparticles toward In Vivo Administration. Molecules. Apr. 3, 2019;24(7): 1303.
Kutchko et al., Transcending the Prediction Paradigm: Novel Applications of SHAPE to RNA Function and Evolution. Wiley Interdiscip Rev RNA. Jan. 2017;8(1):e1374. doi: 10.1002/wrna.1374. Epub Jul. 10, 2016.
Lozano et al., Ribosome-dependent conformational flexibility changes and RNA dynamics of IRES domains revealed by differential SHAPE. Sci Rep. Apr. 3, 2018;8(1):5545. doi: 10.1038/s41598-018-23845-x.
Maclachlan, Lipid Nanoparticle-mediated delivery of messenger RNA. Presentation. 1st International mRNA Health Conference. Tubingen, Germany. Oct. 24, 2013. files.shareholder.com/downloads/ABEA-50QJTB/2628241206x0x699789/47543d12-db34-4e6e-88a9-f3ae5d97b1d2/MacLachlan_mRNA_Conf_2013.pdf. Last accessed Dec. 22, 2016.
Madden et al., Systemic delivery of mRNA therapeutics using lipid nanoparticles (LNP): improved potency for novel LNP and influence of route of administration on protein expression. 2nd International mRNA Health Conference. Nov. 12, 2014. acuitastx.com/wp-content/uploads/2015/01/Poster-Second-International-mRNA-Health-Conference.pdf. 1 page.

(56) References Cited

OTHER PUBLICATIONS

Michel et al., Cationic Nanoliposomes Meet mRNA: Efficient Delivery of Modified mRNA Using Hemocompatible and Stable Vectors for Therapeutic Applications. Mol Ther Nucleic Acids. Sep. 15, 2017;8:459-468. doi: 10.1016/j.omtn.2017.07.013. Epub Jul. 25, 2017.

Mitchell, DA et al., RNA transfected dendritic cells as cancer vaccines. Curr Opin Mol Ther. Apr. 2000;2(2):176-81.

Mitchell, DA et al., RNA-transfected dendritic cells in cancer immunotherapy. J Clin Invest. Nov. 2000;106 (9):1065-9.

Mockey et al., mRNA-based cancer vaccine: prevention of B16 melanoma progression and metastasis by systemic injection of MART1 mRNA histidylated lipopolyplexes, Cancer Gene Therapy, 2007, 14, pp. 802-814.

Monslow et al., Immunogenicity generated by mRNA vaccine encoding VZV gE antigen is comparable to adjuvanted subunit vaccine and better than live attenuated vaccine in nonhuman primates. Vaccine. Aug. 10, 2020;38(36):5793-5802. doi: 10.1016/j.vaccine.2020.06.062. Epub Jul. 20, 2020.

Muller, M.R. et al., Transfection of dendritic cells with RNA induces CD4- and CD8-mediated T cell immunity against breast carcinomas and reveals the immunodominance of presented T cell epitopes. J Immunol. Jun. 15, 2003;170(12):5892-6.

NCT02410733—Evaluation of the Safety and Tolerability of i.v. Administration of a Cancer Vaccine in Patients With Advanced Melanoma (Lipo-MERIT), ClinicalTrials.gov, Jul. 17, 2019, (Online), Viewed online Jan. 2, 2020, URL: www.clinicaltrials.gov/ct2/show/record/NCT02410733?term=NCT02410733&draw=2&rank=1.

Nielsen et al., Toward Personalized Lymphoma Immunotherapy: Identification of Common Driver Mutations Recognized by Patient CD8+ T Cells. Clin Cancer Res. May 1, 2016;22(9):2226-36. doi: 10.1158/1078-0432.CCR-15-2023. Epub Dec. 2, 2015.

Oberli et al., Lipid Nanoparticle Assisted mRNA Delivery for Potent Cancer Immunotherapy. Nano Lett. Mar. 8, 2017;17(3):1326-1335. doi: 10.1021/acs.nanolett.6b03329. Epub Dec. 5, 2016.

Ouranidis et al., Pharma 4.0 Continuous mRNA Drug Products Manufacturing. Pharmaceutics. Aug. 31, 2021;13(9):1371. doi: 10.3390/pharmaceutics13091371.

Pardi et al., Expression Kinetics of Nucleoside-Modified mRNA Delivered in Lipid Nanoparticles to Mice by Various Routes. J Control Release. Nov. 10, 2015;217:345-51. doi: 10.1016/j.jconrel.2015.08.007. Epub Aug. 8, 2015.

Pardi et al., mRNA vaccines—a new era in vaccinology. Nat Rev Drug Discov. Apr. 2018;17(4):261-279. doi: 10.1038/nrd.2017.243. Epub Jan. 12, 2018.

Patel et al., Naturally-occurring cholesterol analogues in lipid nanoparticles induce polymorphic shape and enhance intracellular delivery of mRNA. Nat Commun. Feb. 20, 2020;11(1):983. doi: 10.1038/s41467-020-14527-2.

Phua et al., Messenger RNA (mRNA) nanoparticle tumour vaccination. Nanoscale. Jul. 21, 2014;6(14):7715-29. doi: 10.1039/c4nr01346h. Review.

Ponsaerts, P. et al., Cancer immunotherapy using RNA-loaded dendritic cells. Clin Exp Immunol. Dec. 2003;134 (3):378-84.

Poveda et al., Establishing Preferred Product Characterization for the Evaluation of RNA Vaccine Antigens. Vaccines (Basel). Sep. 27, 2019;7(4):131. doi: 10.3390/vaccines7040131.

Rajasagi et al., Systematic identification of personal tumor-specific neoantigens in chronic lymphocytic leukemia. Blood. Jul. 17, 2014;124(3):453-62. doi: 10.1182/blood-2014-04-567933. Epub Jun. 2, 2014.

Ramamoorth et al., Non viral vectors in gene therapy—an overview. J Clin Diagn Res. Jan. 2015; 9(1): GE01-GE06.

Rammensee et al., Cancer Vaccines: Some Basic Considerations. Genomic and Personalized Medicine. 2009;573-589.

Reichmuth et al., mRNA Vaccine Delivery Using Lipid Nanoparticles. Ther Deliv. 2016;7(5):319-34. doi: 10.4155/tde-2016-0006.

Rittig et al., Intradermal vaccinations with RNA coding for TAA generate CD8+ and CD4+ immune responses and induce clinical benefit in vaccinated patients. Mol Ther. May 2011;19(5):990-9. doi: 10.1038/mt.2010.289. Epub Dec. 28, 2010.

Sabnis et al., A Novel Amino Lipid Series for mRNA Delivery: Improved Endosomal Escape and Sustained Pharmacology and Safety in Non-human Primates. Mol Ther. Jun. 6, 2018;26(6):1509-1519. doi: 10.1016/j.ymthe.2018.03.010. Epub Mar. 14, 2018.

Sahin et al., Personalized RNA mutanome vaccines mobilize poly-specific therapeutic immunity against cancer. Nature. Jul. 13, 2017;547(7662):222-226. doi: 10.1038/nature23003. Epub Jul. 5, 2017.

Sahin et al., Personalized vaccines for cancer immunotherapy. Science. Mar. 23, 2018;359(6382):1355-1360. doi: 10.1126/science.aar7112.

Sayour et al., RNA Nanoparticle Vaccines Facilitate and Sustain Adoptive Cellular Therapy Targeting Pediatric Intracranial Malignancies. Pediatric Blood and Cancer, Jun. 2015, vol. 62, Supplement 2, p. S24, Abstract No. 4012.

Schlake et al., Developing mRNA-vaccine technologies. RNA Biol. Nov. 2012;9(11):1319-30. doi: 10.4161/rna.22269. Epub Oct. 12, 2012.

Schmitt, W.E. et al., In vitro induction of a bladder cancer-specific T-cell response by mRNA-transfected dendritic cells. J Cancer Res Clin Oncol. 2001 ;127(3):203-6.

Shin et al., Recent Advances in RNA Therapeutics and RNA Delivery Systems Based on Nanoparticles. Adv. Therap., Nov. 2018; 1(7):1800065. Review.

Shinu et al., Multi-antigenic Human Cytomegalovirus mRNA Vaccines That Elicit Potent Humoral and Cell-Mediated Immunity. Vaccine. Mar. 14, 2018;36(12):1689-1699. doi: 10.1016/j.vaccine.2018.01.029. Epub Feb. 15, 2018.

Sieber et al., The Definition of Open Reading Frame Revisited. Trends Genet. Mar. 2018;34(3):167-170. doi: 10.1016/j.tig.2017.12.009. Epub Jan. 30, 2018.

Sinai et al., Variational auto-encoding of protein sequences. arXiv:1712.03346; 2018. p. 1-6.

Somarouthu et al., Immune-related tumour response assessment criteria: a comprehensive review. Br J Radiol. Apr. 2018;91(1084):20170457. doi: 10.1259/bjr.20170457. Epub Feb. 14, 2018.

Spitale et al., RNA structural analysis by evolving SHAPE chemistry. Wiley Interdiscip Rev RNA. Nov.-Dec. 2014;5(6):867-81. doi: 10.1002/wrna.1253. Epub Aug. 15, 2014.

Su, Z. et al., Immunological and clinical responses in metastatic renal cancer patients vaccinated with tumor RNA-transfected dendritic cells. Cancer Res. May 1, 2003 ;63(9):2127-33.

Terada et al., Characterization of Lipid Nanoparticles Containing Ionizable Cationic Lipids Using Design-of-Experiments Approach. Langmuir. Jan. 26, 2021;37(3):1120-1128. doi: 10.1021/acs.langmuir.0c03039. Epub Jan. 13, 2021.

Torrecilla et al., Lipid Nanoparticles as Carriers for RNAi Against Viral Infections: Current Status and Future Perspectives. Biomed Res Int. 2014;2014:161794. doi: 10.1155/2014/161794. Epub Aug. 12, 2014.

Tubiana et al., Learning protein constitutive motifs from sequence data. Elife. Mar. 12, 2019;8:e39397. doi: 10.7554/eLife.39397.

Vaziri et al., Extracting information from RNA SHAPE data: Kalman filtering approach. PLoS One. Nov. 21, 2018;13(11):e0207029. doi: 10.1371/journal.pone.0207029. eCollection 2018.

Wang et al., Chapter 3: Lipid Nanoparticles for the Delivery of Nucleic Acids. Book: Nanoparticulate Drug Delivery Systems: Strategies, Technologies, and Applications. 2013. 29 pages.

Wei et al.., The role of balanced training and testing data sets for binary classifiers in bioinformatics. PLoS One. Jul. 9, 2013;8(7):e67863. doi: 10.1371/journal.pone.0067863.

Weide, B. et al., Results of the first phase I/II clinical vaccination trial with direct injection of mRNA. J Immunother. Feb.-Mar. 2008;31(2):180-8.

Weide, B., et al., Direct injection of protamine-protected mRNA: Results of a phase 1/2 vaccination trial in metastatic melanoma patients. J. of Immunotherapy. Jun. 2009; 32(5): 498-507.

(56) References Cited

OTHER PUBLICATIONS

Wilmott et al., Selective BRAF inhibitors induce marked T-cell infiltration into human metastatic melanoma. Clin Cancer Res. Mar. 1, 2012;18(5):1386-94. doi: 10.1158/1078-0432.CCR-11-2479. Epub Dec. 12, 2011.
Woodle et al., Sterically stabilized liposomes. Biochim Biophys Acta. Aug. 14, 1992;1113(2):171-99. doi: 10.1016/0304-4157(92)90038-c. Abstract Only.
Yadav et al., Predicting Immunogenic Tumour Mutations by Combining Mass Spectrometry and Exome Sequencing. Nature. Nov. 27, 2014;515(7528):572-6. doi: 10.1038/nature14001.
Ying, H. et al., Cancer therapy using a self-replicating RNA vaccine. Nat Med. Jul. 1999;5(7):823-7.
Youn et al., Modified mRNA as an alternative to plasmid DNA (pDNA) for transcript replacement and vaccination therapy. Expert Opin Biol Ther. 2015;15(9):1337-48. doi: 10.1517/14712598.2015.1057563. Epub Jun. 30, 2015.
Zeng et al., Formulation and Delivery Technologies for mRNA Vaccines. Curr Top Microbiol Immunol. Jun. 2, 2020;10.1007/82_2020_217. doi: 10.1007/82_2020_217.
Zhang et al., Personalized cancer vaccines: Targeting the cancer mutanome. Vaccine. Feb. 15, 2017;35(7):1094-1100. doi: 10.1016/j.vaccine.2016.05.073. Epub Jul. 20, 2016.
Zhao et al., Chapter Two: Lipid Nanoparticles for Gene Delivery. Book: Advances in Genetics. Elsevier, 2014. 24 pages.
Zhao et al., Nanoparticle vaccines. Vaccine. Jan. 9, 2014;32(3):327-37. doi: 10.1016/j.vaccine.2013.11.069. Epub Dec. 2, 2013.
[No Author Listed], Merck and Moderna Initiate Phase 3 Study Evaluating V940 (mRNA-4157) in Combination with KEYTRUDA® (pembrolizumab) for Adjuvant Treatment of Patients with Resected High-Risk(Stage IIB-IV) Melanoma. Press Release. Jul. 26, 2023. 21 pages.
[No Author Listed], Adding a Personalized mRNA Cancer Vaccine to Immunotherapy May Prolong Recurrence-free Survival in Patients With High-risk Melanoma. American Association for Cancer Research (AACR). Apr. 16, 2023. 2 pages. https://www.aacr.org/about-the-aacr/newsroom/news-releases/adding-a-personalized-mrna-cancer-vaccine-to-immunotherapy-may-prolong-recurrence-free-survival-in-patients-with-high-risk-melanoma/. Last accessed Nov. 7, 2023.
Barbier et al., The clinical progress of mRNA vaccines and immunotherapies. Nat Biotechnol. Jun. 2022;40(6):840-854. doi: 10.1038/s41587-022-01294-2. Epub May 9, 2022.
Bharali et al., Nanoparticles and cancer therapy: a concise review with emphasis on dendrimers. Int J Nanomedicine. 2009;4:1-7. Epub Apr. 1, 2009.
Del Pozo-Rodriguez et al., Lipid nanoparticles as vehicles for macromolecules: nucleic acids and peptides. Recent Pat Drug Deliv Formul. Sep. 2011;5(3):214-26. doi: 10.2174/187221111797200515.
Fan et al., Nanoparticle Drug Delivery Systems Designed to Improve Cancer Vaccines and Immunotherapy. Vaccines (Basel). Aug. 27, 2015;3(3):662-85. doi: 10.3390/vaccines3030662.
Fang et al., Development of lipid-shell and polymer core nanoparticles with water-soluble salidroside for anti-cancer therapy. Int J Mol Sci. Feb. 25, 2014;15(3):3373-88. doi: 10.3390/ijms15033373.
Fotakis et al., Computational cancer neoantigen prediction: current status and recent advances. Immunooncol Technol. Nov. 20, 2021:12:100052. doi: 10.1016/j.iotech.2021.100052. eCollection Dec. 2021.
Hemmer et al., Minimal peptide length requirements for CD4(+) T cell clones—implications for molecular mimicry and T cell survival. Int Immunol. Mar. 2000;12(3):375-83. doi: 10.1093/intimm/12.3.375.
Khattak et al., A Personalized Cancer Vaccine, mRNA-4157 (V940), Combined with Pembrolizumab Versus Pembrolizumab Alone in Patients With Resected High-risk Melanoma: Efficacy and Safety Results From the Randomized, Open-label Phase 2 mRNA-4157-P201/KEYNOTE-942 Trial. Presented at the American Association for Cancer Research (AACR) Annual Meeting, Apr. 14-19, 2023. 23 pages.
Lutz et al., Unmodified mRNA in LNPs constitutes a competitive technology for prophylactic vaccines. NPJ Vaccines. Oct. 19, 2017:2:29. doi: 10.1038/s41541-017-0032-6. eCollection 2017.
Mendonca et al., Design of lipid-based nanoparticles for delivery of therapeutic nucleic acids. Drug Discov Today. Mar. 2023;28(3):103505. doi: 10.1016/j.drudis.2023.103505. Epub Jan. 25, 2023.
Packer et al., A novel mechanism for the loss of mRNA activity in lipid nanoparticle delivery systems. Nat Commun. Nov. 22, 2021;12(1):6777. doi: 10.1038/s41467-021-26926-0.
Pascolo, Messenger RNA-based vaccines. Expert Opin Biol Ther. Aug. 2004;4(8):1285-94. doi: 10.1517/14712598.4.8.1285.
Peek et al., Nanotechnology in vaccine delivery. Adv Drug Deliv Rev. May 22, 2008;60(8):915-28. doi: 10.1016/j.addr.2007.05.017. Epub Feb. 7, 2008.
Sayour, Re-programming Immunity Against Glioblastoma via RNA Nanoparticle Vaccines. 2015. Dissertation. Duke University. 174 pages.
Shidhadye et al., Solid lipid nanoparticles and nanostructured lipid carriers—innovative generations of solid lipid carriers. Curr Drug Deliv. Oct. 2008;5(4):324-31. doi: 10.2174/156720108785915087.
Steenhuysen et al., Moderna/Merck cancer vaccine plus Keytruda delays skin cancer return. Reuters. Apr. 16, 2023. 11 pages. https://www.reuters.com/business/healthcare-pharmaceuticals/moderna-cancer-vaccine-with-mercks-keytruda-delays-return-deadly-skin-cancer-2023-04-16/. Last accessed Nov. 7, 2023.
Su et al., In vitro and in vivo mRNA delivery using lipid-enveloped pH-responsive polymer nanoparticles. Mol Pharm. Jun. 6, 2011;8(3):774-87. doi: 10.1021/mp100390w. Epub Apr. 1, 2011.
Tenchov et al., Lipid Nanoparticles-From Liposomes to mRNA Vaccine Delivery, a Landscape of Research Diversity and Advancement. ACS Nano. Nov. 23, 2021;15(11):16982-17015. doi: 10.1021/acsnano.1c04996. Epub Jun. 28, 2021.
Weden et al., Long-term follow-up of patients with resected pancreatic cancer following vaccination against mutant K-ras. Int J Cancer. Mar. 1, 2011;128(5):1120-8. doi: 10.1002/ijc.25449.
Adnan et al., "A Personalized Cancer Vaccine, mRNA-4157 (V940), Combined with Pembrolizumab Versus Pembrolizumab Alone in Patients With Resected High-risk Melanoma: Efficacy and Safety Results From the Randomized, Open-label Phase 2 mRNA-4157-P201/KEYNOTE-942 Trial", AACR Annual Meeting Apr. 14-19, 2023, pp. 1-23, Article XP093142420.
Barbier et al, "The clinical progress of mRNA vaccines and irnrnunotherapies", 2022 Nature Biotechnology, Nature Publishing Group US, New York, vol. 40, Issue 6, pp. 840-854, Article XP03789781.
Bauman et al., Safety, tolerability, and immunogenicity of mRNA-4157 in combination with pembrolizumab in subjects with unresectable solid tumors (KEYNOTE-603): An update. J Immunother Cancer. 2020;8(Suppl 3):A4 77. https:/ /jitc.bmj.com/content/8/Suppl_3/A477.1.
Boumber, Tumor mutational burden (TMB) as a biomarker of response to immunotherapy in small cell lung cancer, J Thorac Dis 2018; 10(8):4689-4693.
Buyens et al., Liposome based systems for systemic siRNA delivery: stability in blood sets the requirements for optimal carrier design. J Control Release. Mar. 28, 2012;158(3):362-70. doi: 10.1016/j.jconrel.2011.10.009. Epub Oct. 14, 2011.
Collins et al.Combining vaccines and immune checkpoint inhibitors to prime, expand, and facilitate effective tumor immunotherapy, Expert Rev Vaccines. Aug. 2018; 17(8), pp. 1-19.
Deering et al., Nucleic acid vaccines: prospects for non-viral delivery of mRNA vaccines. Expert Opin Drug Deliv. Jun. 2014;I 1(6):885-99. doi: 10.1517/17425247.2014.901308. Epub Mar. 26, 2014.
DMG-PEG 2000. Sigma-Aldrich. Accessed from https://www.sigmaaldrich.com/catalog/product/avanti/880151 p?lang=en@ion=US Jan. 4, 2021. 3 pages.
Gainor et al., T-cell Responses to Individualized Neoantigen Therapy mRNA-4157 (V940) as Monotherapy or in Combination With Pembrolizumab. Presented at the Society for Immunotherapy of Cancer. Nov. 3-5, 2023. San Diego, CA, USA. Poster. 1 page.

(56) References Cited

OTHER PUBLICATIONS

Geall et al., Nonviral delivery of self-amplifying RNA vaccines. Proc Natl Acad Sci US A. Sep. 4, 2012;109(36):14604-9. With Supporting Information. doi:10.1073/pnas.1209367109. Epub Aug. 20, 2012.
Hekele et al., "Rapidly produced SAM(®) vaccine against H7N9 influenza is immunogenic in mice," Emerg Microbes Infect. Aug. 2013;2(8):e52. doi: 10.1038/emi.2013.54. Epub Aug. 14, 2013. PMID: 26038486; PMCID: PMC3821287.
Japanese Cancer Association, General Article, vol. 90, Suppl, 1999, p. 639 (2110).
Kutikuppala et al., Prospects and Challenges in Developing mRNA Vaccines for Infectious Diseases and Oncogenic Viruses. Med Sci (Basel). May 22, 2024;12(2):28. doi: 10.3390/medsci12020028.
Lin et al., Progress and challenges of mRNA vaccines. Interdisc Med. Dec. 22, 2022;1(1).
Liu et al., Advances and prospects of mRNA vaccines in cancer immunotherapy. Biochim Biophys Acta Rev Cancer. Mar. 2024; 1879(2): 189068. doi: 10.1016/j. bbcan.2023 . 189068. Epub Jan. 1, 2024.
Mcdonnell et al. DNA vaccines. N Engl J Med. Jan. 4, 1996;334(1):42-5.
Midoux et al., "Lipid-based mRNA vaccine delivery systems," Expert Review Vaccines, Feb. 2015, vol. 14, No. 2 (pp. 221-234).
Milagre et al., A mouse model of melanoma driven by oncogenic KRAS. Cancer Res. Jul. 1, 2010;70(13):5549-57. doi: 10.1158/0008-5472.CAN-09-4254. Epub Jun. 1, 2010.
National Cancer Institute (sponsor), "Messenger RNA (mRNA)-Based, Personalized Cancer Vaccine Against Neoantigens Expressed by the Autologous Cancer," NCT03480152, https://www.clinicaltrials.gov/study/NCT03480152 (Mar. 28, 2013).
Peng et al, "Current Status of research in various tumor antigen-related tumor vaccines" West China Medical Journal vol. 23, No. 04 p. 928-930 (2008).
Rosenberg, mRNA-Based, Cancer Vaccine, CC Protocol No. 18-C-0074 E, 2019, pp. 1-65.
Sahin, U. "An RNA vaccine drives immunity in checkpoint-inhibitor-treated melanoma", 2020, Nature, vol. 585, Issue 7823, pp. 107-112.
Shemesh et al, "Personalized Cancer Vaccines: Clinical Landscape, Challenges, and Opportunities," Molecular Therapy, 2021, pp. 555-570.
Sjoblom et al., The consensus coding sequences of human breast and colorectal cancers. Science. Oct. 13, 2006;314(5797):268-74. doi: 10.1126/science.1133427. Epub Sep. 7, 2006.
Ulmer et al., RNA-based vaccines. Vaccine. Jun. 22, 2012;30(30):4414-8.
Wang et al., Delivery of oligonucleotides with lipid nanoparticles. Adv Drug Deliv Rev. Jun. 29, 2015;87:68-80. doi: 10.1016/j.addr.2015.02.007. Epub Feb. 27, 2015.
Wang et al., Recent advances in mRNA cancer vaccines: meeting challenges and embracing opportunities. Front Immunol. Sep. 6, 2023;14:1246682. doi: 10.3389/fimmu.2023.1246682.
Weber et al, "Individualized neoantigen therapy mRNA-4157 (V940) plus pembrolizumab versus pembrolizumab monotherapy in resected melanoma (KEYNOTE-942): a randomized, phase 2b study", The Lancet, Elsevier, 2024 Volume 403, Issue 10427, pp. 632-644, Article XP087469992.
Weber, J., "mRNA-4157 (V940) individualized neoantigen therapy pembrolizumab versus pembrolizumab in high-risk resected melanoma: clinical efficacy and correlates of response", 2023, Article XP093153038.
Weissman, mRNA transcript therapy. Expert Rev Vaccines. Feb. 2015;14(2):265-81. doi: 10.1586/14760584.2015.973859. Epub Oct. 31, 2014.
Wenjie et al. "The current situation of epitope peptide in cancer therapy" Journal of Modern Oncology vol. 24, No. 34, pp. 3937-3840 (Dec. 31, 2016).
Xie et al., "Neoantigens: Promising targets for cancer therapy, Signal Transduction and Targeted Therapy," 2023, pp. 1-38.
Xu et al., Enhanced pH-Responsiveness, Cellular Trafficking, Cytotoxicity and Long-circulation of PEGylated Liposomes with Post-insertion Technique Using Gemcitabine as a Model Drug. Pharm Res. Jul. 2015;32(7):2428-38. doi: 10.1007/sl 1095-015-1635-0. Epub Feb. 6, 2015.
Zhang et al., Personalized cancer vaccines: Targeting the cancer mutanome. Vaccine. Feb. 15, 2017;35(7): 1094-1100. doi: 10.1016/i.vaccine.2016.05.073. Epub Jul. 20, 2016.

* cited by examiner

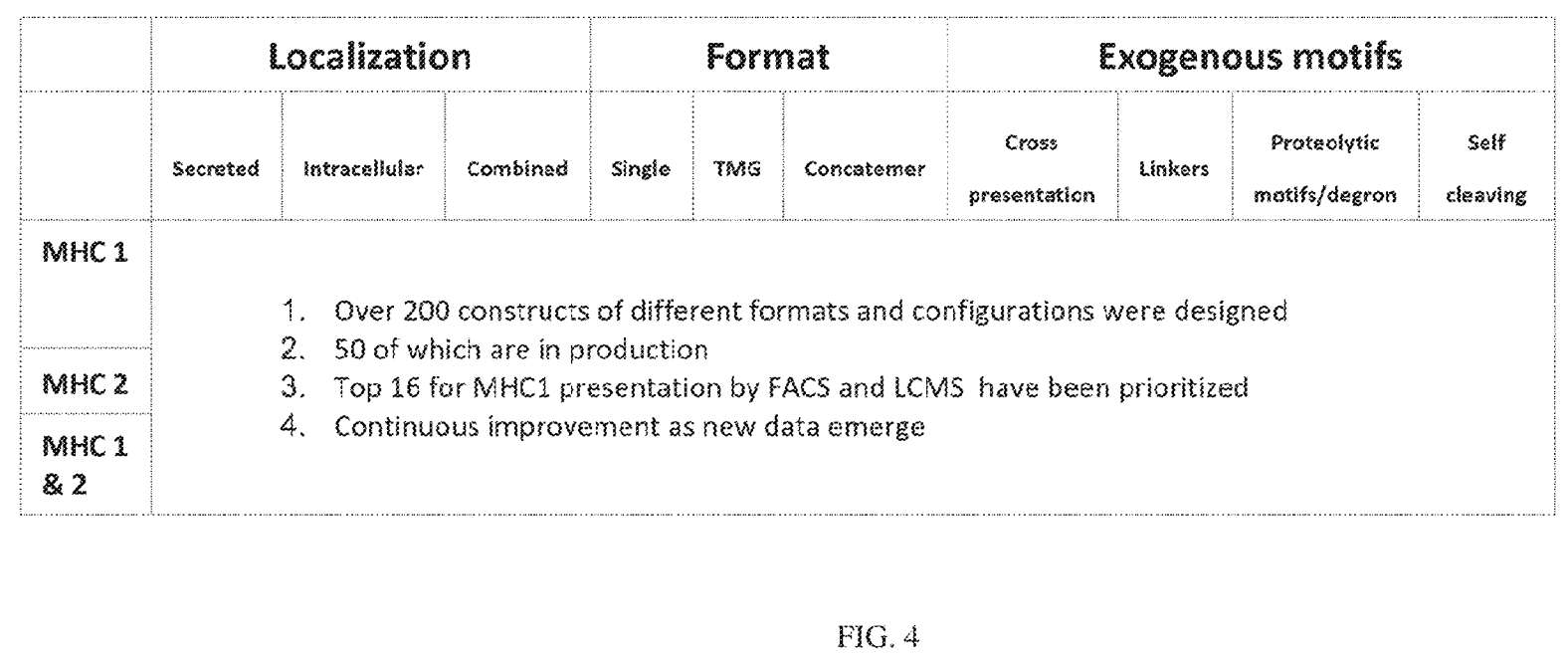

| | Localization | | | Format | | | Exogenous motifs | | | |
|---|---|---|---|---|---|---|---|---|---|---|
| | Secreted | Intracellular | Combined | Single | TMG | Concatemer | Cross presentation | Linkers | Proteolytic motifs/degron | Self cleaving |
| MHC 1 | 1. Over 200 constructs of different formats and configurations were designed<br>2. 50 of which are in production<br>3. Top 16 for MHC1 presentation by FACS and LCMS have been prioritized<br>4. Continuous improvement as new data emerge | | | | | | | | | |
| MHC 2 | | | | | | | | | | |
| MHC 1 & 2 | | | | | | | | | | |

FIG. 4

| Dose group | # positive Class I epitopes* | # positive Class II epitopes* |
|---|---|---|
| 10 µg | 8/10 | 3/5 |
| 3.33 µg | 7/10 | 2/5 |
| 1.11 µg | 3/10 | 1/5 |

* 8x > vehicle

FIG. 9B

UTR = untranslated region; ORF = open reading frame

5'-$^{7Me}G_{ppp}G_{2'OMe}$GGAAAUAAGAGAGAAAAGAAGAGUAAGAAGAAAUAUAAGAGCCACCAUG $(N)_{\sim1,800}$
UGAUAAUAGGCUGGAGCCUCGGUGGCCAUGCUUCUUGCCCCUUGGGCCUCCCCCCAGCCCCUCCUCCCCUUC
CUGCACCCGUACCCCCGUGGUCUUUGAAUAAAGUCUGAGUGGGCGGCAAAAAAAAAAAAAAAAAAAAAAAA
AAAAAAAAAAAAAAAAAAAAAAAAAAAAAAAAAAAAAAAAAAAAAAAAAAAAAAAAAAAAAAAAAAAAAAAAAAAAAAAAA
AAAAAAUCUAG$_{OH}$3'

A,C G & U = AMP, CMP, GMP & N1-ΨUMP, respectively; Me = methyl; p = inorganic phosphate; N = Patient-specific coding sequence comprised of A,C, G or N1-ΨUMP

FIG. 14

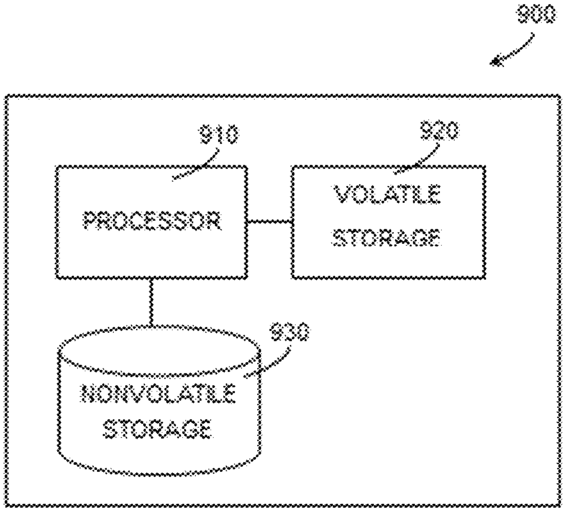

FIG. 15

SEQUENCE LISTING

```
<160> NUMBER OF SEQ ID NOS: 27

<210> SEQ ID NO 1
<211> LENGTH: 56
<212> TYPE: PRT
<213> ORGANISM: Artificial Sequence
<220> FEATURE:
<223> OTHER INFORMATION: Synthetic Polypeptide

<400> SEQUENCE: 1

Thr Ala Lys Ser Val Thr Cys Thr Val Ser Cys Pro Glu Gly Leu Ala
1               5                   10                  15

Ser Met Arg Leu Gln Cys Leu Ala Val Ser Pro Cys Ile Ser Phe Val
            20                  25                  30

Trp Asn Phe Gly Ile Pro Leu His Pro Leu Ala Ser Cys Gln Cys Phe
```

35 40 45

Phe Ile Val Tyr Pro Leu Asn Val
50 55

<210> SEQ ID NO 2
<211> LENGTH: 10
<212> TYPE: PRT
<213> ORGANISM: Artificial Sequence
<220> FEATURE:
<223> OTHER INFORMATION: Synthetic Polypeptide

<400> SEQUENCE: 2

Ala Val Ser Pro Cys Ile Ser Phe Val Trp
1 5 10

<210> SEQ ID NO 3
<211> LENGTH: 10
<212> TYPE: PRT
<213> ORGANISM: Artificial Sequence
<220> FEATURE:
<223> OTHER INFORMATION: Synthetic Polypeptide

<400> SEQUENCE: 3

His Pro Leu Ala Ser Cys Gln Cys Phe Phe
1 5 10

<210> SEQ ID NO 4
<211> LENGTH: 9
<212> TYPE: PRT
<213> ORGANISM: Artificial Sequence
<220> FEATURE:
<223> OTHER INFORMATION: Synthetic Polypeptide

<400> SEQUENCE: 4

Phe Val Trp Asn Phe Gly Ile Pro Leu
1 5

<210> SEQ ID NO 5
<211> LENGTH: 44
<212> TYPE: PRT
<213> ORGANISM: Artificial Sequence
<220> FEATURE:
<223> OTHER INFORMATION: Synthetic Polypeptide

<400> SEQUENCE: 5

Glu Tyr Phe Thr Leu Gln Val Leu Ser Leu Gly Thr Ser Tyr Gln Val
1 5 10 15

Glu Ser Phe Gln Ser Asn Thr Gln Asn Ala Val Phe Phe Leu Thr Val
20 25 30

Leu Pro Ala Ile Gly Ala Phe Ala Ile Arg Gly Gln
35 40

<210> SEQ ID NO 6
<211> LENGTH: 10
<212> TYPE: PRT
<213> ORGANISM: Artificial Sequence
<220> FEATURE:
<223> OTHER INFORMATION: Synthetic Polypeptide

<400> SEQUENCE: 6

Leu Gln Val Leu Ser Leu Gly Thr Ser Tyr
1 5 10

<210> SEQ ID NO 7
<211> LENGTH: 10

<212> TYPE: PRT
<213> ORGANISM: Artificial Sequence
<220> FEATURE:
<223> OTHER INFORMATION: Synthetic Polypeptide

<400> SEQUENCE: 7

Phe Gln Ser Asn Thr Gln Asn Ala Val Phe
1 5 10

<210> SEQ ID NO 8
<211> LENGTH: 14
<212> TYPE: PRT
<213> ORGANISM: Artificial Sequence
<220> FEATURE:
<223> OTHER INFORMATION: Synthetic Polypeptide

<400> SEQUENCE: 8

Ala Lys Ser Val Thr Cys Thr Met Phe Cys Gln Leu Ala Lys
1 5 10

<210> SEQ ID NO 9
<211> LENGTH: 9
<212> TYPE: PRT
<213> ORGANISM: Artificial Sequence
<220> FEATURE:
<223> OTHER INFORMATION: Synthetic Polypeptide

<400> SEQUENCE: 9

Cys Thr Met Phe Cys Gln Leu Ala Lys
1 5

<210> SEQ ID NO 10
<211> LENGTH: 8
<212> TYPE: PRT
<213> ORGANISM: Artificial Sequence
<220> FEATURE:
<223> OTHER INFORMATION: Synthetic Polypeptide

<400> SEQUENCE: 10

Lys Ser Val Thr Cys Thr Met Phe
1 5

<210> SEQ ID NO 11
<211> LENGTH: 22
<212> TYPE: PRT
<213> ORGANISM: Artificial Sequence
<220> FEATURE:
<223> OTHER INFORMATION: Synthetic Polypeptide

<400> SEQUENCE: 11

Val Pro Tyr Glu Pro Pro Glu Val Trp Leu Ala Leu Thr Val Pro Pro
1 5 10 15

Ser Thr Ala Trp Ala Ala
20

<210> SEQ ID NO 12
<211> LENGTH: 9
<212> TYPE: PRT
<213> ORGANISM: Artificial Sequence
<220> FEATURE:
<223> OTHER INFORMATION: Synthetic Polypeptide

<400> SEQUENCE: 12

Val Pro Tyr Glu Pro Pro Glu Val Trp
1 5

-continued

<210> SEQ ID NO 13
<211> LENGTH: 9
<212> TYPE: PRT
<213> ORGANISM: Artificial Sequence
<220> FEATURE:
<223> OTHER INFORMATION: Synthetic Polypeptide

<400> SEQUENCE: 13

Leu Thr Val Pro Pro Ser Thr Ala Trp
1               5

<210> SEQ ID NO 14
<211> LENGTH: 8
<212> TYPE: PRT
<213> ORGANISM: Artificial Sequence
<220> FEATURE:
<223> OTHER INFORMATION: Synthetic Polypeptide
<220> FEATURE:
<221> NAME/KEY: misc_feature
<222> LOCATION: (5)..(8)
<223> OTHER INFORMATION: Xaa can be any naturally occurring amino acid

<400> SEQUENCE: 14

Glu Asn Ser Thr Xaa Xaa Xaa Xaa
1               5

<210> SEQ ID NO 15
<211> LENGTH: 10
<212> TYPE: PRT
<213> ORGANISM: Artificial Sequence
<220> FEATURE:
<223> OTHER INFORMATION: Synthetic Polypeptide

<400> SEQUENCE: 15

Glu Ala Ala Gly Ile Gly Ile Leu Thr Val
1               5                   10

<210> SEQ ID NO 16
<211> LENGTH: 10
<212> TYPE: PRT
<213> ORGANISM: Artificial Sequence
<220> FEATURE:
<223> OTHER INFORMATION: Synthetic Polypeptide

<400> SEQUENCE: 16

Glu Leu Ala Gly Ile Gly Ile Leu Thr Val
1               5                   10

<210> SEQ ID NO 17
<211> LENGTH: 9
<212> TYPE: PRT
<213> ORGANISM: Artificial Sequence
<220> FEATURE:
<223> OTHER INFORMATION: Synthetic Polypeptide

<400> SEQUENCE: 17

Tyr Met Asp Gly Thr Met Ser Gln Val
1               5

<210> SEQ ID NO 18
<211> LENGTH: 140
<212> TYPE: PRT
<213> ORGANISM: Artificial Sequence
<220> FEATURE:
<223> OTHER INFORMATION: Synthetic Polypeptide

<400> SEQUENCE: 18

Met His His His His His His His His His His Lys Glu Asn Gln Pro

-continued

```
1               5                   10                  15

Glu Asn Ser Gln Thr Pro Gly Gly Gly Ser Val Pro Leu Ala His Ser
            20                  25                  30

Ser Ser Ala Phe Thr Ile Met Asp Gln Val Pro Phe Ser Val Ser Val
        35                  40                  45

Ser Gln Leu Gln Ser Ser Met His Asn Ala Leu His Ile Tyr Met Asp
    50                  55                  60

Gly Thr Met Ser Gln Val Gln Gly Ser Ala Asn Asp Gly Val Gly Ala
65                  70                  75                  80

Tyr Gly Thr Val Tyr Lys Ala Cys Asp Pro His Ser Gly His Phe Val
                85                  90                  95

Ala Leu Lys Ser Val Gly His Gly His Ser Tyr Thr Thr Ala Glu Glu
            100                 105                 110

Leu Ala Gly Ile Gly Ile Leu Thr Val Ile Leu Gly Val Leu Gly Lys
        115                 120                 125

Pro Ile Pro Asn Pro Leu Leu Gly Leu Asp Ser Thr
    130                 135                 140


<210> SEQ ID NO 19
<211> LENGTH: 115
<212> TYPE: PRT
<213> ORGANISM: Artificial Sequence
<220> FEATURE:
<223> OTHER INFORMATION: Synthetic Polypeptide

<400> SEQUENCE: 19

Met His His His His His His His His His His Lys Glu Asn Gln Pro
1               5                   10                  15

Glu Asn Ser Gln Thr Pro Gly Gly Gly Ser Val Pro Leu Ala His Ser
            20                  25                  30

Ser Ser Ala Phe Thr Ile Met Asp Gln Val Pro Phe Ser Val Ser Val
        35                  40                  45

Ser Gln Leu Val Pro Leu Ala His Ser Ser Ser Ala Phe Thr Ile Met
    50                  55                  60

Asp Gln Val Pro Phe Ser Val Ser Val Ser Gln Leu Val Pro Leu Ala
65                  70                  75                  80

His Ser Ser Ser Ala Phe Thr Ile Met Asp Gln Val Pro Phe Ser Val
                85                  90                  95

Ser Val Ser Gln Leu Gly Lys Pro Ile Pro Asn Pro Leu Leu Gly Leu
            100                 105                 110

Asp Ser Thr
        115


<210> SEQ ID NO 20
<211> LENGTH: 51
<212> TYPE: RNA
<213> ORGANISM: Artificial Sequence
<220> FEATURE:
<223> OTHER INFORMATION: Synthetic Polynucleotide

<400> SEQUENCE: 20

ggggaaauaa gagagaaaag aagaguaaga agaaauauaa gagccaccau g             51


<210> SEQ ID NO 21
<211> LENGTH: 224
<212> TYPE: RNA
<213> ORGANISM: Artificial Sequence
<220> FEATURE:
<223> OTHER INFORMATION: Synthetic Polynucleotide
```

-continued

<400> SEQUENCE: 21

```
ugauaauagg cuggagccuc gguggccaug cuucuugccc cuugggccuc cccccagccc      60

cuccuccccu uccugcaccc guacccccgu ggucuuugaa uaaagucuga gugggcggca     120

aaaaaaaaaa aaaaaaaaaa aaaaaaaaaa aaaaaaaaaa aaaaaaaaaa aaaaaaaaaa     180

aaaaaaaaaa aaaaaaaaaa aaaaaaaaaa aaaaaaaaau cuag                      224
```

<210> SEQ ID NO 22
<211> LENGTH: 8
<212> TYPE: PRT
<213> ORGANISM: Artificial Sequence
<220> FEATURE:
<223> OTHER INFORMATION: Synthetic Polypeptide

<400> SEQUENCE: 22

```
Ser Ile Ile Asn Phe Glu Lys Leu
1               5
```

<210> SEQ ID NO 23
<211> LENGTH: 9
<212> TYPE: PRT
<213> ORGANISM: Artificial Sequence
<220> FEATURE:
<223> OTHER INFORMATION: Synthetic Polypeptide

<400> SEQUENCE: 23

```
Phe Gln Ser Asn Thr Gln Asn Ala Val
1               5
```

<210> SEQ ID NO 24
<211> LENGTH: 9
<212> TYPE: PRT
<213> ORGANISM: Artificial Sequence
<220> FEATURE:
<223> OTHER INFORMATION: Synthetic Polypeptide

<400> SEQUENCE: 24

```
Val Leu Pro Ala Ile Gly Ala Phe Ala
1               5
```

<210> SEQ ID NO 25
<211> LENGTH: 9
<212> TYPE: PRT
<213> ORGANISM: Artificial Sequence
<220> FEATURE:
<223> OTHER INFORMATION: Synthetic Polypeptide

<400> SEQUENCE: 25

```
Phe Phe Leu Thr Val Leu Pro Ala Ile
1               5
```

<210> SEQ ID NO 26
<211> LENGTH: 12
<212> TYPE: PRT
<213> ORGANISM: Artificial Sequence
<220> FEATURE:
<223> OTHER INFORMATION: Synthetic

<400> SEQUENCE: 26

```
His Glu Tyr Gly Ala Glu Ala Leu Glu Arg Ala Gly
1               5                   10
```

<210> SEQ ID NO 27
<211> LENGTH: 5

-continued

<212> TYPE: PRT
<213> ORGANISM: Artificial Sequence
<220> FEATURE:
<223> OTHER INFORMATION: Synthetic

<400> SEQUENCE: 27

Lys Phe Glu Arg Gln
1 5

CANCER VACCINES

RELATED APPLICATIONS

This application is a national stage filing under 35 U.S.C. § 371 of international patent application number PCT/US2016/058317, filed Oct. 21, 2016, which claims priority under 35 U.S.C. § 119 (e) to U.S. provisional application No. 62/245,129, filed Oct. 22, 2015, U.S. provisional application No. 62/245,031, filed Oct. 22, 2015, U.S. provisional application No. 62/247,317, filed Oct. 28, 2015, U.S. provisional application No. 62/247,472, filed Oct. 28, 2015, and U.S. provisional application No. 62/368,810, filed Jul. 29, 2016, the contents of each of which are incorporated herein by reference in their entireties.

INCORPORATION BY REFERENCE OF SEQUENCE LISTING

This application contains a Sequence Listing which has been submitted in ASCII format via EFS-Web and is hereby incorporated by reference in its entirety. Said ASCII copy, created on Mar. 10, 2023, is named M137870024US03-SUBSEQ-COB and is 8,937 bytes in size.

BACKGROUND OF INVENTION

Cancer vaccines include preventive or prophylactic vaccines, which are intended to prevent cancer from developing in healthy people; and therapeutic vaccines, which are intended to treat an existing cancer by strengthening the body's natural defenses against the cancer. Cancer preventive vaccines may, for instance, target infectious agents that cause or contribute to the development of cancer in order to prevent infectious diseases from causing cancer. Gardasil® and Cervarix®, are two examples of commercially available prophylactic vaccines. Each vaccine protects against HPV infection. Other preventive cancer vaccines may target host proteins or fragments that are predicted to increase the likelihood of an individual developing cancer in the future.

Most commercial or developing vaccines are based on whole microorganisms, protein antigens, peptides, polysaccharides or deoxyribonucleic acid (DNA) vaccines and their combinations. DNA vaccination is one technique used to stimulate humoral and cellular immune responses to antigens. The direct injection of genetically engineered DNA (e.g., naked plasmid DNA) into a living host results in a small number of its cells directly producing an antigen, resulting in a protective immunological response. With this technique, however, comes potential problems of DNA integration into the vaccine's genome, including the possibility of insertional mutagenesis, which could lead to the activation of oncogenes or the inhibition of tumor suppressor genes.

SUMMARY OF INVENTION

Provided herein is a ribonucleic acid (RNA) cancer vaccine of an RNA (e.g., messenger RNA (mRNA)) that can safely direct the body's cellular machinery to produce nearly any cancer protein or fragment thereof of interest. In some embodiments, the RNA is a modified RNA. The RNA vaccines of the present disclosure may be used to induce a balanced immune response against cancers, comprising both cellular and humoral immunity, without risking the possibility of insertional mutagenesis, for example.

The RNA vaccines may be utilized in various settings depending on the prevalence of the cancer or the degree or level of unmet medical need. The RNA vaccines may be utilized to treat and/or prevent a cancer of various stages or degrees of metastasis. The RNA vaccines have superior properties in that they produce much larger antibody titers and produce responses earlier than alternative anti-cancer therapies including cancer vaccines. While not wishing to be bound by theory, it is believed that the RNA vaccines, as mRNA polynucleotides, are better designed to produce the appropriate protein conformation upon translation as the RNA vaccines co-opt natural cellular machinery. Unlike traditional vaccines which are manufactured ex vivo and may trigger unwanted cellular responses, the RNA vaccines are presented to the cellular system in a more native fashion.

Some embodiments of the present disclosure provide cancer vaccines that include at least one ribonucleic acid (RNA) polynucleotide having an open reading frame encoding at least one cancer antigenic polypeptide or an immunogenic fragment thereof (e.g., an immunogenic fragment capable of inducing an immune response to cancer). Other embodiments include at least one ribonucleic acid (RNA) polynucleotide having an open reading frame encoding two or more antigens or epitopes capable of inducing an immune response to cancer.

The invention in some aspects is a vaccine of a mRNA having an open reading frame encoding a cancer antigen and a mRNA having an open reading frame encoding an immune checkpoint modulator. In some embodiments the immune checkpoint modulator is an inhibitory checkpoint polypeptide. In some embodiments, the inhibitory checkpoint polypeptide is an antibody or fragment thereof that specifically binds to a molecule selected from the group consisting of PD-1. TIM-3, VISTA, A2AR, B7-H3, B7-H4, BTLA, CTLA-4, IDO, KIR and LAG3. The inhibitory checkpoint polypeptide is an anti-CTLA4 or anti-PD1 antibody in some embodiments. Optionally the vaccine includes a lipid nanoparticle. In some embodiments a vaccine of a mRNA having an open reading frame encoding a cancer antigen is administered to a subject. In other embodiments a checkpoint inhibitor 3-10 weeks later. In some embodiments the checkpoint inhibitor is administered 4 weeks later.

In other aspects the invention is a personalized cancer vaccine of a mRNA having an open reading frame encoding at least 2 cancer antigens, wherein the at least 2 cancer antigens are patient specific cancer antigens, and a lipid nanoparticle carrier. In some embodiments the lipid nanoparticle has a mean diameter of 50-200 nm.

In yet other aspects, the invention is a personalized cancer vaccine of a mRNA having an open reading frame encoding at least 2 cancer antigens wherein the at least 2 cancer antigens are representative of antigens of a patient. In some embodiments, the antigens of a patient are exosome identified antigens of the patient. In some embodiments a single mRNA encodes the cancer antigens. In other embodiments a plurality of mRNA encode the cancer antigens.

Each mRNA may encode 5-10 cancer antigens or a single cancer antigen in other embodiments. In some embodiments the mRNA encodes 2-100 cancer antigens. In other embodiments mRNA encodes 10-100, 20-100, 50-100, 100-200, 300-400, 500-600, 600-700, 700-800, 900-1,000, or 1,000-10,000 cancer antigens.

In some embodiments, a) the mRNA encoding each cancer antigen is interspersed by cleavage sensitive sites;

b) the mRNA encoding each cancer antigen is linked directly to one another without a linker;

c) the mRNA encoding each cancer antigen is linked to one another with a single nucleotide linker;

d) each cancer antigen comprises a 25-35 amino acids and includes a centrally located SNP mutation;

e) at least 30% of the cancer antigens have a highest affinity for class I MHC molecules from the subject;

f) at least 30% of the cancer antigens have a highest affinity for class II MHC molecules from the subject;

g) at least 50% of the cancer antigens have a predicted binding affinity of IC >500 nM for HLA-A, HLA-B and/or DRB1;

h) the mRNA encodes 20 cancer antigens;

i) 50% of the cancer antigens have a binding affinity for class I MHC and 50% of the cancer antigens have a binding affinity for class II MHC; and/or j) the mRNA encoding the cancer antigens is arranged such that the cancer antigens are ordered to minimize pseudo-epitopes.

In some embodiments, each cancer antigen comprises 31 amino acids and includes a centrally located SNP mutation with 15 flanking amino acids on each side of the SNP mutation.

In some embodiments the vaccine is a personalized cancer vaccine and wherein the cancer antigen is a subject specific cancer antigen. In some embodiments, the subject specific cancer antigen may be representative of an exome of a tumor sample of the subject, or of a transcriptome of a tumor sample of the subject. In some embodiments, the subject specific cancer antigen may be representative of an exosome of the subject.

In some embodiments, the open reading frame further encodes one or more traditional cancer antigens. In some embodiments, the traditional cancer antigen is a non-mutated antigen. In some embodiments, the traditional cancer antigen is a mutated antigen.

In some embodiments, the mRNA vaccine further comprises an mRNA having an open reading frame encoding one or more traditional cancer antigens.

In some embodiments a single mRNA encodes the cancer antigens. In other embodiments a plurality of mRNA encode the cancer antigens. Each cancer antigen is 10-50 amino acids in length in some embodiments. In other embodiments each cancer antigen is 15-20 amino acids in length. In other embodiments the cancer antigen is 20-50, 25-100, 100-200, 200-300, 300-400, 400-500, 500-1,000, or 1,000-10,000 amino acids in length.

In some embodiments, the vaccines further comprise an adjuvant.

Some embodiments of the present disclosure provide a cancer vaccine that includes at least one ribonucleic acid (RNA) polynucleotide having an open reading frame encoding at least one cancer polypeptide, at least one 5' terminal cap and at least one chemical modification, formulated within a lipid nanoparticle. In some embodiments, a 5' terminal cap is 7 mG (5')ppp(5')NlmpNp.

In some embodiments, at least one chemical modification is selected from pseudouridine, N1-methylpseudouridine, N1-ethylpseudouridine, 2-thiouridine, 4'-thiouridine, 5-methylcytosine, 2-thio-1-methyl-1-deaza-pseudouridine, 2-thio-1-methyl-pseudouridine, 2-thio-5-aza-uridine, 2-thio-dihydropseudouridine, 2-thio-dihydrouridine, 2-thio-pseudouridine, 4-methoxy-2-thio-pseudouridine, 4-methoxy-pseudouridine, 4-thio-1-methyl-pseudouridine, 4-thio-pseudouridine, 5-aza-uridine, dihydropseudouridine, 5-methyluridine, 5-methoxyuridine and 2'-O-methyl uridine. In some embodiments the extent of incorporation of chemically modified nucleotides has been optimized for improved immune responses to the vaccine formulation.

In some embodiments, a lipid nanoparticle comprises a cationic lipid, a PEG-modified lipid, a sterol and a non-cationic lipid. In some embodiments, a cationic lipid is an ionizable cationic lipid and the non-cationic lipid is a neutral lipid, and the sterol is a cholesterol. In some embodiments, a cationic lipid is selected from 2,2-dilinoleyl-4-dimethylaminoethyl-[1,3]-dioxolane (DLin-KC2-DMA), dilinoleyl-methyl-4-dimethylaminobutyrate (DLin-MC3-DMA), and di((Z)-non-2-en-1-yl) 9-((4-(dimethylamino) butanoyl)oxy) heptadecanedioate (L319).

In some embodiments the lipid nanoparticle formulation includes an immune potentiator (e.g., TLR agonist) to enhance immunogenicity of the vaccine (formulation).

In some embodiments, 100% of the uracil in the open reading frame have a chemical modification. In some embodiments, a chemical modification is in the 5-position of the uracil. In some embodiments, a chemical modification is a N1-methyl pseudouridine.

In other embodiments a mRNA encoding an APC reprograming molecule is included in the vaccine or coadministered with the vaccine. The APC reprograming molecule may be a CIITA, a chaperone protein such as CLIP, HLA-DO, HLA-DM, a costimulatory molecule such as CD40, CD80, CD86, a CIITA fragment such as amino acids 26-137 of CIITA or a protein having 80% sequence identity to CIITA.

In other aspects a method of eliciting an immune response in a subject by identifying at least 2 cancer antigens from a sample of a subject, wherein the at least 2 cancer antigens include mutations selected from the group consisting of frame-shift mutations and recombinations, and administering a mRNA vaccine having an open reading frame encoding the at least 2 cancer antigens to the subject is provided.

In some embodiments, the cancer antigens are identified from an exosome of the subject. In some embodiments 2-100 antigens are identified from the exosome. In other embodiments the mRNA vaccine has an open reading frame encoding the 2-100 antigens. A single mRNA or a plurality of mRNA may encode the antigens.

In some embodiments the antigens are cancer antigens. The cancer antigens may have mutations selected from point mutations, frame-shift mutations and recombinations. The method may further involve confirming that the cancer antigens are subject specific by exome analysis. In some embodiments the method may further involve confirming that the cancer antigens are subject specific by transcriptome analysis.

In some embodiments the method also involves at least one month after the administration of the mRNA vaccine, identifying at least 2 cancer antigens from a sample of the subject to produce a second set of cancer antigens, and administering to the subject a mRNA vaccine having an open reading frame encoding the second set of cancer antigens to the subject. In other embodiments the sample of the subject is a tumor sample.

In other aspects the invention comprises a method of eliciting an immune response in a subject by identifying at least 2 cancer antigens from a sample of a subject to produce a first set of cancer antigens, administering to the subject a mRNA vaccine having an open reading frame encoding the first set of cancer antigens to the subject, at least one month after the administration of the mRNA vaccine, identifying at least 2 cancer antigens from a sample of a subject to produce a second set of cancer antigens, and administering to the subject a mRNA vaccine having an open reading frame encoding the second set of cancer antigens to the subject.

The mRNA vaccine having an open reading frame encoding second set of antigens, in some embodiments, is administered to the subject 6 months to 1 year after the mRNA vaccine having an open reading frame encoding first set of cancer antigens. In other embodiments the mRNA vaccine having an open reading frame encoding second set of antigens is administered to the subject 1-2 years after the mRNA vaccine having an open reading frame encoding first set of cancer antigens.

In some embodiments a single mRNA has an open reading frame encoding the cancer antigens. In other embodiments a plurality of mRNA encode the antigens. In some embodiments the second set of cancer antigens includes 2-100 antigens. In other embodiments the cancer antigens have mutations selected from point mutations, frame-shift mutations and recombinations.

In other aspects the invention comprises a method of eliciting an immune response in a subject, by identifying at least 2 cancer antigens from a sample of a subject, administering a mRNA having an open reading frame encoding the at least 2 cancer antigens to the subject, and administering a cancer therapeutic agent to the subject. In some embodiments the cancer therapeutic agent is a targeted therapy. The targeted therapy may be a BRAF inhibitor such as vemurafenib (PLX4032) or dabrafenib.

In other embodiments the cancer therapeutic agent is a T-cell therapeutic agent. The T-cell therapeutic agent may be a checkpoint inhibitor such as an anti-PD-1 antibody or an anti-CTLA-4 antibody. In some embodiments the anti-PD-1 antibody is BMS-936558 (nivolumab). In other embodiments the anti-CTLA-4 antibody is ipilimumab. The T-cell therapeutic agent in other embodiments is OX40L. In yet other embodiments the cancer therapeutic agent is a vaccine comprising a population based tumor specific antigen.

In other embodiments the cancer therapeutic agent is a vaccine comprising an mRNA having an open reading frame encoding one or more traditional cancer antigens.

In some embodiments, the mRNA having an open reading frame encoding the at least 2 cancer antigens is administered to the subject simultaneously with the cancer therapeutic agent. In some embodiments, the mRNA having an open reading frame encoding the at least 2 cancer antigens is administered to the subject before administration of the cancer therapeutic agent. In some embodiments, the mRNA having an open reading frame encoding the at least 2 cancer antigens is administered to the subject after administration of the cancer therapeutic agent.

A method comprising mixing a mRNA having an open reading frame encoding a cancer antigen with a lipid nanoparticle formulation to produce a mRNA cancer vaccine, and administering the mRNA cancer vaccine to a subject within 24 hours of mixing is provided in other aspects of the invention. In some embodiments the mRNA cancer vaccine is administered to the subject within 12 hours of mixing. In other embodiments the mRNA cancer vaccine is administered to the subject within 1 hour of mixing. The mRNA cancer vaccine encodes 2-100 cancer antigens or 10-100 cancer antigens in some embodiments.

In some embodiments the vaccine is a personalized cancer vaccine and wherein the cancer antigen is a subject specific cancer antigen.

In some embodiments a single mRNA encodes the cancer antigens. In other embodiments a plurality of mRNA encode the cancer antigens. Each mRNA encodes 5-10 cancer antigens or a single cancer antigen in other embodiments. In yet other embodiments each cancer antigen is 10-50 amino acids in length or 15-20 amino acids in length.

A kit is provided in other aspects of the invention. The kit includes a container housing a lipid nanoparticle formulation, a container housing a vaccine formulation, and instructions for adding a personalized mRNA cancer vaccine to the vaccine formulation to produce a personalized mRNA cancer vaccine formulation, mixing the personalized mRNA cancer vaccine formulation with the lipid nanoparticle formulation within 24 hours of administration to a subject. In some embodiments the kit includes a mRNA having an open reading frame encoding 2-100 cancer antigens.

Further provided herein are uses of cancer vaccines in the manufacture of a medicament for use in a method of inducing an antigen specific immune response in a subject, the method comprising administering the cancer vaccine to the subject in an amount effective to produce an antigen specific immune response.

A method of treating cancer in a subject in need thereof by identifying at least 2 cancer antigens from an exosome isolated from the subject; producing, based on the identified antigens, a mRNA vaccine having an open reading frame encoding the antigens; and administering the mRNA vaccine to the subject, wherein the mRNA vaccine induces a tumor-specific immune response in the subject, thereby treating cancer in the subject is provided in other aspects.

The invention in other aspects is a RNA vaccine preparable according to a method involving identifying at least 2 cancer antigens from an exosome isolated from a subject; producing, based on the identified antigens, a mRNA vaccine having an open reading frame encoding the antigens.

A method of eliciting an immune response in a subject against a cancer antigen is provided in aspects of the invention. The method involves administering to the subject a RNA vaccine comprising at least one RNA polynucleotide having an open reading frame encoding at least one antigenic polypeptide or an immunogenic fragment thereof, thereby inducing in the subject an immune response specific to the antigenic polypeptide or an immunogenic fragment thereof, wherein the anti-antigenic polypeptide antibody titer in the subject is increased following vaccination relative to anti-antigenic polypeptide antibody titer in a subject vaccinated with a prophylactically effective dose of a traditional vaccine against the cancer. An "anti-antigenic polypeptide antibody" is a serum antibody the binds specifically to the antigenic polypeptide.

A prophylactically effective dose is a therapeutically effective dose that prevents advancement of cancer at a clinically acceptable level. In some embodiments the therapeutically effective dose is a dose listed in a package insert for the vaccine. A traditional vaccine, as used herein, refers to a vaccine other than the mRNA vaccines of the invention. For instance, a traditional vaccine includes but is not limited to live microorganism vaccines, killed microorganism vaccines, subunit vaccines, protein antigen vaccines, DNA vaccines, etc. In exemplary embodiments, a traditional vaccine is a vaccine that has achieved regulatory approval and/or is registered by a national drug regulatory body, for example the Food and Drug Administration (FDA) in the United States or the European Medicines Agency (EMA.)

In some embodiments the anti-antigenic polypeptide antibody titer in the subject is increased 1 log to 10 log following vaccination relative to anti-antigenic polypeptide antibody titer in a subject vaccinated with a prophylactically effective dose of a traditional vaccine against the cancer.

In some embodiments the anti-antigenic polypeptide antibody titer in the subject is increased 1 log following vaccination relative to anti-antigenic polypeptide antibody titer in a subject vaccinated with a prophylactically effective dose of a traditional vaccine against the cancer.

In some embodiments the anti-antigenic polypeptide antibody titer in the subject is increased 2 log following vaccination relative to anti-antigenic polypeptide antibody titer in a subject vaccinated with a prophylactically effective dose of a traditional vaccine against the cancer.

In some embodiments the anti-antigenic polypeptide antibody titer in the subject is increased 3 log following vaccination relative to anti-antigenic polypeptide antibody titer in a subject vaccinated with a prophylactically effective dose of a traditional vaccine against the cancer.

In some embodiments the anti-antigenic polypeptide antibody titer in the subject is increased 5 log following vaccination relative to anti-antigenic polypeptide antibody titer in a subject vaccinated with a prophylactically effective dose of a traditional vaccine against the or cancer.

In some embodiments the anti-antigenic polypeptide antibody titer in the subject is increased 10 log following vaccination relative to anti-antigenic polypeptide antibody titer in a subject vaccinated with a prophylactically effective dose of a traditional vaccine against the or cancer.

A method of eliciting an immune response in a subject against a cancer antigen is provided in other aspects of the invention. The method involves administering to the subject a RNA vaccine comprising at least one RNA polynucleotide having an open reading frame encoding at least one antigenic polypeptide or an immunogenic fragment thereof, thereby inducing in the subject an immune response specific to antigenic polypeptide or an immunogenic fragment thereof, wherein the immune response in the subject is equivalent to an immune response in a subject vaccinated with a traditional vaccine against the cancer antigen at 2 times to 100 times the dosage level relative to the RNA vaccine.

In some embodiments the immune response in the subject is equivalent to an immune response in a subject vaccinated with a traditional vaccine at twice the dosage level relative to the RNA vaccine.

In some embodiments the immune response in the subject is equivalent to an immune response in a subject vaccinated with a traditional vaccine at three times the dosage level relative to the RNA vaccine.

In some embodiments the immune response in the subject is equivalent to an immune response in a subject vaccinated with a traditional vaccine at 4 times the dosage level relative to the RNA vaccine.

In some embodiments the immune response in the subject is equivalent to an immune response in a subject vaccinated with a traditional vaccine at 5 times the dosage level relative to the RNA vaccine.

In some embodiments the immune response in the subject is equivalent to an immune response in a subject vaccinated with a traditional vaccine at 10 times the dosage level relative to the RNA vaccine.

In some embodiments the immune response in the subject is equivalent to an immune response in a subject vaccinated with a traditional vaccine at 50 times the dosage level relative to the RNA vaccine.

In some embodiments the immune response in the subject is equivalent to an immune response in a subject vaccinated with a traditional vaccine at 100 times the dosage level relative to the RNA vaccine.

In some embodiments the immune response in the subject is equivalent to an immune response in a subject vaccinated with a traditional vaccine at 10 times to 1000 times the dosage level relative to the RNA vaccine.

In some embodiments the immune response in the subject is equivalent to an immune response in a subject vaccinated with a traditional vaccine at 100 times to 1000 times the dosage level relative to the RNA vaccine.

In other embodiments the immune response is assessed by determining antibody titer in the subject.

In other aspects the invention comprises a method of eliciting an immune response in a subject against a by administering to the subject a RNA vaccine comprising at least one RNA polynucleotide having an open reading frame encoding at least one cancer antigenic polypeptide or an immunogenic fragment thereof, thereby inducing in the subject an immune response specific to the antigenic polypeptide or an immunogenic fragment thereof, wherein the immune response in the subject is induced 2 days to 10 weeks earlier relative to an immune response induced in a subject vaccinated with a prophylactically effective dose of a traditional vaccine against the cancer antigen. In some embodiments the immune response in the subject is induced in a subject vaccinated with a prophylactically effective dose of a traditional vaccine at 2 times to 100 times the dosage level relative to the RNA vaccine.

In some embodiments the immune response in the subject is induced 2 days earlier relative to an immune response induced in a subject vaccinated with a prophylactically effective dose of a traditional vaccine.

In some embodiments the immune response in the subject is induced 3 days earlier relative to an immune response induced in a subject vaccinated a prophylactically effective dose of a traditional vaccine.

In some embodiments the immune response in the subject is induced 1 week earlier relative to an immune response induced in a subject vaccinated with a prophylactically effective dose of a traditional vaccine.

In some embodiments the immune response in the subject is induced 2 weeks earlier relative to an immune response induced in a subject vaccinated with a prophylactically effective dose of a traditional vaccine.

In some embodiments the immune response in the subject is induced 3 weeks earlier relative to an immune response induced in a subject vaccinated with a prophylactically effective dose of a traditional vaccine.

In some embodiments the immune response in the subject is induced 5 weeks earlier relative to an immune response induced in a subject vaccinated with a prophylactically effective dose of a traditional vaccine.

In some embodiments the immune response in the subject is induced 10 weeks earlier relative to an immune response induced in a subject vaccinated with a prophylactically effective dose of a traditional vaccine.

A method of eliciting an immune response in a subject against an cancer by administering to the subject a cancer RNA vaccine having an open reading frame encoding a first antigenic polypeptide, wherein the RNA polynucleotide does not include a stabilization element, and wherein an adjuvant is not coformulated or co-administered with the vaccine.

In yet other aspects the invention comprises a method of producing an mRNA encoding a concatemeric cancer antigen comprising between 1000 and 3000 nucleotides, the method by (a) binding a first polynucleotide comprising an open reading frame encoding the concatemeric cancer antigen and a second polynucleotide comprising a 5'-UTR to a polynucleotide conjugated to a solid support;

(b) ligating 3'-terminus of the second polynucleotide to 5'-terminus of the first polynucleotide under suitable conditions, wherein the suitable conditions comprise a DNA Ligase, thereby producing a first ligation product;

(c) ligating the 5' terminus of a third polynucleotide comprising a 3'-UTR to 3'-terminus of the first ligation product under suitable conditions, wherein the suitable conditions comprise an RNA Ligase, thereby producing a second ligation product; and (d) releasing the second ligation product from the solid support, thereby producing an mRNA encoding the concatemeric cancer antigen comprising between 1000 and 3000 nucleotides.

In some embodiments of any one of the provided compositions or methods, the mRNA encodes one or more recurrent polymorphisms. In some embodiments, the one or more recurrent polymorphisms comprises a recurrent somatic cancer mutation in p53. In some such embodiments, the one or more recurrent somatic cancer mutation in p53 are selected from the group consisting of:

(1) mutations at the canonical 5' splice site neighboring codon p.T125, inducing a retained intron having peptide sequence TAKSVTCTVSCPEGLASMRLQCLAVSPCISFVWNFGIPLHPLASCQCFFIVYPLNV (SEQ ID NO: 1) that contains epitopes AVSPCISFVW (SEQ ID NO: 2) (HLA-B*57:01, HLA-B*58:01), HPLASCQCFF (SEQ ID NO: 3) (HLA-B*35:01, HLA-B*53:01), FVWNFGIPL (SEQ ID NO: 4) (HLA-A*02:01, HLA-A*02:06, HLA-B*35:01);

(2) mutations at the canonical 5' splice site neighboring codon p.331, inducing a retained intron having peptide sequence EYFTLQVLSLGTSYQVESFQSNTQNAVFFLTVLPAIGAFAIRGQ (SEQ ID NO: 5) that contains epitopes LQVLSLGTSY (SEQ ID NO: 6) (HLA-B*15:01), FQSNTQNAVF (SEQ ID NO: 7) (HLA-B*15:01);

(3) mutations at the canonical 3' splice site neighboring codon p.126, inducing a cryptic alternative exonic 3' splice site producing the novel spanning peptide sequence AKSVTCTMFCQLAK (SEQ ID NO: 8) that contains epitopes CTMFCQLAK (SEQ ID NO: 9) (HLA-A*11:01), KSVTCTMF (SEQ ID NO: 10) (HLA-B*58:01); and/or (4) mutations at the canonical 5' splice site neighboring codon p.224, inducing a cryptic alternative intronic 5' splice site producing the novel spanning peptide sequence VPYEPPEVWLALTVPPSTAWAA (SEQ ID NO: 11) that contains epitopes VPYEPPEVW (SEQ ID NO: 12) (HLA-B*53:01, HLA-B*51:01), LTVPPSTAW (SEQ ID NO: 13) (HLA-B*58:01, HLA-B*57:01), wherein the transcript codon positions refer to the canonical full-length p53 transcript ENST00000269305 (SEQ ID NO: 14) from the Ensembl v83 human genome annotation.

In one embodiment, the invention provides a cancer therapeutic vaccine comprising mRNA encoding an open reading frame (ORF) coding for one or more of neoantigen peptides (1) through (4). In one embodiment, the invention provides the selective administration of a vaccine containing or coding for one or more of peptides (1)-(4), based on the patient's tumor containing any of the above mutations. In one embodiment, the invention provides the selective administration of the vaccine based on the dual criteria of the subject's tumor containing any of the above mutations and the subject's normal HLA type containing the corresponding HLA allele predicted to bind to the resulting neoantigen.

A kit for preparing an mRNA cancer vaccine is provided in other aspects of the invention. The kit has one or more containers housing one or more polynucleotides comprising a 5'-ORF, one or more polynucleotides comprising a 3'-ORF, one or more polynucleotides comprising a poly(A) tail, a ligase enzyme, and instructions for ligating one or more polynucleotides comprising an ORF encoding a patient specific epitope to the one or more polynucleotides comprising the a 5'-ORF, 3'-ORF, and poly(A) tail.

A method for treating a subject with a personalized mRNA cancer vaccine, by isolating a sample from a subject, identifying a set of neoepitopes by analyzing a patient transcriptome and/or a patient exome from the sample to produce a patient specific mutanome, selecting a set of neoepitopes for the vaccine from the mutanome based on MHC binding strength, MHC binding diversity, predicted degree of immunogenicity, low self reactivity, and/or T cell reactivity, preparing the mRNA vaccine to encode the set of neoepitopes and administering the mRNA vaccine to the subject within two months of isolating the sample from the subject is provided in other aspects of the invention. In some embodiments the mRNA vaccine is administered to the subject within one month of isolating the sample from the subject.

In other aspects the invention comprises a method of identifying a set of neoepitopes for use in a personalized mRNA cancer vaccine having one or more polynucleotides that encode the set of neoepitopes by a. identifying a patient specific mutanome by analyzing a patient transcriptome and a patient exome, b. selecting a subset of 15-500 neoepitopes from the mutanome using a weighted value for the neoepitopes based on at least three of: an assessment of gene or transcript-level expression in patient RNA-seq; variant call confidence score; RNA-seq allele-specific expression; conservative vs. non-conservative amino acid substitution; position of point mutation (Centering Score for increased TCR engagement); position of point mutation (Anchoring Score for differential HLA binding); Selfness: <100% core epitope homology with patient WES data; HLA-A and —B IC50 for 8mers-11mers; HLA-DRB1 IC50 for 15mers-20mers; promiscuity Score (i.e. number of patient HLAs predicted to bind); HLA-C IC50 for 8mers-11mers; HLA-DRB3-5 IC50 for 15mers-20mers; HLA-DQB1/A1 IC50 for 15mers-20mers; HLA-DPB1/A1 IC50 for 15mers-20mers; Class I vs Class II proportion; Diversity of patient HLA-A, -B and DRB1 allotypes covered; proportion of point mutation vs complex epitopes (e.g. frameshifts); and/or pseudo-epitope HLA binding scores, and c. selecting the set of neoepitopes for use in a personalized mRNA cancer vaccine from the subset based on the highest weighted value, wherein the set of neoepitopes comprise 15-40 neoepitopes.

In some embodiments the nucleic acid vaccines described herein are chemically modified. In other embodiments the nucleic acid vaccines are unmodified.

Yet other aspects provide compositions for and methods of vaccinating a subject comprising administering to the subject a nucleic acid vaccine comprising one or more RNA polynucleotides having an open reading frame encoding a first antigenic polypeptide or a concatemeric polypeptide, wherein the RNA polynucleotide does not include a stabilization element, and wherein an adjuvant is not coformulated or co-administered with the vaccine.

In other aspects the invention is a composition for or method of vaccinating a subject comprising administering to the subject a nucleic acid vaccine comprising one or more RNA polynucleotides having an open reading frame encoding a first antigenic polypeptide wherein a dosage of between 10 μg/kg and 400 μg/kg of the nucleic acid vaccine is administered to the subject. In some embodiments the dosage of the RNA polynucleotide is 1-5 ug, 5-10 ug, 10-15 ug, 15-20 ug, 10-25 ug, 20-25 ug, 20-50 ug, 30-50 ug, 40-50 ug, 40-60 ug, 60-80 ug, 60-100 ug, 50-100 ug, 80-120 ug, 40-120 ug, 40-150 ug, 50-150 ug, 50-200 ug, 80-200 ug, 100-200 ug, 120-250 ug, 150-250 ug, 180-280 ug, 200-300 ug, 50-300 ug, 80-300 ug, 100-300 ug, 40-300 ug, 50-350 ug, 100-350 ug, 200-350 ug, 300-350 ug, 320-400 ug, 40-380 ug, 40-100 ug, 100-400 ug, 200-400 ug, or 300-400 ug per dose. In some embodiments, the nucleic acid vaccine is administered to the subject by intradermal or intramuscular injection. In some embodiments, the nucleic acid vaccine is administered to the subject on day zero. In some embodiments, a second dose of the nucleic acid vaccine is administered to the subject on day twenty one.

In some embodiments, a dosage of 25 micrograms of the RNA polynucleotide is included in the nucleic acid vaccine administered to the subject. In some embodiments, a dosage of 100 micrograms of the RNA polynucleotide is included in the nucleic acid vaccine administered to the subject. In some embodiments, a dosage of 50 micrograms of the RNA polynucleotide is included in the nucleic acid vaccine administered to the subject. In some embodiments, a dosage of 75 micrograms of the RNA polynucleotide is included in the nucleic acid vaccine administered to the subject. In some embodiments, a dosage of 150 micrograms of the RNA polynucleotide is included in the nucleic acid vaccine administered to the subject. In some embodiments, a dosage of 400 micrograms of the RNA polynucleotide is included in the nucleic acid vaccine administered to the subject. In some embodiments, a dosage of 200 micrograms of the RNA polynucleotide is included in the nucleic acid vaccine administered to the subject. In some embodiments, the RNA polynucleotide accumulates at a 100 fold higher level in the local lymph node in comparison with the distal lymph node. In other embodiments the nucleic acid vaccine is chemically modified and in other embodiments the nucleic acid vaccine is not chemically modified.

Aspects of the invention provide a nucleic acid vaccine comprising one or more RNA polynucleotides having an open reading frame encoding a first antigenic polypeptide or a concatemeric polypeptide, wherein the RNA polynucleotide does not include a stabilization element, and a pharmaceutically acceptable carrier or excipient, wherein an adjuvant is not included in the vaccine. In some embodiments, the stabilization element is a histone stem-loop. In some embodiments, the stabilization element is a nucleic acid sequence having increased GC content relative to wild type sequence.

Aspects of the invention provide nucleic acid vaccines comprising one or more RNA polynucleotides having an open reading frame encoding a first antigenic polypeptide, wherein the RNA polynucleotide is present in the formulation for in vivo administration to a host, which confers an antibody titer superior to the criterion for seroprotection for the first antigen for an acceptable percentage of human subjects. In some embodiments, the antibody titer produced by the mRNA vaccines of the invention is a neutralizing antibody titer. In some embodiments the neutralizing antibody titer is greater than a protein vaccine. In other embodiments the neutralizing antibody titer produced by the mRNA vaccines of the invention is greater than an adjuvanted protein vaccine. In yet other embodiments the neutralizing antibody titer produced by the mRNA vaccines of the invention is 1,000-10,000, 1,200-10,000, 1,400-10,000, 1,500-10,000, 1,000-5,000, 1,000-4,000, 1,800-10,000, 2000-10,000, 2,000-5,000, 2,000-3,000, 2,000-4,000, 3,000-5,000, 3,000-4,000, or 2,000-2,500. A neutralization titer is typically expressed as the highest serum dilution required to achieve a 50% reduction in the number of plaques.

In preferred aspects, vaccines of the invention (e.g., LNP-encapsulated mRNA vaccines) produce prophylactically—and/or therapeutically-efficacious levels, concentrations and/or titers of antigen-specific antibodies in the blood or serum of a vaccinated subject. As defined herein, the term antibody titer refers to the amount of antigen-specific antibody produces in s subject, e.g., a human subject. In exemplary embodiments, antibody titer is expressed as the inverse of the greatest dilution (in a serial dilution) that still gives a positive result. In exemplary embodiments, antibody titer is determined or measured by enzyme-linked immunosorbent assay (ELISA). In exemplary embodiments, antibody titer is determined or measured by neutralization assay, e.g., by microneutralization assay. In certain aspects, antibody titer measurement is expressed as a ratio, such as 1:40, 1:100, etc.

In exemplary embodiments of the invention, an efficacious vaccine produces an antibody titer of greater than 1:40, greater that 1:100, greater than 1:400, greater than 1:1000, greater than 1:2000, greater than 1:3000, greater than 1:4000, greater than 1:500, greater than 1:6000, greater than 1:7500, greater than 1:10000. In exemplary embodiments, the antibody titer is produced or reached by 10 days following vaccination, by 20 days following vaccination, by 30 days following vaccination, by 40 days following vaccination, or by 50 or more days following vaccination. In exemplary embodiments, the titer is produced or reached following a single dose of vaccine administered to the subject. In other embodiments, the titer is produced or reached following multiple doses, e.g., following a first and a second dose (e.g., a booster dose.)

In exemplary aspects of the invention, antigen-specific antibodies are measured in units of μg/ml or are measured in units of IU/L (International Units per liter) or mIU/ml (milli International Units per ml). In exemplary embodiments of the invention, an efficacious vaccine produces >0.5 μg/ml, >0.1 μg/ml, >0.2 μg/ml, >0.35 μg/ml, >0.5 μg/ml, >1 μg/ml, >2 μg/ml, >5 μg/ml or >10 μg/ml. In exemplary embodiments of the invention, an efficacious vaccine produces >10 mIU/ml, >20 mIU/ml, >50 mIU/ml, >100 mIU/ml, >200 mIU/ml, >500 mIU/ml or >1000 mIU/ml. In exemplary embodiments, the antibody level or concentration is produced or reached by 10 days following vaccination, by 20 days following vaccination, by 30 days following vaccination, by 40 days following vaccination, or by 50 or more days following vaccination. In exemplary embodiments, the level or concentration is produced or reached following a single dose of vaccine administered to the subject. In other embodiments, the level or concentration is produced or reached following multiple doses, e.g., following a first and a second dose (e.g., a booster dose.) In exemplary embodiments, antibody level or concentration is determined or measured by enzyme-linked immunosorbent assay (ELISA). In exemplary embodiments, antibody level or concentration is determined or measured by neutralization assay, e.g., by microneutralization assay. Also provided are nucleic acid vaccines comprising one or more RNA polynucleotides having an open reading frame encoding a first antigenic polypeptide or a concatemeric polypeptide, wherein the RNA polynucleotide is present in a formulation for in vivo administration to a host for eliciting a longer lasting high antibody titer than an antibody titer elicited by an mRNA vaccine having a stabilizing element or formulated with an adjuvant and encoding the first antigenic polypeptide. In some embodiments, the RNA polynucleotide is formulated to produce a neutralizing antibodies within one week of a single administration. In some embodiments, the adjuvant is selected from a cationic peptide and an immunostimulatory nucleic acid. In some embodiments, the cationic peptide is protamine.

Aspects provide nucleic acid vaccines comprising one or more RNA polynucleotides having an open reading frame comprising at least one chemical modification or optionally no nucleotide modification, the open reading frame encoding a first antigenic polypeptide or a concatemeric polypeptide, wherein the RNA polynucleotide is present in the formulation for in vivo administration to a host such that the level of antigen expression in the host significantly exceeds a level of antigen expression produced by an mRNA vaccine having a stabilizing element or formulated with an adjuvant and encoding the first antigenic polypeptide.

Other aspects provide nucleic acid vaccines comprising one or more RNA polynucleotides having an open reading frame comprising at least one chemical modification or optionally no nucleotide modification, the open reading frame encoding a first antigenic polypeptide or a concatemeric polypeptide, wherein the vaccine has at least 10 fold less RNA polynucleotide than is required for an unmodified mRNA vaccine to produce an equivalent antibody titer. In some embodiments, the RNA polynucleotide is present in a dosage of 25-100 micrograms.

Aspects of the invention also provide a unit of use vaccine, comprising between 10 ug and 400 ug of one or more RNA polynucleotides having an open reading frame comprising at least one chemical modification or optionally no nucleotide modification, the open reading frame encoding a first antigenic polypeptide or a concatemeric polypeptide, and a pharmaceutically acceptable carrier or excipient, formulated for delivery to a human subject. In some embodiments, the vaccine further comprises a cationic lipid nanoparticle.

Aspects of the invention provide methods of creating, maintaining or restoring antigenic memory to a tumor in an individual or population of individuals comprising administering to said individual or population an antigenic memory booster nucleic acid vaccine comprising (a) at least one RNA polynucleotide, said polynucleotide comprising at least one chemical modification or optionally no nucleotide modification and two or more codon-optimized open reading frames, said open reading frames encoding a set of reference antigenic polypeptides, and (b) optionally a pharmaceutically acceptable carrier or excipient. In some embodiments, the vaccine is administered to the individual via a route selected from the group consisting of intramuscular administration, intradermal administration and subcutaneous administration. In some embodiments, the administering step comprises contacting a muscle tissue of the subject with a device suitable for injection of the composition. In some embodiments, the administering step comprises contacting a muscle tissue of the subject with a device suitable for injection of the composition in combination with electroporation.

Aspects of the invention provide methods of vaccinating a subject comprising administering to the subject a single dosage of between 25 μg/kg and 400 μg/kg of a nucleic acid vaccine comprising one or more RNA polynucleotides having an open reading frame encoding a first antigenic polypeptide or a concatemeric polypeptide in an effective amount to vaccinate the subject.

Other aspects provide nucleic acid vaccines comprising one or more RNA polynucleotides having an open reading frame comprising at least one chemical modification, the open reading frame encoding a first antigenic polypeptide or a concatemeric polypeptide, wherein the vaccine has at least 10 fold less RNA polynucleotide than is required for an unmodified mRNA vaccine to produce an equivalent antibody titer. In some embodiments, the RNA polynucleotide is present in a dosage of 25-100 micrograms.

Other aspects provide nucleic acid vaccines comprising an LNP formulated RNA polynucleotide having an open reading frame comprising no nucleotide modifications (unmodified), the open reading frame encoding a first antigenic polypeptide or a concatemeric polypeptide, wherein the vaccine has at least 10 fold less RNA polynucleotide than is required for an unmodified mRNA vaccine not formulated in a LNP to produce an equivalent antibody titer. In some embodiments, the RNA polynucleotide is present in a dosage of 25-100 micrograms.

The data presented in the Examples demonstrate significant enhanced immune responses using the formulations of the invention. Surprisingly, in contrast to prior art reports that it was preferable to use chemically unmodified mRNA formulated in a carrier for the production of vaccines, it is described herein that chemically modified mRNA-LNP vaccines required a much lower effective mRNA dose than unmodified mRNA, i.e., tenfold less than unmodified mRNA when formulated in carriers other than LNP. Both the chemically modified and unmodified RNA vaccines of the invention produce better immune responses than mRNA vaccines formulated in a different lipid carrier.

In other aspects the invention encompasses a method of treating an elderly subject age 60 years or older comprising administering to the subject a nucleic acid vaccine comprising one or more RNA polynucleotides having an open reading frame encoding an antigenic polypeptide or a concatemeric polypeptide in an effective amount to vaccinate the subject.

In other aspects the invention encompasses a method of treating a young subject age 17 years or younger comprising administering to the subject a nucleic acid vaccine comprising one or more RNA polynucleotides having an open reading frame encoding an antigenic polypeptide or a concatemeric polypeptide in an effective amount to vaccinate the subject.

In other aspects the invention encompasses a method of treating an adult subject comprising administering to the subject a nucleic acid vaccine comprising one or more RNA polynucleotides having an open reading frame encoding an antigenic polypeptide or a concatemeric polypeptide in an effective amount to vaccinate the subject.

In some aspects the invention comprises a method of vaccinating a subject with a combination vaccine including at least two nucleic acid sequences encoding antigens wherein the dosage for the vaccine is a combined therapeutic dosage wherein the dosage of each individual nucleic acid encoding an antigen is a sub therapeutic dosage. In some embodiments, the combined dosage is 25 micrograms of the RNA polynucleotide in the nucleic acid vaccine administered to the subject. In some embodiments, the combined dosage is 100 micrograms of the RNA polynucleotide in the nucleic acid vaccine administered to the subject. In some embodiments the combined dosage is 50 micrograms of the RNA polynucleotide in the nucleic acid vaccine administered to the subject. In some embodiments, the combined dosage is 75 micrograms of the RNA polynucleotide in the nucleic acid vaccine administered to the subject. In some embodiments, the combined dosage is 150 micrograms of the RNA polynucleotide in the nucleic acid vaccine administered to the subject. In some embodiments, the combined dosage is 400 micrograms of the RNA polynucleotide in the nucleic acid vaccine administered to the subject. In some embodiments, the sub therapeutic dosage of each individual nucleic acid encoding an antigen is 1, 2, 3, 4, 5, 6, 7, 8, 9, 10, 11, 12, 13, 14, 15, 16, 17, 18, 19, or 20 micrograms. In other embodiments the nucleic acid vaccine is chemically modified and in other embodiments the nucleic acid vaccine is not chemically modified.

The details of various embodiments of the invention are set forth in the description below. Other features, objects, and advantages of the invention will be apparent from the description and the drawings, and from the claims.

BRIEF DESCRIPTION OF THE DRAWINGS

The foregoing and other objects, features and advantages will be apparent from the following description of particular embodiments of the invention, as illustrated in the accompanying drawings in which like reference characters refer to the same parts throughout the different views. The drawings are not necessarily to scale, emphasis instead being placed upon illustrating the principles of various embodiments of the invention.

FIG. 4 is a table depicting a multi-factorial consideration of antigen design of mRNA-based neoepitopes.

FIGS. 9A and 9B depict exemplary dose response elicited with mRNA encoding concatamer CA-80. A loss of hits was observed as the amount of vaccine administered decreased.

FIG. 14 is a schematic of an exemplary general molecular sequence of mRNA-1, in which the patient specific coding region is depicted by reference as (N). The sequence corresponds to SEQ ID NOs: 20 and 21.

FIG. 15 is a block diagram of an exemplary computer system on which some embodiments may be implemented.

DETAILED DESCRIPTION

Figure 1A:
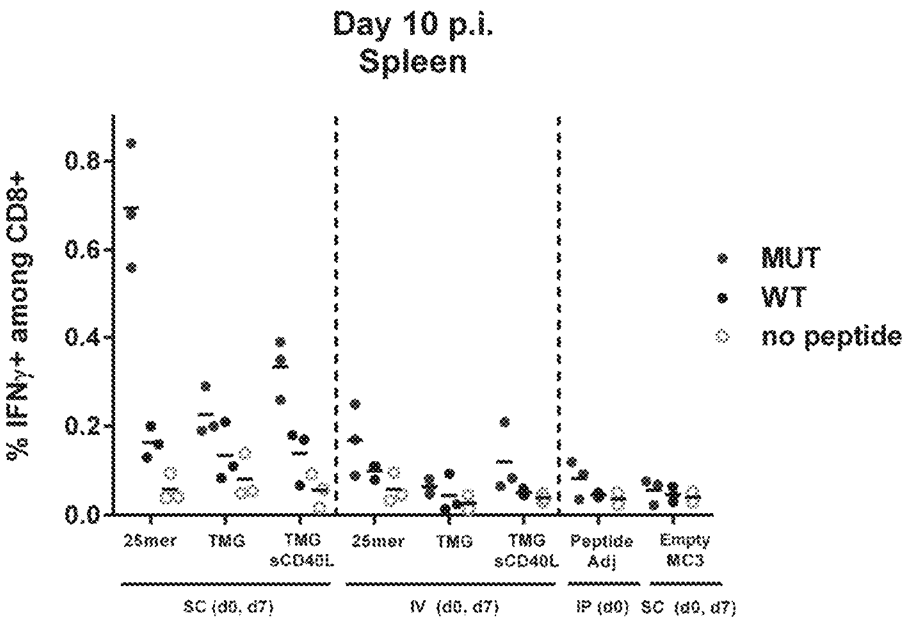
FIGS. 1A-1D show the results of an assay to demonstrate a mRNA vaccine antigen specific CD8 response.
Figure 1B:
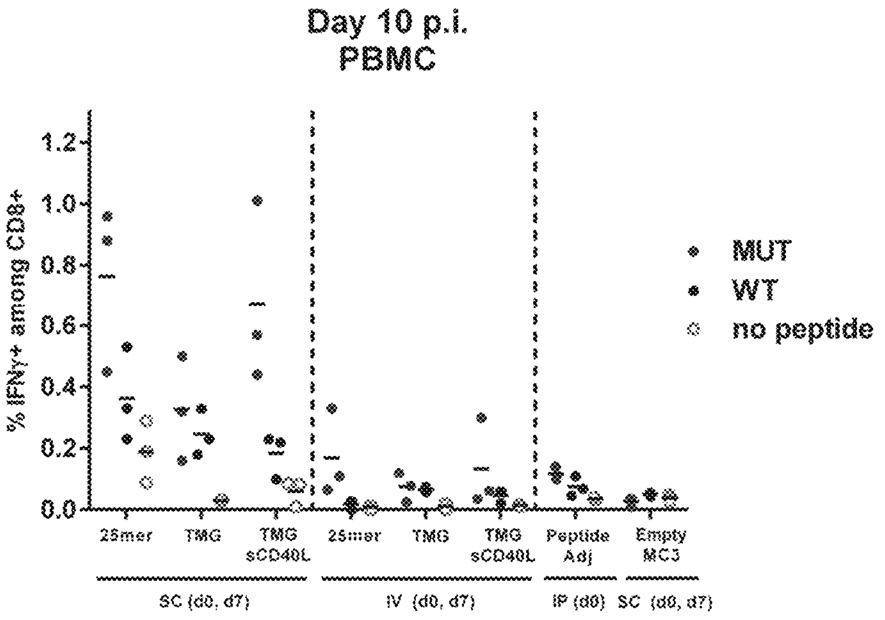
Figure 1C:
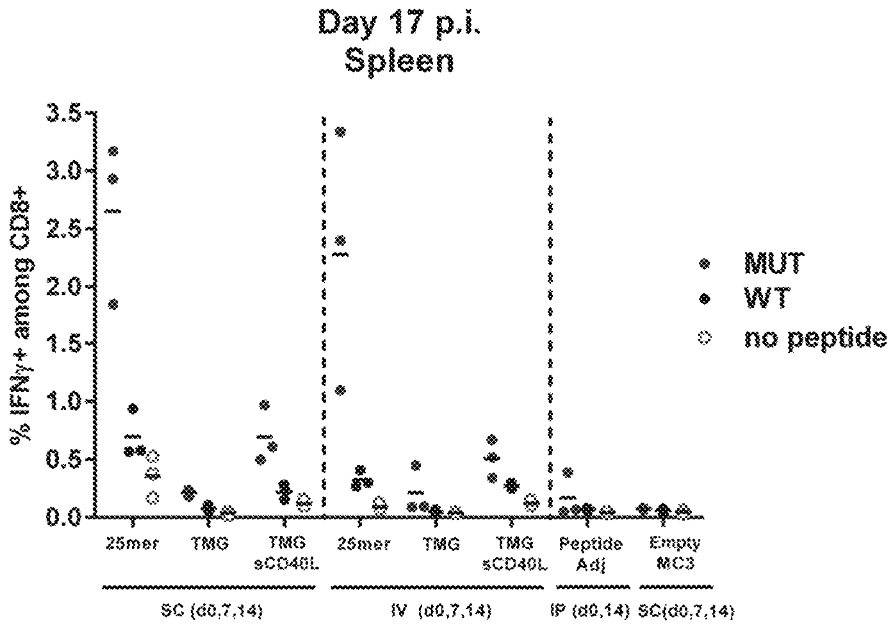
Figure 1D:
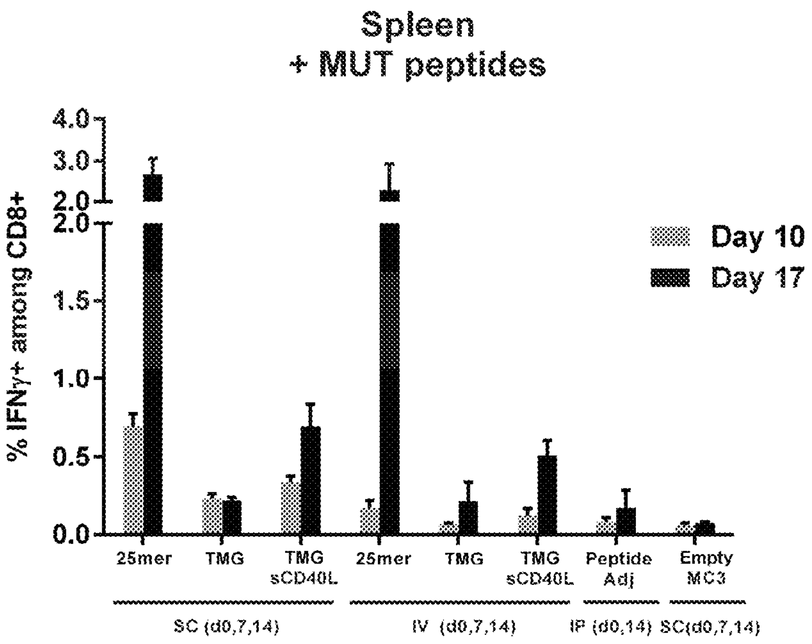

Embodiments of the present disclosure provide RNA (e.g., mRNA) vaccines that include a polynucleotide encoding a cancer antigen. Cancer RNA vaccines, as provided herein may be used to induce a balanced immune response, comprising cellular and/or humoral immunity, without many of the risks associated with DNA vaccination. In some embodiments, a vaccine comprises at least one RNA (e.g., mRNA) polynucleotide having an open reading frame encoding a cancer antigen.

Although attempts have been made to produce functional RNA vaccines, including mRNA cancer vaccines, the therapeutic efficacy of these RNA vaccines have not yet been fully established. Quite surprisingly, the inventors have discovered a class of formulations for delivering mRNA vaccines that results in significantly enhanced, and in many respects synergistic, immune responses including enhanced T cell responses. The vaccines of the invention include traditional cancer vaccines as well as personalized cancer vaccines. The invention involves, in some aspects, the surprising finding that lipid nanoparticle formulations significantly enhance the effectiveness of mRNA vaccines, including chemically modified and unmodified mRNA vaccines.

The lipid nanoparticle used in the studies described herein has been used previously to deliver siRNA various in animal models as well as in humans. In view of the observations made in association with the siRNA delivery of lipid nanoparticle formulations, the fact that lipid nanoparticle is useful in vaccines is quite surprising. It has been observed that therapeutic delivery of siRNA formulated in lipid nanoparticle causes an undesirable inflammatory response associated with a transient IgM response, typically leading to a reduction in antigen production and a compromised immune response. In contrast to the findings observed with siRNA, the lipid nanoparticle-mRNA vaccine formulations are demonstrated to generate enhanced IgG levels, sufficient for prophylactic and therapeutic methods rather than transient IgM responses.

The generation of cancer antigens that elicit a desired immune response (e.g. T-cell responses) against targeted polypeptide sequences in vaccine development remains a challenging task. The invention involves technology that overcome hurdles associated with vaccine development. Through the use of the technology of the invention, it is possible to tailor the desired immune response by selecting appropriate T or B cell cancer epitopes and formulating the epitopes or antigens for effective delivery in vivo.

Thus, the invention relates to mRNA vaccines. mRNA vaccines are described in International Patent Application No. PCT/US2015/027400, filed on Apr. 23, 2015, herein incorporated by reference in its entirety.

The mRNA cancer vaccines provide unique therapeutic alternatives to peptide based or DNA vaccines. When the mRNA cancer vaccine is delivered to a cell, the mRNA will be processed into a polypeptide by the intracellular machinery which can then process the polypeptide into immunosensitive fragments capable of stimulating an immune response against the tumor.

The cancer vaccines described herein include at least one ribonucleic acid (RNA) polynucleotide having an open reading frame encoding at least one cancer antigenic polypeptide or an immunogenic fragment thereof (e.g., an immunogenic fragment capable of inducing an immune response to cancer). The cancer vaccines may be traditional or personalized cancer vaccines. A traditional cancer vaccine is a vaccine including a cancer antigen that is known to be found in cancers or tumors generally or in a specific type of cancer or tumor. Antigens that are expressed in or by tumor cells are referred to as "tumor associated antigens". A particular tumor associated antigen may or may not also be expressed in non-cancerous cells. Many tumor mutations are known in the art.

Personalized vaccines, for instance, may include RNA encoding for one or more known cancer antigens specific for the tumor or cancer antigens specific for each subject, referred to as neoepitopes or subject specific epitopes or antigens. A "subject specific cancer antigen" is an antigen that has been identified as being expressed in a tumor of a particular patient. The subject specific cancer antigen may or may not be typically present in tumor samples generally. Tumor associated antigens that are not expressed or rarely expressed in non-cancerous cells, or whose expression in non-cancerous cells is sufficiently reduced in comparison to that in cancerous cells and that induce an immune response induced upon vaccination, are referred to as neoepitopes. Neoepitopes, like tumor associated antigens, are completely foreign to the body and thus would not produce an immune response against healthy tissue or be masked by the protective components of the immune system. In some embodiments personalized vaccines based on neoepitopes are desirable because such vaccine formulations will maximize specificity against a patient's specific tumor. Mutation-derived neoepitopes can arise from point mutations, non-synonymous mutations leading to different amino acids in the protein; read-through mutations in which a stop codon is modified or deleted, leading to translation of a longer protein with a novel tumor-specific sequence at the C-terminus; splice site mutations that lead to the inclusion of an intron in the mature mRNA and thus a unique tumor-specific protein sequence; chromosomal rearrangements that give rise to a chimeric protein with tumor-specific sequences at the junction of 2 proteins (i.e., gene fusion); frameshift mutations or deletions that lead to a new open reading frame with a novel tumor-specific protein sequence; and translocations. Thus, in some embodiments the mRNA cancer vaccines include at least 2 cancer antigens including mutations selected from the group consisting of frame-shift mutations and recombinations or any of the other mutations described herein.

Methods for generating personalized cancer vaccines generally involve identification of mutations, e.g., using deep nucleic acid or protein sequencing techniques, identification of neoepitopes, e.g., using application of validated peptide-MHC binding prediction algorithms or other analytical techniques to generate a set of candidate T cell epitopes that may bind to patient HLA alleles and are based on mutations present in tumors, optional demonstration of antigen-specific T cells against selected neoepitopes or demonstration that a candidate neoepitope is bound to HLA proteins on the tumor surface and development of the vaccine. The mRNA cancer vaccines of the invention may include multiple copies of a single neoepitope, multiple different neoepitopes based on a single type of mutation, i.e. point mutation, multiple different neoepitopes based on a variety of mutation types, neoepitopes and other antigens, such as tumor associated antigens or recall antigens.

Examples of techniques for identifying mutations include but are not limited to dynamic allele-specific hybridization (DASH), microplate array diagonal gel electrophoresis (MADGE), pyrosequencing, oligonucleotide-specific ligation, the TaqMan system as well as various DNA "chip" technologies i.e. Affymetrix SNP chips, and methods based on the generation of small signal molecules by invasive cleavage followed by mass spectrometry or immobilized padlock probes and rolling-circle amplification.

The deep nucleic acid or protein sequencing techniques are known in the art. Any type of sequence analysis method can be used. Nucleic acid sequencing may be performed on whole tumor genomes, tumor exomes (protein-encoding DNA), tumor transcriptomes, or exosomes. Real-time single molecule sequencing-by-synthesis technologies rely on the detection of fluorescent nucleotides as they are incorporated into a nascent strand of DNA that is complementary to the template being sequenced. Other rapid high throughput sequencing methods also exist. Protein sequencing may be performed on tumor proteomes. Additionally, protein mass spectrometry may be used to identify or validate the presence of mutated peptides bound to MHC proteins on tumor cells. Peptides can be acid-eluted from tumor cells or from HLA molecules that are immunoprecipitated from tumor, and then identified using mass spectrometry. The results of the sequencing may be compared with known control sets or with sequencing analysis performed on normal tissue of the patient.

Accordingly, the present invention relates to methods for identifying and/or detecting neoepitopes of an antigen, such as T-cell epitopes. Specifically, the invention provides methods of identifying and/or detecting tumor specific neoepitopes that are useful in inducing a tumor specific immune response in a subject. Optionally, these neoepitopes bind to class I HLA proteins with a greater affinity than the wild-type peptide and/or are capable of activating anti-tumor CD8 T-cells. Identical mutations in any particular gene are rarely found across tumors.

Proteins of MHC class I are present on the surface of almost all cells of the body, including most tumor cells. The proteins of MHC class I are loaded with antigens that usually originate from endogenous proteins or from pathogens present inside cells, and are then presented to cytotoxic T-lymphocytes (CTLs). T-Cell receptors are capable of recognizing and binding peptides complexed with the molecules of MHC class I. Each cytotoxic T-lymphocyte expresses a unique T-cell receptor which is capable of binding specific MHC/peptide complexes.

Using computer algorithms, it is possible to predict potential neoepitopes such as T-cell epitopes, i.e. peptide sequences, which are bound by the MHC molecules of class I or class II in the form of a peptide-presenting complex and then, in this form, recognized by the T-cell receptors of T-lymphocytes. Examples of programs useful for identifying peptides which will bind to MHC include for instance: Lonza Epibase, SYFPEITHI (Rammensee et al., Immunogenetics, 50 (1999), 213-219) and HLA_BIND (Parker et al., J. Immunol., 152 (1994), 163-175).

Once putative neoepitopes are selected, they can be further tested using in vitro and/or in vivo assays. Conventional in vitro lab assays, such as Elispot assays may be used with an isolate from each patient, to refine the list of neoepitopes selected based on the algorithm1s predictions.

The mRNA cancer vaccines of the invention are compositions, including pharmaceutical compositions. The invention also encompasses methods for the selection, design, preparation, manufacture, formulation, and/or use of mRNA cancer vaccines. Also provided are systems, processes, devices and kits for the selection, design and/or utilization of the mRNA cancer vaccines described herein.

The mRNA vaccines of the invention may include one or more cancer antigens. In some embodiments the mRNA vaccine is composed of 3 or more, 4 or more, 5 or more 6 or more 7 or more, 8 or more, 9 or more antigens. In other embodiments the mRNA vaccine is composed of 1000 or less, 900 or less, 500 or less, 100 or less, 75 or less, 50 or less, 40 or less, 30 or less, 20 or less or 100 or less cancer antigens. In yet other embodiments the mRNA vaccine has 3-100, 5-100, 10-100, 15-100, 20-100, 25-100, 30-100, 35-100, 40-100, 45-100, 50-100, 55-100, 60-100, 65-100, 70-100, 75-100, 80-100, 90-100, 5-50, 10-50, 15-50, 20-50, 25-50, 30-50, 35-50, 40-50, 45-50, 100-150, 100-200, 100-300, 100-400, 100-500, 50-500, 50-800, 50-1,000, or 100-1,000 cancer antigens.

In some embodiments the mRNA cancer vaccines and vaccination methods include epitopes or antigens based on specific mutations (neoepitopes) and those expressed by cancer-germline genes (antigens common to tumors found in multiple patients).

An epitope, also known as an antigenic determinant, as used herein is a portion of an antigen that is recognized by the immune system in the appropriate context, specifically by antibodies, B cells, or T cells. Epitopes include B cell epitopes and T cell epitopes. B-cell epitopes are peptide sequences which are required for recognition by specific antibody producing B-cells. B cell epitopes refer to a specific region of the antigen that is recognized by an antibody. The portion of an antibody that binds to the epitope is called a paratope. An epitope may be a conformational epitope or a linear epitope, based on the structure and interaction with the paratope. A linear, or continuous, epitope is defined by the primary amino acid sequence of a particular region of a protein. The sequences that interact with the antibody are situated next to each other sequentially on the protein, and the epitope can usually be mimicked by a single peptide. Conformational epitopes are epitopes that are defined by the conformational structure of the native protein. These epitopes may be continuous or discontinuous, i.e. components of the epitope can be situated on disparate parts of the protein, which are brought close to each other in the folded native protein structure.

T-cell epitopes are peptide sequences which, in association with proteins on APC, are required for recognition by specific T-cells. T cell epitopes are processed intracellularly and presented on the surface of APCs, where they are bound to MHC molecules including MHC class II and MHC class I. The peptide epitope may be any length that is reasonable for an epitope. In some embodiments the peptide epitope is 9-30 amino acids. In other embodiments the length is 9-22, 9-29, 9-28, 9-27, 9-26, 9-25, 9-24, 9-23, 9-21, 9-20, 9-19, 9-18, 10-22, 10-21, 10-20, 11-22, 22-21, 11-20, 12-22, 12-21, 12-20,13-22, 13-21, 13-20, 14-19, 15-18, or 16-17 amino acids.

In some embodiments, the peptide epitopes comprise at least one MHC class I epitope and at least one MHC class II epitope. In some embodiments, at least 10% of the epitopes are MHC class I epitopes. In some embodiments, at least 20% of the epitopes are MHC class I epitopes. In some embodiments, at least 30% of the epitopes are MHC class I epitopes. In some embodiments, at least 40% of the epitopes are MHC class I epitopes. In some embodiments, at least 50%, 60%, 70%, 80%, 90% or 100% of the epitopes are MHC class I epitopes. In some embodiments, at least 10% of the epitopes are MHC class II epitopes. In some embodiments, at least 20% of the epitopes are MHC class II epitopes. In some embodiments, at least 30% of the epitopes are MHC class II epitopes. In some embodiments, at least 40% of the epitopes are MHC class II epitopes. In some embodiments, at least 50%, 60%, 70%, 80%, 90% or 100% of the epitopes are MHC class II epitopes. In some embodiments, the ratio of MHC class I epitopes to MHC class II epitopes is a ratio selected from about 10%: about 90%; about 20%: about 80%; about 30%: about 70%; about 40%: about 60%; about 50%: about 50%; about 60%: about 40%; about 70%: about 30%; about 80%: about 20%; about 90%: about 10% MHC class 1: MHC class II epitopes. In some embodiments, the ratio of MHC class II epitopes to MHC class I epitopes is a ratio selected from about 10%: about 90%; about 20%: about 80%; about 30%: about 70%; about 40%: about 60%; about 50%: about 50%; about 60%: about 40%; about 70%: about 30%; about 80%: about 20%; about 90%: about 10% MHC class I1: MHC class I epitopes. In some embodiments, at least one of the peptide epitopes of the cancer vaccine is a B cell epitope. In some embodiments, the T cell epitope of the cancer vaccine comprises between 8-11 amino acids. In some embodiments, the B cell epitope of the cancer vaccine comprises between 13-17 amino acids.

The cancer vaccine of the invention, in some aspects comprises an mRNA vaccine encoding multiple peptide epitope antigens arranged with a single nucleotide spacer between the epitopes or directly to one another without a spacer between the epitopes. The multiple epitope antigens includes a mixture of MHC class I epitopes and MHC class II epitopes. For instance, the multiple peptide epitope antigens may be a polypeptide having the structure:

(X-G-X)$_{1-10}$ (G-Y-G-Y)$_{1-10}$ (G-X-G-X)$_{0-10}$(G-Y-G-Y)$_{0-10}$, (X-G)$_{1-10}$ (G-Y)$_{1-10}$ (G-X)$_{0-10}$ (G-Y)$_{0-10}$, (X-G-X-G-X)$_{1-10}$ (G-Y-G-Y)$_{1-10}$ (X-G-X)$_{0-10}$(G-Y-G-Y)$_{0-10}$, (X-G-X)$_{1-10}$ (G-Y-G-Y-G-Y)$_{1-10}$ (X-G-X)$_{0-10}$ (G-Y-G-Y)$_{0-10}$, (X-G-X-G-X-G-X)$_{1-10}$ (G-Y-G-Y)$_{1-10}$ (X-G-X)$_{0-10}$(G-Y-G-Y)$_{0-10}$, (X-G-X)$_{1-10}$ (G-Y-G-Y-G-Y-G-Y)$_{1-10}$ (X-G-X)$_{0-10}$(G-Y-G-Y)$_{0-10}$. (X)$_{1-10}$ (Y)$_{1-10}$ (X)$_{0-10}$ (Y)$_{0-10}$, (Y)$_{1-10}$ (X)$_{1-10}$ (Y)$_{0-10}$(X)$_{0-10}$, (XX)$_{1-10}$ (Y)$_{1-10}$ (X)$_{0-10}$(Y)$_{0-10}$, (YY)$_{1-10}$ (XX)$_{1-10}$ (Y)$_{0-10}$ (X)$_{0-10}$, (X)$_{1-10}$ (YY)$_{1-10}$ (X)$_{0-10}$(Y)$_{0-10}$, (XXX)$_{1-10}$ (YYY)$_{1-10}$ (XX)$_{0-10}$(YY)$_{0-10}$, (YYY)$_{1-10}$ (XXX)$_{1-10}$ (YY)$_{0-10}$(XX)$_{0-10}$, (XY)$_{1-10}$ (Y)$_{1-10}$ (X)$_{1-10}$ (Y) 1-10, (YX)$_{1-10}$ (Y)$_{1-10}$ (X)$_{1-10}$ (Y) 1-10, (YX)$_{1-10}$ (X)$_{1-10}$ (Y)$_{1-10}$ (Y) 1-10, (Y-G-Y)$_{1-10}$ (G-X-G-X)$_{1-10}$ (G-Y-G-Y)$_{0-10}$(G-X-G-X)$_{0-10}$, (Y-G)$_{1-10}$ (G-X)$_{1-10}$ (G-Y)$_{0-10}$ (G-X)$_{0-10}$, (Y-G-Y-G-Y)$_{1-10}$ (G-X-G-X)$_{1-10}$ (Y-G-Y)$_{0-10}$(G-X-G-X)$_{0-10}$, (Y-G-Y)$_{1-10}$ (G-X-G-X-G-X)$_{1-10}$ (Y-G-Y)$_{0-10}$(G-X-G-X)$_{0-10}$, (Y-G-Y-G-Y-G-Y)$_{1-10}$ (G-X-G-X)$_{1-10}$ (Y-G-Y)$_{0-10}$(G-X-G-X)$_{0-10}$, (Y-G-Y)$_{1-10}$ (G-X-G-X-G-X-G-X)$_{1-10}$ (Y-G-Y)$_{0-10}$(G-X-G-X)$_{0-10}$, (XY)$_{1-10}$ (YX)$_{1-10}$ (XY)$_{0-10}$(YX)$_{0-10}$, (YX)$_{1-10}$ (XY)$_{1-10}$ (Y)$_{0-10}$(X)$_{0-10}$, (YY)$_{1-10}$ (X)$_{1-10}$ (Y)$_{0-10}$(X)$_{0-10}$, (XY)$_{1-10}$ (XY)$_{1-10}$ (X)$_{0-10}$(X)$_{0-10}$, (Y)$_{1-10}$ (YX)$_{1-10}$ (X)$_{0-10}$(Y)$_{0-10}$, (XYX)$_{1-10}$ (YXX)$_{1-10}$ (YX)$_{0-10}$(YY)$_{0-10}$, or (YYX)$_{1-10}$ (XXY)$_{1-10}$ (YX)$_{0-10}$ (XY)$_{0-10}$,

X is an MHC class I epitope of 10-40 amino acids in length, Y is an MHC class II epitope of 10-40 amino acids in length, and G is glycine.

In some embodiments the RNA vaccines can be combined with agents for promoting the production of antigen presenting cells (APCs), for instance, by converting non-APCs into pseudo-APCs. Antigen presentation is a key step in the initiation, amplification and duration of an immune response. In this process fragments of antigens are presented through the Major Histocompatibility Complex (MHC) or Human Leukocyte Antigens (HLA) to T cells driving an antigen-specific immune response. For immune prophylaxis and therapy, enhancing this response is important for improved efficacy. The RNA vaccines of the invention may be designed or enhanced to drive efficient antigen presentation. One method for enhancing APC processing and presentation, is to provide better targeting of the RNA vaccines to antigen presenting cells (APC). Another approach involves activating the APC cells with immune-stimulatory formulations and/or components.

Alternatively, methods for reprograming non-APC into becoming APC may be used with the RNA vaccines of the invention. Importantly, most cells that take up mRNA formulations and are targets of their therapeutic actions are not APC. Therefore, designing a way to convert these cells into APC would be beneficial for efficacy. Methods and approaches for delivering RNA vaccines, e.g., mRNA vaccines to cells while also promoting the shift of a non-APC to an APC are provided herein. In some embodiments a mRNA encoding an APC reprograming molecule is included in the RNA vaccine or coadministered with the RNA vaccine.

An APC reprograming molecule, as used herein, is a molecule that promotes a transition in a non APC cell to an APC-like phenotype. An APC-like phenotype is property that enables MHC class II processing. Thus, an APC cell having an APC-like phenotype is a cell having one or more exogenous molecules (APC reprograming molecule) which has enhanced MHC class II processing capabilities in comparison to the same cell not having the one or more exogenous molecules. In some embodiments an APC reprograming molecule is a CIITA (a central regulator of MHC Class II expression); a chaperone protein such as CLIP, HLA-DO, HLA-DM etc. (enhancers of loading of antigen fragments into MHC Class II) and/or a costimulatory molecule like CD40, CD80, CD86 etc. (enhancers of T cell antigen recognition and T cell activation).

A CIITA protein is a transactivator that enhances activation of transcription of MHC Class II genes (Steimle et al., 1993, Cell 75:135-146) by interacting with a conserved set of DNA binding proteins that associate with the class II promoter region. The transcriptional activation function of CIITA has been mapped to an amino terminal acidic domain (amino acids 26-137). A nucleic acid molecule encoding a protein that interacts with CIITA, termed CIITA-interacting protein 104 (also referred to herein as CIP104). Both CITTA and CIP104 have been shown to enhance transcription from MHC class II promoters and thus are useful as APC reprograming molecule of the invention. In some embodiments the APC reprograming molecule are full length CIITA, CIP104 or other related molecules or active fragments thereof, such as amino acids 26-137 of CIITA, or amino acids having at least 80% sequence identity thereto and maintaining the ability to enhance activation of transcription of MHC Class II genes.

In preferred embodiments the APC reprograming molecule is delivered to a subject in the form of an mRNA encoding the APC reprograming molecule. As such the RNA vaccines of the invention may include an mRNA encoding an APC reprograming molecule. In some embodiments the mRNA in monocistronic. In other embodiments it is polycistronic. In some embodiments the mRNA encoding the one or more antigens is in a separate formulation from the mRNA encoding the APC reprograming molecule. In other embodiments the mRNA encoding the one or more antigens is in the same formulation as the mRNA encoding the APC reprograming molecule. In some embodiments the mRNA encoding the one or more antigens is administered to a subject at the same time as the mRNA encoding the APC reprograming molecule. In other embodiments the mRNA encoding the one or more antigens is administered to a subject at a different time than the mRNA encoding the APC reprograming molecule. For instance, the mRNA encoding the APC reprograming molecule may be administered prior to the mRNA encoding the one or more antigens. The mRNA encoding the APC reprograming molecule may be administered immediately prior to, at least 1 hour prior to, at least 1 day prior to, at least one week prior to, or at least one month prior to the mRNA encoding the antigens.

Alternatively, the mRNA encoding the APC reprograming molecule may be administered after the mRNA encoding the one or more antigens. The mRNA encoding the APC reprograming molecule may be administered immediately after, at least 1 hour after, at least 1 day after, at least one week after, or at least one month after the mRNA encoding the antigens. In some embodiments the antigen is a cancer antigen, such as a patient specific antigen. In other embodiments the antigen is an infectious disease antigen.

In some embodiments the mRNA vaccine may include a recall antigen, also sometimes referred to as a memory antigen. A recall antigen is an antigen that has previously been encountered by an individual and for which there are pre-existent memory lymphocytes. In some embodiments the recall antigen may be an infectious disease antigen that the individual has likely encountered such as an influenza antigen. The recall antigen helps promote a more robust immune response.

The antigens or neoepitopes selected for inclusion in the mRNA vaccine typically will be high affinity binding peptides. In some aspect the antigens or neoepitopes binds an HLA protein with greater affinity than a wild-type peptide. The antigen or neoepitope has an IC50 of at least less than 5000 nM, at least less than 500 nM, at least less than 250 nM, at least less than 200 nM, at least less than 150 nM, at least less than 100 nM, at least less than 50 nM or less in some embodiments. Typically, peptides with predicted IC50<50 nM, are generally considered medium to high affinity binding peptides and will be selected for testing their affinity empirically using biochemical assays of HLA-binding.

In a personalized cancer vaccine, the subject specific cancer antigens may be identified in a sample of a patient. For instance, the sample may be a tissue sample or a tumor sample. For instance, a sample of one or more tumor cells may be examined for the presence of subject specific cancer antigens. The tumor sample may be examined using whole genome, exome or transcriptome analysis in order to identify the subject specific cancer antigens.

Alternatively the subject specific cancer antigens may be identified in an exosome of the subject. When the antigens for a vaccine are identified in an exosome of the subject, such antigens are said to be representative of exosome antigens of the subject.

Exosomes are small microvesicles shed by cells, typically having a diameter of approximately 30-100 nm. Exosomes are classically formed from the inward invagination and pinching off of the late endosomal membrane, resulting in the formation of a multivesicular body (MVB) laden with small lipid bilayer vesicles, each of which contains a sample of the parent cell's cytoplasm. Fusion of the MVB with the cell membrane results in the release of these exosomes from the cell, and their delivery into the blood, urine, cerebrospinal fluid, or other bodily fluids. Exosomes can be recovered from any of these biological fluids for further analysis.

Nucleic acids within exosomes have a role as biomarkers for tumor antigens. An advantage of analyzing exosomes in order to identify subject specific cancer antigens, is that the method circumvents the need for biopsies. This can be particularly advantageous when the patient needs to have several rounds of therapy including identification of cancer antigens, and vaccination.

A number of methods of isolating exosomes from a biological sample have been described in the art. For example, the following methods can be used: differential centrifugation, low speed centrifugation, anion exchange and/or gel permeation chromatography, sucrose density gradients or organelle electrophoresis, magnetic activated cell sorting (MACS), nanomembrane ultrafiltration concentration, Percoll gradient isolation and using microfluidic devices. Exemplary methods are described in US Patent Publication No. 2014/0212871 for instance.

The term "biological sample" refers to a sample that contains biological materials such as a DNA, a RNA and a protein. In some embodiments, the biological sample may suitably comprise a bodily fluid from a subject. The bodily fluids can be fluids isolated from anywhere in the body of the subject, preferably a peripheral location, including but not limited to, for example, blood, plasma, serum, urine, sputum, spinal fluid, cerebrospinal fluid, pleural fluid, nipple aspirates, lymph fluid, fluid of the respiratory, intestinal, and genitourinary tracts, tear fluid, saliva, breast milk, fluid from the lymphatic system, semen, cerebrospinal fluid, intra-organ system fluid, ascitic fluid, tumor cyst fluid, amniotic fluid and combinations thereof.

In some embodiments, the progression of the cancer can be monitored to identify changes in the expressed antigens. Thus, in some embodiments the method also involves at least one month after the administration of a cancer mRNA vaccine, identifying at least 2 cancer antigens from a sample of the subject to produce a second set of cancer antigens, and administering to the subject a mRNA vaccine having an open reading frame encoding the second set of cancer antigens to the subject. The mRNA vaccine having an open reading frame encoding second set of antigens, in some embodiments, is administered to the subject 2 months, 3 months, 4 months, 5 months, 6 months, 8 months, 10 months, or 1 year after the mRNA vaccine having an open reading frame encoding the first set of cancer antigens. In other embodiments the mRNA vaccine having an open reading frame encoding second set of antigens is administered to the subject 1½, 2, 2½, 3, 3½, 4, 4½, or 5 years after the mRNA vaccine having an open reading frame encoding the first set of cancer antigens.

Hotspot Mutations as Neoantigens

In population analyses of cancer, certain mutations occur in a higher percentage of patients than would be expected by chance. These "recurrent" or "hotspot" mutations have often been shown to have a "driver" role in the tumor, producing some change in the cancer cell function that is important to tumor initiation, maintenance, or metastasis, and is therefore selected for in the evolution of the tumor. In addition to their importance in tumor biology and therapy, recurrent mutations provide the opportunity for precision medicine, in which the patient population is stratified into groups more likely to respond to a particular therapy, including but not limited to targeting the mutated protein itself.

Much effort and research on recurrent mutations has focused on non-synonymous (or "missense") single nucleotide variants (SNVs), but population analyses have revealed that a variety of more complex (non-SNV) variant classifications, such as synonymous (or "silent"), splice site, multinucleotide variants, insertions, and deletions, can also occur at high frequencies.

The p53 gene (official symbol TP53) is mutated more frequently than any other gene in human cancers. Large cohort studies have shown that, for most p53 mutations, the genomic position is unique to one or only a few patients and the mutation cannot be used as recurrent neoantigens for therapeutic vaccines designed for a specific population of patients. Surprisingly, a small subset of p53 loci do, however, exhibit a "hotspot" pattern, in which several positions in the gene are mutated with relatively high frequency. Strikingly, a large portion of these recurrently mutated regions occur near exon-intron boundaries, disrupting the canonical nucleotide sequence motifs recognized by the mRNA splicing machinery. Mutation of a splicing motif can alter the final mRNA sequence even if no change to the local amino acid sequence is predicted (i.e., for synonymous or intronic mutations). Therefore, these mutations are often annotated as "noncoding" by common annotation tools and neglected for further analysis, even though they may alter mRNA splicing in unpredictable ways and exert severe functional impact on the translated protein. If an alternatively spliced isoform produces an in-frame sequence change (i.e., no PTC is produced), it can escape depletion by NMD and be readily expressed, processed, and presented on the cell surface by the HLA system. Further, mutation-derived alternative splicing is usually "cryptic", i.e., not expressed in normal tissues, and therefore may be recognized by T-cells as non-self neoantigens.

In some aspects, the present invention provides neoantigen peptide sequences resulting from certain recurrent somatic cancer mutations in p53, not limited to missense SNVs and often resulting in alternative splicing, for use as targets for therapeutic vaccination. In some embodiments, the mutation, mRNA splicing events, resulting neoantigen peptides, and/or HLA-restricted epitopes include mutations at the canonical 5' splice site neighboring codon p.T125, inducing a retained intron having peptide sequence TAKSVTCTVSCPEGLASMRLQCLAVSPCISFVWNF-GIPLHPLASCQCFFIVYPLNV (SEQ ID NO: 1) that contains epitopes AVSPCISFVW (SEQ ID NO: 2) (HLA-B*57:01, HLA-B*58:01), HPLASCQCFF (SEQ ID NO: 3) (HLA-B*35:01, HLA-B*53:01), FVWNFGIPL (SEQ ID NO: 4) (HLA-A*02:01, HLA-A*02:06, HLA-B*35:01).

In some embodiments, the mutation, mRNA splicing events, resulting neoantigen peptides, and/or HLA-restricted epitopes include mutations at the canonical 5' splice site neighboring codon p.331, inducing a retained intron having peptide sequence EYFTLQVLSLGTSYQVESFQSNTQ-NAVFFLTVLPAIGAFAIRGQ (SEQ ID NO: 5) that contains epitopes LQVLSLGTSY (SEQ ID NO: 6) (HLA-B*15:01), FQSNTQNAVF (SEQ ID NO: 7) (HLA-B*15:01).

In some embodiments, the mutation, mRNA splicing events, resulting neoantigen peptides, and/or HLA-restricted epitopes include mutations at the canonical 3' splice site neighboring codon p.126, inducing a cryptic alternative exonic 3' splice site producing the novel spanning peptide sequence AKSVTCTMFCQLAK (SEQ ID NO: 8) that contains epitopes CTMFCQLAK (SEQ ID NO: 9) (HLA-A*11:01), KSVTCTMF (SEQ ID NO: 10) (HLA-B*58:01).

In some embodiments, the mutation, mRNA splicing events, resulting neoantigen peptides, and/or HLA-restricted epitopes include mutations at the canonical 5' splice site neighboring codon p.224, inducing a cryptic alternative intronic 5' splice site producing the novel spanning peptide sequence VPYEPPEVWLALTVPPSTAWAA (SEQ ID NO: 11) that contains epitopes VPYEPPEVW (SEQ ID NO: 12) (HLA-B*53:01, HLA-B*51:01), LTVPPSTAW (SEQ ID NO: 13) (HLA-B*58:01, HLA-B*57:01)

In the foregoing sequences, the transcript codon positions refer to the canonical full-length p53 transcript ENST00000269305 (SEQ ID NO: 14) from the Ensembl v83 human genome annotation.

In one embodiment, the invention provides an mRNA vaccine comprising a concatemeric polyepitope construct or set of individual epitope constructs containing open reading frame (ORF) coding for neoantigen peptides 1 through 4.

In one embodiment, the invention provides the selective administration of a vaccine containing or coding for peptides 1-4, based on the patient's tumor containing any of the above mutations.

In one embodiment, the invention provides the selective administration of the vaccine based on the dual criteria of the 1) patient's tumor containing any of the above mutations and 2) the patient's normal HLA type containing the corresponding HLA allele predicted to bind to the resulting neoantigen.

It has been discovered that the mRNA vaccines described herein are superior to current vaccines in several ways. First, the lipid nanoparticle (LNP) delivery is superior to other formulations including liposome or protamine based approachs described in the literature and no additional adjuvants are to be necessary. The use of LNPs enables the effective delivery of chemically modified or unmodified mRNA vaccines. Both modified and unmodified LNP formulated mRNA vaccines are superior to conventional vaccines by a significant degree. In some embodiments the mRNA vaccines of the invention are superior to conventional vaccines by a factor of at least 10 fold, 20 fold, 40 fold, 50 fold, 100 fold, 500 fold or 1,000 fold.

Although attempts have been made to produce functional RNA vaccines, including mRNA vaccines and self-replicating RNA vaccines, the therapeutic efficacy of these RNA vaccines have not yet been fully established. Quite surprisingly, the inventors have discovered, according to aspects of the invention a class of formulations for delivering mRNA vaccines in vivo that results in significantly enhanced, and in many respects synergistic, immune responses including enhanced antigen generation and functional antibody production with neutralization capability. These results can be achieved even when significantly lower doses of the mRNA are administered in comparison with mRNA doses used in other classes of lipid based formulations. The formulations of the invention have demonstrated significant unexpected in vivo immune responses sufficient to establish the efficacy of functional mRNA vaccines as prophylactic and therapeutic agents. Additionally, self-replicating RNA vaccines rely on viral replication pathways to deliver enough RNA to a cell to produce an immunogenic response. The formulations of the invention do not require viral replication to produce enough protein to result in a strong immune response. Thus, the mRNA of the invention are not self-replicating RNA and do not include components necessary for viral replication.

The invention involves, in some aspects, the surprising finding that lipid nanoparticle (LNP) formulations significantly enhance the effectiveness of mRNA vaccines, including chemically modified and unmodified mRNA vaccines. The efficacy of mRNA vaccines formulated in LNP was examined in vivo using several distinct tumor antigens. In addition to providing an enhanced immune response, the formulations of the invention generate a more rapid immune response with fewer doses of antigen than other vaccines tested. The mRNA-LNP formulations of the invention also produce quantitatively and qualitatively better immune responses than vaccines formulated in a different carriers. Additionally, the mRNA-LNP formulations of the invention are superior to other vaccines even when the dose of mRNA is lower than other vaccines.

The LNP used in the studies described herein has been used previously to deliver siRNA in various animal models as well as in humans. In view of the observations made in association with the siRNA delivery of LNP formulations, the fact that LNP is useful in vaccines is quite surprising. It has been observed that therapeutic delivery of siRNA formulated in LNP causes an undesirable inflammatory response associated with a transient IgM response, typically leading to a reduction in antigen production and a compromised immune response. In contrast to the findings observed with siRNA, the LNP-mRNA formulations of the invention are demonstrated herein to generate enhanced IgG levels, sufficient for prophylactic and therapeutic methods rather than transient IgM responses.

Nucleic Acids/Polynucleotides

Cancer vaccines, as provided herein, comprise at least one (one or more) ribonucleic acid (RNA) polynucleotide having an open reading frame encoding at least one cancer antigenic polypeptide. The term "nucleic acid," in its broadest sense, includes any compound and/or substance that comprises a polymer of nucleotides. These polymers are referred to as polynucleotides.

Nucleic acids (also referred to as polynucleotides) may be or may include, for example, ribonucleic acids (RNAs), deoxyribonucleic acids (DNAs), threose nucleic acids (TNAs), glycol nucleic acids (GNAs), peptide nucleic acids (PNAs), locked nucleic acids (LNAs, including LNA having a β-D-ribo configuration, α-LNA having an α-L-ribo configuration (a diastereomer of LNA), 2'-amino-LNA having a 2'-amino functionalization, and 2'-amino-α-LNA having a 2'-amino functionalization), ethylene nucleic acids (ENA), cyclohexenyl nucleic acids (CeNA) or chimeras or combinations thereof.

In some embodiments, polynucleotides of the present disclosure function as messenger RNA (mRNA). "Messenger RNA" (mRNA) refers to any polynucleotide that encodes a (at least one) polypeptide (a naturally-occurring, non-naturally-occurring, or modified polymer of amino acids) and can be translated to produce the encoded polypeptide in vitro, in vivo, in situ or ex vivo.

The basic components of an mRNA molecule typically include at least one coding region, a 5' untranslated region (UTR), a 3' UTR, a 5' cap and a poly-A tail. Polynucleotides of the present disclosure may function as mRNA but can be distinguished from wild-type mRNA in their functional and/or structural design features which serve to overcome existing problems of effective polypeptide expression using nucleic-acid based therapeutics.

In some embodiments, a RNA polynucleotide of a cancer vaccine encodes 2-10, 2-9, 2-8, 2-7, 2-6, 2-5, 2-4, 2-3, 3-10, 3-9, 3-8, 3-7, 3-6, 3-5, 3-4, 4-10, 4-9, 4-8, 4-7, 4-6, 4-5, 5-10, 5-9, 5-8, 5-7, 5-6, 6-10, 6-9, 6-8, 6-7, 7-10, 7-9, 7-8, 8-10, 8-9 or 9-10 antigenic polypeptides. In some embodiments, a RNA polynucleotide of a cancer vaccine encodes at least 10, 20, 30, 40, 50, 60, 70, 80, 90 or 100 antigenic polypeptides. In some embodiments, a RNA polynucleotide of a cancer vaccine encodes at least 100 or at least 200 antigenic polypeptides. In some embodiments, a RNA polynucleotide of a cancer vaccine encodes 1-10, 5-15, 10-20, 15-25, 20-30, 25-35, 30-40, 35-45, 40-50, 1-50, 1-100, 2-50 or 2-100 antigenic polypeptides.

Polynucleotides of the present disclosure, in some embodiments, are codon optimized. Codon optimization methods are known in the art and may be used as provided herein. Codon optimization, in some embodiments, may be used to match codon frequencies in target and host organisms to ensure proper folding; bias GC content to increase mRNA stability or reduce secondary structures; minimize tandem repeat codons or base runs that may impair gene construction or expression; customize transcriptional and translational control regions; insert or remove protein trafficking sequences; remove/add post translation modification sites in encoded protein (e.g. glycosylation sites); add, remove or shuffle protein domains; insert or delete restriction sites; modify ribosome binding sites and mRNA degradation sites; adjust translational rates to allow the various domains of the protein to fold properly; or to reduce or eliminate problem secondary structures within the polynucleotide. Codon optimization tools, algorithms and services are known in the art-non-limiting examples include services from GeneArt (Life Technologies), DNA2.0 (Menlo Park CA) and/or proprietary methods. In some embodiments, the open reading frame (ORF) sequence is optimized using optimization algorithms.

In some embodiments, a codon optimized sequence shares less than 95% sequence identity to a naturally-occurring or wild-type sequence (e.g., a naturally-occurring or wild-type mRNA sequence encoding a polypeptide or protein of interest (e.g., an antigenic protein or polypeptide. In some embodiments, a codon optimized sequence shares less than 90% sequence identity to a naturally-occurring or wild-type sequence (e.g., a naturally-occurring or wild-type mRNA sequence encoding a polypeptide or protein of interest (e.g., an antigenic protein or polypeptide. In some embodiments, a codon optimized sequence shares less than 85% sequence identity to a naturally-occurring or wild-type sequence (e.g., a naturally-occurring or wild-type mRNA sequence encoding a polypeptide or protein of interest (e.g., an antigenic protein or polypeptide. In some embodiments, a codon optimized sequence shares less than 80% sequence identity to a naturally-occurring or wild-type sequence (e.g., a naturally-occurring or wild-type mRNA sequence encoding a polypeptide or protein of interest (e.g., an antigenic protein or polypeptide. In some embodiments, a codon optimized sequence shares less than 75% sequence identity to a naturally-occurring or wild-type sequence (e.g., a naturally-occurring or wild-type mRNA sequence encoding a polypeptide or protein of interest (e.g., an antigenic protein or polypeptide.

In some embodiments, a codon optimized sequence shares between 65% and 85% (e.g., between about 67% and about 85% or between about 67% and about 80%) sequence identity to a naturally-occurring or wild-type sequence (e.g., a naturally-occurring or wild-type mRNA sequence encoding a polypeptide or protein of interest (e.g., an antigenic protein or polypeptide. In some embodiments, a codon optimized sequence shares between 65% and 75 or about 80% sequence identity to a naturally-occurring or wild-type sequence (e.g., a naturally-occurring or wild-type mRNA sequence encoding a polypeptide or protein of interest (e.g., an antigenic protein or polypeptide.

In some embodiments a codon optimized RNA may, for instance, be one in which the levels of G/C are enhanced. The G/C-content of nucleic acid molecules may influence the stability of the RNA. RNA having an increased amount of guanine (G) and/or cytosine (C) residues may be functionally more stable than nucleic acids containing a large amount of adenine (A) and thymine (T) or uracil (U) nucleotides. WO02/098443 discloses a pharmaceutical composition containing an mRNA stabilized by sequence modifications in the translated region. Due to the degeneracy of the genetic code, the modifications work by substituting existing codons for those that promote greater RNA stability without changing the resulting amino acid. The approach is limited to coding regions of the RNA.

Antigens/Antigenic Polypeptides

In some embodiments, a cancer antigenic polypeptide is longer than 25 amino acids and shorter than 50 amino acids. Thus, polypeptides include gene products, naturally occurring polypeptides, synthetic polypeptides, homologs, orthologs, paralogs, fragments and other equivalents, variants, and analogs of the foregoing. A polypeptide may be a single molecule or may be a multi-molecular complex such as a dimer, trimer or tetramer. Polypeptides may also comprise single chain or multichain polypeptides such as antibodies or insulin and may be associated or linked. Most commonly, disulfide linkages are found in multichain polypeptides. The term polypeptide may also apply to amino acid polymers in which at least one amino acid residue is an artificial chemical analogue of a corresponding naturally-occurring amino acid.

The term "polypeptide variant" refers to molecules which differ in their amino acid sequence from a native or reference sequence. The amino acid sequence variants may possess substitutions, deletions, and/or insertions at certain positions within the amino acid sequence, as compared to a native or reference sequence. Ordinarily, variants possess at least 50% identity to a native or reference sequence. In some embodiments, variants share at least 80%, or at least 90% identity with a native or reference sequence.

In some embodiments "variant mimics" are provided. As used herein, the term "variant mimic" is one which contains at least one amino acid that would mimic an activated sequence. For example, glutamate may serve as a mimic for phosphoro-threonine and/or phosphoro-serine. Alternatively, variant mimics may result in deactivation or in an inactivated product containing the mimic, for example, phenylalanine may act as an inactivating substitution for tyrosine; or alanine may act as an inactivating substitution for serine.

"Orthologs" refers to genes in different species that evolved from a common ancestral gene by speciation. Normally, orthologs retain the same function in the course of evolution. Identification of orthologs is critical for reliable prediction of gene function in newly sequenced genomes.

"Analogs" is meant to include polypeptide variants which differ by one or more amino acid alterations, for example, substitutions, additions or deletions of amino acid residues that still maintain one or more of the properties of the parent or starting polypeptide.

The present disclosure provides several types of compositions that are polynucleotide or polypeptide based, including variants and derivatives. These include, for example, substitutional, insertional, deletion and covalent variants and derivatives. The term "derivative" is used synonymously with the term "variant" but generally refers to a molecule that has been modified and/or changed in any way relative to a reference molecule or starting molecule.

As such, polynucleotides encoding peptides or polypeptides containing substitutions, insertions and/or additions, deletions and covalent modifications with respect to reference sequences, in particular the polypeptide sequences disclosed herein, are included within the scope of this disclosure. For example, sequence tags or amino acids, such as one or more lysines, can be added to peptide sequences (e.g., at the N-terminal or C-terminal ends). Sequence tags can be used for peptide detection, purification or localization. Lysines can be used to increase peptide solubility or to allow for biotinylation. Alternatively, amino acid residues located at the carboxy and amino terminal regions of the amino acid sequence of a peptide or protein may optionally be deleted providing for truncated sequences. Certain amino acids (e.g., C-terminal or N-terminal residues) may alternatively be deleted depending on the use of the sequence, as for example, expression of the sequence as part of a larger sequence which is soluble, or linked to a solid support.

"Substitutional variants" when referring to polypeptides are those that have at least one amino acid residue in a native or starting sequence removed and a different amino acid inserted in its place at the same position. Substitutions may be single, where only one amino acid in the molecule has been substituted, or they may be multiple, where two or more amino acids have been substituted in the same molecule.

As used herein the term "conservative amino acid substitution" refers to the substitution of an amino acid that is normally present in the sequence with a different amino acid of similar size, charge, or polarity. Examples of conservative substitutions include the substitution of a non-polar (hydrophobic) residue such as isoleucine, valine and leucine for another non-polar residue. Likewise, examples of conservative substitutions include the substitution of one polar (hydrophilic) residue for another such as between arginine and lysine, between glutamine and asparagine, and between glycine and serine. Additionally, the substitution of a basic residue such as lysine, arginine or histidine for another, or the substitution of one acidic residue such as aspartic acid or glutamic acid for another acidic residue are additional examples of conservative substitutions. Examples of non-conservative substitutions include the substitution of a non-polar (hydrophobic) amino acid residue such as isoleucine, valine, leucine, alanine, methionine for a polar (hydrophilic) residue such as cysteine, glutamine, glutamic acid or lysine and/or a polar residue for a non-polar residue.

"Features" when referring to polypeptide or polynucleotide are defined as distinct amino acid sequence-based or nucleotide-based components of a molecule respectively. Features of the polypeptides encoded by the polynucleotides include surface manifestations, local conformational shape, folds, loops, half-loops, domains, half-domains, sites, termini or any combination thereof.

As used herein when referring to polypeptides the term "domain" refers to a motif of a polypeptide having one or more identifiable structural or functional characteristics or properties (e.g., binding capacity, serving as a site for protein-protein interactions).

As used herein when referring to polypeptides the terms "site" as it pertains to amino acid based embodiments is used synonymously with "amino acid residue" and "amino acid side chain." As used herein when referring to polynucleotides the terms "site" as it pertains to nucleotide based embodiments is used synonymously with "nucleotide." A site represents a position within a peptide or polypeptide or polynucleotide that may be modified, manipulated, altered, derivatized or varied within the polypeptide or polynucleotide based molecules.

As used herein the terms "termini" or "terminus" when referring to polypeptides or polynucleotides refers to an extremity of a polypeptide or polynucleotide respectively. Such extremity is not limited only to the first or final site of the polypeptide or polynucleotide but may include additional amino acids or nucleotides in the terminal regions. Polypeptide-based molecules may be characterized as having both an N-terminus (terminated by an amino acid with a free amino group (NH2)) and a C-terminus (terminated by an amino acid with a free carboxyl group (COOH)). Proteins are in some cases made up of multiple polypeptide chains brought together by disulfide bonds or by non-covalent forces (multimers, oligomers). These proteins have multiple N- and C-termini. Alternatively, the termini of the polypeptides may be modified such that they begin or end, as the case may be, with a non-polypeptide based moiety such as an organic conjugate.

As recognized by those skilled in the art, protein fragments, functional protein domains, and homologous proteins are also considered to be within the scope of polypeptides of interest. For example, provided herein is any protein fragment (meaning a polypeptide sequence at least one amino acid residue shorter than a reference polypeptide sequence but otherwise identical) of a reference protein 10, 20, 30, 40, 50, 60, 70, 80, 90, 100 or greater than 100 amino acids in length. In another example, any protein that includes a stretch of 20, 30, 40, 50, or 100 amino acids which are 40%, 50%, 60%, 70%, 80%, 90%, 95%, or 100% identical to any of the sequences described herein can be utilized in accordance with the disclosure. In some embodiments, a polypeptide includes 2, 3, 4, 5, 6, 7, 8, 9, 10, or more mutations as shown in any of the sequences provided or referenced herein. In another example, any protein that includes a stretch of 20, 30, 40, 50, or 100 amino acids that are greater than 80%, 90%, 95%, or 100% identical to any of the sequences described herein, wherein the protein has a stretch of 5, 10, 15, 20, 25, or 30 amino acids that are less than 80%, 75%, 70%, 65% or 60% identical to any of the sequences described herein can be utilized in accordance with the disclosure.

Polypeptide or polynucleotide molecules of the present disclosure may share a certain degree of sequence similarity or identity with the reference molecules (e.g., reference polypeptides or reference polynucleotides), for example, with art-described molecules (e.g., engineered or designed molecules or wild-type molecules). The term "identity" as known in the art, refers to a relationship between the sequences of two or more polypeptides or polynucleotides, as determined by comparing the sequences. In the art, identity also means the degree of sequence relatedness between them as determined by the number of matches between strings of two or more amino acid residues or nucleic acid residues. Identity measures the percent of identical matches between the smaller of two or more sequences with gap alignments (if any) addressed by a particular mathematical model or computer program (e.g., "algorithms"). Identity of related peptides can be readily calculated by known methods. "% identity" as it applies to polypeptide or polynucleotide sequences is defined as the percentage of residues (amino acid residues or nucleic acid residues) in the candidate amino acid or nucleic acid sequence that are identical with the residues in the amino acid sequence or nucleic acid sequence of a second sequence after aligning the sequences and introducing gaps, if necessary, to achieve the maximum percent identity. Methods and computer programs for the alignment are well known in the art. It is understood that identity depends on a calculation of percent identity but may differ in value due to gaps and penalties introduced in the calculation. Generally, variants of a particular polynucleotide or polypeptide have at least 40%, 45%, 50%, 55%, 60%, 65%, 70%, 75%, 80%, 85%, 90%, 91%, 92%, 93%, 94%, 95%, 96%, 97%, 98%, 99% but less than 100% sequence identity to that particular reference polynucleotide or polypeptide as determined by sequence alignment programs and parameters described herein and known to those skilled in the art. Such tools for alignment include those of the BLAST suite (Stephen F. Altschul, et al (1997), "Gapped BLAST and PSI-BLAST: a new generation of protein database search programs", Nucleic Acids Res. 25:3389-3402). Another popular local alignment technique is based on the Smith-Waterman algorithm (Smith, T. F. & Waterman, M. S. (1981) "Identification of common molecular subsequences." J. Mol. Biol. 147:195-197). A general global alignment technique based on dynamic programming is the Needleman-Wunsch algorithm (Needleman, S. B. & Wunsch, C. D. (1970) "A general method applicable to the search for similarities in the amino acid sequences of two proteins." J. Mol. Biol. 48:443-453). More recently a Fast Optimal Global Sequence Alignment Algorithm (FOGSAA) has been developed that purportedly produces global alignment of nucleotide and protein sequences faster than other optimal global alignment methods, including the Needleman-Wunsch algorithm. Other tools are described herein, specifically in the definition of "identity" below.

As used herein, the term "homology" refers to the overall relatedness between polymeric molecules, e.g. between nucleic acid molecules (e.g. DNA molecules and/or RNA molecules) and/or between polypeptide molecules. Polymeric molecules (e.g. nucleic acid molecules (e.g. DNA molecules and/or RNA molecules) and/or polypeptide molecules) that share a threshold level of similarity or identity determined by alignment of matching residues are termed homologous. Homology is a qualitative term that describes a relationship between molecules and can be based upon the quantitative similarity or identity. Similarity or identity is a quantitative term that defines the degree of sequence match between two compared sequences. In some embodiments, polymeric molecules are considered to be "homologous" to one another if their sequences are at least 25%, 30%, 35%, 40%, 45%, 50%, 55%, 60%, 65%, 70%, 75%, 80%, 85%, 90%, 95%, or 99% identical or similar. The term "homologous" necessarily refers to a comparison between at least two sequences (polynucleotide or polypeptide sequences). Two polynucleotide sequences are considered homologous if the polypeptides they encode are at least 50%, 60%, 70%, 80%, 90%, 95%, or even 99% for at least one stretch of at least 20 amino acids. In some embodiments, homologous polynucleotide sequences are characterized by the ability to encode a stretch of at least 4-5 uniquely specified amino acids. For polynucleotide sequences less than 60 nucleotides in length, homology is determined by the ability to encode a stretch of at least 4-5 uniquely specified amino acids. Two protein sequences are considered homologous if the proteins are at least 50%, 60%, 70%, 80%, or 90% identical for at least one stretch of at least 20 amino acids.

Homology implies that the compared sequences diverged in evolution from a common origin. The term "homolog" refers to a first amino acid sequence or nucleic acid sequence (e.g., gene (DNA or RNA) or protein sequence) that is related to a second amino acid sequence or nucleic acid sequence by descent from a common ancestral sequence. The term "homolog" may apply to the relationship between genes and/or proteins separated by the event of speciation or to the relationship between genes and/or proteins separated by the event of genetic duplication. "Orthologs" are genes (or proteins) in different species that evolved from a common ancestral gene (or protein) by speciation. Typically, orthologs retain the same function in the course of evolution. "Paralogs" are genes (or proteins) related by duplication within a genome. Orthologs retain the same function in the course of evolution, whereas paralogs evolve new functions, even if these are related to the original one.

The term "identity" refers to the overall relatedness between polymeric molecules, for example, between polynucleotide molecules (e.g. DNA molecules and/or RNA molecules) and/or between polypeptide molecules. Calculation of the percent identity of two polynucleic acid sequences, for example, can be performed by aligning the two sequences for optimal comparison purposes (e.g., gaps can be introduced in one or both of a first and a second nucleic acid sequences for optimal alignment and non-identical sequences can be disregarded for comparison purposes). In certain embodiments, the length of a sequence aligned for comparison purposes is at least 30%, at least 40%, at least 50%, at least 60%, at least 70%, at least 80%, at least 90%, at least 95%, or 100% of the length of the reference sequence. The nucleotides at corresponding nucleotide positions are then compared. When a position in the first sequence is occupied by the same nucleotide as the corresponding position in the second sequence, then the molecules are identical at that position. The percent identity between the two sequences is a function of the number of identical positions shared by the sequences, taking into account the number of gaps, and the length of each gap, which needs to be introduced for optimal alignment of the two sequences. The comparison of sequences and determination of percent identity between two sequences can be accomplished using a mathematical algorithm. For example, the percent identity between two nucleic acid sequences can be determined using methods such as those described in Computational Molecular Biology, Lesk, A. M., ed., Oxford University Press, New York, 1988; Biocomputing: Informatics and Genome Projects, Smith, D. W., ed., Academic Press, New York, 1993; Sequence Analysis in Molecular Biology, von Heinje, G., Academic Press, 1987; Computer Analysis of Sequence Data, Part I, Griffin, A. M., and Griffin, H. G., eds., Humana Press, New Jersey, 1994; and Sequence Analysis Primer, Gribskov, M. and Devereux, J., eds., M Stockton Press, New York, 1991; each of which is incorporated herein by reference. For example, the percent identity between two nucleic acid sequences can be determined using the algorithm of Meyers and Miller (CABIOS, 1989, 4:11-17), which has been incorporated into the ALIGN program (version 2.0) using a PAM120 weight residue table, a gap length penalty of 12 and a gap penalty of 4. The percent identity between two nucleic acid sequences can, alternatively, be determined using the GAP program in the GCG software package using an NWSgapdna.CMP matrix. Methods commonly employed to determine percent identity between sequences include, but are not limited to those disclosed in Carillo, H., and Lipman, D., SIAM J Applied Math., 48:1073 (1988); incorporated herein by reference. Techniques for determining identity are codified in publicly available computer programs. Exemplary computer software to determine homology between two sequences include, but are not limited to, GCG program package, Devereux, J., et al., *Nucleic Acids Research,* 12 (1), 387 (1984)), BLASTP, BLASTN, and FASTA Altschul, S. F. et al., *J. Molec. Biol.,* 215, 403 (1990)).

Chemical Modifications RNA (e.g., mRNA) vaccines of the present disclosure comprise, in some embodiments, at least one ribonucleic acid (RNA) polynucleotide having an open reading frame encoding at least one respiratory syncytial virus (RSV) antigenic polypeptide, wherein said RNA comprises at least one chemical modification.

The terms "chemical modification" and "chemically modified" refer to modification with respect to adenosine (A), guanosine (G), uridine (U), thymidine (T) or cytidine (C) ribonucleosides or deoxyribnucleosides in at least one of their position, pattern, percent or population. Generally, these terms do not refer to the ribonucleotide modifications in naturally occurring 5'-terminal mRNA cap moieties.

Modifications of polynucleotides include, without limitation, those described herein, and include, but are expressly not limited to, those modifications that comprise chemical modifications. Polynucleotides (e.g., RNA polynucleotides, such as mRNA polynucleotides) may comprise modifications that are naturally-occurring, non-naturally-occurring or the polynucleotide may comprise a combination of naturally-occurring and non-naturally-occurring modifications. Polynucleotides may include any useful modification, for example, of a sugar, a nucleobase, or an internucleoside linkage (e.g., to a linking phosphate, to a phosphodiester linkage or to the phosphodiester backbone).

With respect to a polypeptide, the term "modification" refers to a modification relative to the canonical set 20 amino acids. Polypeptides, as provided herein, are also considered "modified" of they contain amino acid substitutions, insertions or a combination of substitutions and insertions.

Polynucleotides (e.g., RNA polynucleotides, such as mRNA polynucleotides), in some embodiments, comprise various (more than one) different modifications. In some embodiments, a particular region of a polynucleotide contains one, two or more (optionally different) nucleoside or nucleotide modifications. In some embodiments, a modified RNA polynucleotide (e.g., a modified mRNA polynucleotide), introduced to a cell or organism, exhibits reduced degradation in the cell or organism, respectively, relative to an unmodified polynucleotide. In some embodiments, a modified RNA polynucleotide (e.g., a modified mRNA polynucleotide), introduced into a cell or organism, may exhibit reduced immunogenicity in the cell or organism, respectively (e.g., a reduced innate response).

Polynucleotides (e.g., RNA polynucleotides, such as mRNA polynucleotides), in some embodiments, comprise non-natural modified nucleotides that are introduced during synthesis or post-synthesis of the polynucleotides to achieve desired functions or properties. The modifications may be present on an internucleotide linkages, purine or pyrimidine bases, or sugars. The modification may be introduced with chemical synthesis or with a polymerase enzyme at the terminal of a chain or anywhere else in the chain. Any of the regions of a polynucleotide may be chemically modified.

The present disclosure provides for modified nucleosides and nucleotides of a polynucleotide (e.g., RNA polynucleotides, such as mRNA polynucleotides). A "nucleoside" refers to a compound containing a sugar molecule (e.g., a pentose or ribose) or a derivative thereof in combination with an organic base (e.g., a purine or pyrimidine) or a derivative thereof (also referred to herein as "nucleobase"). A nucleotide" refers to a nucleoside, including a phosphate group. Modified nucleotides may by synthesized by any useful method, such as, for example, chemically, enzymatically, or recombinantly, to includ e one or more modified or non-natural nucleosides. Polynucleotides may comprise a region or regions of linked nucleosides. Such regions may have variable backbone linkages. The linkages may be standard phosphdioester linkages, in which case the polynucleotides would comprise regions of nucleotides.

Modified nucleotide base pairing encompasses not only the standard adenosine-thymine, adenosine-uracil, or guanosine-cytosine base pairs, but also base pairs formed between nucleotides and/or modified nucleotides comprising non-standard or modified bases, wherein the arrangement of hydrogen bond donors and hydrogen bond acceptors permits hydrogen bonding between a non-standard base and a standard base or between two complementary non-standard base structures, such as, for example, in those polynucleotides having at least one chemical modification. One example of such non-standard base pairing is the base pairing between the modified nucleotide inosine and adenine, cytosine or uracil. Any combination of base/sugar or linker may be incorporated into polynucleotides of the present disclosure.

Modifications of polynucleotides (e.g., RNA polynucleotides, such as mRNA polynucleotides), including but not limited to chemical modification, that are useful in the compositions, vaccines, methods and synthetic processes of the present disclosure include, but are not limited to the following: 2-methylthio-N6-(cis-hydroxyisopentenyl) adenosine; 2-methylthio-N6-methyladenosine; 2-methylthio-N6-threonyl carbamoyladenosine; N6-glycinylcarbamoyladenosine; N6-isopentenyladenosine; N6-methyladenosine; N6-threonylcarbamoyladenosine; 1,2'-O-dimethyladenosine; 1-methyladenosine; 2'-O-methyladenosine; 2'-O-ribosyladenosine (phosphate); 2-methyladenosine; 2-methylthio-N6 isopentenyladenosine; 2-methylthio-N6-hydroxynorvalyl carbamoyladenosine; 2'-O-methyladenosine; 2'-O-ribosyladenosine (phosphate); Isopentenyladenosine; N6-(cis-hydroxyisopentenyl) adenosine; N6,2'-O-dimethyladenosine; N6,2'-O-dimethyladenosine; N6,N6,2'-O-trimethyladenosine; N6,N6-dimethyladenosine; N6-acetyladenosine; N6-hydroxynorvalylcarbamoyladenosine; N6-methyl-N6-threonylcarbamoyladenosine; 2-methyladenosine; 2-methylthio-N6-isopentenyladenosine; 7-deaza-adenosine; N1-methyl-adenosine; N6,N6 (dimethyl) adenine; N6-cis-hydroxy-isopentenyl-adenosine; α-thio-adenosine; 2 (amino) adenine; 2 (aminopropyl) adenine; 2 (methylthio) N6 (isopentenyl) adenine; 2-(alkyl) adenine; 2-(aminoalkyl) adenine; 2-(aminopropyl) adenine; 2-(halo) adenine; 2-(halo) adenine; 2-(propyl) adenine; 2'-Amino-2'-deoxy-ATP; 2'-Azido-2'-deoxy-ATP; 2'-Deoxy-2'-a-aminoadenosine TP; 2'-Deoxy-2'-a-azidoadenosine TP; 6 (alkyl) adenine; 6 (methyl) adenine; 6-(alkyl) adenine; 6-(methyl) adenine; 7 (deaza) adenine; 8 (alkenyl) adenine; 8 (alkynyl) adenine; 8 (amino) adenine; 8 (thioalkyl) adenine; 8-(alkenyl) adenine; 8-(alkyl) adenine; 8-(alkynyl) adenine; 8-(amino) adenine; 8-(halo) adenine; 8-(hydroxyl) adenine; 8-(thioalkyl) adenine; 8-(thiol) adenine; 8-azido-adenosine; aza adenine; deaza adenine; N6 (methyl) adenine; N6-(isopentyl) adenine; 7-deaza-8-aza-adenosine; 7-methyladenine; 1-Deazaadenosine TP; 2'Fluoro-N6-Bz-deoxyadenosine TP; 2'-OMe-2-Amino-ATP; 2'O-methyl-N6-Bz-deoxyadenosine TP; 2'-a-Ethynyladenosine TP; 2-aminoadenine; 2-Aminoadenosine TP; 2-Amino-ATP; 2'-a-Trifluoromethyladenosine TP; 2-Azidoadenosine TP; 2'-b-Ethynyladenosine TP; 2-Bromoadenosine TP; 2'-b-Trifluoromethyladenosine TP; 2-Chloroadenosine TP; 2'-Deoxy-2', 2'-difluoroadenosine TP; 2'-Deoxy-2'-a-mercaptoadenosine TP; 2'-Deoxy-2'-a-thiomethoxyadenosine TP; 2'-Deoxy-2'-b-aminoadenosine TP; 2'-Deoxy-2'-b-azidoadenosine TP; 2'-Deoxy-2'-b-bromoadenosine TP; 2'-Deoxy-2'-b-chloroadenosine TP; 2'-Deoxy-2'-b-fluoroadenosine TP; 2'-Deoxy-2'-b-iodoadenosine TP; 2'-Deoxy-2'-b-mercaptoadenosine TP; 2'-Deoxy-2'-b-thiomethoxyadenosine TP; 2-Fluoroadenosine TP; 2-Iodoadenosine TP; 2-Mercaptoadenosine TP; 2-methoxy-adenine; 2-methylthio-adenine; 2-Trifluoromethyladenosine TP; 3-Deaza-3-bromoadenosine TP; 3-Deaza-3-chloroadenosine TP; 3-Deaza-3-fluoroadenosine TP; 3-Deaza-3-iodoadenosine TP; 3-Deazaadenosine TP; 4'-Azidoadenosine TP; 4'-Carbocyclic adenosine TP; 4'-Ethynyladenosine TP; 5'-Homo-adenosine TP; 8-Aza-ATP; 8-bromo-adenosine TP; 8-Trifluoromethyladenosine TP; 9-Deazaadenosine TP; 2-aminopurine; 7-deaza-2,6-diaminopurine; 7-deaza-8-aza-2,6-diaminopurine; 7-deaza-8-aza-2-aminopurine; 2,6-diaminopurine; 7-deaza-8-aza-adenine, 7-deaza-2-aminopurine; 2-thiocytidine; 3-methylcytidine; 5-formylcytidine; 5-hydroxymethylcytidine; 5-methylcytidine; N4-acetylcytidine; 2'-O-methylcytidine; 2'-O-methylcytidine; 5,2'-O-dimethylcytidine; 5-formyl-2'-O-methylcytidine; Lysidine; N4,2'-O-dimethylcytidine; N4-acetyl-2'-O-methylcytidine; N4-methylcytidine; N4,N4-Dimethyl-2'-OMe-Cytidine TP; 4-methylcytidine; 5-aza-cytidine; Pseudo-iso-cytidine; pyrrolo-cytidine; α-thio-cytidine; 2-(thio) cytosine; 2'-Amino-2'-deoxy-CTP; 2'-Azido-2'-deoxy-CTP; 2'-Deoxy-2'-a-aminocytidine TP; 2'-Deoxy-2'-a-azidocytidine TP; 3 (deaza) 5 (aza) cytosine; 3 (methyl) cytosine; 3-(alkyl) cytosine; 3-(deaza) 5 (aza) cytosine; 3-(methyl) cytidine; 4,2'-O-dimethylcytidine; 5 (halo) cytosine; 5 (methyl) cytosine; 5 (propynyl) cytosine; 5 (trifluoromethyl) cytosine; 5-(alkyl) cytosine; 5-(alkynyl) cytosine; 5-(halo) cytosine; 5-(propynyl) cytosine; 5-(trifluoromethyl) cytosine; 5-bromo-cytidine; 5-iodo-cytidine; 5-propynyl cytosine; 6-(azo) cytosine; 6-aza-cytidine; aza cytosine; deaza cytosine; N4 (acetyl) cytosine; 1-methyl-1-deaza-pseudoisocytidine; 1-methyl-pseudoisocytidine; 2-methoxy-5-methyl-cytidine; 2-methoxy-cytidine; 2-thio-5-methyl-cytidine; 4-methoxy-1-methyl-pseudoisocytidine; 4-methoxy-pseudoisocytidine; 4-thio-1-methyl-1-deaza-pseudoisocytidine; 4-thio-1-methyl-pseudoisocytidine; 4-thio-pseudoisocytidine; 5-aza-zebularine; 5-methyl-zebularine; pyrrolo-pseudoisocytidine; Zebularine; (E)-5-(2-Bromo-vinyl) cytidine TP; 2,2'-anhydro-cytidine TP hydrochloride; 2'Fluor-N4-Bz-cytidine TP; 2'Fluoro-N4-Acetyl-cytidine TP; 2'-O-Methyl-N4-Acetyl-cytidine TP; 2'O-methyl-N4-Bz-cytidine TP; 2'-a-Ethynylcytidine TP; 2'-a-Trifluoromethylcytidine TP; 2'-b-Ethynylcytidine TP; 2'-b-Trifluoromethylcytidine TP; 2'-Deoxy-2', 2'-difluorocytidine TP; 2'-Deoxy-2'-a-mercaptocytidine TP; 2'-Deoxy-2'-a-thiomethoxycytidine TP; 2'-Deoxy-2'-b-aminocytidine TP; 2'-Deoxy-2'-b-azidocytidine TP; 2'-Deoxy-2'-b-bromocytidine TP; 2'-Deoxy-2'-b-chlorocytidine TP; 2'-Deoxy-2'-b-fluorocytidine TP; 2'-Deoxy-2'-b-iodocytidine TP; 2'-Deoxy-2'-b-mercaptocytidine TP; 2'-Deoxy-2'-b-thiomethoxycytidine TP; 2'-O-Methyl-5-(1-propynyl) cytidine TP; 3'-Ethynylcytidine TP; 4'-Azidocytidine TP; 4'-Carbocyclic cytidine TP; 4'-Ethynylcytidine TP; 5-(1-Propynyl) ara-cytidine TP; 5-(2-Chloro-phenyl)-2-thiocytidine TP; 5-(4-Amino-phenyl)-2-thiocytidine TP; 5-Aminoallyl-CTP; 5-Cyanocytidine TP; 5-Ethynylara-cytidine TP; 5-Ethynylcytidine TP; 5'-Homo-cytidine TP; 5-Methoxycytidine TP; 5-Trifluoromethyl-Cytidine TP; N4-Amino-cytidine TP; N4-Benzoyl-cytidine TP; Pseudoisocytidine; 7-methylguanosine; N2,2'-O-dimethylguanosine; N2-methylguanosine; Wyosine; 1,2'-O-dimethylguanosine; 1-methylguanosine; 2'-O-methylguanosine; 2'-O-ribosylguanosine (phosphate); 2'-O-methylguanosine; 2'-O-ribosylguanosine (phosphate); 7-aminomethyl-7-deazaguanosine; 7-cyano-7-deazaguanosine;

Archacosine; Methylwyosine; N2,7-dimethylguanosine; N2,N2,2'-O-trimethylguanosine; N2,N2,7-trimethylguanosine; N2,N2-dimethylguanosine; N2,7,2'-O-trimethylguanosine; 6-thio-guanosine; 7-deaza-guanosine; 8-oxo-guanosine; N1-methyl-guanosine; a-thio-guanosine; 2 (propyl) guanine; 2-(alkyl) guanine; 2'-Amino-2'-deoxy-GTP; 2'-Azido-2'-deoxy-GTP; 2'-Deoxy-2'-a-aminoguanosine TP; 2'-Deoxy-2'-a-azidoguanosine TP; 6 (methyl) guanine; 6-(alkyl) guanine; 6-(methyl) guanine; 6-methyl-guanosine; 7 (alkyl) guanine; 7 (deaza) guanine; 7 (methyl) guanine; 7-(alkyl) guanine; 7-(deaza) guanine; 7-(methyl) guanine; 8 (alkyl) guanine; 8 (alkynyl) guanine; 8 (halo) guanine; 8 (thioalkyl) guanine; 8-(alkenyl) guanine; 8-(alkyl) guanine; 8-(alkynyl) guanine; 8-(amino) guanine; 8-(halo) guanine; 8-(hydroxyl) guanine; 8-(thioalkyl) guanine; 8-(thiol) guanine; aza guanine;

deaza guanine; N (methyl) guanine; N-(methyl) guanine; 1-methyl-6-thio-guanosine; 6-methoxy-guanosine; 6-thio-7-deaza-8-aza-guanosine; 6-thio-7-deaza-guanosine; 6-thio-7-methyl-guanosine; 7-deaza-8-aza-guanosine; 7-methyl-8-oxo-guanosine; N2,N2-dimethyl-6-thio-guanosine; N2-methyl-6-thio-guanosine; 1-Me-GTP; 2'Fluoro-N2-isobutyl-guanosine TP; 2'O-methyl-N2-isobutyl-guanosine TP; 2'-a-Ethynylguanosine TP; 2'-a-Trifluoromethylguanosine TP; 2'-b-Ethynylguanosine TP; 2'-b-Trifluoromethylguanosine TP; 2'-Deoxy-2', 2'-difluoroguanosine TP; 2'-Deoxy-2'-a-mercaptoguanosine TP; 2'-Deoxy-2'-a-thiomethoxyguanosine TP; 2'-Deoxy-2'-b-aminoguanosine TP; 2'-Deoxy-2'-b-azidoguanosine TP; 2'-Deoxy-2'-b-bromoguanosine TP; 2'-Deoxy-2'-b-chloroguanosine TP; 2'-Deoxy-2'-b-fluoroguanosine TP; 2'-Deoxy-2'-b-iodoguanosine TP; 2'-Deoxy-2'-b-mercaptoguanosine TP;

2'-Deoxy-2'-b-thiomethoxyguanosine TP; 4'-Azidoguanosine TP; 4'-Carbocyclic guanosine TP;

4'-Ethynylguanosine TP; 5'-Homo-guanosine TP; 8-bromo-guanosine TP; 9-Deazaguanosine TP; N2-isobutyl-guanosine TP; 1-methylinosine; Inosine; 1,2'-O-dimethylinosine; 2'-O-methylinosine; 7-methylinosine; 2'-O-methylinosine; Epoxyqueuosine; galactosyl-queuosine; Mannosylqueuosine; Queuosine; allyamino-thymidine; aza thymidine; deaza thymidine; deoxy-thymidine; 2'-O-methyluridine; 2-thiouridine; 3-methyluridine; 5-carboxymethyluridine; 5-hydroxyuridine; 5-methyluridine; 5-taurinomethyl-2-thiouridine; 5-taurinomethyluridine; Dihydrouridine; Pseudouridine; (3-(3-amino-3-carboxypropyl) uridinc; 1-methyl-3-(3-amino-5-carboxypropyl) pseudouridinc; 1-methylpscduouridine; 1-ethyl-pseudouridine; 2'-O-methyluridine; 2'-O-methylpseudouridinc; 2'-O-methyluridine; 2-thio-2'-O-methyluridine; 3-(3-amino-3-carboxypropyl) uridine; 3,2'-O-dimethyluridine; 3-Methyl-pscudo-Uridine TP; 4-thiouridine; 5-(carboxyhydroxymethyl) uridine; 5-(carboxyhydroxymethyl) uridine methyl ester; 5,2'-O-dimethyluridine; 5,6-dihydro-uridine; 5-aminomethyl-2-thiouridine; 5-carbamoylmethyl-2'-O-methyluridine; 5-carbamoylmethyluridine; 5-carboxyhydroxymethyluridinc; 5-carboxyhydroxymethyluridine methyl ester; 5-carboxymethylaminomethyl-2'-O-methyluridine; 5-carboxymethylaminomethyl-2-thiouridine; 5-carboxymethylaminomethyl-2-thiouridine; 5-carboxymethylaminomethyluridine; 5-carboxymethylaminomethyluridine; 5-Carbamoylmethyluridine TP; 5-methoxycarbonylmethyl-2'-O-methyluridine; 5-methoxycarbonylmethyl-2-thiouridine; 5-methoxycarbonylmethyluridine; 5-methyluridinc), 5-methoxyuridine; 5-methyl-2-thiouridine; 5-methylaminomethyl-2-selenouridine; 5-methylaminomethyl-2-thiouridine; 5-methylaminomethyluridine; 5-Methyldihydrouridine; 5-Oxyacetic acid-Uridine TP; 5-Oxyacetic acid-methyl ester-Uridine TP; N1-methyl-pseudo-uracil; N1-ethyl-pseudo-uracil; uridine 5-oxyacetic acid; uridine 5-oxyacetic acid methyl ester; 3-(3-Amino-3-carboxypropyl)-Uridine TP; 5-(iso-Pentenylaminomethyl)-2-thiouridine TP; 5-(iso-Pentenylaminomethyl)-2'-O-methyluridine TP; 5-(iso-Pentenylaminomethyl) uridine TP; 5-propynyl uracil; a-thio-uridine; 1 (aminoalkylamino-carbonylethylenyl)-2 (thio)-pseudouracil; 1 (aminoalkylaminocarbonylethylenyl)-2,4-(dithio) pseudouracil; 1 (aminoalkylaminocarbonylethylenyl)-4 (thio) pseudouracil; 1 (aminoalkylaminocarbonylethylenyl)-pseudouracil; 1 (aminocarbonylethylenyl)-2 (thio)-pseudouracil; 1 (aminocarbonylethylenyl)-2,4-(dithio) pseudouracil; 1 (aminocarbonylethylenyl)-4 (thio) pseudouracil; 1 (aminocarbonylethylenyl)-pseudouracil; 1 substituted 2 (thio)-pseudouracil; 1 substituted 2,4-(dithio) pseudouracil; 1 substituted 4 (thio) pseudouracil; 1 substituted pseudouracil; 1-(aminoalkylamino-carbonylethylenyl)-2-(thio)-pseudouracil; 1-Methyl-3-(3-amino-3-carboxypropyl) pseudouridine TP; 1-Methyl-3-(3-amino-3-carboxypropyl) pseudo-UTP; 1-Methyl-pseudo-UTP; 1-Ethyl-pseudo-UTP; 2 (thio) pseudouracil; 2' deoxy uridine; 2' fluorouridine; 2-(thio) uracil; 2,4-(dithio) psuedouracil; 2' methyl, 2'amino, 2'azido, 2'fluro-guanosine; 2'-Amino-2'-deoxy-UTP; 2'-Azido-2'-deoxy-UTP; 2'-Azido-deoxyuridine TP; 2'-O-methylpseudouridine; 2' deoxy uridine; 2' fluorouridine; 2'-Deoxy-2'-a-aminouridine TP; 2'-Deoxy-2'-a-azidouridine TP; 2-methylpseudouridine; 3 (3 amino-3 carboxypropyl) uracil; 4 (thio) pseudouracil; 4-(thio) pseudouracil; 4-(thio) uracil; 4-thiouracil; 5 (1,3-diazole-1-alkyl) uracil; 5 (2-aminopropyl) uracil; 5 (aminoalkyl) uracil; 5 (dimethylaminoalkyl) uracil; 5 (guanidiniumalkyl) uracil; 5 (methoxycarbonylmethyl)-2-(thio) uracil; 5 (methoxycarbonyl-methyl) uracil; 5 (methyl) 2 (thio) uracil; 5 (methyl) 2,4 (dithio) uracil; 5 (methyl) 4 (thio) uracil; 5 (methylaminomethyl)-2 (thio) uracil; 5 (methylaminomethyl)-2.4 (dithio) uracil; 5 (methylaminomethyl)-4 (thio) uracil; 5 (propynyl) uracil; 5 (trifluoromethyl) uracil; 5-(2-aminopropyl) uracil; 5-(alkyl)-2-(thio) pseudouracil; 5-(alkyl)-2.4 (dithio) pseudouracil; 5-(alkyl)-4 (thio) pseudouracil; 5-(alkyl) pseudouracil; 5-(alkyl) uracil; 5-(alkynyl) uracil; 5-(allylamino) uracil; 5-(cyanoalkyl) uracil; 5-(dialkylaminoalkyl) uracil; 5-(dimethylaminoalkyl) uracil; 5-(guanidiniumalkyl) uracil; 5-(halo) uracil; 5-(1,3-diazole-1-alkyl) uracil; 5-(methoxy) uracil; 5-(methoxycarbonylmethyl)-2-(thio) uracil; 5-(methoxycarbonyl-methyl) uracil; 5-(methyl) 2 (thio) uracil; 5-(methyl) 2,4 (dithio) uracil; 5-(methyl) 4 (thio) uracil; 5-(methyl)-2-(thio) pseudouracil; 5-(methyl)-2.4 (dithio) pseudouracil; 5-(methyl)-4 (thio) pseudouracil; 5-(methyl) pseudouracil; 5-(methylaminomethyl)-2 (thio) uracil; 5-(methylaminomethyl)-2,4 (dithio) uracil; 5-(methylaminomethyl)-4-(thio) uracil; 5-(propynyl) uracil; 5-(trifluoromethyl) uracil; 5-aminoallyl-uridine; 5-bromo-uridine; 5-iodo-uridine; 5-uracil; 6 (azo) uracil; 6-(azo) uracil; 6-aza-uridine; allyamino-uracil;

aza uracil; deaza uracil; N3 (methyl) uracil; P scudo-UTP-1-2-cthanoic acid; Pseudouracil; 4-Thio-pseudo-UTP; 1-carboxymethyl-pseudouridine; 1-methyl-1-deaza-pseudouridine; 1-propynyl-uridine; 1-taurinomethyl-1-methyl-uridine; 1-taurinomethyl-4-thio-uridine; 1-taurinomethyl-pseudouridine; 2-methoxy-4-thio-pseudouridine; 2-thio-1-methyl-1-deaza-pseudouridine; 2-thio-1-methyl-pseudouridine; 2-thio-5-aza-uridine; 2-thio-dihydropseudouridine; 2-thio-dihydrouridine; 2-thio-pseudouridine; 4-methoxy-2-thio-pseudouridine; 4-methoxy-pseudouridine; 4-thio-1-methyl-pseudouridine; 4-thio-pseudouridine; 5-aza-uridine; Dihydropseudouridine; (+) 1-(2-Hydroxypropyl) pseudouridine TP; (2R)-1-(2-Hydroxypropyl) pseudouridine TP; (2S)-1-(2-Hydroxypropyl) pseudouridine TP; (E)-5-(2-Bromo-vinyl) ara-uridine TP; (E)-5-(2-Bromo-vinyl) uridine TP; (Z)-5-(2-Bromo-vinyl) ara-uridine TP; (Z)-5-(2-Bromo-vinyl) uridinc TP; 1-(2,2,2-Trifluoroethyl)-pseudo-UTP; 1-(2,2,3,3,3-Pentafluoropropyl) pseudouridine TP; 1-(2,2-Dicthoxyethyl) pseudouridine TP; 1-(2,4,6-Trimethylbenzyl) pseudouridine TP; 1-(2,4,6-Trimethyl-benzyl) pseudo-UTP; 1-(2,4,6-Trimethyl-phenyl) pseudo-UTP; 1-(2-Amino-2-carboxyethyl) pseudo-UTP; 1-(2-Amino-ethyl) pseudo-UTP; 1-(2-Hydroxyethyl) pseudouridine TP; 1-(2-Methoxyethyl) pseudouridine TP; 1-(3,4-Bis-trifluoromethoxybenzyl) pseudouridine TP; 1-(3,4-Dimethoxybenzyl) pseudouridine TP; 1-(3-Amino-3-carboxypropyl) pseudo-UTP; 1-(3-Amino-propyl) pseudo-UTP; 1-(3-Cyclopropyl-prop-2-ynyl) pseudouridine TP; 1-(4-Amino-4-carboxybutyl) pseudo-UTP; 1-(4-Amino-benzyl) pseudo-UTP; 1-(4-Amino-butyl) pseudo-UTP; 1-(4-Amino-phenyl) pseudo-UTP; 1-(4-Azidobenzyl) pseudouridine TP; 1-(4-Bromobenzyl) pseudouridine TP; 1-(4-Chlorobenzyl) pseudouridine TP; 1-(4-Fluorobenzyl) pseudouridine TP; 1-(4-Iodobenzyl)

pseudouridine TP; 1-(4-Methanesulfonylbenzyl) pseudouridine TP; 1-(4-Methoxybenzyl) pseudouridine TP; 1-(4-Methoxy-benzyl) pseudo-UTP; 1-(4-Methoxy-phenyl) pseudo-UTP; 1-(4-Methylbenzyl) pseudouridine TP; 1-(4-Methyl-benzyl) pseudo-UTP; 1-(4-Nitrobenzyl) pseudouridine TP; 1-(4-Nitro-benzyl) pseudo-UTP; 1 (4-Nitro-phenyl) pseudo-UTP; 1-(4-Thiomethoxybenzyl) pseudouridine TP; 1-(4-Trifluoromethoxybenzyl) pseudouridine TP; 1-(4-Trifluoromethylbenzyl) pseudouridine TP; 1-(5-Amino-pentyl) pseudo-UTP; 1-(6-Amino-hexyl) pseudo-UTP; 1,6-Dimethyl-pseudo-UTP; 1-[3-(2-{2-[2-(2-Aminocthoxy)-ethoxy]-ethoxy}-ethoxy)-propionyl] pseudouridine TP; 1-{3-[2-(2-Aminoethoxy)-ethoxy]-propionyl} pseudouridine TP; 1-Acetylpseudouridine TP; 1-Alkyl-6-(1-propynyl)-pseudo-UTP; 1-Alkyl-6-(2-propynyl)-pseudo-UTP; 1-Alkyl-6-allyl-pseudo-UTP; 1-Alkyl-6-ethynyl-pseudo-UTP; 1-Alkyl-6-homoallyl-pseudo-UTP; 1-Alkyl-6-vinyl-pseudo-UTP; 1-Allylpseudouridine TP; 1-Aminomethyl-pseudo-UTP; 1-Benzoylpseudouridine TP; 1-Benzyloxymethylpseudouridine TP; 1-Benzyl-pseudo-UTP; 1-Biotinyl-PEG2-pseudouridine TP; 1-Biotinylpseudouridine TP; 1-Butyl-pseudo-UTP; 1-Cyanomethylpscudouridinc TP; 1-Cyclobutylmethyl-pseudo-UTP; 1-Cyclobutyl-pseudo-UTP; 1-Cycloheptylmethyl-pseudo-UTP; 1-Cycloheptyl-pseudo-UTP; 1-Cyclohexylmethyl-pseudo-UTP; 1-Cyclohexyl-pseudo-UTP; 1-Cyclooctylmethyl-pseudo-UTP; 1-Cyclooctyl-pseudo-UTP; 1-Cyclopentylmethyl-pseudo-UTP; 1-Cyclopentyl-pseudo-UTP; 1-Cyclopropylmethyl-pseudo-UTP; 1-Cyclopropyl-pseudo-UTP; 1-Ethyl-pseudo-UTP; 1-Hexyl-pseudo-UTP; 1-Homoallylpseudouridine TP; 1-Hydroxymethylpseudouridine TP; 1-iso-propyl-pseudo-UTP; 1-Me-2-thio-pseudo-UTP; 1-Me-4-thio-pseudo-UTP; 1-Mc-alpha-thio-pseudo-UTP; 1-Methanesulfonylmethylpseudouridine TP; 1-Methoxymethylpseudouridine TP; 1-Methyl-6-(2,2,2-Trifluoroethyl) pseudo-UTP; 1-Methyl-6-(4-morpholino)-pseudo-UTP; 1-Methyl-6-(4-thiomorpholino)-pseudo-UTP; 1-Methyl-6-(substituted phenyl) pseudo-UTP; 1-Methyl-6-amino-pseudo-UTP; 1-Methyl-6-azido-pseudo-UTP; 1-Methyl-6-bromo-pseudo-UTP; 1-Methyl-6-butyl-pseudo-UTP; 1-Methyl-6-chloro-pseudo-UTP; 1-Methyl-6-cyano-pseudo-UTP; 1-Methyl-6-dimethylamino-pseudo-UTP; 1-Methyl-6-ethoxy-pseudo-UTP; 1-Methyl-6-ethylcarboxylate-pseudo-UTP; 1-Methyl-6-ethyl-pseudo-UTP; 1-Methyl-6-fluoro-pseudo-UTP; 1-Methyl-6-formyl-pscudo-UTP; 1-Methyl-6-hydroxyamino-pseudo-UTP; 1-Methyl-6-hydroxy-pseudo-UTP; 1-Methyl-6-iodo-pscudo-UTP; 1-Methyl-6-iso-propyl-pseudo-UTP; 1-Methyl-6-methoxy-pseudo-UTP; 1-Methyl-6-methylamino-pseudo-UTP; 1-Methyl-6-phenyl-pseudo-UTP; 1-Methyl-6-propyl-pseudo-UTP; 1-Methyl-6-tert-butyl-pseudo-UTP; 1-Methyl-6-trifluoromethoxy-pseudo-UTP; 1-Methyl-6-trifluoromethyl-pseudo-UTP; 1-Morpholinomethylpseudouridine TP; 1-Pentyl-pseudo-UTP; 1-Phenyl-pseudo-UTP; 1-Pivaloylpseudouridine TP; 1-Propargylpseudouridinc TP; 1-Propyl-pseudo-UTP; 1-propynyl-pseudouridine; 1-p-tolyl-pseudo-UTP; 1-tert-Butyl-pseudo-UTP; 1-Thiomethoxymethylpseudouridine TP; 1-Thiomorpholinomethylpseudouridine TP; 1-Trifluoroacetylpseudouridine TP; 1-Trifluoromethyl-pseudo-UTP; 1-Vinylpseudouridine TP; 2,2'-anhydro-uridine TP; 2'-bromo-deoxyuridine TP; 2'-F-5-Methyl-2'-deoxy-UTP; 2'-OMe-5-Me-UTP; 2'-OMe-pseudo-UTP; 2'-a-Ethynyluridine TP; 2'-a-Trifluoromethyluridine TP; 2'-b-Ethynyluridine TP; 2'-b-Trifluoromethyluridine TP; 2'-Deoxy-2', 2'-difluorouridine TP; 2'-Deoxy-2'-a-mercaptouridine TP; 2'-Deoxy-2'-a-thiomethoxyuridine TP; 2'-Deoxy-2'-b-aminouridine TP; 2'-Deoxy-2'-b-azidouridine TP; 2'-Deoxy-2'-b-bromouridine TP; 2'-Deoxy-2'-b-chlorouridine TP; 2'-Deoxy-2'-b-fluorouridine TP; 2'-Deoxy-2'-b-iodouridine TP; 2'-Deoxy-2'-b-mercaptouridine TP; 2'-Deoxy-2'-b-thiomethoxyuridine TP; 2-methoxy-4-thio-uridine; 2-methoxyuridine; 2'-O-Methyl-5-(1-propynyl) uridine TP; 3-Alkyl-pseudo-UTP; 4'-Azidouridine TP; 4'-Carbocyclic uridine TP; 4'-Ethynyluridine TP; 5-(1-Propynyl) ara-uridine TP; 5-(2-Furanyl) uridine TP; 5-Cyanouridine TP; 5-Dimethylaminouridine TP; 5'-Homo-uridine TP; 5-iodo-2'-fluoro-deoxyuridine TP; 5-Phenylethynyluridine TP; 5-Trideuteromethyl-6-deuterouridine TP; 5-Trifluoromethyl-Uridine TP; 5-Vinylarauridine TP; 6-(2,2,2-Trifluoroethyl)-pseudo-UTP; 6-(4-Morpholino)-pseudo-UTP; 6-(4-Thiomorpholino)-pseudo-UTP; 6-(Substituted-Phenyl)-pseudo-UTP; 6-Amino-pseudo-UTP; 6-Azido-pseudo-UTP; 6-Bromo-pseudo-UTP; 6-Butyl-pseudo-UTP; 6-Chloro-pseudo-UTP; 6-Cyano-pseudo-UTP; 6-Dimethylamino-pseudo-UTP; 6-Ethoxy-pseudo-UTP; 6-Ethylcarboxylate-pseudo-UTP; 6-Ethyl-pseudo-UTP; 6-Fluoro-pseudo-UTP; 6-Formyl-pseudo-UTP; 6-Hydroxyamino-pseudo-UTP; 6-Hydroxy-pseudo-UTP; 6-lodo-pseudo-UTP; 6-iso-Propyl-pseudo-UTP; 6-Methoxy-pseudo-UTP; 6-Methylamino-pseudo-UTP; 6-Methyl-pseudo-UTP; 6-Phenyl-pseudo-UTP; 6-Phenyl-pseudo-UTP; 6-Propyl-pseudo-UTP; 6-tert-Butyl-pseudo-UTP; 6-Trifluoromethoxy-pseudo-UTP; 6-Trifluoromethyl-pseudo-UTP; Alpha-thio-pseudo-UTP; Pseudouridine 1-(4-methylbenzenesulfonic acid) TP; Pseudouridine 1-(4-methylbenzoic acid) TP; Pseudouridine TP 1-[3-(2-ethoxy)]propionic acid; Pseudouridine TP 1-[3-{2-(2-[2-(2-ethoxy)-ethoxy]-ethoxy)-ethoxy}]propionic acid; Pseudouridine TP 1-[3-{2-(2-[2-{2 (2-ethoxy)-ethoxy}-ethoxy]-ethoxy)-ethoxy}]propionic acid; Pseudouridine TP 1-[3-{2-(2-[2-ethoxy]-ethoxy)-ethoxy}]propionic acid; Pseudouridine TP 1-[3-{2-(2-ethoxy)-ethoxy}]propionic acid;

Pseudouridine TP 1-methylphosphonic acid; Pseudouridine TP 1-methylphosphonic acid diethyl ester; Pseudo-UTP-N1-3-propionic acid; Pseudo-UTP-N1-4-butanoic acid; Pseudo-UTP-N1-5-pentanoic acid; Pseudo-UTP-N1-6-hexanoic acid; Pseudo-UTP-N1-7-heptanoic acid; Pseudo-UTP-N1-methyl-p-benzoic acid; Pseudo-UTP-N1-p-benzoic acid; Wybutosine; Hydroxywybutosine; Isowyosine; Peroxywybutosine; undermodified hydroxywybutosine; 4-demethylwyosine; 2,6-(diamino) purine; 1-(aza)-2-(thio)-3-(aza)-phenoxazin-1-yl: 1,3-(diaza)-2-(oxo)-phenthiazin-1-yl; 1,3-(diaza)-2-(oxo)-phenoxazin-1-yl; 1,3,5-(triaza)-2,6-(dioxa)-naphthalene; 2 (amino) purine; 2,4,5-(trimethyl)phenyl; 2' methyl, 2'amino, 2'azido, 2'fluro-cytidine; 2' methyl, 2'amino, 2'azido, 2'fluro-adenine; 2'methyl, 2'amino, 2'azido, 2'fluro-uridine; 2'-amino-2'-deoxyribose; 2-amino-6-Chloro-purine; 2-aza-inosinyl; 2'-azido-2'-deoxyribose; 2'fluoro-2'-deoxyribose; 2'-fluoro-modified bases; 2'-O-methyl-ribose; 2-oxo-7-aminopyridopyrimidin-3-yl; 2-oxo-pyridopyrimidine-3-yl; 2-pyridinone; 3 nitropyrrole;

3-(methyl)-7-(propynyl) isocarbostyrilyl; 3-(methyl) isocarbostyrilyl; 4-(fluoro)-6-(methyl)benzimidazole; 4-(methyl)benzimidazole; 4-(methyl) indolyl; 4,6-(dimethyl) indolyl; 5 nitroindole; 5 substituted pyrimidines; 5-(methyl) isocarbostyrilyl; 5-nitroindole; 6-(aza)pyrimidine; 6-(azo) thymine; 6-(methyl)-7-(aza) indolyl; 6-chloro-purine; 6-phenyl-pyrrolo-pyrimidin-2-on-3-yl; 7-(aminoalkylhydroxy)-1-(aza)-2-(thio)-3-(aza)-phenthiazin-1-yl; 7-(aminoalkylhydroxy)-1-(aza)-2-(thio)-3-(aza)-phenoxazin-1-yl; 7-(aminoalkylhydroxy)-1,3-(diaza)-2-(oxo)-phenoxazin-1-yl; 7-(aminoalkylhydroxy)-1,3-(diaza)-2-(oxo)-phenthiazin-1-yl; 7-(aminoalkylhydroxy)-1,3-(diaza)-2-(oxo)-phenoxazin-1-yl; 7-(aza) indolyl; 7-(guanidiniumalkylhydroxy)-1-(aza)-2-(thio)-3-(aza)-phenoxazinl-yl; 7-(guanidiniumalkylhydroxy)-1-(aza)-2-(thio)-3-(aza)-phenthiazin-1-yl; 7-(guanidiniumalkylhydroxy)-1-(aza)-2-(thio)-3-(aza)-phenoxazin-1-yl; 7-(guanidiniumalkylhydroxy)-1,3-(diaza)-2-(oxo)-phenoxazin-1-yl; 7-(guanidiniumalkyl-hydroxy)-1,3-(diaza)-2-(oxo)-phenthiazin-1-yl; 7-(guanidiniumalkylhydroxy)-1,3-(diaza)-2-(oxo)-phenoxazin-1-yl; 7-(propynyl) isocarbostyrilyl; 7-(propynyl) isocarbostyrilyl, propynyl-7-(aza) indolyl; 7-deaza-inosinyl; 7-substituted 1-(aza)-2-(thio)-3-(aza)-phenoxazin-1-yl; 7-substituted 1,3-(diaza)-2-(oxo)-phenoxazin-1-yl; 9-(methyl)-imidizopyridinyl; Aminoindolyl; Anthracenyl; bis-ortho-(aminoalkylhydroxy)-6-phenyl-pyrrolo-pyrimidin-2-on-3-yl; bis-ortho-substituted-6-phenyl-pyrrolo-pyrimidin-2-on-3-yl; Difluorotolyl; Hypoxanthine; Imidizopyridinyl; Inosinyl; Isocarbostyrilyl; Isoguanisine; N2-substituted purines; N6-methyl-2-amino-purine; N6-substituted purines; N-alkylated derivative; Napthalenyl; Nitrobenzimidazolyl; Nitroimidazolyl; Nitroindazolyl; Nitropyrazolyl; Nubularine; 06-substituted purines; O-alkylated derivative; ortho-(aminoalkylhydroxy)-6-phenyl-pyrrolo-pyrimidin-2-on-3-yl; ortho-substituted-6-phenyl-pyrrolo-pyrimidin-2-on-3-yl; Oxoformycin TP; para-(aminoalkylhydroxy)-6-phenyl-pyrrolo-pyrimidin-2-on-3-yl; para-substituted-6-phenyl-pyrrolo-pyrimidin-2-on-3-yl; Pentacenyl; Phenanthracenyl; Phenyl; propynyl-7-(aza) indolyl; Pyrenyl; pyridopyrimidin-3-yl; pyridopyrimidin-3-yl, 2-oxo-7-amino-pyridopyrimidin-3-yl; pyrrolo-pyrimidin-2-on-3-yl; Pyrrolopyrimidinyl; Pyrrolopyrizinyl;

Stilbenzyl; substituted 1,2,4-triazoles; Tetracenyl; Tubercidine; Xanthine; Xanthosine-5'-TP; 2-thio-zebularine; 5-aza-2-thio-zebularine; 7-deaza-2-amino-purine; pyridin-4-one ribonucleoside; 2-Amino-riboside-TP; Formycin A TP; Formycin B TP; Pyrrolosine TP; 2'-OH-ara-adenosine TP; 2'-OH-ara-cytidine TP; 2'-OH-ara-uridine TP; 2'-OH-ara-guanosine TP; 5-(2-carbomethoxyvinyl) uridine TP; and N6-(19-Amino-pentaoxanonadecyl) adenosine TP.

In some embodiments, polynucleotides (e.g., RNA polynucleotides, such as mRNA polynucleotides) include a combination of at least two (e.g., 2, 3, 4 or more) of the aforementioned modified nucleobases.

In some embodiments, modified nucleobases in polynucleotides (e.g., RNA polynucleotides, such as mRNA polynucleotides) are selected from the group consisting of pseudouridine (w), 2-thiouridine (s2U), 4'-thiouridine, 5-methylcytosine, 2-thio-1-methyl-1-deaza-pseudouridine, 2-thio-1-methyl-pseudouridine, 2-thio-5-aza-uridine, 2-thio-dihydropseudouridine, 2-thio-dihydrouridine, 2-thio-pseudouridine, 4-methoxy-2-thio-pseudouridine, 4-methoxy-pseudouridine, 4-thio-1-methyl-pseudouridine, 4-thio-pseudouridine, 5-aza-uridine, dihydropseudouridine, 5-methyluridine, 5-methoxyuridine, 2'-O-methyl uridine, 1-methyl-pseudouridine (mlψ), 1-ethyl-pseudouridine (e1ψ), 5-methoxy-uridine (mo5U), 5-methyl-cytidine (m5C), a-thio-guanosine, a-thio-adenosine, 5-cyano uridine, 4'-thio uridine 7-deaza-adenine, 1-methyl-adenosine (m1A), 2-methyl-adenine (m2A), N6-methyl-adenosine (m6A), and 2,6-Diaminopurine, (I), 1-methyl-inosine (m1I), wyosine (imG), methylwyosine (mimG), 7-deaza-guanosine, 7-cyano-7-deaza-guanosine (prcQ0), 7-aminomethyl-7-deaza-guanosine (preQ1), 7-methyl-guanosine (m7G), 1-methyl-guanosine (m1G), 8-oxo-guanosine, 7-methyl-8-oxo-guanosine, 2,8-dimethyladenosine, 2-geranylthiouridine, 2-lysidine, 2-selenouridine, 3-(3-amino-3-carboxypropyl)-5,6-dihydrouridine, 3-(3-amino-3-carboxypropyl) pseudouridine, 3-methylpseudouridine, 5-(carboxyhydroxymethyl)-2'-O-methyluridine methyl ester, 5-aminomethyl-2-geranylthiouridine, 5-aminomethyl-2-selenouridine, 5-aminomethyluridine, 5-carbamoylhydroxymethyluridine, 5-carbamoylmethyl-2-thiouridine, 5-carboxymethyl-2-thiouridine, 5-carboxymethylaminomethyl-2-geranylthiouridine, 5-carboxymethylaminomethyl-2-selenouridine, 5-cyanomethyluridine, 5-hydroxycytidine, 5-methylaminomethyl-2-geranylthiouridine, 7-aminocarboxypropyl-demethylwyosine, 7-aminocarboxypropylwyosine, 7-aminocarboxypropylwyosine methyl ester, 8-methyladenosine, N4,N4-dimethylcytidine, N6-formyladenosine, N6-hydroxymethyladenosine, agmatidine, cyclic N6-threonylcarbamoyladenosine, glutamyl-queuosine, methylated undermodified hydroxywybutosine, N4,N4,2'-O-trimethylcytidine, geranylated 5-methylaminomethyl-2-thiouridine, geranylated 5-carboxymethylaminomethyl-2-thiouridine, Qbase, preQObase, preQ1 base, and two or more combinations thereof. In some embodiments, the at least one chemically modified nucleoside is selected from the group consisting of pseudouridine, 1-methyl-pseudouridine, 1-ethyl-pseudouridine, 5-methylcytosine, 5-methoxyuridine, and a combination thereof. In some embodiments, the polyribonucleotide (e.g., RNA polyribonucleotide, such as mRNA polyribonucleotide) includes a combination of at least two (e.g., 2, 3, 4 or more) of the aforementioned modified nucleobases. In some embodiments, polynucleotides (e.g., RNA polynucleotides, such as mRNA polynucleotides) include a combination of at least two (e.g., 2, 3, 4 or more) of the aforementioned modified nucleobases.

In some embodiments, modified nucleobases in polynucleotides (e.g., RNA polynucleotides, such as mRNA polynucleotides) are selected from the group consisting of 1-methyl-pseudouridine (m1ψ), 1-ethyl-pseudouridine (e1ψ), 5-methoxy-uridine (mo5U), 5-methyl-cytidine (m5C), pseudouridine (v), a-thio-guanosine and a-thio-adenosine. In some embodiments, the polyribonucleotide includes a combination of at least two (e.g., 2, 3, 4 or more) of the aforementioned modified nucleobases, including but not limited to chemical modifications.

In some embodiments, polynucleotides (e.g., RNA polynucleotides, such as mRNA polynucleotides) comprise pseudouridine (w) and 5-methyl-cytidine (m5C). In some embodiments, the polyribonucleotides (e.g., RNA, such as mRNA) comprise 1-methyl-pseudouridine (m1ψ). In some embodiments, the polyribonucleotides (e.g., RNA, such as mRNA) comprise 1-ethyl-pseudouridine (e1ψ). In some embodiments, the polyribonucleotides (e.g., RNA, such as mRNA) comprise 1-methyl-pseudouridine (m1ψ) and 5-methyl-cytidine (m5C). In some embodiments, the polyribonucleotides (e.g., RNA, such as mRNA) comprise 1-ethyl-pseudouridine (e1ψ) and 5-methyl-cytidine (m5C). In some embodiments, the polyribonucleotides (e.g., RNA, such as mRNA) comprise 2-thiouridine (s2U). In some embodiments, the polyribonucleotides (e.g., RNA, such as mRNA) comprise 2-thiouridine and 5-methyl-cytidine (m5C). In some embodiments, the polyribonucleotides (e.g., RNA, such as mRNA) comprise methoxy-uridine (mo5U). In some embodiments, the polyribonucleotides (e.g., RNA, such as mRNA) comprise 5-methoxy-uridine (mo5U) and 5-methyl-cytidine (m5C). In some embodiments, the polyribonucleotides (e.g., RNA, such as mRNA) comprise 2'-O-methyl uridine. In some embodiments, the polyribonucleotides (e.g., RNA, such as mRNA) comprise 2'-O-methyl uridine and 5-methyl-cytidine (m5C). In some embodiments, the polyribonucleotides (e.g., RNA, such as mRNA) comprise N6-methyl-adenosine (m6A). In some embodiments, the polyribonucleotides (e.g., RNA, such as mRNA) comprise N6-methyl-adenosine (m6A) and 5-methyl-cytidine (m5C).

In some embodiments, polynucleotides (e.g., RNA polynucleotides, such as mRNA polynucleotides) are uniformly modified (e.g., fully modified, modified throughout the entire sequence) for a particular modification. For example, a polynucleotide can be uniformly modified with 1-methyl-pseudouridine, meaning that all uridine residues in the mRNA sequence are replaced with 1-methyl-pseudouridine. Similarly, a polynucleotide can be uniformly modified for any type of nucleoside residue present in the sequence by replacement with a modified residue such as those set forth above.

Exemplary nucleobases and nucleosides having a modified cytosine include N4-acetyl-cytidine (ac4C), 5-methyl-cytidine (m5C), 5-halo-cytidine (e.g., 5-iodo-cytidine), 5-hydroxymethyl-cytidine (hm5C), 1-methyl-pseudoisocytidine, 2-thio-cytidine (s2C), and 2-thio-5-methyl-cytidine.

In some embodiments, a modified nucleobase is a modified uridine. Exemplary nucleobases and nucleosides having a modified uridine include 1-methyl-pseudouridine (mlψ), 1-ethyl-pseudouridine (e1ψ), 5-methoxy uridine, 2-thio uridine, 5-cyano uridine, 2'-O-methyl uridine and 4'-thio uridine.

In some embodiments, a modified nucleobase is a modified adenine. Exemplary nucleobases and nucleosides having a modified adenine include 7-deaza-adenine, 1-methyl-adenosine (m1A), 2-methyl-adenine (m2A), and N6-methyl-adenosine (m6A).

In some embodiments, a modified nucleobase is a modified guanine. Exemplary nucleobases and nucleosides having a modified guanine include inosine (I), 1-methyl-inosine (mlI), wyosine (imG), methylwyosine (mimG), 7-deaza-guanosine, 7-cyano-7-deaza-guanosine (preQ0), 7-aminomethyl-7-deaza-guanosine (preQ1), 7-methyl-guanosine (m7G), 1-methyl-guanosine (m1G), 8-oxo-guanosinc, 7-methyl-8-oxo-guanosinc.

The polynucleotides of the present disclosure may be partially or fully modified along the entire length of the molecule. For example, one or more or all or a given type of nucleotide (e.g., purine or pyrimidine, or any one or more or all of A, G, U. C) may be uniformly modified in a polynucleotide of the invention, or in a given predetermined sequence region thereof (e.g., in the mRNA including or excluding the poly A tail). In some embodiments, all nucleotides X in a polynucleotide of the present disclosure (or in a given sequence region thereof) are modified nucleotides, wherein X may any one of nucleotides A. G. U. C, or any one of the combinations A+G, A+U, A+C, G+U, G+C, U+C. A+G+U, A+G+C. G+U+C or A+G+C.

The polynucleotide may contain from about 1% to about 100% modified nucleotides (either in relation to overall nucleotide content, or in relation to one or more types of nucleotide, i.e., any one or more of A, G. U or C) or any intervening percentage (e.g., from 1% to 20%, from 1% to 25%, from 1% to 50%, from 1% to 60%, from 1% to 70%, from 1% to 80%, from 1% to 90%, from 1% to 95%, from 10% to 20%, from 10% to 25%, from 10% to 50%, from 10% to 60%, from 10% to 70%, from 10% to 80%, from 10% to 90%, from 10% to 95%, from 10% to 100%, from 20% to 25%, from 20% to 50%, from 20% to 60%, from 20% to 70%, from 20% to 80%, from 20% to 90%, from 20% to 95%, from 20% to 100%, from 50% to 60%, from 50% to 70%, from 50% to 80%, from 50% to 90%, from 50% to 95%, from 50% to 100%, from 70% to 80%, from 70% to 90%, from 70% to 95%, from 70% to 100%, from 80% to 90%, from 80% to 95%, from 80% to 100%, from 90% to 95%, from 90% to 100%, and from 95% to 100%). It will be understood that any remaining percentage is accounted for by the presence of unmodified A, G, U, or C.

The polynucleotides may contain at a minimum 1% and at maximum 100% modified nucleotides, or any intervening percentage, such as at least 5% modified nucleotides, at least 10% modified nucleotides, at least 25% modified nucleotides, at least 50% modified nucleotides, at least 80% modified nucleotides, or at least 90% modified nucleotides. For example, the polynucleotides may contain a modified pyrimidine such as a modified uracil or cytosine. In some embodiments, at least 5%, at least 10%, at least 25%, at least 50%, at least 80%, at least 90% or 100% of the uracil in the polynucleotide is replaced with a modified uracil (e.g., a 5-substituted uracil). The modified uracil can be replaced by a compound having a single unique structure, or can be replaced by a plurality of compounds having different structures (e.g., 2, 3, 4 or more unique structures). In some embodiments, at least 5%, at least 10%, at least 25%, at least 50%, at least 80%, at least 90% or 100% of the cytosine in the polynucleotide is replaced with a modified cytosine (e.g., a 5-substituted cytosine). The modified cytosine can be replaced by a compound having a single unique structure, or can be replaced by a plurality of compounds having different structures (e.g., 2, 3, 4 or more unique structures).

Thus, in some embodiments, the RNA vaccines comprise a 5'UTR element, an optionally codon optimized open reading frame, and a 3'UTR element, a poly(A) sequence and/or a polyadenylation signal wherein the RNA is not chemically modified.

In some embodiments, the modified nucleobase is a modified uracil. Exemplary nucleobases and nucleosides having a modified uracil include pseudouridine (w), pyridin-4-one ribonucleoside, 5-aza-uridine, 6-aza-uridine, 2-thio-5-aza-uridine, 2-thio-uridine ($s^2U$), 4-thio-uridine ($s^4U$), 4-thio-pseudouridine, 2-thio-pseudouridine, 5-hydroxy-uridine ($ho^5U$), 5-aminoallyl-uridine, 5-halo-uridine (e.g., 5-iodo-uridincor 5-bromo-uridine), 3-methyl-uridine ($m^3U$), 5-methoxy-uridine ($mo^5U$), uridine 5-oxyacetic acid ($cmo^5U$), uridine 5-oxyacetic acid methyl ester ($memo^5U$), 5-carboxymethyl-uridine ($cm^5U$), 1-carboxymethyl-pseudouridine, 5-carboxyhydroxymethyl-uridine ($chm^5U$), 5-carboxyhydroxymethyl-uridine methyl ester ($mchm^5U$), 5-methoxycarbonylmethyl-uridine (mcmSU), 5-methoxycarbonylmethyl-2-thio-uridine ($mcm^5s^2U$), 5-aminomethyl-2-thio-uridine ($nm5s^2U$), 5-methylaminomethyl-uridine ($mnm^5U$), 5-methylaminomethyl-2-thio-uridine ($mnm^5s^2U$), 5-methylaminomethyl-2-seleno-uridine ($mnm^5se^2U$), 5-carbamoylmethyl-uridine (ncmSU), 5-carboxymethylaminomethyl-uridine ($cmnm^5U$), 5-carboxymethylaminomethyl-2-thio-uridine ($cmnm^5s^2U$), 5-propynyl-uridine, 1-propynyl-pseudouridine, 5-taurinomethyl-uridine ($\tau m^5U$), 1-taurinomethyl-pseudouridine, 5-taurinomethyl-2-thio-uridine ($\tau m^5s^2U$), 1-taurinomethyl-4-thio-pseudouridine, 5-methyl-uridine ($m^5U$, i.e., having the nucleobase deoxythymine), 1-methyl-pseudouridine ($m^1\psi$), 1-ethyl-pseudouridine ($e1\psi$), 5-methyl-2-thio-uridine ($m^5s^2U$), 1-methyl-4-thio-pseudouridine ($m^1s^4\psi$), 4-thio-1-methyl-pseudouridine, 3-methyl-pseudouridine ($m^3v$), 2-thio-1-methyl-pseudouridine, 1-methyl-1-deaza-pseudouridine, 2-thio-1-methyl-1-deaza-pseudouridine, dihydrouridine (D), dihydropseudouridine, 5,6-dihydrouridine, 5-methyl-dihydrouridine ($m^5D$), 2-thio-dihydrouridine, 2-thio-dihydropseudouridine, 2-methoxy-uridine, 2-methoxy-4-thio-uridine, 4-methoxy-pseudouridine, 4-methoxy-2-thio-pseudouridine, N1-methyl-pseudouridine, 3-(3-amino-3-carboxypropyl) uridine ($acp^3U$), 1-methyl-3-(3-amino-3-carboxypropyl) pseudouridine ($acp^3$ v), 5-(isopentenylaminomethyl) uridine ($inm^5U$), 5-(isopentenylaminomethyl)-2-thio-uridine ($inm^5s^2U$), a-thio-uridine, 2'-O-methyl-uridine (Um), 5,2'-O-dimethyl-uridine ($m^5Um$), 2'-O-methyl-pseudouridine (vm), 2-thio-2'-O-methyl-uridine ($s^2Um$), 5-methoxycarbonylmethyl-2'-O-methyl-uridine ($mcm^5Um$), 5-carbamoylmethyl-2'-O-methyl-uridine ($ncm^5Um$), 5-carboxymethylaminomethyl-2'-O-methyl-uridine ($cmnm^5Um$), 3,2'-O-dimethyl-uridine ($m^3Um$), and 5-(isopentenylaminomethyl)-2'-O-methyl-uridine ($inm^5Um$), 1-thio-uridine, deoxythymidine, 2'-F-ara-uridine, 2'-F-uridine, 2'-OH-ara-uridine, 5-(2-carbomethoxyvinyl) uridine, and 5-[3-(1-E-propenylamino)] uridine.

In some embodiments, the modified nucleobase is a modified cytosine. Exemplary nucleobases and nucleosides having a modified cytosine include 5-aza-cytidine, 6-aza-cytidine, pseudoisocytidine, 3-methyl-cytidine ($m^3C$), N4-acetyl-cytidine (ac+C), 5-formyl-cytidine ($f^5C$), N4-methyl-cytidine ($m^4C$), 5-methyl-cytidine ($m^5C$), 5-halo-cytidine (e.g., 5-iodo-cytidine), 5-hydroxymethyl-cytidine ($hm^5C$), 1-methyl-pseudoisocytidine, pyrrolo-cytidine, pyrrolo-pseudoisocytidine, 2-thio-cytidine ($s^2C$), 2-thio-5-methyl-cytidine, 4-thio-pseudoisocytidine, 4-thio-1-methyl-pseudoisocytidine, 4-thio-1-methyl-1-deaza-pseudoisocytidine, 1-methyl-1-deaza-pseudoisocytidine, zebularine, 5-aza-zebularine, 5-methyl-zebularine, 5-aza-2-thio-zebularine, 2-thio-zebularine, 2-methoxy-cytidine, 2-methoxy-5-methyl-cytidine, 4-methoxy-pseudoisocytidine, 4-methoxy-1-methyl-pseudoisocytidine, lysidine ($k_2C$), a-thio-cytidine, 2'-O-methyl-cytidine (Cm), 5,2'-O-dimethyl-cytidine ($m^5Cm$), N4-acetyl-2'-O-methyl-cytidine ($ac^4Cm$), N4,2'-O-dimethyl-cytidine ($m^4Cm$), 5-formyl-2'-O-methyl-cytidine ($f^5Cm$), N4,N4,2'-O-trimethyl-cytidine ($m^4{}_2Cm$), 1-thio-cytidine, 2'-F-ara-cytidine, 2'-F-cytidine, and 2'-OH-ara-cytidine.

In some embodiments, the modified nucleobase is a modified adenine. Exemplary nucleobases and nucleosides having a modified adenine include 2-amino-purine, 2, 6-diaminopurine, 2-amino-6-halo-purine (e.g., 2-amino-6-chloro-purine), 6-halo-purine (e.g., 6-chloro-purine), 2-amino-6-methyl-purine, 8-azido-adenosine, 7-deaza-adenine, 7-deaza-8-aza-adenine, 7-deaza-2-amino-purine, 7-deaza-8-aza-2-amino-purine, 7-deaza-2,6-diaminopurine, 7-deaza-8-aza-2,6-diaminopurine, 1-methyl-adenosine (m'A), 2-methyl-adenine ($m^2A$), N6-methyl-adenosine ($m^6A$), 2-methylthio-N6-methyl-adenosine ($ms^2m^6A$), N6-isopentenyl-adenosine ($i^6A$), 2-methylthio-N6-isopentenyl-adenosine ($ms^2i^6A$), N6-(cis-hydroxyisopentenyl) adenosine ($io^6A$), 2-methylthio-N6-(cis-hydroxyisopentenyl) adenosine ($ms^2io^6A$), N6-glycinylcarbamoyl-adenosine ($g^6A$), N6-threonylcarbamoyl-adenosine (t6A), N6-methyl-N6-threonylcarbamoyl-adenosine ($m^6t^6A$), 2-methylthio-N6-threonylcarbamoyl-adenosine ($ms^2g^6A$), N6,N6-dimethyl-adenosine ($m^6{}_2A$), N6-hydroxynorvalylcarbamoyl-adenosine (hn6A), 2-methylthio-N6-hydroxynorvalylcarbamoyl-adenosine ($ms^2hn6A$), N6-acetyl-adenosine (ac6A), 7-methyl-adenine, 2-methylthio-adenine, 2-methoxy-adenine, a-thio-adenosine, 2'-O-methyl-adenosine (Am), N6,2'-O-dimethyl-adenosine ($m^6Am$), N6,N6,2'-O-trimethyl-adenosine ($m^6{}_2Am$), 1,2'-O-dimethyl-adenosine ($m^1Am$), 2'-O-ribosyladenosine (phosphate) (Ar (p)), 2-amino-N6-methyl-purine, 1-thio-adenosine, 8-azido-adenosine, 2'-F-ara-adenosine, 2'-F-adenosine, 2'-OH-ara-adenosine, and N6-(19-amino-pentaoxanonadecyl)-adenosine.

In some embodiments, the modified nucleobase is a modified guanine. Exemplary nucleobases and nucleosides having a modified guanine include inosine (I), 1-methyl-inosine ($m^1I$), wyosine (imG), methylwyosine (mimG), 4-demethyl-wyosine (imG-14), isowyosine (imG2), wybutosine (yW), peroxywybutosine ($o_2yW$), hydroxywybutosine (OhyW), undermodified hydroxywybutosine (OhyW*), 7-deaza-guanosine, queuosine (Q), epoxyqueuosine (oQ), galactosyl-queuosine (galQ), mannosyl-queuosine (manQ), 7-cyano-7-deaza-guanosine ($preQ_0$), 7-aminomethyl-7-deaza-guanosine (preQ1), archaeosine (G+), 7-deaza-8-aza-guanosine, 6-thio-guanosine, 6-thio-7-deaza-guanosine, 6-thio-7-deaza-8-aza-guanosine, 7-methyl-guanosine ($m^7G$), 6-thio-7-methyl-guanosine, 7-methyl-inosine, 6-methoxy-guanosine, 1-methyl-guanosine ($m^1G$), N2-methyl-guanosine ($m^2G$), N2,N2-dimethyl-guanosine ($m^2{}_2G$), N2,7-dimethyl-guanosine ($m^{2,7}G$), N2,N2,7-dimethyl-guanosine ($m^{2,2,7}G$), 8-oxo-guanosine, 7-methyl-8-oxo-guanosine, 1-methyl-6-thio-guanosine, N2-methyl-6-thio-guanosine, N2,N2-dimethyl-6-thio-guanosine, a-thio-guanosine, 2'-O-methyl-guanosine (Gm), N2-methyl-2'-O-methyl-guanosine ($m^2Gm$), N2,N2-dimethyl-2'-O-methyl-guanosine ($m^2{}_2Gm$), 1-methyl-2'-O-methyl-guanosine ($m^1Gm$), N2,7-dimethyl-2'-O-methyl-guanosine ($m^{2,7}Gm$), 2'-O-methyl-inosine (Im), 1,2'-O-dimethyl-inosine ($m^1Im$), 2'-O-ribosylguanosine (phosphate) (Gr (p)). 1-thio-guanosine, 06-methyl-guanosine, 2'-F-ara-guanosine, and 2'-F-guanosine.

In Vitro Transcription of RNA (e.g., mRNA)

Cancer vaccines of the present disclosure comprise at least one RNA polynucleotide, such as a mRNA (e.g., modified mRNA). mRNA, for example, is transcribed in vitro from template DNA, referred to as an "in vitro transcription template." In some embodiments, an in vitro transcription template encodes a 5' untranslated (UTR) region, contains an open reading frame, and encodes a 3' UTR and a polyA tail. The particular nucleic acid sequence composition and length of an in vitro transcription template will depend on the mRNA encoded by the template.

A "5' untranslated region" (UTR) refers to a region of an mRNA that is directly upstream (i.e., 5') from the start codon (i.e., the first codon of an mRNA transcript translated by a ribosome) that does not encode a polypeptide.

A "3' untranslated region" (UTR) refers to a region of an mRNA that is directly downstream (i.e., 3') from the stop codon (i.e., the codon of an mRNA transcript that signals a termination of translation) that does not encode a polypeptide.

An "open reading frame" is a continuous stretch of DNA beginning with a start codon (e.g., methionine (ATG)), and ending with a stop codon (e.g., TAA, TAG or TGA) and encodes a polypeptide.

A "polyA tail" is a region of mRNA that is downstream, e.g., directly downstream (i.e., 3'), from 3' UTR that contains multiple, consecutive adenosine monophosphates. A polyA tail may contain 10 to 300 adenosine monophosphates. For example, a polyA tail may contain 10, 20, 30, 40, 50, 60, 70, 80, 90, 100, 110, 120, 130, 140, 150, 160, 170, 180, 190, 200, 210, 220, 230, 240, 250, 260, 270, 280, 290 or 300 adenosine monophosphates. In some embodiments, a polyA tail contains 50 to 250 adenosine monophosphates. In a relevant biological setting (e.g., in cells, in vivo) the poly(A) tail functions to protect mRNA from enzymatic degradation, e.g., in the cytoplasm, and aids in transcription termination, export of the mRNA from the nucleus and translation.

In some embodiments, a polynucleotide includes 200 to 3,000 nucleotides. For example, a polynucleotide may include 200 to 500, 200 to 1000, 200 to 1500, 200 to 3000, 500 to 1000, 500 to 1500, 500 to 2000, 500 to 3000, 1000 to 1500, 1000 to 2000, 1000 to 3000, 1500 to 3000, or 2000 to 3000 nucleotides).

In other aspects, the invention relates to a method for preparing an mRNA cancer vaccine by IVT methods. In vitro transcription (IVT) methods permit template-directed synthesis of RNA molecules of almost any sequence. The size of the RNA molecules that can be synthesized using IVT methods range from short oligonucleotides to long nucleic acid polymers of several thousand bases. IVT methods permit synthesis of large quantities of RNA transcript (e.g., from microgram to milligram quantities) (Beckert et al., Synthesis of RNA by in vitro transcription, *Methods Mol Biol.* 703:29-41 (2011); Rio et al. *RNA: A Laboratory Manual*. Cold Spring Harbor: Cold Spring Harbor Laboratory Press, 2011, 205-220; Cooper, Geoffery M. The Cell: A Molecular Approach. 4th ed. Washington D.C.: ASM Press, 2007. 262-299). Generally, IVT utilizes a DNA template featuring a promoter sequence upstream of a sequence of interest. The promoter sequence is most commonly of bacteriophage origin (ex. the T7, T3 or SP6 promoter sequence) but many other promotor sequences can be tolerated including those designed de novo. Transcription of the DNA template is typically best achieved by using the RNA polymerase corresponding to the specific bacteriophage promoter sequence. Exemplary RNA polymerases include, but are not limited to T7 RNA polymerase, T3 RNA polymerase, or SP6 RNA polymerase, among others. IVT is generally initiated at a dsDNA but can proceed on a single strand.

It will be appreciated that mRNA vaccines of the present disclosure, e.g., mRNAs encoding the cancer antigen, may be made using any appropriate synthesis method. For example, in some embodiments, mRNA vaccines of the present disclosure are made using IVT from a single bottom strand DNA as a template and complementary oligonucleotide that serves as promotor. The single bottom strand DNA may act as a DNA template for in vitro transcription of RNA, and may be obtained from, for example, a plasmid, a PCR product, or chemical synthesis. In some embodiments, the single bottom strand DNA is lincarized from a circular template. The single bottom strand DNA template generally includes a promoter sequence, e.g., a bacteriophage promoter sequence, to facilitate IVT. Methods of making RNA using a single bottom strand DNA and a top strand promoter complementary oligonucleotide are known in the art. An exemplary method includes, but is not limited to, annealing the DNA bottom strand template with the top strand promoter complementary oligonucleotide (e.g., T7 promoter complementary oligonucleotide, T3 promoter complementary oligonucleotide, or SP6 promoter complementary oligonucleotide), followed by IVT using an RNA polymerase corresponding to the promoter sequence, e.g., aT7 RNA polymerase, a T3 RNA polymerase, or an SP6 RNA polymerase.

IVT methods can also be performed using a double-stranded DNA template. For example, in some embodiments, the double-stranded DNA template is made by extending a complementary oligonucleotide to generate a complementary DNA strand using strand extension techniques available in the art. In some embodiments, a single bottom strand DNA template containing a promoter sequence and sequence encoding one or more epitopes of interest is annealed to a top strand promoter complementary oligonucleotide and subjected to a PCR-like process to extend the top strand to generate a double-stranded DNA template. Alternatively or additionally, a top strand DNA containing a sequence complementary to the bottom strand promoter sequence and complementary to the sequence encoding one or more epitopes of interest is annealed to a bottom strand promoter oligonucleotide and subjected to a PCR-like process to extend the bottom strand to generate a double-stranded DNA template. In some embodiments, the number of PCR-like cycles ranges from 1 to 20 cycles, e.g., 3 to 10 cycles. In some embodiments, a double-stranded DNA template is synthesized wholly or in part by chemical synthesis methods. The double-stranded DNA template can be subjected to in vitro transcription as described herein.

In another aspect, mRNA vaccines of the present disclosure, e.g., mRNAs encoding the cancer antigen, may be made using two DNA strands that are complementary across an overlapping portion of their sequence, leaving single-stranded overhangs (i.e., sticky ends) when the complementary portions are annealed. These single-stranded overhangs can be made double-stranded by extending using the other strand as a template, thereby generating double-stranded DNA. In some cases, this primer extension method can permit larger ORFs to be incorporated into the template DNA sequence, e.g., as compared to sizes incorporated into the template DNA sequences obtained by top strand DNA synthesis methods. In the primer extension method, a portion of 3'-end of a first strand (in the 5"-3' direction) is complementary to a portion 3'-end of a second strand (in 3'-5' direction). In some such embodiments, the single first strand DNA may include a sequence of a promoter (e.g., T7, T3, or SP6), optionally a 5'-UTR, and some or all of an ORF (e.g., a portion of 5'-end of the ORF). In some embodiments, the single second strand DNA may include complementary sequences for some or all of an ORF (e.g., a portion complementary to 3'-end of the ORF), and optionally a 3'-UTR, a stop sequence, and/or a poly(A) tail. Methods of making RNA using two synthetic DNA strands may include annealing the two strands with overlapping complementary portions, followed by primer extension using one or more PCR-like cycles to extend the strands to generate a double-stranded DNA template. In some embodiments, the number of PCR-like cycles ranges from 1 to 20 cycles, e.g., 3 to10 cycles. Such double-stranded DNA can be subjected to in vitro transcription as described herein.

In another aspect, mRNA vaccines of the present disclosure, e.g., mRNAs encoding the cancer antigen, may be made using synthetic double-stranded linear DNA molecules, such as gBlocks® (Integrated DNA Technologies, Coralville, lowa), as the double-stranded DNA template. An advantage to such synthetic double-stranded linear DNA molecules is that they provide a longer template from which to generate mRNAs. For example, gBlocks® can range in size from 45-1000 (e.g., 125-750 nucleotides). In some embodiments, a synthetic double-stranded linear DNA template includes a full length 5'-UTR, a full length 3'-UTR, or both. A full length 5'-UTR may be up to 100 nucleotides in length, e.g., about 40-60 nucleotides. A full length 3'-UTR may be up to 300 nucleotides in length, e.g., about 100-150 nucleotides.

To facilitate generation of longer constructs, two or more double-stranded linear DNA molecules and/or gene fragments that are designed with overlapping sequences on 3' strands may be assembled together using methods known in art. For example, the Gibson Assembly™ Method (Synthetic Genomics, Inc., La Jolla, C A) may be performed with the use of a mesophilic exonuclease that cleaves bases from 5'-end of the double-stranded DNA fragments, followed by annealing of the newly formed complementary single-stranded 3'-ends, polymerase-dependent extension to fill in any single-stranded gaps, and finally, covalent joining of the DNA segments by a DNA ligase.

In another aspect, mRNA vaccines of the present disclosure, e.g., mRNAs encoding the cancer antigen, may be made using chemical synthesis of the RNA. Methods, for instance, involve annealing a first polynucleotide comprising an open reading frame encoding the polypeptide and a second polynucleotide comprising a 5'-UTR to a complementary polynucleotide conjugated to a solid support. The 3'-terminus of the second polynucleotide is then ligated to 5'-terminus of the first polynucleotide under suitable conditions. Suitable conditions include the use of a DNA Ligase. The ligation reaction produces a first ligation product. The 5' terminus of a third polynucleotide comprising a 3'-UTR is then ligated to the 3'-terminus of the first ligation product under suitable conditions. Suitable conditions for the second ligation reaction include an RNA Ligase. A second ligation product is produced in the second ligation reaction. The second ligation product is released from the solid support to produce an mRNA encoding a polypeptide of interest. In some embodiments the mRNA is between 30 and 1000 nucleotides.

An mRNA encoding a polypeptide of interest may also be prepared by binding a first polynucleotide comprising an open reading frame encoding the polypeptide to a second polynucleotide comprising 3'-UTR to a complementary polynucleotide conjugated to a solid support. The 5'-terminus of the second polynucleotide is ligated to 3'-terminus of the first polynucleotide under suitable conditions. The suitable conditions include a DNA Ligase. The method produces a first ligation product. A third polynucleotide comprising a 5'-UTR is ligated to the first ligation product under suitable conditions to produce a second ligation product. The suitable conditions include an RNA Ligase, such as T4 RNA. The second ligation product is released from the solid support to produce an mRNA encoding a polypeptide of interest.

In some embodiments the first polynucleotide features a 5'-triphosphate and a 3'-OH. In other embodiments the second polynucleotide comprises a 3'-OH. In yet other embodiments, the third polynucleotide comprises a 5'-triphosphate and a 3'-OH. The second polynucleotide may also include a 5'-cap structure. The method may also involve the further step of ligating a fourth polynucleotide comprising a poly-A region at 3'-terminus of the third polynucleotide. The fourth polynucleotide may comprise a 5'-triphosphate.

The method may or may not comprise reverse phase purification. The method may also include a washing step wherein the solid support is washed to remove unreacted polynucleotides. The solid support may be, for instance, a capture resin. In some embodiments the method involves dT purification.

In accordance with the present disclosure, template DNA encoding the mRNA vaccines of the present disclosure includes an open reading frame (ORF) encoding one or more cancer epitopes. In some embodiments, the template DNA includes an ORF of up to 1000 nucleotides, e.g., about 10-350, 30-300 nucleotides or about 50-250 nucleotides. In some embodiments, the template DNA includes an ORF of about 150 nucleotides. In some embodiments, the template DNA includes an ORF of about 200 nucleotides.

In some embodiments, IVT transcripts are purified from the components of the IVT reaction mixture after the reaction takes place. For example, the crude IVT mix may be treated with RNase-free DNase to digest the original template. The mRNA can be purified using methods known in the art, including but not limited to, precipitation using an organic solvent or column based purification method. Commercial kits are available to purify RNA, e.g., MEGA-CLEAR™ Kit (Ambion, Austin, TX). The mRNA can be quantified using methods known in the art, including but not limited to, commercially available instruments, e.g., NanoDrop. Purified mRNA can be analyzed, for example, by agarose gel electrophoresis to confirm the RNA is the proper size and/or to confirm that no degradation of the RNA has occurred.

The template DNA may include one or more stabilizing elements, including, but not limited to untranslated regions (UTR) at their 5'-end (5'UTR) and/or at their 3'-end (3'UTR), in addition to other structural features, such as a 5'-cap structure or a 3'-poly(A) tail. In some embodiments, the template DNA includes a 5'-UTR of about 1-30 nucleotides, e.g., about 5-25 nucleotides or about 10-20 nucleotides. In some embodiments, the template DNA includes a 5'-UTR of 13 nucleotides. In some embodiments, the template DNA does not include a 5'-UTR. In some embodiments, the template DNA includes a 3'-UTR of about 1-60 nucleotides, e.g., 10-50 nucleotides. In some embodiments, the template DNA includes a 3'-UTR of 40 nucleotides. In some embodiments, the template DNA does not include a 3'-UTR. In some embodiments, the template DNA includes a 3'-poly(A) tail of 1-150 nucleotides, e.g., 10-100 nucleotides, e.g., 30 nucleotides. Such stabilizing elements may be included in the DNA for transcription in the IVT reaction, or may be synthesized separately and added to the resulting RNA generated from the IVT reaction.

A 3'-poly(A) tail may be added to an RNA of the present disclosure. Methods for poly(A) tail addition are well known in the art. Such methods include, but are not limited to poly(A) polymerase catalysis or periodate treatment. Alternatively or additionally, a poly(A) tail can be synthesized separately and then added to the RNA using any appropriate technique, such as click chemistry, orthoclick chemistry, solulink, or other bioconjugate chemistries known to those in the art.

A 7-methyl guanosine ($m^7G$) cap may be added to an RNA of the present disclosure.

Methods for $m^7G$ cap addition are well known in the art. Examples include, but are not limited to, co-transcriptional incorporation of anti-reverse cap analog (ARCA) using RNA polymerase, such as T7 polymerase. Commercial kits are available for T7 ARCA mRNA generation, such as the HiScribe™ T7 ARCA mRNA kit (New England BioLabs).

According to the present disclosure, two regions or parts of a chimeric polynucleotide may be joined or ligated, for example, using triphosphate chemistry. In some embodiments, a first region or part of 100 nucleotides or less is chemically synthesized with a 5'-monophosphate and terminal 3'-desOH or blocked OH. If the region is longer than 80 nucleotides, it may be synthesized as two or more strands that will subsequently be chemically linked by ligation. If the first region or part is synthesized as a non-positionally modified region or part using IVT, conversion to the 5'-monophosphate with subsequent capping of 3'-terminus may follow. Monophosphate protecting groups may be selected from any of those known in the art. A second region or part of the chimeric polynucleotide may be synthesized using either chemical synthesis or IVT methods, e.g., as described herein. IVT methods may include use of an RNA polymerase that can utilize a primer with a modified cap. Alternatively, a cap may be chemically synthesized and coupled to the IVT region or part.

It is noted that for ligation methods, ligation with DNA T4 ligase followed by DNAse treatment (to eliminate the DNA splint required for DNA T4 Ligase activity) should readily prevent the undesirable formation of concatenation products.

The entire chimeric polynucleotide need not be manufactured with a phosphate-sugar backbone. If one of the regions or parts encodes a polypeptide, then it is preferable that such region or part comprise a phosphate-sugar backbone.

Ligation may be performed using any appropriate technique, such as enzymatic ligation, click chemistry, orthoclick chemistry, solulink, or other bioconjugate chemistries known to those in the art. In some embodiments, the ligation is directed by a complementary oligonucleotide splint. In some embodiments, the ligation is performed without a complementary oligonucleotide splint.

In other aspects, the invention relates to kits for preparing an mRNA cancer vaccine by IVT methods. In personalized cancer vaccines, it is important to identify patient specific mutations and vaccinate the patient with one or more neoepitopes. In such vaccines, the antigen(s) encoded by the ORFs of an mRNA will be specific to the patient. The 5'- and 3'-ends of RNAs encoding the antigen(s) may be more broadly applicable, as they include untranslated regions and stabilizing regions that are common to many RNAs. Among other things, the present disclosure provides kits that include one or parts of a chimeric polynucleotide, such as one or more 5'- and/or 3'-regions of RNA, which may be combined with an ORF encoding a patient-specific epitope. For example, a kit may include a polynucleotide containing one or more of a 5'-ORF, a 3'-ORF, and a poly(A) tail. In some embodiments, each polynucleotide component is in an individual container. In other embodiments, more than one polynucleotide component is present together in a single container. In some embodiments, the kit includes a ligase enzyme. In some embodiments, provided kits include instructions for use. In some embodiments, the instructions include an instruction to ligate the epitope encoding ORF to one or more other components from the kit, e.g., 5'-ORF, a 3'-ORF, and/or a poly(A) tail.

Methods for generating personalized cancer vaccines according to the invention involve identification of mutations using techniques such as deep nucleic acid or protein sequencing methods as described herein of tissue samples. In some embodiments an initial identification of mutations in a patient's transcriptome is performed. The data from the patient's transcriptome is compared with sequence information from the patients exome in order to identify patient specific and tumor specific mutations that are expressed. The comparison produces a dataset of putative neoepitopes, referred to as a mutanome. The mutanome may include approximately 100-10,000 candidate mutations per patients. The mutanome is subject to a data probing analysis using a set of inquiries or algorithms to identify an optimal mutation set for generation of a neoantigen vaccine. In some embodiments an mRNA neoantigen vaccine is designed and manufactured. The patient is then treated with the vaccine.

The neoantigen vaccine may be a polycistronic vaccine including multiple neoepitopes or one or more single RNA vaccines or a combination thereof.

In some embodiments the entire method from the initiation of the mutation identification process to the start of patient treatment is achieved in less than 2 months. In other embodiments the whole process is achieved in 7 weeks or less, 6 weeks or less, 5 weeks or less, 4 weeks or less, 3 weeks or less, 2 weeks or less or less than 1 week. In some embodiments the whole method is performed in less than 30 days.

The mutation identification process may involve both transcriptome and exome analysis or only transcriptome or exome analysis. In some embodiments transcriptome analysis is performed first and exome analysis is performed second. The analysis is performed on a biological or tissue sample. In some embodiments a biological or tissue sample is a blood or serum sample. In other embodiments the sample is a tissue bank sample or EBV transformation of B-cells.

It has been recognized and appreciated that, by analyzing certain properties of cancer associated mutations, optimal neoepitopes may be assessed and/or selected for inclusion in an mRNA vaccine. For example, at a given time, one or more of several properties may be assessed and weighted in order to select a set of neoepitopes for inclusion in a vaccine. A property of a neoepitope or set of neoepitopes may include, for instance, an assessment of gene or transcript-level expression in patient RNA-seq or other nucleic acid analysis, tissue-specific expression in available databases, known oncogenes/tumor suppressors, variant call confidence score, RNA-seq allele-specific expression, conservative vs. non-conservative AA substitution, position of point mutation (Centering Score for increased TCR engagement), position of point mutation (Anchoring Score for differential HLA binding), Selfness: <100% core epitope homology with patient WES data, HLA-A and -B IC50 for 8mers-11mers, HLA-DRB1 IC50 for 15mers-20mers, promiscuity Score (i.e. number of patient HLAs predicted to bind), HLA-C IC50 for 8mers-11mers, HLA-DRB3-5 IC50 for 15mers-20mers, HLA-DQB1/A1 IC50 for 15mers-20mers, HLA-DPB1/A1 IC50 for 15mers-20mers, Class I vs Class II proportion, Diversity of patient HLA-A, -B and DRB1 allotypes covered, proportion of point mutation vs complex epitopes (e.g. frameshifts), and/or pseudo-epitope HLA binding scores.

In some embodiments, the properties of cancer associated mutations used to identify optimal neoepitopes are properties related to the type of mutation, abundance of mutation in patient sample, immunogenicity, lack of self-reactivity, and nature of peptide composition.

The type of mutation should be determined and considered as a factor in determining whether a putative epitope should be included in a vaccine. The type of mutation may vary. In some instances it may be desirable to include multiple different types of mutations in a single vaccine. In other instances a single type of mutation may be more desirable. A value for particular mutation can be weighted and calculated. In some embodiments, a particular mutation is a single nucleotide polymorphism (SNP). In some embodiments, a particular mutation is a complex variant, for example, a peptide sequence resulting from intron retention, complex splicing events, or insertion/deletion mutations changing the reading frame of a sequence.

The abundance of the mutation in patient sample may also be scored and factored into the decision of whether a putative epitope should be included in a vaccine. Highly abundant mutations may promote a more robust immune response.

The consideration of the immunogenicity is an important component in the selection of optimal neoepitopes for inclusion in a vaccine. Immunogenicity may be assessed for instance, by analyzing the MHC binding capacity of a neoepitope, HLA promiscuity, mutation position, predicted T cell reactivity, actual T cell reactivity, structure leading to particular conformations and resultant solvent exposure, and representation of specific amino acids. Known algorithms such as the NetMHC prediction algorithm can be used to predict capacity of a peptide to bind to common HLA-A and -B alleles. Structural assessment of a MHC bound peptide may also be conducted by in silico 3-dimensional analysis and/or protein docking programs. Use of a predicted epitope structure when bound to a MHC molecule, such as acquired from a Rosetta algorithm, may be used to evaluate the degree of solvent exposure of an amino acid residues of an epitope when the epitope is bound to a MHC molecule. T cell reactivity may be assessed experimentally with epitopes and T cells in vitro. Alternatively T cell reactivity may be assessed using T cell response/sequence datasets.

An important component of a neoepitope included in a vaccine, is a lack of self-reactivity. The putative neoepitopes may be screened to confirm that the epitope is restricted to tumor tissue, for instance, arising as a result of genetic change within malignant cells. Ideally, the epitope should not be present in normal tissue of the patient and thus, self-similar epitopes are filtered out of the dataset. A personalized coding genome may be used as a reference for comparison of neoantigen candidates to determine lack of self-reactivity. In some embodiments, a personalized coding genome is generated from an individualized transcriptome and/or exome.

The nature of peptide composition may also be considered in the epitope design. For instance a score can be provided for each putative epitope on the value of conserved versus non-conserved amino acids found in the epitope.

In some embodiments, the analysis performed by the tools described herein may include comparing different sets of properties acquired at different times from a patient, i.e. prior to and following a therapeutic intervention, from different tissue samples, from different patients having similar tumors, etc. In some embodiments, an average of peak values from one set of properties may be compared with an average of peak values from another set of properties. For example, an average value for HLA binding may be compared between two different sets of distributions. The two sets of distributions may be determined for time durations separated by days, months, or years, for instance.

Moreover, the inventors have recognized and appreciated that such data on properties of cancer mutations may be collected and analyzed using the algorithms described herein. The data is useful for identifying neoepitopes and sets of neoepitopes for the development of personalized cancer vaccines.

In some embodiments, all annotated transcripts of a tumor variant peptide are included in a vaccine in accordance with the invention. In some embodiments, translations of RNA identified in RNAseq are included in a vaccine in accordance with the present invention.

It will be appreciated that a concatamer of 2 or more peptides, e.g., 2 or more neoantigens, may create unintended new epitopes (pseudoepitopes) at peptide boundaries. To prevent or eliminate such pseudoepitopes, class I alleles may be scanned for hits across peptide boundaries in a concatamer. In some embodiments, the peptide order within the concatamer is shuffled to reduce or eliminate pseudoepitope formation. In some embodiments, a linker is used between peptides, e.g., a single amino acid linker such as glycine, to reduce or eliminate pseudoepitope formation. In some embodiments, anchor amino acids can be replaced with other amino acids which will reduce or eliminate pseudoepitope formation. In some embodiments, peptides are trimmed at the peptide boundary within the concatamer to reduce or eliminate pseudoepitope formation.

In some embodiments the multiple peptide epitope antigens are arranged and ordered to minimize pseudoepitopes. In other embodiments the multiple peptide epitope antigens are a polypeptide that is free of pseudoepitopes. When the cancer antigen epitopes are arranged in a concatemeric structure in a head to tail formation a junction is formed between each of the cancer antigen epitopes. That includes several, i.e. 1-10, amino acids from an epitope on a N-terminus of the peptide and several, i.e. 1-10, amino acids on a C-terminus of an adjacent directly linked epitope. It is important that the junction not be an immunogenic peptide that may produce an immune response. In some embodiments the junction forms a peptide sequence that binds to an HLA protein of a subject for which the personalized cancer vaccine is designed with an IC50 greater than about 50 nM. In other embodiments the junction peptide sequence binds to an HLA protein of a subject with an IC50 greater than about 10 nM, 150 nM, 200 nM, 250 nM, 300 nM, 350 nM, 400 nM, 450 nm, or 500 nM.

A neoepitope characterization system in accordance with the techniques described herein may take any suitable form, as embodiments are not limited in this respect. An illustrative implementation of a computer system 900 that may be used in connection with some embodiments is shown in FIG. 15. One or more computer systems such as computer system 900 may be used to implement any of the functionality described above. The computer system 900 may include one or more processors 910 and one or more computer-readable storage media (i.e., tangible, non-transitory computer-readable media), e.g., volatile storage 920 and one or more non-volatile storage media 930, which may be formed of any suitable data storage media. The processor 910 may control writing data to and reading data from the volatile storage 920 and the non-volatile storage device 930 in any suitable manner, as embodiments are not limited in this respect. To perform any of the functionality described herein, the processor 910 may execute one or more instructions stored in one or more computer-readable storage media (e.g., volatile storage 920 and/or non-volatile storage 930), which may serve as tangible, non-transitory computer-readable media storing instructions for execution by the processor 910.

The above-described embodiments can be implemented in any of numerous ways.

For example, the embodiments may be implemented using hardware, software or a combination thereof. When implemented in software, the software code can be executed on any suitable processor or collection of processors, whether provided in a single computer or distributed among multiple computers. It should be appreciated that any component or collection of components that perform the functions described above can be generically considered as one or more controllers that control the above-discussed functions. The one or more controllers can be implemented in numerous ways, such as with dedicated hardware, or with general purpose hardware (e.g., one or more processors) that is programmed using microcode or software to perform the functions recited above.

In this respect, it should be appreciated that one implementation comprises at least one computer-readable storage medium (i.e., at least one tangible, non-transitory computer-readable medium), such as a computer memory (e.g., hard drive, flash memory, processor working memory, etc.), a floppy disk, an optical disk, a magnetic tape, or other tangible, non-transitory computer-readable medium, encoded with a computer program (i.e., a plurality of instructions), which, when executed on one or more processors, performs above-discussed functions. The computer-readable storage medium can be transportable such that the program stored thereon can be loaded onto any computer resource to implement techniques discussed herein. In addition, it should be appreciated that the reference to a computer program which, when executed, performs above-discussed functions, is not limited to an application program running on a host computer. Rather, the term "computer program" is used herein in a generic sense to reference any type of computer code (e.g., software or microcode) that can be employed to program one or more processors to implement above-techniques.

Methods of Treatment

Provided herein are compositions (e.g., pharmaceutical compositions), methods, kits and reagents for prevention and/or treatment of cancer in humans and other mammals. Cancer RNA vaccines can be used as therapeutic or prophylactic agents. They may be used in medicine to prevent and/or treat cancer. In exemplary aspects, the cancer RNA vaccines of the present disclosure are used to provide prophylactic protection from cancer. Prophylactic protection from cancer can be achieved following administration of a cancer RNA vaccine of the present disclosure. Vaccines can be administered once, twice, three times, four times or more but it is likely sufficient to administer the vaccine once (optionally followed by a single booster). It is more desirable, to administer the vaccine to an individual having cancer to achieve a therapeutic response. Dosing may need to be adjusted accordingly.

Once an mRNA vaccine is synthesized, it is administered to the patient. In some embodiments the vaccine is administered on a schedule for up to two months, up to three months, up to four month, up to five months, up to six months, up to seven months, up to eight months, up to nine months, up to ten months, up to eleven months, up to 1 year, up to 1 and ½ years, up to two years, up to three years, or up to four years. The schedule may be the same or varied. In some embodiments the schedule is weekly for the first 3 weeks and then monthly thereafter.

The vaccine may be administered by any route. In some embodiments the vaccine is administered by an IM or IV route.

At any point in the treatment the patient may be examined to determine whether the mutations in the vaccine are still appropriate. Based on that analysis the vaccine may be adjusted or reconfigured to include one or more different mutations or to remove one or more mutations.

Therapeutic and Prophylactic Compositions

Provided herein are compositions (e.g., pharmaceutical compositions), methods, kits and reagents for prevention, treatment or diagnosis of cancer in humans and other mammals, for example. cancer RNA vaccines can be used as therapeutic or prophylactic agents. They may be used in medicine to prevent and/or treat cancer. In some embodiments, the cancer vaccines of the invention can be envisioned for use in the priming of immune effector cells, for example, to activate peripheral blood mononuclear cells (PBMCs) ex vivo, which are then infused (re-infused) into a subject.

In exemplary embodiments, a cancer vaccine containing RNA polynucleotides as described herein can be administered to a subject (e.g., a mammalian subject, such as a human subject), and the RNA polynucleotides are translated in vivo to produce an antigenic polypeptide.

The cancer RNA vaccines may be induced for translation of a polypeptide (e.g., antigen or immunogen) in a cell, tissue or organism. In exemplary embodiments, such translation occurs in vivo, although there can be envisioned embodiments where such translation occurs ex vivo, in culture or in vitro. In exemplary embodiments, the cell, tissue or organism is contacted with an effective amount of a composition containing a cancer RNA vaccine that contains a polynucleotide that has at least one a translatable region encoding an antigenic polypeptide.

An "effective amount" of a cancer RNA vaccine is provided based, at least in part, on the target tissue, target cell type, means of administration, physical characteristics of the polynucleotide (e.g., size, and extent of modified nucleosides) and other components of the cancer RNA vaccine, and other determinants. In general, an effective amount of the cancer RNA vaccine composition provides an induced or boosted immune response as a function of antigen production in the cell, preferably more efficient than a composition containing a corresponding unmodified polynucleotide encoding the same antigen or a peptide antigen. Increased antigen production may be demonstrated by increased cell transfection (the percentage of cells transfected with the RNA vaccine), increased protein translation from the polynucleotide, decreased nucleic acid degradation (as demonstrated, for example, by increased duration of protein translation from a modified polynucleotide), or altered antigen specific immune response of the host cell.

In some embodiments, RNA vaccines (including polynucleotides their encoded polypeptides) in accordance with the present disclosure may be used for treatment of cancer.

Cancer RNA vaccines may be administered prophylactically or therapeutically as part of an active immunization scheme to healthy individuals or early in cancer or during active cancer after onset of symptoms. In some embodiments, the amount of RNA vaccines of the present disclosure provided to a cell, a tissue or a subject may be an amount effective for immune prophylaxis.

Cancer RNA vaccines may be administered with other prophylactic or therapeutic compounds. As a non-limiting example, a prophylactic or therapeutic compound may be an adjuvant or a booster. As used herein, when referring to a composition, such as a vaccine, the term "booster" refers to an extra administration of the prophylactic (vaccine) composition. A booster (or booster vaccine) may be given after an earlier administration of the prophylactic composition. The time of administration between the initial administration of the prophylactic composition and the booster may be, but is not limited to, 1 minute, 2 minutes, 3 minutes, 4 minutes, 5 minutes, 6 minutes, 7 minutes, 8 minutes, 9 minutes, 10 minutes, 15 minutes, 20 minutes 35 minutes, 40 minutes, 45 minutes, 50 minutes, 55 minutes, 1 hour, 2 hours, 3 hours, 4 hours, 5 hours, 6 hours, 7 hours, 8 hours, 9 hours, 10 hours, 11 hours, 12 hours, 13 hours, 14 hours, 15 hours, 16 hours, 17 hours, 18 hours, 19 hours, 20 hours, 21 hours, 22 hours, 23 hours, 1 day, 36 hours, 2 days, 3 days, 4 days, 5 days, 6 days, 1 week, 10 days, 2 weeks, 3 weeks, 1 month, 2 months, 3 months, 4 months, 5 months, 6 months, 7 months, 8 months, 9 months, 10 months, 11 months, 1 year, 18 months, 2 years, 3 years, 4 years. 5 years, 6 years, 7 years, 8 years, 9 years, 10 years, 11 years, 12 years, 13 years, 14 years, 15 years, 16 years, 17 years, 18 years, 19 years, 20 years, 25 years, 30 years, 35 years, 40 years, 45 years, 50 years, 55 years, 60 years, 65 years, 70 years, 75 years, 80 years, 85 years, 90 years, 95 years or more than 99 years. In exemplary embodiments, the time of administration between the initial administration of the prophylactic composition and the booster may be, but is not limited to, 1 week, 2 weeks, 3 weeks, 1 month, 2 months, 3 months, 6 months or 1 year.

In one embodiment, the polynucleotides may be administered intramuscularly or intradermally similarly to the administration of vaccines known in the art.

The mRNA cancer vaccines may be utilized in various settings depending on the severity of the cancer or the degree or level of unmet medical need. As a non-limiting example, the mRNA cancer vaccines may be utilized to treat any stage of cancer. The mRNA cancer vaccines have superior properties in that they produce much larger antibody titers, T cell responses and produce responses early than commercially available anti-cancer vaccines. While not wishing to be bound by theory, the inventors hypothesize that the mRNA cancer vaccines, as mRNAs, are better designed to produce the appropriate protein conformation on translation as the mRNA cancer vaccines co-opt natural cellular machinery. Unlike traditional vaccines which are manufactured ex vivo and may trigger unwanted cellular responses, the mRNA cancer vaccines are presented to the cellular system in a more native fashion.

A non-limiting list of cancers that the mRNA cancer vaccines may treat is presented below. Peptide epitopes or antigens may be derived from any antigen of these cancers or tumors. Such epitopes are referred to as cancer or tumor antigens. Cancer cells may differentially express cell surface molecules during different phases of tumor progression. For example, a cancer cell may express a cell surface antigen in a benign state, yet down-regulate that particular cell surface antigen upon metastasis. As such, it is envisioned that the tumor or cancer antigen may encompass antigens produced during any stage of cancer progression. The methods of the invention may be adjusted to accommodate for these changes. For instance, several different mRNA vaccines may be generated for a particular patient. For instance a first vaccine may be used at the start of the treatment. At a later time point, a new mRNA vaccine may be generated and administered to the patient to account for different antigens being expressed.

In some embodiments, the tumor antigen is one of the following antigens: CD2, CD19, CD20, CD22, CD27, CD33, CD37, CD38, CD40, CD44, CD47, CD52, CD56, CD70, CD79, CD137, 4-IBB, 5T4, AGS-5, AGS-16, Angiopoietin 2, B7.1, B7.2, B7DC, B7H1, B7H2, B7H3, BT-062, BTLA, CAIX, Carcinoembryonic antigen, CTLA4, Cripto, ED-B, ErbB1, ErbB2, ErbB3, ErbB4, EGFL7, EpCAM, EphA2, EphA3, EphB2, FAP, Fibronectin, Folate Receptor, Ganglioside GM3, GD2, glucocorticoid-induced tumor necrosis factor receptor (GITR), gplOO, gpA33, GPNMB, ICOS, IGFIR, Integrin av, Integrin avß, LAG-3, Lewis Y, Mesothelin, c-MET, MN Carbonic anhydrase IX, MUC1, MUC16, Nectin-4, NKGD2, NOTCH, OX40, OX40L, PD-1, PDL1, PSCA, PSMA, RANKL, ROR1, ROR2, SLC44A4, Syndecan-1, TACI, TAG-72, Tenascin, TIM3, TRAILR1, TRAILR2, VEGFR-1, VEGFR-2, VEGFR-3, and variants thereof.

Cancers or tumors include but are not limited to neoplasms, malignant tumors, metastases, or any disease or disorder characterized by uncontrolled cell growth such that it would be considered cancerous. The cancer may be a primary or metastatic cancer. Specific cancers that can be treated according to the present invention include, but are not limited to, those listed below (for a review of such disorders, see Fishman et al., 1985, Medicine, 2d Ed., J. B. Lippincott Co., Philadelphia). Cancers include, but are not limited to, biliary tract cancer; bladder cancer; brain cancer including glioblastomas and medulloblastomas; breast cancer;

cervical cancer; choriocarcinoma; colon cancer; endometrial cancer; esophageal cancer;

gastric cancer; hematological neoplasms including acute lymphocytic and myelogenous leukemia; multiple myeloma; AIDS-associated leukemias and adult T-cell leukemia lymphoma; intraepithelial neoplasms including Bowen's disease and Paget's disease; liver cancer; lung cancer; lymphomas including Hodgkin's disease and lymphocytic lymphomas;

neuroblastomas; oral cancer including squamous cell carcinoma; ovarian cancer including those arising from epithelial cells, stromal cells, germ cells and mesenchymal cells;

pancreatic cancer; prostate cancer; rectal cancer; sarcomas including leiomyosarcoma, rhabdomyosarcoma, liposarcoma, fibrosarcoma, and osteosarcoma; skin cancer including melanoma, Kaposi's sarcoma, basocellular cancer, and squamous cell cancer; testicular cancer including germinal tumors such as seminoma, non-seminoma, teratomas, choriocarcinomas; stromal tumors and germ cell tumors; thyroid cancer including thyroid adenocarcinoma and medullar carcinoma; and renal cancer including adenocarcinoma and Wilms' tumor. Commonly encountered cancers include breast, prostate, lung, ovarian, colorectal, and brain cancer.

Provided herein are pharmaceutical compositions including cancer RNA vaccines and RNA vaccine compositions and/or complexes optionally in combination with one or more pharmaceutically acceptable excipients.

Cancer RNA vaccines may be formulated or administered alone or in conjunction with one or more other components. For instance, cancer RNA vaccines (vaccine compositions) may comprise other components including, but not limited to, adjuvants. In some embodiments, cancer RNA vaccines do not include an adjuvant (they are adjuvant free).

In other embodiments the mRNA cancer vaccines described herein may be combined with any other therapy useful for treating the patient. For instance a patient may be treated with the mRNA cancer vaccine and an anti-cancer agent. Thus, in one embodiment, the methods of the invention can be used in conjunction with one or more cancer therapeutics, for example, in conjunction with an anti-cancer agent, a traditional cancer vaccine, chemotherapy, radiotherapy, etc. (e.g., simultaneously, or as part of an overall treatment procedure). Parameters of cancer treatment that may vary include, but are not limited to, dosages, timing of administration or duration or therapy; and the cancer treatment can vary in dosage, timing, or duration. Another treatment for cancer is surgery, which can be utilized either alone or in combination with any of the previous treatment methods. Any agent or therapy (e.g., traditional cancer vaccines, chemotherapies, radiation therapies, surgery, hormonal therapies, and/or biological therapies/immunotherapies) which is known to be useful, or which has been used or is currently being used for the prevention or treatment of cancer can be used in combination with a composition of the invention in accordance with the invention described herein. One of ordinary skill in the medical arts can determine an appropriate treatment for a subject.

Examples of such agents (i.e., anti-cancer agents) include, but are not limited to, DNA-interactive agents including, but not limited to, the alkylating agents (e.g., nitrogen mustards, e.g. Chlorambucil, Cyclophosphamide, Isofamide, Mechlorethamine, Melphalan, Uracil mustard; Aziridine such as Thiotepa; methanesulphonate esters such as Busulfan; nitroso ureas, such as Carmustine, Lomustine, Streptozocin; platinum complexes, such as Cisplatin, Carboplatin; bioreductive alkylator, such as Mitomycin, and Procarbazine, Dacarbazine and Altretamine); the DNA strand—breakage agents, e.g., Bleomycin; the intercalating topoisomerase II inhibitors, e.g., Intercalators, such as Amsacrine, Dactinomycin, Daunorubicin, Doxorubicin, Idarubicin, Mitoxantrone, and nonintercalators, such as Etoposide and Teniposide; the nonintercalating topoisomerase II inhibitors, e.g., Etoposide and Teniposde; and the DNA minor groove binder, e.g., Plicamydin; the antimetabolites including, but not limited to, folate antagonists such as Methotrexate and trimetrexate; pyrimidine antagonists, such as Fluorouracil, Fluorodeoxyuridine, CB3717, Azacitidine and Floxuridine; purine antagonists such as Mercaptopurine, 6-Thioguanine, Pentostatin; sugar modified analogs such as Cytarabine and Fludarabine; and ribonucleotide reductase inhibitors such as hydroxyurea; tubulin Interactive agents including, but not limited to, colchicine, Vincristine and Vinblastine, both alkaloids and Paclitaxel and cytoxan; hormonal agents including, but not limited to, estrogens, conjugated estrogens and Ethinyl Estradiol and Diethylstilbesterol, Chlortrianisen and Idenestrol; progestins such as Hydroxyprogesterone caproate, Medroxyprogesterone, and Megestrol; and androgens such as testosterone, testosterone propionate; fluoxymesterone, methyltestosterone; adrenal corticosteroid, e.g., Prednisone, Dexamethasone, Methylprednisolone, and Prednisolone; leutinizing hormone releasing hormone agents or gonadotropin-releasing hormone antagonists, e.g., leuprolide acetate and goserelin acetate; antihormonal antigens including, but not limited to, antiestrogenic agents such as Tamoxifen, antiandrogen agents such as Flutamide; and antiadrenal agents such as Mitotane and Aminoglutethimide; cytokines including, but not limited to, IL-1.alpha., IL-1β, IL-2, IL-3, IL-4, IL-5, IL-6, IL-7, IL-8, IL-9, IL-10, IL-11, IL-12, IL-13, IL-18, TGF-β, GM-CSF, M-CSF, G-CSF, TNF-α, TNF-β, LAF, TCGF, BCGF, TRF, BAF, BDG, MP, LIF, OSM, TMF, PDGF, IFN-α, IFN-β, IFN-.γ, and Uteroglobins (U.S. Pat. No. 5,696,092); anti-angiogenics including, but not limited to, agents that inhibit VEGF (e.g., other neutralizing antibodies), soluble receptor constructs, tyrosine kinase inhibitors, antisense strategies, RNA aptamers and ribozymes against VEGF or VEGF receptors, Immunotoxins and coaguligands, tumor vaccines, and antibodies.

Specific examples of anti-cancer agents which can be used in accordance with the methods of the invention include, but not limited to: acivicin; aclarubicin; acodazole hydrochloride; acronine; adozelesin; aldesleukin; altretamine; ambomycin; ametantrone acetate; aminoglutethimide; amsacrine; anastrozole; anthramycin; asparaginase; asperlin; azacitidine; azetepa; azotomycin; batimastat; benzodepa; bicalutamide; bisantrene hydrochloride; bisnafide dimesylate; bizelesin; bleomycin sulfate; brequinar sodium;

bropirimine; busulfan; cactinomycin; calusterone; caracemide; carbetimer; carboplatin;

carmustine; carubicin hydrochloride; carzelesin; cedefingol; chlorambucil; cirolemycin;

cisplatin; cladribine; crisnatol mesylate; cyclophosphamide; cytarabine; dacarbazine;

dactinomycin; daunorubicin hydrochloride; decitabine; dexormaplatin; dezaguanine;

dezaguanine mesylate; diaziquone; docetaxel; doxorubicin; doxorubicin hydrochloride;

droloxifene; droloxifene citrate; dromostanolone propionate; duazomycin; cdatrexate;

cflomithine hydrochloride; elsamitrucin; enloplatin; enpromate; epipropidine; cpirubicin hydrochloride; erbulozole; esorubicin hydrochloride; estramustine; estramustine phosphate sodium; ctanidazole; etoposide; etoposide phosphate; etoprine; fadrozole hydrochloride; fazarabine; fenretinide; floxuridine; fludarabine phosphate; fluorouracil; flurocitabine;

fosquidone; fostriecin sodium; gemcitabine; gemcitabine hydrochloride; hydroxyurca;

idarubicin hydrochloride; ifosfamide; ilmofosine; interleukin II (including recombinant intericukin II, or rIL2), interferon alpha-2a; interferon alpha-2b; interferon alpha-n1;

interferon alpha-n3; interferon beta-I a; interferon gamma-I b; iproplatin; irinotecan hydrochloride; lanreotide acetate; letrozole; leuprolide acetate; liarozole hydrochloride;

lometrexol sodium; lomustine; losoxantrone hydrochloride; masoprocol; maytansine;

mechlorethamine hydrochloride; megestrol acetate; melengestrol acetate; melphalan;

menogaril; mercaptopurine; methotrexate; methotrexate sodium; metoprine; meturedepa;

mitindomide; mitocarcin; mitocromin; mitogillin; mitomalcin; mitomycin; mitosper;

mitotane; mitoxantrone hydrochloride; mycophenolic acid; nocodazole; nogalamycin;

ormaplatin; oxisuran; paclitaxel; pegaspargase; peliomycin; pentamustine; peplomycin sulfate; perfosfamide; pipobroman; piposulfan; piroxantrone hydrochloride; plicamycin;

plomestane; porfimer sodium; porfiromycin; prednimustine; procarbazine hydrochloride;

puromycin; puromycin hydrochloride; pyrazofurin; riboprine; rogletimide; safingol; safingol hydrochloride; semustine; simtrazene; sparfosate sodium; sparsomycin; spirogermanium hydrochloride; spiromustine; spiroplatin; streptonigrin; streptozocin; sulofenur; talisomycin; tecogalan sodium; tegafur; teloxantrone hydrochloride; temoporfin; teniposide; teroxirone; testolactone; thiamiprine; thioguanine; thiotepa; tiazofurin; tirapazamine; toremifene citrate; trestolone acetate; triciribine phosphate; trimetrexate; trimetrexate glucuronate; triptorelin;

tubulozole hydrochloride; uracil mustard; uredepa; vapreotide; verteporfin; vinblastine sulfate; vincristine sulfate; vindesine; vindesine sulfate; vinepidine sulfate; vinglycinate sulfate; vinleurosine sulfate; vinorelbine tartrate; vinrosidine sulfate; vinzolidine sulfate; vorozole; zeniplatin; zinostatin; and zorubicin hydrochloride.

Other anti-cancer drugs include, but are not limited to: 20-epi-1,25 dihydroxyvitamin D3; 5-ethynyluracil; angiogenesis inhibitors; anti-dorsalizing morphogenetic protein-1; ara-CDP-DL-PTBA; BCR/ABL antagonists; CaRest M3; CARN 700; cascin kinase inhibitors (ICOS); clotrimazole; collismycin A; collismycin B; combretastatin A4; crambescidin 816; cryptophycin 8; curacin A; dehydrodidemnin B;

didemnin B; dihydro-5-azacytidine; dihydrotaxol, duocarmycin SA; kahalalide F; lamellarin-N triacetate;

leuprolide+estrogen+progesterone; lissoclinamide 7; monophosphoryl lipid A+myobacterium cell wall sk; N-acetyldinaline; N-substituted benzamides; 06-benzylguanine; placetin A;

placetin B; platinum complex; platinum compounds; platinum-triamine complex; rhenium Re 186 etidronate; RII retinamide; rubiginone B 1; SarCNU; sarcophytol A; sargramostim;

senescence derived inhibitor 1; spicamycin D; tallimustine; 5-fluorouracil; thrombopoietin;

thymotrinan; thyroid stimulating hormone; variolin B; thalidomide; velaresol; veramine;

verdins; verteporfin; vinorelbine; vinxaltine; vitaxin; zanoterone; zeniplatin; and zilascorb.

The invention also encompasses administration of a composition comprising a mRNA cancer vaccine in combination with radiation therapy comprising the use of x-rays, gamma rays and other sources of radiation to destroy the cancer cells. In preferred embodiments, the radiation treatment is administered as external beam radiation or teletherapy wherein the radiation is directed from a remote source. In other preferred embodiments, the radiation treatment is administered as internal therapy or brachytherapy wherein a radioactive source is placed inside the body close to cancer cells or a tumor mass.

In specific embodiments, an appropriate anti-cancer regimen is selected depending on the type of cancer. For instance, a patient with ovarian cancer may be administered a prophylactically or therapeutically effective amount of a composition comprising a mRNA cancer vaccine in combination with a prophylactically or therapeutically effective amount of one or more other agents useful for ovarian cancer therapy, including but not limited to, intraperitoneal radiation therapy, such as P32 therapy, total abdominal and pelvic radiation therapy, cisplatin, the combination of paclitaxel (Taxol) or docetaxel (Taxotere) and cisplatin or carboplatin, the combination of cyclophosphamide and cisplatin, the combination of cyclophosphamide and carboplatin, the combination of 5-FU and leucovorin, etoposide, liposomal doxorubicin, gemcitabine or topotecan. Cancer therapies and their dosages, routes of administration and recommended usage are known in the art and have been described in such literature as the *Physician's Desk Reference* (56th ed., 2002).

In some preferred embodiments of the invention the mRNA cancer vaccines are administered with a T cell activator such as be an immune checkpoint modulator. Immune checkpoint modulators include both stimulatory checkpoint molecules and inhibitory checkpoint molecules i.e., an anti-CTLA4 and anti-PD1 antibody.

Stimulatory checkpoint inhibitors function by promoting the checkpoint process. Several stimulatory checkpoint molecules are members of the tumor necrosis factor (TNF) receptor superfamily-CD27, CD40, OX40, GITR and CD137, while others belong to the B7-CD28 superfamily-CD28 and ICOS. OX40 (CD134), is involved in the expansion of effector and memory T cells. Anti-OX40 monoclonal antibodies have been shown to be effective in treating advanced cancer. MEDI0562 is a humanized OX40 agonist. GITR, Glucocorticoid-Induced TNFR family Related gene, is involved in T cell expansion Several antibodies to GITR have been shown to promote an anti-tumor responses. ICOS, Inducible T-cell costimulator, is important in T cell effector function. CD27 supports antigen-specific expansion of naïve T cells and is involved in the generation of T and B cell memory. Several agonistic anti-CD27 antibodies are in development. CD122 is the Interleukin-2 receptor beta subunit. NKTR-214 is a CD122-biased immune-stimulatory cytokine.

Inhibitory checkpoint molecules include but are not limited to PD-1, TIM-3, VISTA, A2AR, B7-H3, B7-H4, BTLA, CTLA-4, IDO, KIR and LAG3. CTLA-4, PD-1 and its ligands are members of the CD28-B7 family of co-signaling molecules that play important roles throughout all stages of T-cell function and other cell functions. CTLA-4, Cytotoxic T-Lymphocyte-Associated protein 4 (CD152), is involved in controlling T cell proliferation.

The PD-1 receptor is expressed on the surface of activated T cells (and B cells) and, under normal circumstances, binds to its ligands (PD-L1 and PD-L2) that are expressed on the surface of antigen-presenting cells, such as dendritic cells or macrophages. This interaction sends a signal into the T cell and inhibits it. Cancer cells take advantage of this system by driving high levels of expression of PD-L1 on their surface. This allows them to gain control of the PD-1 pathway and switch off T cells expressing PD-1 that may enter the tumor microenvironment, thus suppressing the anticancer immune response. Pembrolizumab (formerly MK-3475 and lambrolizumab, trade name Keytruda) is a human antibody used in cancer immunotherapy. It targets the PD-1 receptor.

IDO, Indoleamine 2,3-dioxygenase, is a tryptophan catabolic enzyme, which suppresses T and NK cells, generates and activates Tregs and myeloid-derived suppressor cells, and promotes tumor angiogenesis. TIM-3, T-cell Immunoglobulin domain and Mucin domain 3, acts as a negative regulator of Th1/Tel function by triggering cell death upon interaction with its ligand, galectin-9. VISTA, V-domain Ig suppressor of T cell activation.

The checkpoint inhibitor is a molecule such as a monoclonal antibody, a humanized antibody, a fully human antibody, a fusion protein or a combination thereof or a small molecule. For instance, the checkpoint inhibitor inhibits a checkpoint protein which may be CTLA-4, PDL1, PDL2, PD1, B7-H3, B7-H4, BTLA, HVEM, TIM3, GAL9, LAG3, VISTA, KIR, 2B4, CD160, CGEN-15049, CHK 1, CHK2, A2aR, B-7 family ligands or a combination thereof. Ligands of checkpoint proteins include but are not limited to CTLA-4, PDL1, PDL2, PD1, B7-H3, B7-H4, BTLA, HVEM, TIM3, GAL9, LAG3, VISTA, KIR, 2B4, CD160, CGEN-15049, CHK 1, CHK2, A2aR, and B-7 family ligands. In some embodiments the anti-PD-1 antibody is BMS-936558 (nivolumab). In other embodiments the anti-CTLA-4 antibody is ipilimumab (trade name Yervoy, formerly known as MDX-010 and MDX-101).

In some preferred embodiments the cancer therapeutic agents, including the checkpoint modulators, are delivered in the form of mRNA encoding the cancer therapeutic agents, e.g., anti-PD1, cytokines, chemokines or stimulatory receptors/ligands (e.g., OX40.

In some embodiments the cancer therapeutic agent is a targeted therapy. The targeted therapy may be a BRAF inhibitor such as vemurafenib (PLX4032) or dabrafenib. The BRAF inhibitor may be PLX 4032, PLX 4720, PLX 4734, GDC-0879, PLX 4032, PLX-4720, PLX 4734 and Sorafenib Tosylate. BRAF is a human gene that makes a protein called B-Raf, also referred to as proto-oncogene B-Raf and v-Raf murine sarcoma viral oncogene homolog B1. The B-Raf protein is involved in sending signals inside cells, which are involved in directing cell growth. Vemurafenib, a BRAF inhibitor, was approved by FDA for treatment of late-stage melanoma.

The T-cell therapeutic agent in other embodiments is OX40L. OX40 is a member of the tumor necrosis factor/nerve growth factor receptor (TNFR/NGFR) family. OX40 may play a role in T-cell activation as well as regulation of differentiation, proliferation or apoptosis of normal and malignant lymphoid cells.

In other embodiments the cancer therapeutic agent is a cytokine. In yet other embodiments the cancer therapeutic agent is a vaccine comprising a population based tumor specific antigen.

In other embodiments, the cancer therapeutic agent is vaccine containing one or more traditional antigens expressed by cancer-germline genes (antigens common to tumors found in multiple patients, also referred to as "shared cancer antigens"). In some embodiments, a traditional antigen is one that is known to be found in cancers or tumors generally or in a specific type of cancer or tumor. In some embodiments, a traditional cancer antigen is a non-mutated tumor antigen. In some embodiments, a traditional cancer antigen is a mutated tumor antigen.

Figure 16:
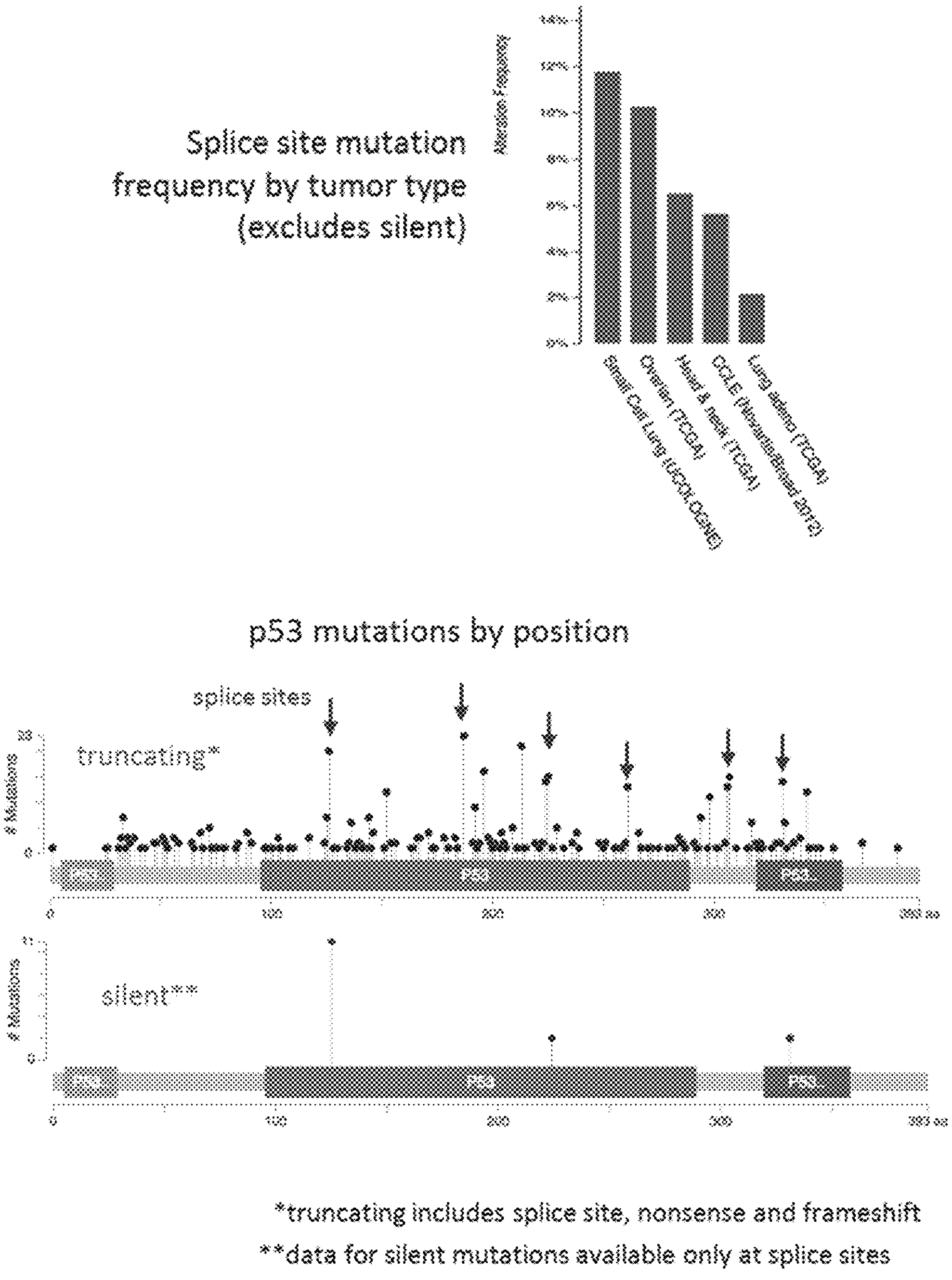
FIG. 16 is a schematic depicting splice site mutation frequency by tumor type, excluding silent mutations (top panel), and p53 mutations by position (lower panel).

The p53 gene (official symbol TP53) is mutated more frequently than any other gene in human cancers. Large cohort studies have shown that, for most p53 mutations, the genomic position is unique to one or only a few patients and the mutation cannot be used as recurrent neoantigens for therapeutic vaccines designed for a specific population of patients. A small subset of p53 loci do, however, exhibit a "hotspot" pattern, in which several positions in the gene are mutated with relatively high frequency. Strikingly, a large portion of these recurrently mutated regions occur near exon-intron boundaries, disrupting the canonical nucleotide sequence motifs recognized by the mRNA splicing machinery (FIG. 16). Mutation of a splicing motif can alter the final mRNA sequence even if no change to the local amino acid sequence is predicted (i.e. for synonymous or intronic mutations). Therefore, these mutations are often annotated as "noncoding" by common annotation tools and neglected for further analysis, even though they may alter mRNA splicing in unpredictable ways and exert severe functional impact on the translated protein. If an alternatively spliced isoform produces an in-frame sequence change (i.e., no premature termination codon (PTC) is produced), it can escape depletion by nonsense-mediated mRNA decay (NMD) and be readily expressed, processed, and presented on the cell surface by the HLA system. Further, mutation-derived alternative splicing is usually "cryptic", i.e., not expressed in normal tissues, and therefore may be recognized by T-cells as non-self neoantigens.

In some instances, the the cancer therapeutic agent is a vaccine which includes one or more neoantigens which are recurrent polymorphisms ("hot spot mutations"). For example, among other things, the present invention provides neoantigen peptide sequences resulting from certain recurrent somatic cancer mutations in p53. Exemplary mutations and mRNA splicing events resulting neoantigen peptides and HLA-restricted epitopes include, but are not limited to those depicted in FIG. 17, and the following:

(1) mutations at the canonical 5' splice site neighboring codon p.T125, inducing a retained intron having peptide sequence TAKSVTCTVSCPEGLASMRLQCLAVSPCISFVWNFGIPLHPLASCQCFFIVYPLNV (SEQ ID NO: 1) that contains epitopes AVSPCISFVW (SEQ ID NO: 2) (HLA-B*57:01, HLA-B*58:01), HPLASCQCFF (SEQ ID NO: 3) (HLA-B*35:01, HLA-B*53:01), FVWNFGIPL (SEQ ID NO: 4) (HLA-A*02:01, HLA-A*02:06, HLA-B*35:01);

(2) mutations at the canonical 5' splice site neighboring codon p.331, inducing a retained intron having peptide sequence EYFTLQVLSLGTSYQVESFQSNTQNAVFFLTVLPAIGAFAIRGQ (SEQ ID NO: 5) that contains epitopes LQVLSLGTSY (SEQ ID NO: 6) (HLA-B*15:01), FQSNTQNAVF (SEQ ID NO: 7) (HLA-B*15:01);

(3) mutations at the canonical 3' splice site neighboring codon p.126, inducing a cryptic alternative exonic 3' splice site producing the novel spanning peptide sequence AKSVTCTMFCQLAK (SEQ ID NO: 8) that contains epitopes CTMFCQLAK (SEQ ID NO: 9) (HLA-A*11:01), KSVTCTMF (SEQ ID NO: 10) (HLA-B*58:01); and/or (4) mutations at the canonical 5' splice site neighboring codon p.224, inducing a cryptic alternative intronic 5' splice site producing the novel spanning peptide sequence VPYEPPEVWLALTVPPSTAWAA (SEQ ID NO: 11) that contains epitopes VPYEPPEVW (SEQ ID NO: 12) (HLA-B*53:01, HLA-B*51:01), LTVPPSTAW (SEQ ID NO: 13) (HLA-B*58:01, HLA-B*57:01), wherein the transcript codon positions refer to the canonical full-length p53 transcript ENST00000269305 (SEQ ID NO: 14) from the Ensembl v83 human genome annotation.

In one embodiment, the invention provides a cancer therapeutic vaccine comprising mRNA encoding an open reading frame (ORF) coding for one or more of neoantigen peptides (1) through (4). In one embodiment, the invention provides the selective administration of a vaccine containing or coding for one or more of peptides (1)-(4), based on the patient's tumor containing any of the above mutations. In one embodiment, the invention provides the selective administration of the vaccine based on the dual criteria of the subject's tumor containing any of the above mutations and the subject's normal HLA type containing the corresponding HLA allele predicted to bind to the resulting neoantigen.

In some embodiments, the cancer therapeutic vaccine comprises one or more mRNAs encoding one or more recurrent polymorphisms. In some embodiments, the cancer therapeutic vaccine comprises one or more mRNAs encoding one or more patient specific neoantigens. In some embodiments, the cancer therapeutic vaccine comprises one or more mRNAs encoding an immune checkpoint modulator. The one or more recurrent polymorphisms, the one or more patient specific neoantigens, and/or the one or more immune checkpoint modulator can be combined in any manner. For example, it may desirable for one or more concatameric constructs to encode one the one or more recurrent polymorphisms, the one or more patient specific neoantigens, and/or the one or more immune checkpoint modulator. In other instances, it may be desirable for the one or more recurrent polymorphisms, the one or more patient specific neoantigens, and/or the one or more immune checkpoint modulator to be encoded by separate mRNA constructs. It will be appreciated that the one or more recurrent polymorphisms, the one or more patient specific neoantigens, and/or the one or more immune checkpoint modulator can be administered concurrently, or can be administered sequentially.

The mRNA cancer vaccine and anti-cancer therapeutic can be combined to enhance immune therapeutic responses even further. The mRNA cancer vaccine and other therapeutic agent may be administered simultaneously or sequentially. When the other therapeutic agents are administered simultaneously they can be administered in the same or separate formulations, but are administered at the same time.

The other therapeutic agents are administered sequentially with one another and with the mRNA cancer vaccine, when the administration of the other therapeutic agents and the mRNA cancer vaccine is temporally separated. The separation in time between the administration of these compounds may be a matter of minutes or it may be longer, e.g. hours, days, weeks, months. For example, in some embodiments, the separation in time between the administration of these compounds is 1 hour, 2 hours, 3 hours 4 hours, 5 hours, 6 hours, 8 hours, 12 hours, 24 hours or more. In some embodiments, the separation in time between the administration of these compounds is 2 days, 3 days, 4 days, 5 days, 6 days, or 7 days or more. In some embodiments, the mRNA cancer vaccine is administered before the anti-cancer therapeutic. In some embodiments, the mRNA cancer vaccine is administered after the anti-cancer therapeutic.

Other therapeutic agents include but are not limited to anti-cancer therapeutic, adjuvants, cytokines, antibodies, antigens, etc.

RNA vaccines may be formulated or administered in combination with one or more pharmaceutically-acceptable excipients. In some embodiments, vaccine compositions comprise at least one additional active substances, such as, for example, a therapeutically-active substance, a prophylactically-active substance, or a combination of both. Vaccine compositions may be sterile, pyrogen-free or both sterile and pyrogen-free. General considerations in the formulation and/or manufacture of pharmaceutical agents, such as vaccine compositions, may be found, for example, in Remington: The Science and Practice of Pharmacy 21 st ed., Lippincott Williams & Wilkins, 2005 (incorporated herein by reference in its entirety).

In some embodiments, cancer RNA vaccines are administered to humans, human patients or subjects. For the purposes of the present disclosure, the phrase "active ingredient" generally refers to the RNA vaccines or the polynucleotides contained therein, for example, RNA polynucleotides (e.g., mRNA polynucleotides) encoding antigenic polypeptides. Formulations of the vaccine compositions described herein may be prepared by any method known or hereafter developed in the art of pharmacology. In general, such preparatory methods include the step of bringing the active ingredient (e.g., mRNA polynucleotide) into association with an excipient and/or one or more other accessory ingredients, and then, if necessary and/or desirable, dividing, shaping and/or packaging the product into a desired single- or multi-dose unit.

Cancer RNA vaccines can be formulated using one or more excipients to: (1) increase stability; (2) increase cell transfection; (3) permit the sustained or delayed release (e.g., from a depot formulation); (4) alter the biodistribution (e.g., target to specific tissues or cell types); (5) increase the translation of encoded protein in vivo; and/or (6) alter the release profile of encoded protein (antigen) in vivo. In addition to traditional excipients such as any and all solvents, dispersion media, diluents, or other liquid vehicles, dispersion or suspension aids, surface active agents, isotonic agents, thickening or emulsifying agents, preservatives, excipients can include, without limitation, lipidoids, liposomes, lipid nanoparticles, polymers, lipoplexes, core-shell nanoparticles, peptides, proteins, cells transfected with cancer RNA vaccines (e.g., for transplantation into a subject), hyaluronidase, nanoparticle mimics and combinations thereof.

Stabilizing Elements

Naturally-occurring eukaryotic mRNA molecules have been found to contain stabilizing elements, including, but not limited to untranslated regions (UTR) at their 5'-end (5'UTR) and/or at their 3'-end (3'UTR), in addition to other structural features, such as a 5'-cap structure or a 3'-poly(A) tail. Both 5'UTR and 3'UTR are typically transcribed from the genomic DNA and are elements of the premature mRNA. Characteristic structural features of mature mRNA, such as 5'-cap and 3'-poly(A) tail are usually added to the transcribed (premature) mRNA during mRNA processing. The 3'-poly(A) tail is typically a stretch of adenine nucleotides added to 3'-end of the transcribed mRNA. It can comprise up to about 400 adenine nucleotides. In some embodiments the length of 3'-poly(A) tail may be an essential element with respect to the stability of the individual mRNA.

In some embodiments the RNA vaccine may include one or more stabilizing elements. Stabilizing elements may include for instance a histone stem-loop. A stem-loop binding protein (SLBP), a 32 kDa protein has been identified. It is associated with the histone stem-loop at 3'-end of the histone messages in both the nucleus and the cytoplasm. Its expression level is regulated by the cell cycle; it is peaks during the S-phase, when histone mRNA levels are also elevated. The protein has been shown to be essential for efficient 3'-end processing of histone pre-mRNA by the U7 snRNP. SLBP continues to be associated with the stem-loop after processing, and then stimulates the translation of mature histone mRNAs into histone proteins in the cytoplasm. The RNA binding domain of SLBP is conserved through metazoa and protozoa; its binding to the histone stem-loop depends on the structure of the loop. The minimum binding site includes at least three nucleotides 5' and two nucleotides 3' relative to the stem-loop.

In some embodiments, the RNA vaccines include a coding region, at least one histone stem-loop, and optionally, a poly(A) sequence or polyadenylation signal. The poly(A) sequence or polyadenylation signal generally should enhance the expression level of the encoded protein. The encoded protein, in some embodiments, is not a histone protein, a reporter protein (e.g. Luciferase, GFP, EGFP, B-Galactosidase, EGFP), or a marker or selection protein (e.g. alpha-Globin, Galactokinase and Xanthine: guanine phosphoribosyl transferase (GPT)).

In some embodiments, the combination of a poly(A) sequence or polyadenylation signal and at least one histone stem-loop, even though both represent alternative mechanisms in nature, acts synergistically to increase the protein expression beyond the level observed with either of the individual elements. It has been found that the synergistic effect of the combination of poly(A) and at least one histone stem-loop does not depend on the order of the elements or the length of the poly(A) sequence.

In some embodiments, the RNA vaccine does not comprise a histone downstream element (HDE). "Histone downstream element" (HDE) includes a purine-rich polynucleotide stretch of approximately 15 to 20 nucleotides 3' of naturally occurring stem-loops, representing the binding site for the U7 snRNA, which is involved in processing of histone pre-mRNA into mature histone mRNA. Ideally, the inventive nucleic acid does not include an intron.

In some embodiments, the RNA vaccine may or may not contain a enhancer and/or promoter sequence, which may be modified or unmodified or which may be activated or inactivated. In some embodiments, the histone stem-loop is generally derived from histone genes, and includes an intramolecular base pairing of two neighbored partially or entirely reverse complementary sequences separated by a spacer, consisting of a short sequence, which forms the loop of the structure. The unpaired loop region is typically unable to base pair with either of the stem loop elements. It occurs more often in RNA, as is a key component of many RNA secondary structures, but may be present in single-stranded DNA as well. Stability of the stem-loop structure generally depends on the length, number of mismatches or bulges, and base composition of the paired region. In some embodiments, wobble base pairing (non-Watson-Crick base pairing) may result. In some embodiments, the at least one histone stem-loop sequence comprises a length of 15 to 45 nucleotides.

In other embodiments the RNA vaccine may have one or more AU-rich sequences removed. These sequences, sometimes referred to as AURES are destabilizing sequences found in 3'UTR. The AURES may be removed from the RNA vaccines. Alternatively the AURES may remain in the RNA vaccine.

Nanoparticle Formulations

In some embodiments, cancer RNA vaccines are formulated in a nanoparticle. In some embodiments, cancer RNA vaccines are formulated in a lipid nanoparticle. In some embodiments, cancer RNA vaccines are formulated in a lipid-polycation complex, referred to as a cationic lipid nanoparticle. The formation of the lipid nanoparticle may be accomplished by methods known in the art and/or as described in U.S. Pub. No. 20120178702, herein incorporated by reference in its entirety. As a non-limiting example, the polycation may include a cationic peptide or a polypeptide such as, but not limited to, polylysine, polyornithine and/or polyarginine and the cationic peptides described in International Pub. No. WO2012013326 or US Patent Pub. No. US20130142818; each of which is herein incorporated by reference in its entirety. In some embodiments, cancer RNA vaccines are formulated in a lipid nanoparticle that includes a non-cationic lipid such as, but not limited to, cholesterol or dioleoyl phosphatidylethanolamine (DOPE).

A lipid nanoparticle formulation may be influenced by, but not limited to, the selection of the cationic lipid component, the degree of cationic lipid saturation, the nature of the PEGylation, ratio of all components and biophysical parameters such as size. In one example by Semple et al. (*Nature Biotech.* 2010 28:172-176; herein incorporated by reference in its entirety), the lipid nanoparticle formulation is composed of 57.1% cationic lipid, 7.1% dipalmitoylphosphatidylcholine, 34.3% cholesterol, and 1.4% PEG-c-DMA. As another example, changing the composition of the cationic lipid can more effectively deliver siRNA to various antigen presenting cells (Basha et al. *Mol Ther.* 2011 19:2186-2200; herein incorporated by reference in its entirety).

In some embodiments, lipid nanoparticle formulations may comprise 35 to 45% cationic lipid, 40% to 50% cationic lipid, 50% to 60% cationic lipid and/or 55% to 65% cationic lipid. In some embodiments, the ratio of lipid to RNA (e.g., mRNA) in lipid nanoparticles may be 5:1 to 20:1, 10:1 to 25:1, 15:1 to 30:1 and/or at least 30:1.

In some embodiments, the ratio of PEG in the lipid nanoparticle formulations may be increased or decreased and/or the carbon chain length of the PEG lipid may be modified from C14 to C18 to alter the pharmacokinetics and/or biodistribution of the lipid nanoparticle formulations. As a non-limiting example, lipid nanoparticle formulations may contain 0.5% to 3.0%, 1.0% to 3.5%, 1.5% to 4.0%, 2.0% to 4.5%, 2.5% to 5.0% and/or 3.0% to 6.0% of the lipid molar ratio of PEG-c-DOMG (R-3-[(ω-methoxy-poly(ethyleneglycol) 2000) carbamoyl)]-1,2-dimyristyloxypropyl-3-amine) (also referred to herein as PEG-DOMG) as compared to the cationic lipid, DSPC and cholesterol. In some embodiments, the PEG-c-DOMG may be replaced with a PEG lipid such as, but not limited to, PEG-DSG (1,2-Distearoyl-sn-glycerol, methoxypolyethylene glycol), PEG-DMG (1,2-Dimyristoyl-sn-glycerol) and/or PEG-DPG (1,2-Dipalmitoyl-sn-glycerol, methoxypolyethylene glycol). The cationic lipid may be selected from any lipid known in the art such as, but not limited to, DLin-MC3-DMA, DLin-DMA, C12-200 and DLin-KC2-DMA.

In some embodiments, a cancer RNA vaccine formulation is a nanoparticle that comprises at least one lipid. The lipid may be selected from, but is not limited to, DLin-DMA, DLin-K-DMA, 98N12-5, C12-200, DLin-MC3-DMA, DLin-KC2-DMA, DODMA, PLGA, PEG, PEG-DMG, PEGylated lipids and amino alcohol lipids. In some embodiments, the lipid may be a cationic lipid such as, but not limited to, DLin-DMA, DLin-D-DMA, DLin-MC3-DMA, DLin-KC2-DMA, DODMA and amino alcohol lipids. The amino alcohol cationic lipid may be the lipids described in and/or made by the methods described in US Patent Publication No. US20130150625, herein incorporated by reference in its entirety. As a non-limiting example, the cationic lipid may be 2-amino-3-[(9Z,12Z)-octadeca-9,12-dien-1-yloxy]-2-{[(9Z,2Z)-octadeca-9,12-dien-1-yloxy]methyl} propan-1-ol (Compound 1 in US20130150625); 2-amino-3-[(9Z)-octadec-9-en-1-yloxy]-2-{[(9Z)-octadec-9-en-1-yloxy|methyl} propan-1-ol (Compound 2 in US20130150625); 2-amino-3-[(9Z,12Z)-octadeca-9,12-dien-1-yloxy]-2-[(octyloxy)methyl]propan-1-ol (Compound 3 in US20130150625); and 2-(dimethylamino)-3-[(9Z,12Z)-octadeca-9,12-dien-1-yloxy]-2-{[(9Z,12Z)-octadeca-9,12-dien-1-yloxy]methyl} propan-1-ol (Compound 4 in US20130150625); or any pharmaceutically acceptable salt or stereoisomer thereof.

Lipid nanoparticle formulations typically comprise a lipid, in particular, an ionizable cationic lipid, for example, 2,2-dilinoleyl-4-dimethylaminoethyl-[1,3]-dioxolane (DLin-KC2-DMA), dilinoleyl-methyl-4-dimethylaminobutyrate (DLin-MC3-DMA), or di((Z)-non-2-en-1-yl) 9-((4-(dimethylamino) butanoyl)oxy) heptadecanedioate (L319), and further comprise a neutral lipid, a sterol and a molecule capable of reducing particle aggregation, for example a PEG or PEG-modified lipid.

In some embodiments, a lipid nanoparticle formulation consists essentially of (i) at least one lipid selected from the group consisting of 2,2-dilinoleyl-4-dimethylaminoethyl-[1,3]-dioxolane (DLin-KC2-DMA), dilinoleyl-methyl-4-dimethylaminobutyrate (DLin-MC3-DMA), and di((Z)-non-2-en-1-yl) 9-((4-(dimethylamino) butanoyl)oxy) heptadecanedioate (L319); (ii) a neutral lipid selected from DSPC, DPPC, POPC, DOPE and SM; (iii) a sterol, e.g., cholesterol; and (iv) a PEG-lipid, e.g., PEG-DMG or PEG-CDMA, in a molar ratio of 20-60% cationic lipid: 5-25% neutral lipid: 25-55% sterol; 0.5-15% PEG-lipid.

In some embodiments, a lipid nanoparticle formulation includes 25% to 75% on a molar basis of a cationic lipid selected from 2,2-dilinoleyl-4-dimethylaminoethyl-[1,3]-dioxolane (DLin-KC2-DMA), dilinoleyl-methyl-4-dimethylaminobutyrate (DLin-MC3-DMA), and di((Z)-non-2-en-1-yl) 9-((4-(dimethylamino) butanoyl)oxy) heptadecanedioate (L319), e.g., 35 to 65%, 45 to 65%, 60%, 57.5%, 50% or 40% on a molar basis.

In some embodiments, a lipid nanoparticle formulation includes 0.5% to 15% on a molar basis of the neutral lipid, e.g., 3 to 12%, 5 to 10% or 15%, 10%, or 7.5% on a molar basis. Examples of neutral lipids include, without limitation, DSPC, POPC, DPPC, DOPE and SM. In some embodiments, the formulation includes 5% to 50% on a molar basis of the sterol (e.g., 15 to 45%, 20 to 40%, 40%, 38.5%, 35%, or 31% on a molar basis. A non-limiting example of a sterol is cholesterol. In some embodiments, a lipid nanoparticle formulation includes 0.5% to 20% on a molar basis of the PEG or PEG-modified lipid (e.g., 0.5 to 10%, 0.5 to 5%, 1.5%, 0.5%, 1.5%, 3.5%, or 5% on a molar basis. In some embodiments, a PEG or PEG modified lipid comprises a PEG molecule of an average molecular weight of 2,000 Da. In some embodiments, a PEG or PEG modified lipid comprises a PEG molecule of an average molecular weight of less than 2,000, for example around 1,500 Da, around 1,000 Da, or around 500 Da. Non-limiting examples of PEG-modified lipids include PEG-distearoyl glycerol (PEG-DMG) (also referred herein as PEG-C14 or C14-PEG), PEG-CDMA (further discussed in Reyes et al. *J. Controlled Release,* 107, 276-287 (2005) the contents of which are herein incorporated by reference in its entirety).

In some embodiments, lipid nanoparticle formulations include 25-75% of a cationic lipid selected from 2,2-dilinoleyl-4-dimethylaminoethyl-[1,3]-dioxolane (DLin-KC2-DMA), dilinoleyl-methyl-4-dimethylaminobutyrate (DLin-MC3-DMA), and di((Z)-non-2-en-1-yl) 9-((4-(dimethylamino) butanoyl)oxy) heptadecanedioate (L319), 0.5-15% of the neutral lipid, 5-50% of the sterol, and 0.5-20% of the PEG or PEG-modified lipid on a molar basis.

In some embodiments, lipid nanoparticle formulations include 35-65% of a cationic lipid selected from 2,2-dilinoleyl-4-dimethylaminoethyl-[1,3]-dioxolane (DLin-KC2-DMA), dilinolcyl-methyl-4-dimethylaminobutyrate (DLin-MC3-DMA), and di((Z)-non-2-en-1-yl) 9-((4-(dimethylamino) butanoyl)oxy) heptadecanedioate (L319), 3-12% of the neutral lipid, 15-45% of the sterol, and 0.5-10% of the PEG or PEG-modified lipid on a molar basis.

In some embodiments, lipid nanoparticle formulations include 45-65% of a cationic lipid selected from 2,2-dilinoleyl-4-dimethylaminoethyl-[1,3]-dioxolane (DLin-KC2-DMA), dilinoleyl-methyl-4-dimethylaminobutyrate (DLin-MC3-DMA), and di((Z)-non-2-en-1-yl) 9-((4-(dimethylamino) butanoyl)oxy) heptadecanedioate (L319), 5-10% of the neutral lipid, 25-40% of the sterol, and 0.5-10% of the PEG or PEG-modified lipid on a molar basis.

In some embodiments, lipid nanoparticle formulations include 60% of a cationic lipid selected from 2,2-dilinoleyl-4-dimethylaminoethyl-[1,3]-dioxolane (DLin-KC2-DMA), dilinoleyl-methyl-4-dimethylaminobutyrate (DLin-MC3-DMA), and di((Z)-non-2-en-1-yl) 9-((4-(dimethylamino) butanoyl)oxy) heptadecanedioate (L319), 7.5% of the neutral lipid, 31% of the sterol, and 1.5% of the PEG or PEG-modified lipid on a molar basis.

In some embodiments, lipid nanoparticle formulations include 50% of a cationic lipid selected from 2,2-dilinoleyl-4-dimethylaminoethyl-[1,3]-dioxolane (DLin-KC2-DMA), dilinoleyl-methyl-4-dimethylaminobutyrate (DLin-MC3-DMA), and di((Z)-non-2-en-1-yl) 9-((4-(dimethylamino) butanoyl)oxy) heptadecanedioate (L319), 10% of the neutral lipid, 38.5% of the sterol, and 1.5% of the PEG or PEG-modified lipid on a molar basis.

In some embodiments, lipid nanoparticle formulations include 50% of a cationic lipid selected from 2,2-dilinoleyl-4-dimethylaminoethyl-[1,3]-dioxolane (DLin-KC2-DMA), dilinoleyl-methyl-4-dimethylaminobutyrate (DLin-MC3-DMA), and di((Z)-non-2-en-1-yl) 9-((4-(dimethylamino) butanoyl)oxy) heptadecanedioate (L319), 10% of the neutral lipid, 35% of the sterol, 4.5% or 5% of the PEG or PEG-modified lipid, and 0.5% of the targeting lipid on a molar basis.

In some embodiments, lipid nanoparticle formulations include 40% of a cationic lipid selected from 2,2-dilinoleyl-4-dimethylaminoethyl-[1,3]-dioxolane (DLin-KC2-DMA), dilinoleyl-methyl-4-dimethylaminobutyrate (DLin-MC3-DMA), and di((Z)-non-2-en-1-yl) 9-((4-(dimethylamino) butanoyl)oxy) heptadecanedioate (L319), 15% of the neutral lipid, 40% of the sterol, and 5% of the PEG or PEG-modified lipid on a molar basis.

In some embodiments, lipid nanoparticle formulations include 57.2% of a cationic lipid selected from 2,2-dilinoleyl-4-dimethylaminoethyl-[1,3]-dioxolane (DLin-KC2-DMA), dilinoleyl-methyl-4-dimethylaminobutyrate (DLin-MC3-DMA), and di((Z)-non-2-en-1-yl) 9-((4-(dimethylamino) butanoyl)oxy) heptadecanedioate (L319), 7.1% of the neutral lipid, 34.3% of the sterol, and 1.4% of the PEG or PEG-modified lipid on a molar basis.

In some embodiments, lipid nanoparticle formulations include 57.5% of a cationic lipid selected from the PEG lipid is PEG-CDMA (PEG-CDMA is further discussed in Reyes et al. (*J. Controlled Release,* 107, 276-287 (2005), the contents of which are herein incorporated by reference in its entirety), 7.5% of the neutral lipid, 31.5% of the sterol, and 3.5% of the PEG or PEG-modified lipid on a molar basis.

In some embodiments, lipid nanoparticle formulations consists essentially of a lipid mixture in molar ratios of 20-70% cationic lipid: 5-45% neutral lipid: 20-55% cholesterol: 0.5-15% PEG-modified lipid. In some embodiments, lipid nanoparticle formulations consists essentially of a lipid mixture in a molar ratio of 20-60% cationic lipid: 5-25% neutral lipid: 25-55% cholesterol: 0.5-15% PEG-modified lipid.

In some embodiments, the molar lipid ratio is 50/10/38.5/1.5 (mol % cationic lipid/neutral lipid, e.g., DSPC/Chol/PEG-modified lipid, e.g., PEG-DMG, PEG-DSG or PEG-DPG), 57.2/7.1134.3/1.4 (mol % cationic lipid/neutral lipid, e.g., DPPC/Chol/PEG-modified lipid, e.g., PEG-cDMA), 40/15/40/5 (mol % cationic lipid/neutral lipid, e.g., DSPC/Chol/PEG-modified lipid, e.g., PEG-DMG), 50/10/35/4.5/0.5 (mol % cationic lipid/neutral lipid, e.g., DSPC/Chol/PEG-modified lipid, e.g., PEG-DSG), 50/10/35/5 (cationic lipid/neutral lipid, e.g., DSPC/Chol/PEG-modified lipid, e.g., PEG-DMG), 40/10/40/10 (mol % cationic lipid/neutral lipid, e.g., DSPC/Chol/PEG-modified lipid, e.g., PEG-DMG or PEG-cDMA), 35/15/40/10 (mol % cationic lipid/neutral lipid, e.g., DSPC/Chol/PEG-modified lipid, e.g., PEG-DMG or PEG-cDMA) or 52/13/30/5 (mol % cationic lipid/neutral lipid, e.g., DSPC/Chol/PEG-modified lipid, e.g., PEG-DMG or PEG-cDMA).

Non-limiting examples of lipid nanoparticle compositions and methods of making them are described, for example, in Semple et al. (2010) *Nat. Biotechnol.* 28:172-176; Jayarama et al. (2012), *Angew. Chem. Int. Ed.,* 51:8529-8533; and Maier et al. (2013) Molecular Therapy 21, 1570-1578 (the contents of each of which are incorporated herein by reference in their entirety).

In some embodiments, lipid nanoparticle formulations may comprise a cationic lipid, a PEG lipid and a structural lipid and optionally comprise a non-cationic lipid. As a non-limiting example, a lipid nanoparticle may comprise 40-60% of cationic lipid, 5-15% of a non-cationic lipid, 1-2% of a PEG lipid and 30-50% of a structural lipid. As another non-limiting example, the lipid nanoparticle may comprise 50% cationic lipid, 10% non-cationic lipid, 1.5% PEG lipid and 38.5% structural lipid. As yet another non-limiting example, a lipid nanoparticle may comprise 55% cationic lipid, 10% non-cationic lipid, 2.5% PEG lipid and 32.5% structural lipid. In some embodiments, the cationic lipid may be any cationic lipid described herein such as, but not limited to, DLin-KC2-DMA, DLin-MC3-DMA and L319.

In some embodiments, the lipid nanoparticle formulations described herein may be 4 component lipid nanoparticles. The lipid nanoparticle may comprise a cationic lipid, a non-cationic lipid, a PEG lipid and a structural lipid. As a non-limiting example, the lipid nanoparticle may comprise 40-60% of cationic lipid, 5-15% of a non-cationic lipid, 1-2% of a PEG lipid and 30-50% of a structural lipid. As another non-limiting example, the lipid nanoparticle may comprise 50% cationic lipid, 10% non-cationic lipid, 1.5% PEG lipid and 38.5% structural lipid. As yet another non-limiting example, the lipid nanoparticle may comprise 55% cationic lipid, 10% non-cationic lipid, 2.5% PEG lipid and 32.5% structural lipid. In some embodiments, the cationic lipid may be any cationic lipid described herein such as, but not limited to, DLin-KC2-DMA, DLin-MC3-DMA and L319.

In some embodiments, the lipid nanoparticle formulations described herein may comprise a cationic lipid, a non-cationic lipid, a PEG lipid and a structural lipid. As a non-limiting example, the lipid nanoparticle comprise 50% of the cationic lipid DLin-KC2-DMA, 10% of the non-cationic lipid DSPC, 1.5% of the PEG lipid PEG-DOMG and 38.5% of the structural lipid cholesterol. As a non-limiting example, the lipid nanoparticle comprise 50% of the cationic lipid DLin-MC3-DMA, 10% of the non-cationic lipid DSPC, 1.5% of the PEG lipid PEG-DOMG and 38.5% of the structural lipid cholesterol. As a non-limiting example, the lipid nanoparticle comprise 50% of the cationic lipid DLin-MC3-DMA, 10% of the non-cationic lipid DSPC, 1.5% of the PEG lipid PEG-DMG and 38.5% of the structural lipid cholesterol. As yet another non-limiting example, the lipid nanoparticle comprise 55% of the cationic lipid L319, 10% of the non-cationic lipid DSPC, 2.5% of the PEG lipid PEG-DMG and 32.5% of the structural lipid cholesterol.

In some embodiments, a nanoparticle comprises compounds of Formula (I):

(I)

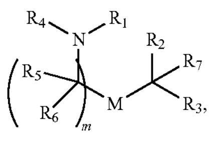

or a salt or isomer thereof, wherein:

$R_1$ is selected from the group consisting of $C_{5-30}$ alkyl, $C_{5-20}$ alkenyl, —R*YR", —YR", and —R"M'R';

$R_2$ and $R_3$ are independently selected from the group consisting of H, $C_{1-14}$ alkyl, $C_{2-14}$ alkenyl, —R*YR", —YR", and —R*OR", or $R_2$ and $R_3$, together with the atom to which they are attached, form a heterocycle or carbocycle;

$R_4$ is selected from the group consisting of a $C_{3-6}$ carbocycle, —$(CH_2)_n$Q, —$(CH_2)_n$CHQR, —CHQR, —CQ(R) 2, and unsubstituted $C_{1-6}$ alkyl, where Q is selected from a carbocycle, heterocycle, —O R, —$O(CH_2)_nN(R)_2$, —C(O)OR, —O C(O)R, —$CX_3$, —$CX_2H$, —$CXH_2$, —CN, —$N(R)_2$, —C(O)N$(R)_2$, —N(R)C(O)R, —N(R) $S(O)_2R$, —N(R)C(O)N$(R)_2$, —N(R)C(S) $N(R)_2$, —N(R)$R_8$, —$O(CH_2)$, OR, —N(R)C(=$NR_9$) $N(R)_2$, —N(R)C(=$CHR_9$) $N(R)_2$, —O C(O)N$(R)_2$, —N(R)C(O)OR, —N(OR)C(O)R, —N(OR) $S(O)_2R$, —N(OR) C(O)OR, —N(OR) C(O) N$(R)_2$, —N(OR) C(S) N$(R)_2$, —N(OR)C(=$NR_9$) N$(R)_2$, —N(OR) C(=$CHR_9$) N$(R)_2$, —C(=$NR_9$) N$(R)_2$, —C(=$NR_9$)R, —C(O)N(R)O R, and —C(R)N $(R)_2$C(O)OR, and each n is independently selected from 1, 2, 3, 4, and 5;

each $R_5$ is independently selected from the group consisting of $C_{1-3}$ alkyl, $C_{2-3}$ alkenyl, and H;

each $R_6$ is independently selected from the group consisting of $C_{1-3}$ alkyl, $C_{2-3}$ alkenyl, and H;

M and M' are independently selected from —C(O)O—, —O C(O)—, —C(O)N(R')—, —N(R') C(O)—, —C(O)—, —C(S)—, —C(S)S—, —S C(S)—, —CH (OH)—, —P(O) (OR')O—, —$S(O)_2$—, —S—S—, an aryl group, and a heteroaryl group;

$R_7$ is selected from the group consisting of $C_{1-3}$ alkyl, $C_{2-3}$ alkenyl, and H;

$R_8$ is selected from the group consisting of $C_{3-6}$ carbocycle and heterocycle;

$R_9$ is selected from the group consisting of H, CN, NO2, $C_{1-6}$ alkyl, —O R, —$S(O)_2R$, —$S(O)_2N(R)_2$, $C_{2-6}$ alkenyl, $C_{3-6}$ carbocycle and heterocycle;

each R is independently selected from the group consisting of C1-3 alkyl, $C_{2-3}$ alkenyl, and H;

each R' is independently selected from the group consisting of $C_{1-18}$ alkyl, $C_{2-18}$ alkenyl, —R*YR", —YR", and H;

each R" is independently selected from the group consisting of $C_{3-14}$ alkyl and $C_{3-14}$ alkenyl;

each R* is independently selected from the group consisting of $C_{1-12}$ alkyl and $C_{2-12}$ alkenyl;

each Y is independently a $C_{3-6}$ carbocycle;

each X is independently selected from the group consisting of F, Cl, Br, and I; and m is selected from 5, 6, 7, 8, 9, 10, 11, 12, and 13.

In some embodiments, a subset of compounds of Formula (I) includes those in which when $R_4$ is —$(CH_2)_n$Q, —$(CH_2)_n$CHQR, —CHQR, or —CQ$(R)_2$, then (i) Q is not-N$(R)_2$ when n is 1, 2, 3, 4 or 5, or (ii) Q is not 5, 6, or 7-membered heterocycloalkyl when n is 1 or 2. In some embodiments, another subset of compounds of Formula (I) includes those in which $R_1$ is selected from the group consisting of $C_{5-30}$ alkyl, $C_{5-20}$ alkenyl, —R*YR", —YR", and —R"M'R';

$R_2$ and $R_3$ are independently selected from the group consisting of H, $C_{1-14}$ alkyl, $C_{2-14}$ alkenyl, —R*YR", —YR", and —R*OR", or $R_2$ and $R_3$, together with the atom to which they are attached, form a heterocycle or carbocycle;

$R_4$ is selected from the group consisting of a $C_{3-6}$ carbocycle, —$(CH_2)_n$Q, —$(CH_2)$ ICHQR, —CHQR, —CQ $(R)_2$, and unsubstituted $C_{1-6}$ alkyl, where Q is selected from a $C_{3-6}$ carbocycle, a 5- to 14-membered heteroaryl having one or more heteroatoms selected from N, O, and S, —OR, —$O(CH_2)_nN(R)_2$, —C(O)OR, —O C(O) R, —CX3, —CX2H, —CXH2, —CN, —C(O)N$(R)_2$, —N(R) C(O)R, —N(R)$S(O)_2R$, —N(R)C(O)N$(R)_2$, —N(R)C(S) N$(R)_2$, —C RN$(R)_2$C(O)OR, —N(R)$R_8$, —$O(CH_2)$, OR, —N(R)C(=NR9) N$(R)_2$, —N(R)C (=CHR9) N$(R)_2$, —O C(O)N$(R)_2$, —N(R)C(O)OR, —N(OR)C(O)R, —N(OR) $S(O)_2R$, —N(OR) C(O) OR, —N(OR) C(O)N$(R)_2$, —N(OR) C(S) N$(R)_2$, —N(OR)C(=NR9) N$(R)_2$, —N(OR) C(=CHR9) N$(R)_2$, —C(=NR9) N$(R)_2$, —C(=NR9)R, —C(O)N (R)O R, and a 5- to 14-membered heterocycloalkyl having one or more heteroatoms selected from N, O, and S which is substituted with one or more substituents selected from oxo (=O), OH, amino, mono- or di-alkylamino, and $C_{1-3}$ alkyl, and each n is independently selected from 1, 2, 3, 4, and 5;

each $R_5$ is independently selected from the group consisting of $C_{1-3}$ alkyl, $C_{2-3}$ alkenyl, and H;

each $R_6$ is independently selected from the group consisting of $C_{1-3}$ alkyl, $C_{2-3}$ alkenyl, and H;

M and M' are independently selected from —C(O)O—, —O C(O)—, —C(O)N(R')—, —N(R') C(O)—, —C(O)—, —C(S)—, —C(S)S—, —S C(S)—, —CH (OH)—, —P(O) (OR')O—, —$S(O)_2$—, —S—S—, an aryl group, and a heteroaryl group;

$R_7$ is selected from the group consisting of $C_{1-3}$ alkyl, $C_{2-3}$ alkenyl, and H; Rg is selected from the group consisting of $C_{3-6}$ carbocycle and heterocycle;

$R_9$ is selected from the group consisting of H, CN, NO2, $C_{1-6}$ alkyl, —O R, —$S(O)_2R$, —$S(O)_2N(R)_2$, C2-6 alkenyl, $C_{3-6}$ carbocycle and heterocycle;

each R is independently selected from the group consisting of C1-3 alkyl, $C_{2-3}$ alkenyl, and H;

each R' is independently selected from the group consisting of $C_{1-18}$ alkyl, $C_{2-18}$ alkenyl, —R*YR", —YR", and H;

each R" is independently selected from the group consisting of $C_{3-14}$ alkyl and $C_{3-14}$ alkenyl;

each R* is independently selected from the group consisting of $C_{1-12}$ alkyl and $C_{2-12}$ alkenyl;

each Y is independently a $C_{3-6}$ carbocycle;

each X is independently selected from the group consisting of F, Cl, Br, and I; and m is selected from 5, 6, 7, 8, 9, 10, 11, 12, and 13, or salts or isomers thereof.

In some embodiments, another subset of compounds of Formula (I) includes those in which $R_1$ is selected from the group consisting of C5-30 alkyl, $C_{5-20}$ alkenyl, —R*YR", —YR", and —R"M'R';

$R_2$ and $R_3$ are independently selected from the group consisting of H, $C_{1-14}$ alkyl, $C_{2-14}$ alkenyl, —R*YR", —YR", and —R*OR", or $R_2$ and $R_3$, together with the atom to which they are attached, form a heterocycle or carbocycle;

$R_4$ is selected from the group consisting of a $C_{3-6}$ carbocycle, —$(CH_2)_nQ$, —$(CH_2)_n$CHQR, —CHQR, —$CQ(R)_2$, and unsubstituted $C_{1-6}$ alkyl, where Q is selected from a $C_{3-6}$ carbocycle, a 5- to 14-membered heterocycle having one or more heteroatoms selected from N, O, and S, —OR, —$O(CH_2)_nN(R)_2$, —C(O)OR, —O C(O)R, —CX3, —CX2H, —CXH2, —CN, —$C(O)N(R)_2$, —N(R) C(O)R, —$N(R)S(O)_2R$, —$N(R)C(O)N(R)_2$, —N(R)C(S) $N(R)_2$, —C $RN(R)_2C(O)OR$, —$N(R)R_8$, —$O(CH_2)$, OR, —N(R)C (=$NR_9$) $N(R)_2$, —N(R)C(=CHR9) $N(R)_2$, —O $C(O)N(R)_2$, —N(R)C(O)OR, —N(OR)C(O)R, —N(OR) $S(O)_2R$, —N(OR) C(O)OR, —N(OR) $C(O)N(R)_2$, —N(OR) C(S) $N(R)_2$, —N(OR)C(=$NR_9$) $N(R)_2$, —N(OR) C(=CHR9) $N(R)_2$, —C(=$NR_9$)R, —C(O)N(R)OR,
and —C(=$NR_9$) $N(R)_2$, and each n is independently selected from 1, 2, 3, 4, and 5; and when Q is a 5- to 14-membered heterocycle and (i) $R_4$ is —$(CH_2)_nQ$ in which n is 1 or 2, or (ii) $R_4$ is —$(CH_2)_n$CHQR in which n is 1, or (iii) $R_4$ is —CHQR, and —$CQ(R)_2$, then Q is either a 5- to 14-membered heteroaryl or 8- to 14-membered heterocycloalkyl;

each $R_5$ is independently selected from the group consisting of $C_{1-3}$ alkyl, $C_{2-3}$ alkenyl, and H;

each $R_6$ is independently selected from the group consisting of $C_{1-3}$ alkyl, $C_{2-3}$ alkenyl, and H;

M and M' are independently selected from —C(O)O—, —O C(O)—, —C(O)N(R')—, —N(R') C(O)—, —C(O)—, —C(S)—, —C(S)S—, —S C(S)—, —CH (OH)—, —P(O) (OR')O—, —$S(O)_2$—, —S—S—, an aryl group, and a heteroaryl group;

$R_7$ is selected from the group consisting of $C_{1-3}$ alkyl, $C_{2-3}$ alkenyl, and H;

$R_8$ is selected from the group consisting of $C_{3-6}$ carbocycle and heterocycle;

$R_9$ is selected from the group consisting of H, CN, NO2, $C_{1-6}$ alkyl, —O R, —$S(O)_2R$, —$S(O)_2N(R)_2$, $C_{2-6}$ alkenyl, $C_{3-6}$ carbocycle and heterocycle;

each R is independently selected from the group consisting of $C_{1-3}$ alkyl, $C_{2-3}$ alkenyl, and H;

each R' is independently selected from the group consisting of $C_{1-18}$ alkyl, $C_{2-18}$ alkenyl, —R*YR", —YR", and H;

each R" is independently selected from the group consisting of $C_{3-14}$ alkyl and $C_{3-14}$ alkenyl;

each R* is independently selected from the group consisting of $C_{1-12}$ alkyl and $C_{2-12}$ alkenyl;

each Y is independently a $C_{3-6}$ carbocycle;

each X is independently selected from the group consisting of F, Cl, Br, and I; and m is selected from 5, 6, 7, 8, 9, 10, 11, 12, and 13, or salts or isomers thereof.

In some embodiments, another subset of compounds of Formula (I) includes those in which $R_1$ is selected from the group consisting of $C_{5-30}$ alkyl, $C_{5-20}$ alkenyl, —R*YR", —YR", and —R"M'R';

$R_2$ and $R_3$ are independently selected from the group consisting of H, $C_{1-14}$ alkyl, $C_{2-14}$ alkenyl, —R*YR", —YR", and —R*OR", or $R_2$ and $R_3$, together with the atom to which they are attached, form a heterocycle or carbocycle;

$R_4$ is selected from the group consisting of a $C_{3-6}$ carbocycle, —$(CH_2)_nQ$, —$(CH_2)$ ICHQR, —CHQR, —CQ $(R)_2$, and unsubstituted $C_{1-6}$ alkyl, where Q is selected from a $C_{3-6}$ carbocycle, a 5- to 14-membered heteroaryl having one or more heteroatoms selected from N, O, and S, —OR, —$O(CH_2)_nN(R)_2$, —C(O)OR, —O C(O)R, —CX3, —CX2H, —CXH2, —CN, —$C(O)N(R)_2$, —N(R) C(O)R, —$N(R)S(O)_2R$, —$N(R)C(O)N(R)_2$, —N(R) C(S) $N(R)_2$, —C $RN(R)_2C(O)OR$, —$N(R)R_8$, —$O(CH_2)$, OR, —N(R)C(=$NR_9$) $N(R)_2$, —N(R)C (=CHR9) $N(R)_2$, —O $C(O)N(R)_2$, —N(R)C(O)OR, —N(OR)C(O)R, —N(OR) $S(O)_2R$, —N(OR) C(O)OR, —N(OR) $C(O)N(R)_2$, —N(OR) C(S) $N(R)_2$, —N(OR)C(=$NR_9$) $N(R)_2$, —N(OR) C(=CHR9) $N(R)_2$, —C(=$NR_9$)R, —C(O)N(R)OR,
and —C(=$NR_9$) $N(R)_2$, and each n is independently selected from 1, 2, 3, 4, and 5; each $R_5$ is independently selected from the group consisting of $C_{1-3}$ alkyl, $C_{2-3}$ alkenyl, and H;

each $R_6$ is independently selected from the group consisting of $C_{1-3}$ alkyl, $C_{2-3}$ alkenyl, and H;

M and M' are independently selected from —C(O)O—, —O C(O)—, —C(O)N(R')—, —N(R') C(O)—, —C(O)—, —C(S)—, —C(S)S—, —S C(S)—, —CH (OH)—, —P(O) (OR')O—, —$S(O)_2$—, —S—S—, an aryl group, and a heteroaryl group;

$R_7$ is selected from the group consisting of $C_{1-3}$ alkyl, $C_{2-3}$ alkenyl, and H;

$R_5$ is selected from the group consisting of $C_{3-6}$ carbocycle and heterocycle;

$R_9$ is selected from the group consisting of H, CN, NO2, $C_{1-6}$ alkyl, —O R, —$S(O)_2R$, —$S(O)_2N(R)_2$, $C_{2-6}$ alkenyl, $C_{3-6}$ carbocycle and heterocycle;

each R is independently selected from the group consisting of $C_{1-3}$ alkyl, $C_{2-3}$ alkenyl, and H;

each R' is independently selected from the group consisting of $C_{1-18}$ alkyl, $C_{2-18}$ alkenyl, —R*YR", —YR", and H;

each R" is independently selected from the group consisting of $C_{3-14}$ alkyl and $C_{3-14}$ alkenyl;

each R* is independently selected from the group consisting of $C_{1-12}$ alkyl and $C_{2-12}$ alkenyl;

each Y is independently a $C_{3-6}$ carbocycle;

each X is independently selected from the group consisting of F, Cl, Br, and I; and m is selected from 5, 6, 7, 8, 9, 10, 11, 12, and 13, or salts or isomers thereof.

In some embodiments, another subset of compounds of Formula (I) includes those in which $R_1$ is selected from the group consisting of $C_{5-30}$ alkyl, $C_{5-20}$ alkenyl, —R*YR", —YR", and —R"M'R';

$R_2$ and $R_3$ are independently selected from the group consisting of H, $C_{2-14}$ alkyl, $C_{2-14}$ alkenyl, —R*YR", —YR", and —R*OR", or $R_2$ and $R_3$, together with the atom to which they are attached, form a heterocycle or carbocycle;

$R_4$ is —$(CH_2)_nQ$ or —$(CH_2)_nCHQR$, where Q is —$N(R)_2$, and n is selected from 3, 4, and 5;

each $R_5$ is independently selected from the group consisting of $C_{1-3}$ alkyl, $C_{2-3}$ alkenyl, and H;

each $R_6$ is independently selected from the group consisting of $C_{1-3}$ alkyl, $C_{2-3}$ alkenyl, and H;

M and M' are independently selected from —C(O)O—, —O C(O)—, —C(O)N(R')—, —N(R') C(O)—, —C(O)—, —C(S)—, —C(S)S—, —S C(S)—, —CH (OH)—, —P(O) (OR')O—, —$S(O)_2$—, —S—S—, an aryl group, and a heteroaryl group;

$R_7$ is selected from the group consisting of $C_{1-3}$ alkyl, $C_{2-3}$ alkenyl, and H; each R is independently selected from the group consisting of $C_{1-3}$ alkyl, $C_{2-3}$ alkenyl, and H;

each R' is independently selected from the group consisting of $C_{1-18}$ alkyl, $C_{2-18}$ alkenyl, —R*YR", —YR", and H;

each R" is independently selected from the group consisting of $C_{3-14}$ alkyl and $C_{3-14}$ alkenyl;

each R* is independently selected from the group consisting of $C_{1-12}$ alkyl and $C_{1-12}$ alkenyl;

each Y is independently a $C_{3-6}$ carbocycle;

each X is independently selected from the group consisting of F, Cl, Br, and I; and m is selected from 5, 6, 7, 8, 9, 10, 11, 12, and 13, or salts or isomers thereof.

In some embodiments, another subset of compounds of Formula (I) includes those in which $R_1$ is selected from the group consisting of $C_{5-30}$ alkyl, $C_{5-20}$ alkenyl, —R*YR", —YR", and —R"M'R';

$R_2$ and $R_3$ are independently selected from the group consisting of $C_{1-14}$ alkyl, $C_{2-14}$ alkenyl, —R*YR", —YR", and —R*OR", or $R_2$ and $R_3$, together with the atom to which they are attached, form a heterocycle or carbocycle;

$R_4$ is selected from the group consisting of —$(CH_2)_nQ$, —$(CH_2)_nCHQR$, —CHQR, and —$CQ(R)_2$, where Q is —$N(R)_2$, and n is selected from 1, 2, 3, 4, and 5;

each $R_5$ is independently selected from the group consisting of $C_{1-3}$ alkyl, $C_{2-3}$ alkenyl, and H;

each $R_6$ is independently selected from the group consisting of $C_{1-3}$ alkyl, $C_{2-3}$ alkenyl, and H;

M and M' are independently selected from —C(O)O—, —O C(O)—, —C(O)N(R')—, —N(R') C(O)—, —C(O)—, —C(S)—, —C(S)S—, —S C(S)—, —CH (OH)—, —P(O) (OR')O—, —$S(O)_2$—, —S—S—, an aryl group, and a heteroaryl group;

$R_7$ is selected from the group consisting of $C_{1-3}$ alkyl, $C_{2-3}$ alkenyl, and H; each R is independently selected from the group consisting of $C_{1-3}$ alkyl, $C_{2-3}$ alkenyl, and H;

each R' is independently selected from the group consisting of $C_{1-18}$ alkyl, $C_{2-18}$ alkenyl, —R*YR", —YR", and H;

each R" is independently selected from the group consisting of $C_{3-14}$ alkyl and $C_{3-14}$ alkenyl;

each R* is independently selected from the group consisting of $C_{1-12}$ alkyl and $C_{1-12}$ alkenyl;

each Y is independently a $C_{3-6}$ carbocycle;

each X is independently selected from the group consisting of F, Cl, Br, and I; and m is selected from 5, 6, 7, 8, 9, 10, 11, 12, and 13, or salts or isomers thereof.

In some embodiments, a subset of compounds of Formula (I) includes those of Formula (IA):

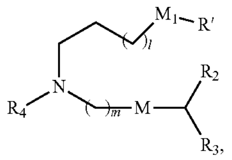

(IA)

or a salt or isomer thereof, wherein 1 is selected from 1, 2, 3, 4, and 5; m is selected from 5, 6, 7, 8, and 9; $M_1$ is a bond or M'; $R_4$ is unsubstituted $C_{1-3}$ alkyl, or —$(CH_2)_nQ$, in which Q is OH, —NHC(S) $N(R)_2$, —NHC(O)$N(R)_2$, —N(R)C(O)R, —N(R)$S(O)_2R$, —N(R)$R_8$, —NHC(=$NR_9$) $N(R)_2$, —NHC(=CHR9) $N(R)_2$, —O C(O)$N(R)_2$, —N(R)C(O)OR, heteroaryl or heterocycloalkyl; M and M' are independently selected from —C(O)O—, —O C(O)—, —C(O)N(R')—, —P(O)(OR')O—, —S—S—, an aryl group, and a heteroaryl group; and $R_2$ and $R_3$ are independently selected from the group consisting of H, $C_{1-14}$ alkyl, and $C_{2-14}$ alkenyl.

In some embodiments, a subset of compounds of Formula (I) includes those of Formula (II):

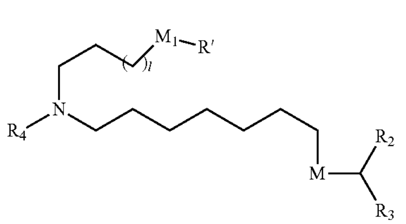

(II)

or a salt or isomer thereof, wherein 1 is selected from 1, 2, 3, 4, and 5; M1 is a bond or M'; $R_4$ is unsubstituted $C_{1-3}$ alkyl, or —$(CH_2)_nQ$, in which n is 2, 3, or 4, and Q is OH, —NHC(S) $N(R)_2$, —NHC(O)$N(R)_2$, —N(R)

C(O)R, —N(R)S(O)$_2$R, —N(R)R$_8$, —NHC(═NR$_9$) N(R)$_2$, —NHC(═CHR9) N(R)$_2$, —O C(O)N(R)$_2$, —N(R)C(O)OR, heteroaryl or heterocycloalkyl; M and M' are independently selected from —C(O)O—, —O C(O)—, —C(O)N(R')—, — P(O)(OR')O—, —S—S—, an aryl group, and a heteroaryl group; and $R_2$ and $R_3$ are independently selected from the group consisting of H, $C_{1-14}$ alkyl, and $C_{2-14}$ alkenyl.

In some embodiments, a subset of compounds of Formula (I) includes those of Formula (IIa), (IIb), (IIc), or (Ie):

(IIa)

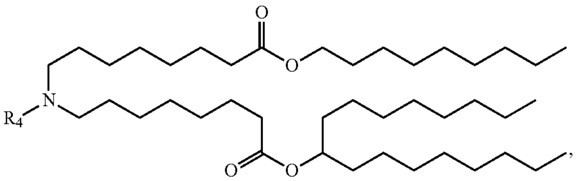

, (IIb)

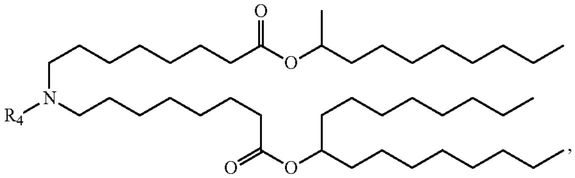

, (IIc)

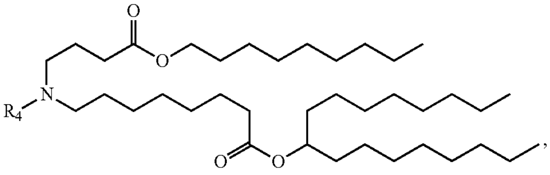

, or (IIe)

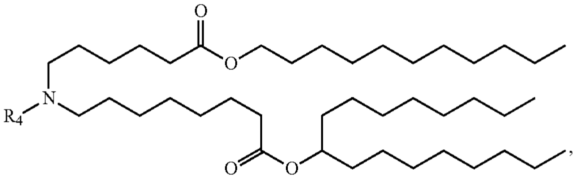

, or a salt or isomer thereof, wherein $R_4$ is as described herein.

In some embodiments, a subset of compounds of Formula (I) includes those of

Formula (IId):

(IId)

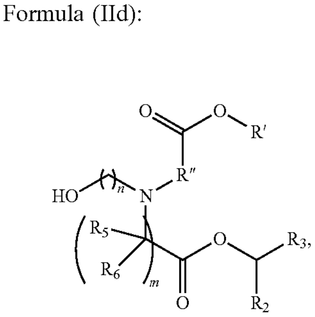

or a salt or isomer thereof, wherein n is 2, 3, or 4; and m, R', R", and $R_2$ through $R_6$ are as described herein. For example, each of $R_2$ and $R_3$ may be independently selected from the group consisting of $C_{5-14}$ alkyl and $C_{5-14}$ alkenyl.

In some embodiments, a subset of compounds of Formula (I) includes those of Formula (IIa), (IIb), (IIc), or (IIe):

(IIa)

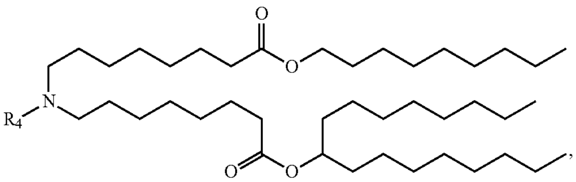

, (IIb)

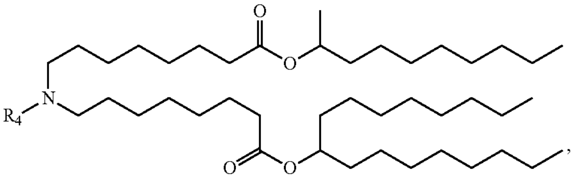

, (IIc)

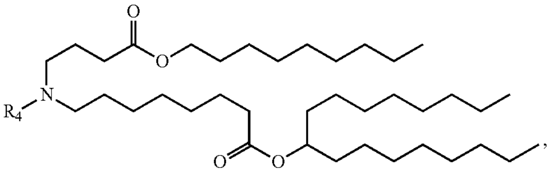

, or (IIe)

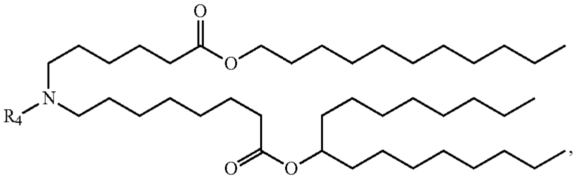

, or a salt or isomer thereof, wherein $R_4$ is as described herein.

In some embodiments, a subset of compounds of Formula (I) includes those of

Formula (IId):

(IId)

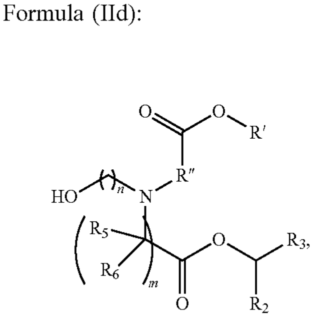

or a salt or isomer thereof, wherein n is 2, 3, or 4; and m, R', R", and $R_2$ through $R_6$ are as described herein. For example, each of $R_2$ and $R_3$ may be independently selected from the group consisting of $C_{5-14}$ alkyl and $C_{5-14}$ alkenyl.

In some embodiments, the compound of Formula (I) is selected from the group consisting of:

(Compound 1)
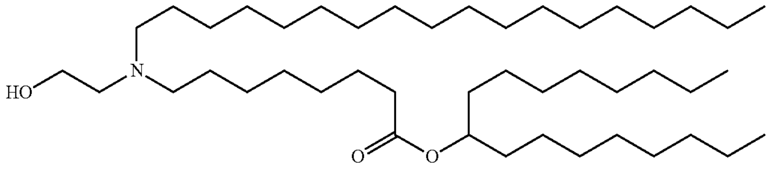,
(Compound 2)
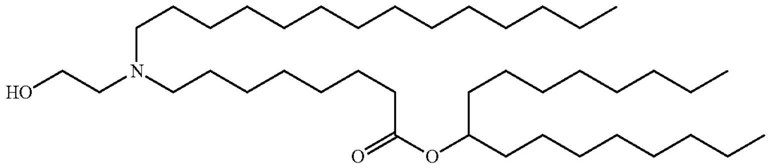,
(Compound 3)
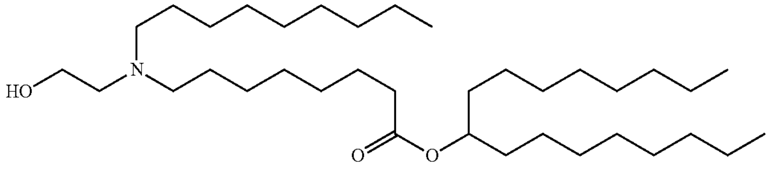,
(Compound 4)
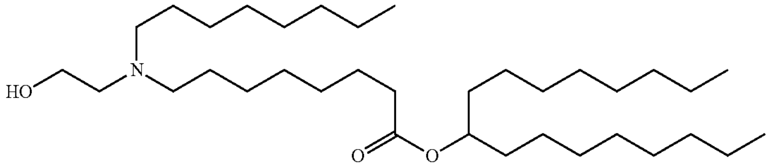,
(Compound 5)
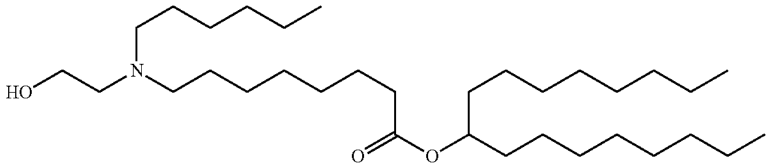,
(Compound 6)
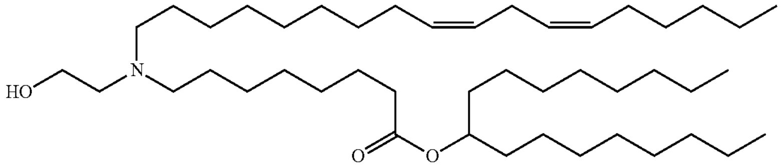,
(Compound 7)
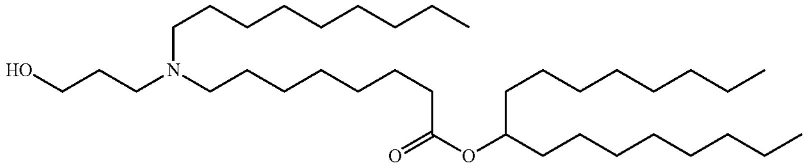,
(Compound 8)
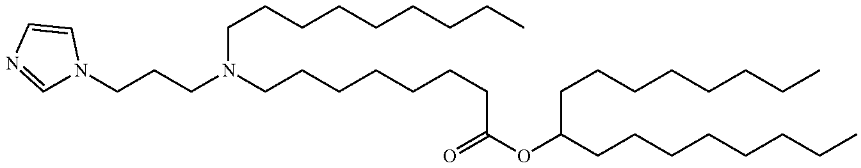,
(Compound 9)
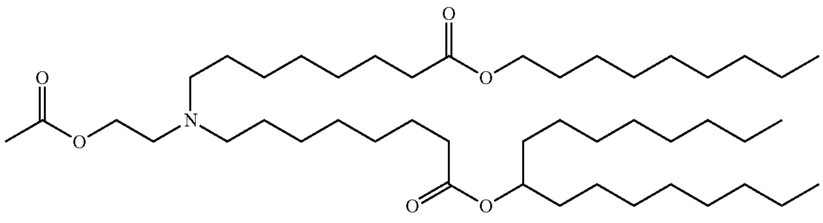, -continued
(Compound 10)
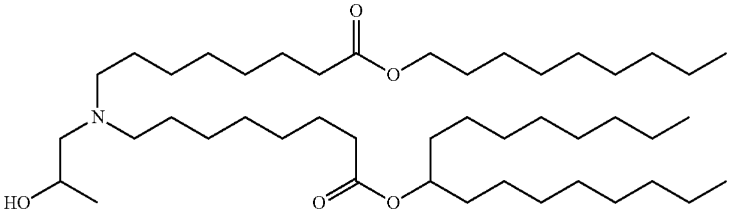
,
(Compound 11)
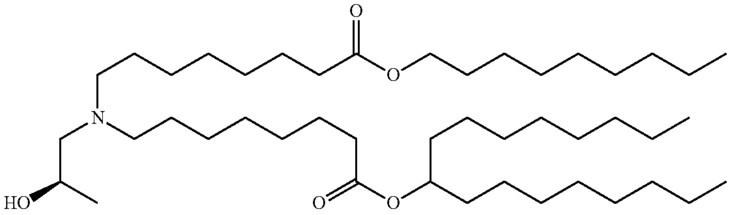
,
(Compound 12)
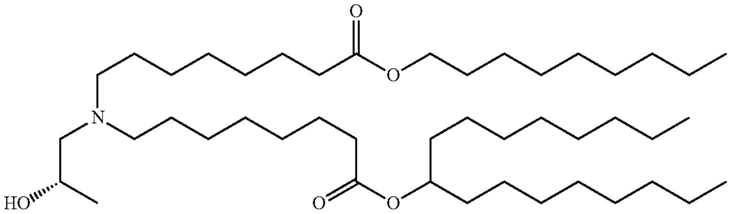
,
(Compound 13)
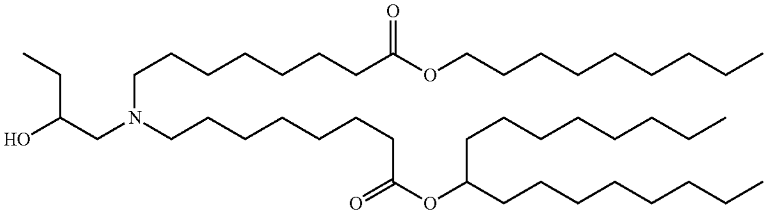
,
(Compound 14)
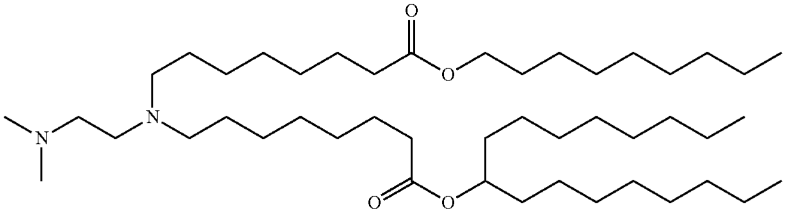
,
(Compound 15)
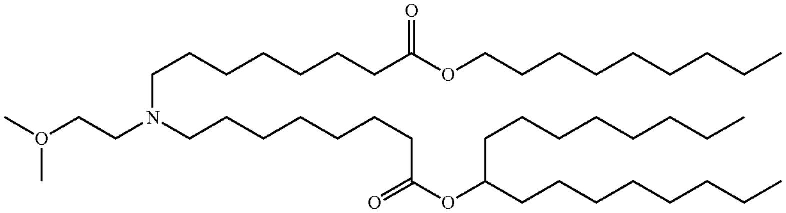
,
(Compound 16)
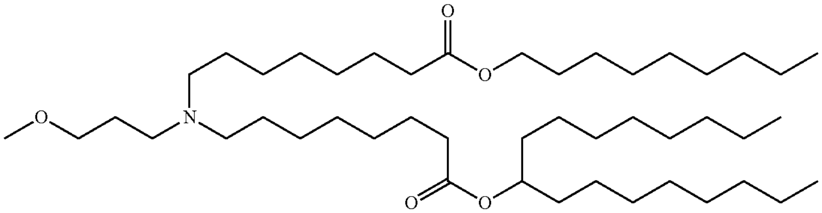
, -continued
(Compound 17)
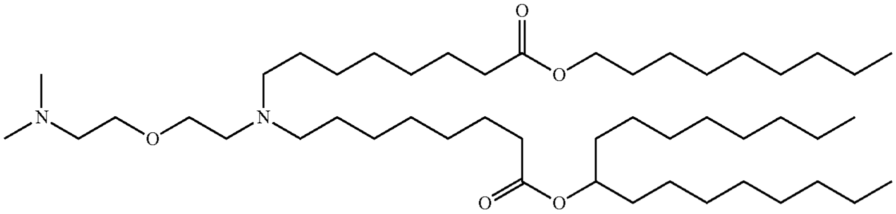
(Compound 18)
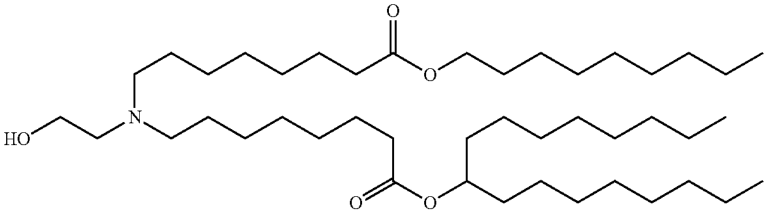
(Compound 19)
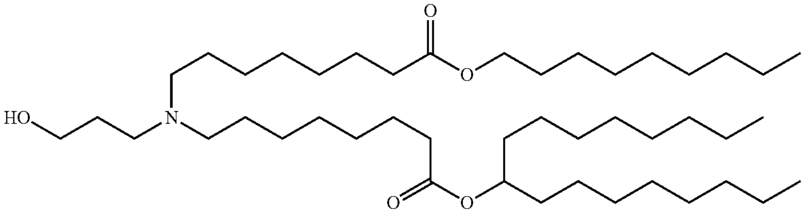
(Compound 20)
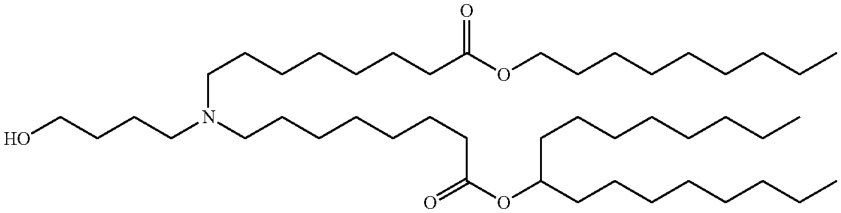
(Compound 21)
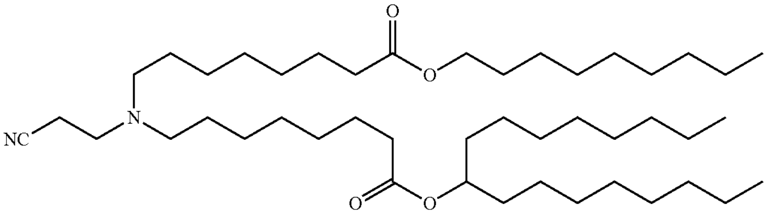
(Compound 22)
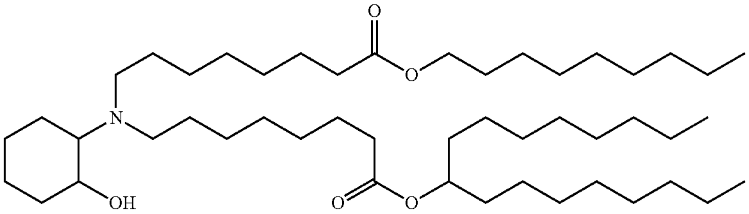
(Compound 23)
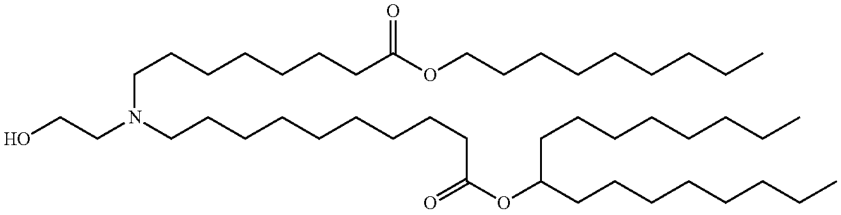
, -continued
(Compound 24)
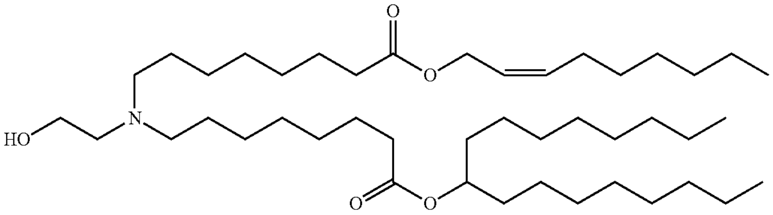
,
(Compound 25)
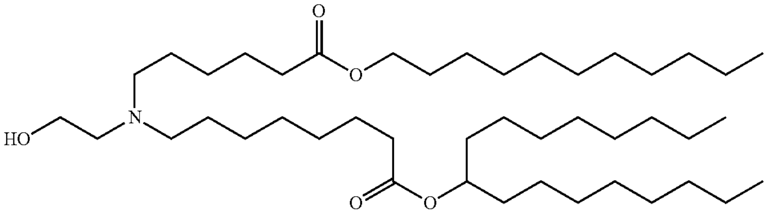
,
(Compound 26)
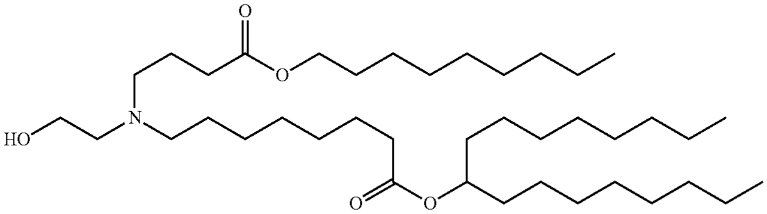
,
(Compound 27)
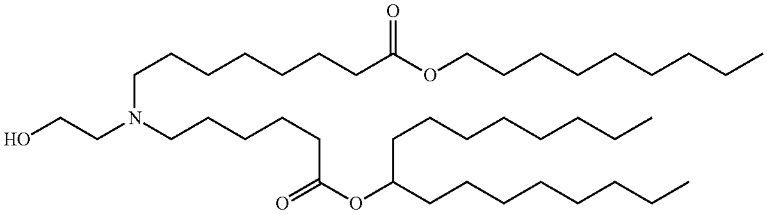
,
(Compound 28)
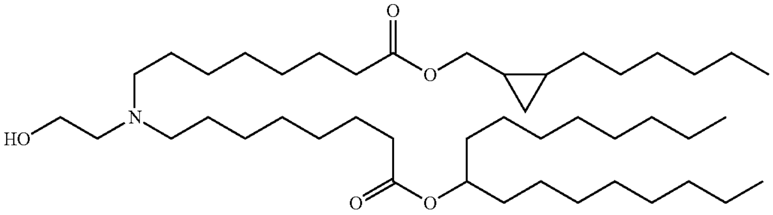
,
(Compound 29)
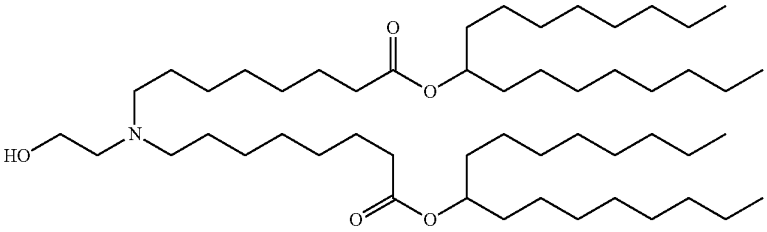
,
(Compound 30)
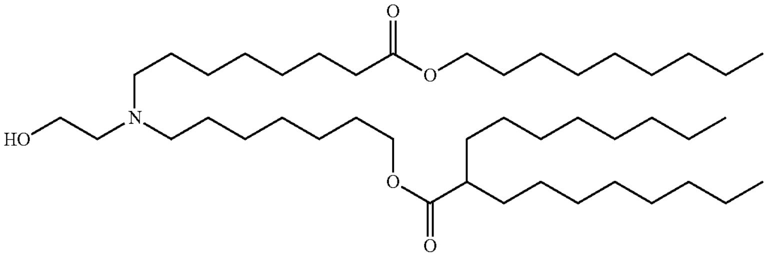
, -continued
(Compound 31)
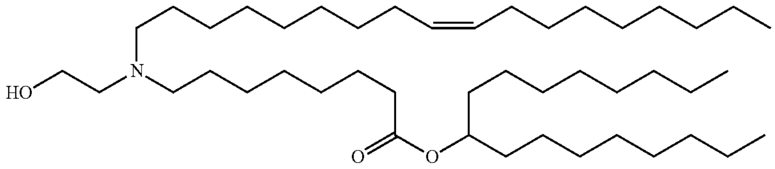
,
(Compound 32)
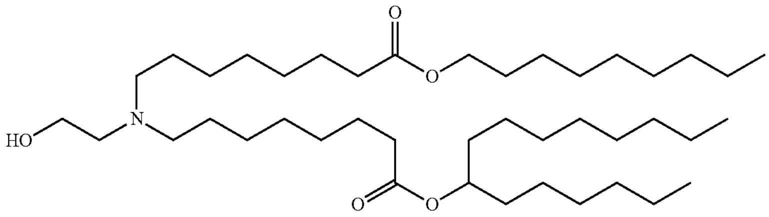
,
(Compound 33)
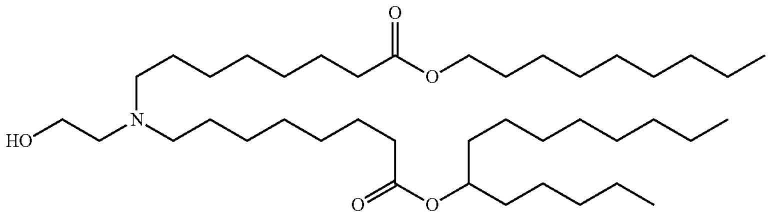
,
(Compound 34)
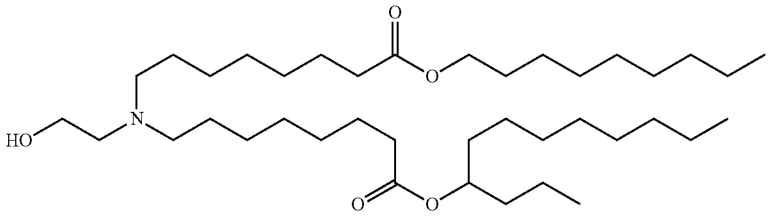
,
(Compound 35)
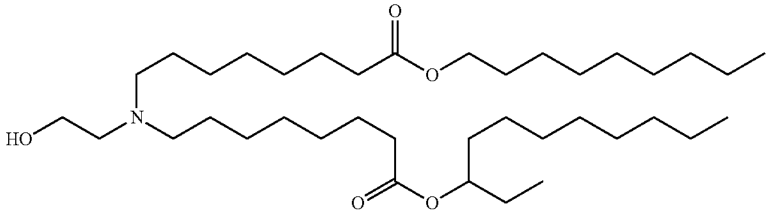
,
(Compound 36)
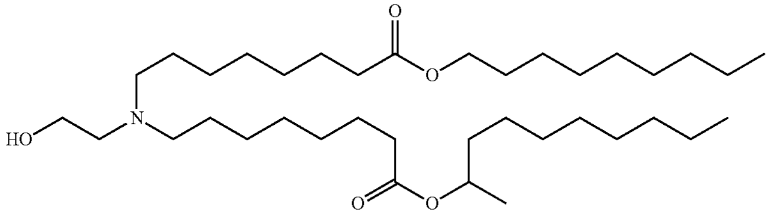
,
(Compound 37)
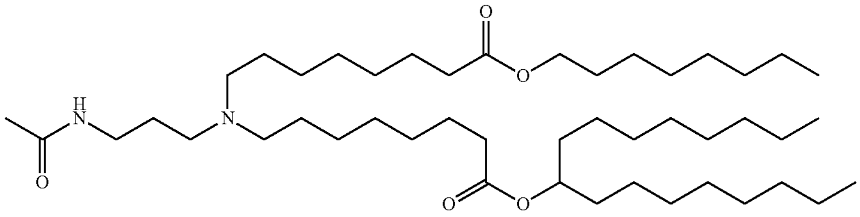
, -continued
(Compound 38)
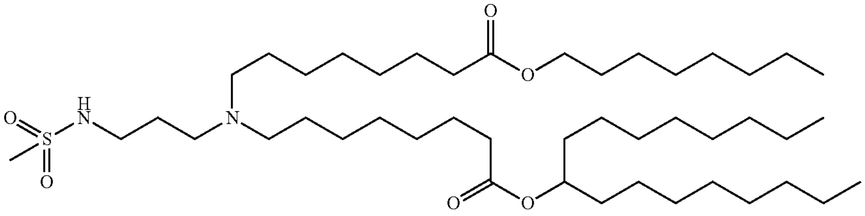
,
(Compound 39)
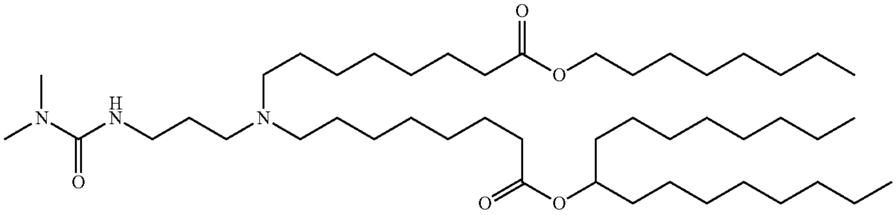
,
(Compound 40)
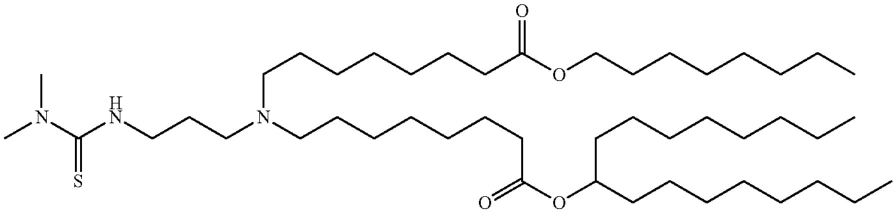
,
(Compound 41)
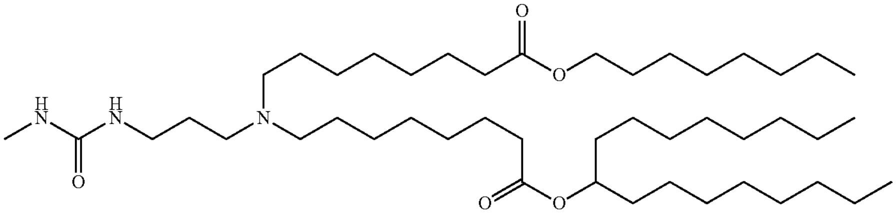
,
(Compound 42)
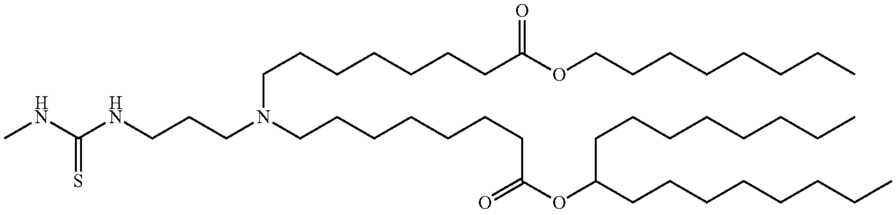
,
(Compound 43)
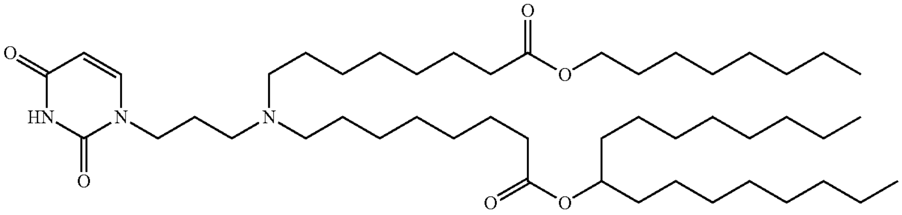
,
(Compound 44)
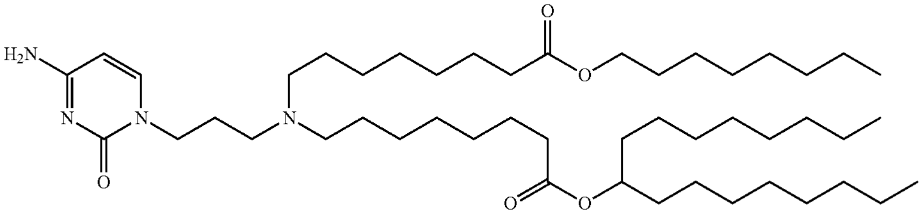
, -continued
(Compound 45)
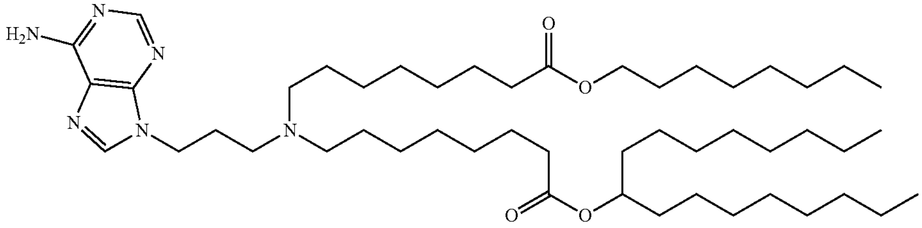
,
(Compound 46)
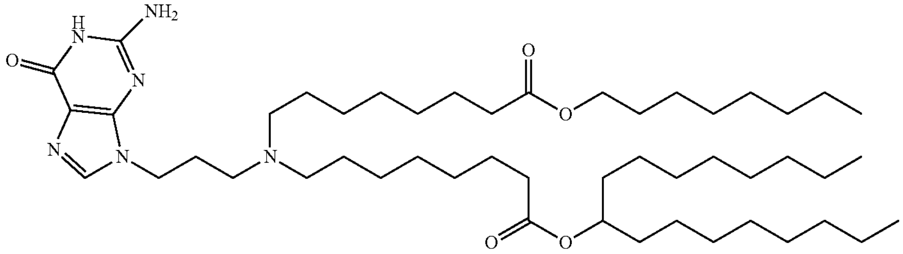
,
(Compound 47)
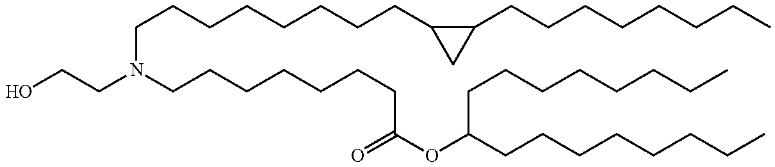
,
(Compound 48)
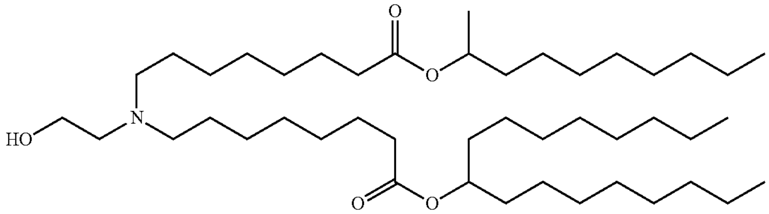
,
(Compound 49)
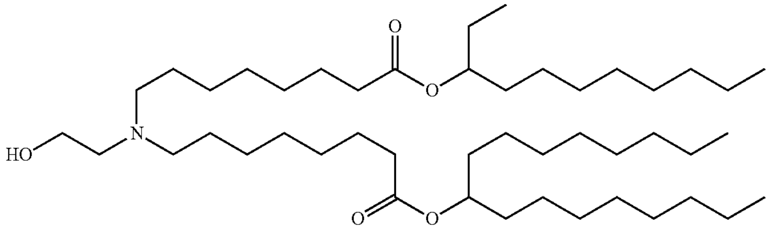
,
(Compound 50)
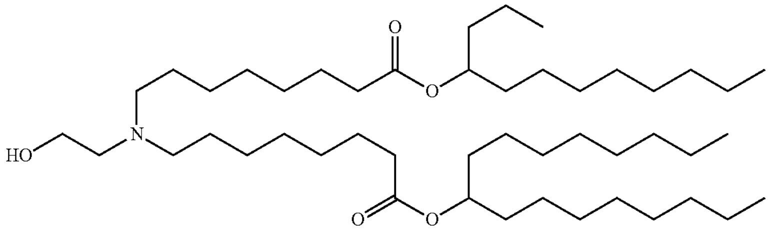
,
(Compound 51)
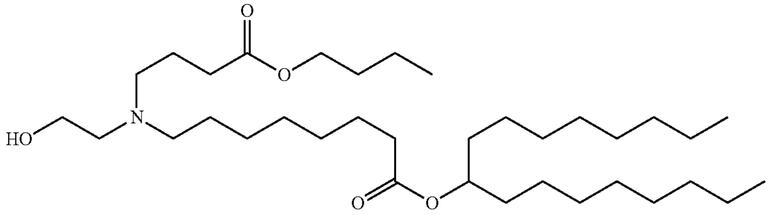
, -continued
(Compound 52)
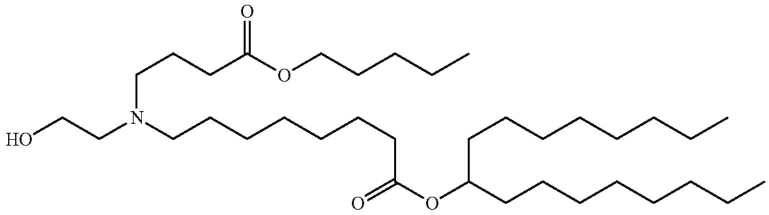
,
(Compound 53)
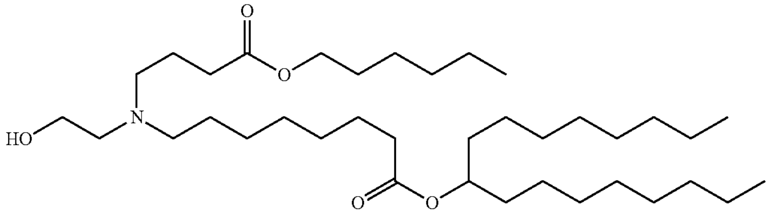
,
(Compound 54)
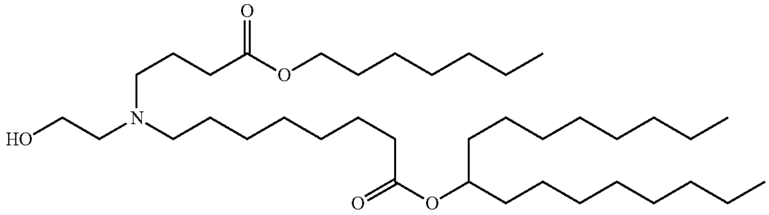
,
(Compound 55)
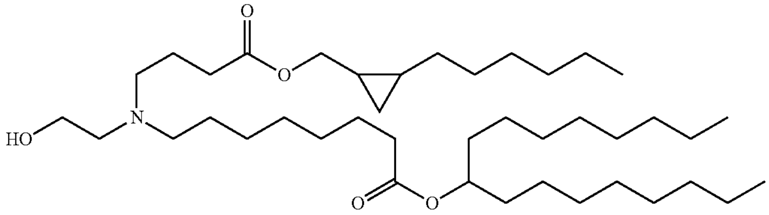
,
(Compound 56)
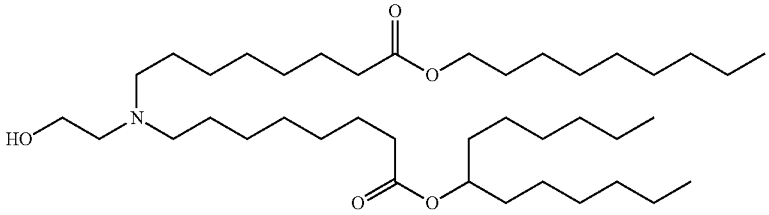
,
(Compound 57)
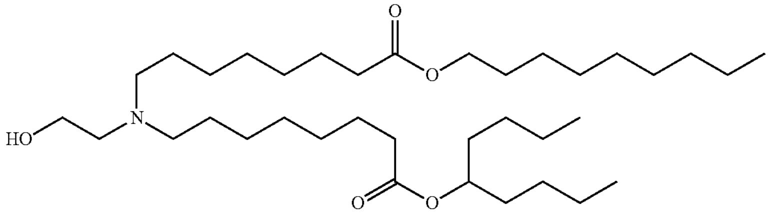
,
(Compound 58)
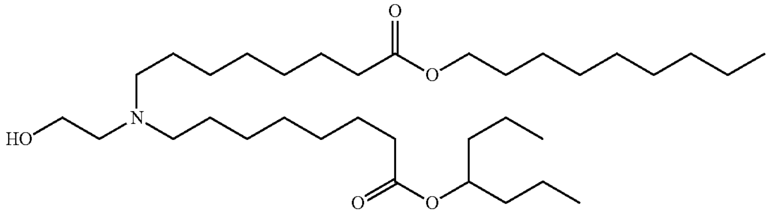
, -continued
(Compound 59)
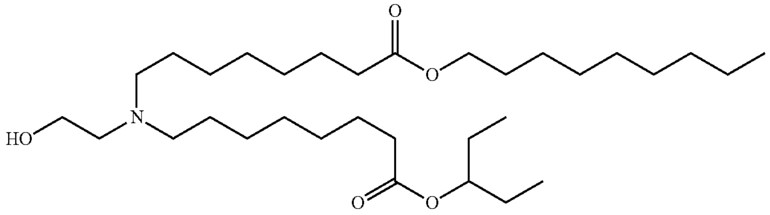
,
(Compound 60)
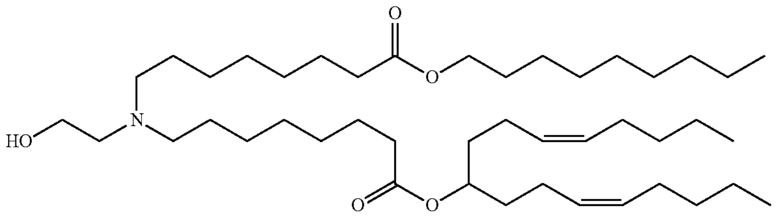
, and
(Compound 61)
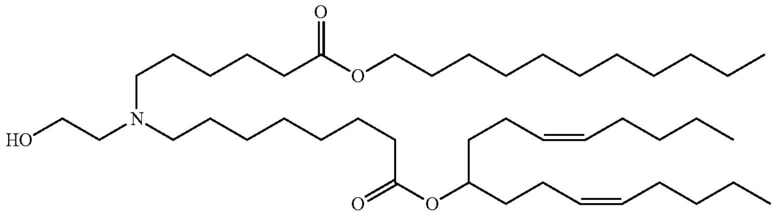
.
In further embodiments, the compound of Formula (I) is selected from the group consisting of:
(Compound 62)
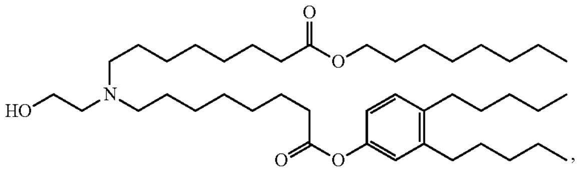
,
-continued
(Compound 63)
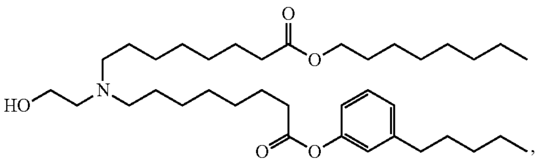
, and
(Compound 64)
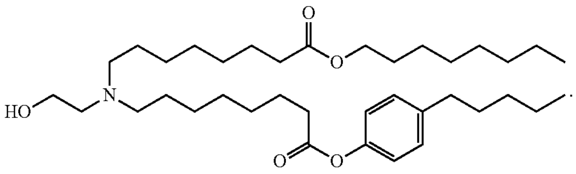
.
In some embodiments, the compound of Formula (I) is selected from the group consisting of:
(Compound 65)
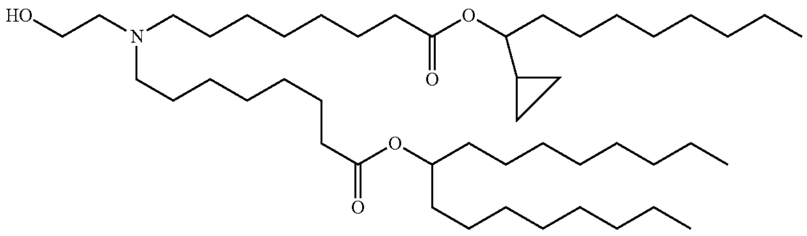
, -continued
(Compound 66)
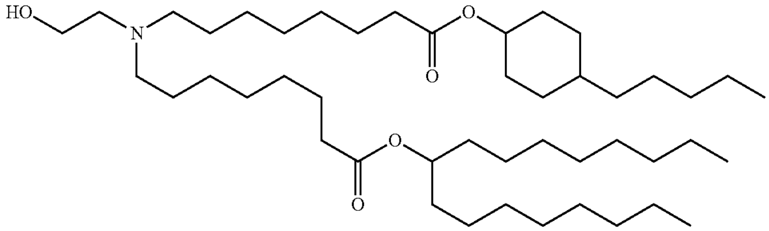
,
(Compound 67)
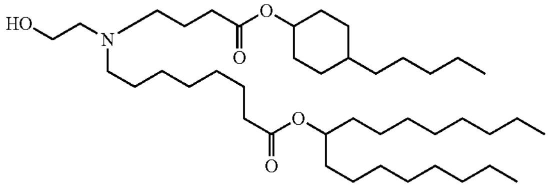
,
(Compound 68)
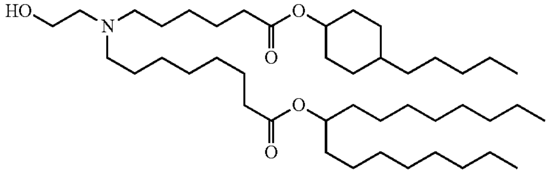
,
(Compound 69)
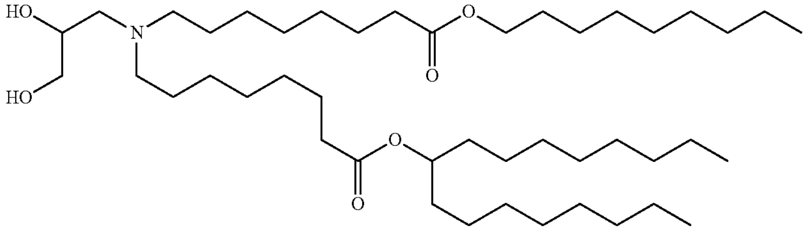
,
(Compound 70)
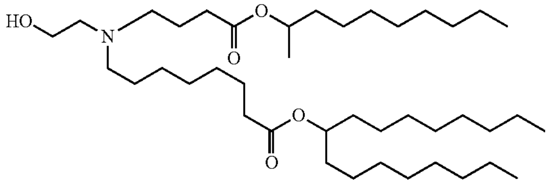
,
(Compound 71)
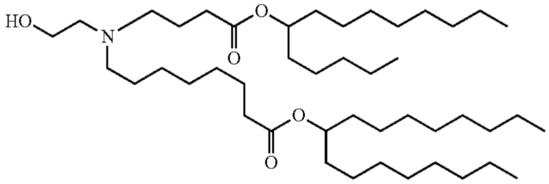
,
(Compound 72)
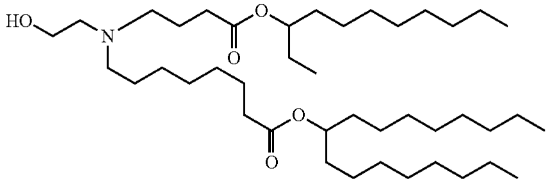
,
(Compound 73)
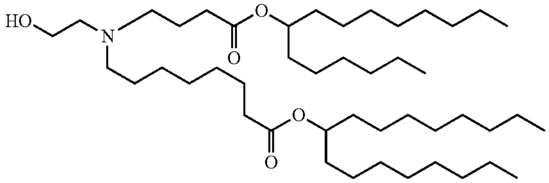
,
(Compound 74)
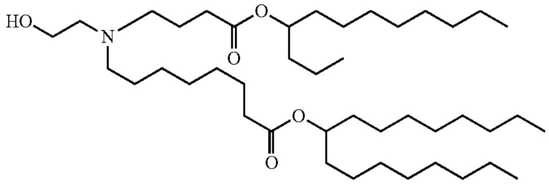
,
(Compound 75)
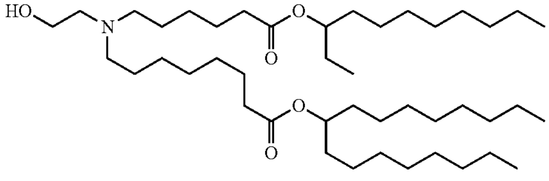
,
(Compound 76)
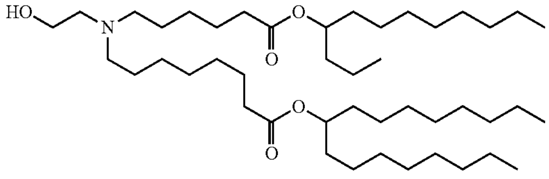
,
(Compound 77)
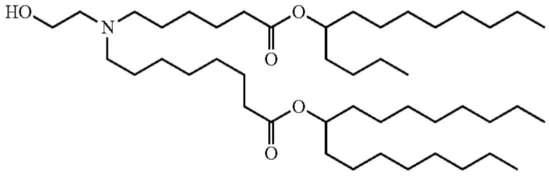
, -continued
(Compound 78)
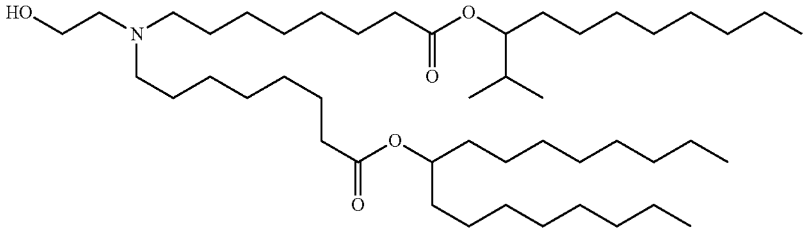
,
(Compound 79)
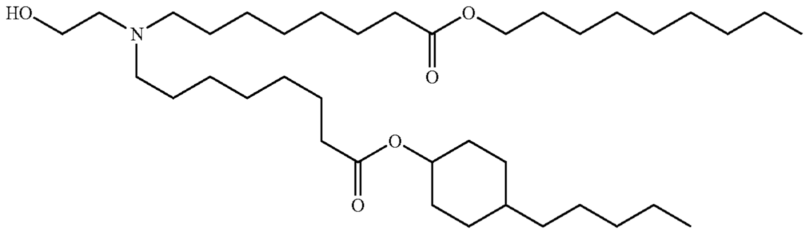
,
(Compound 80)
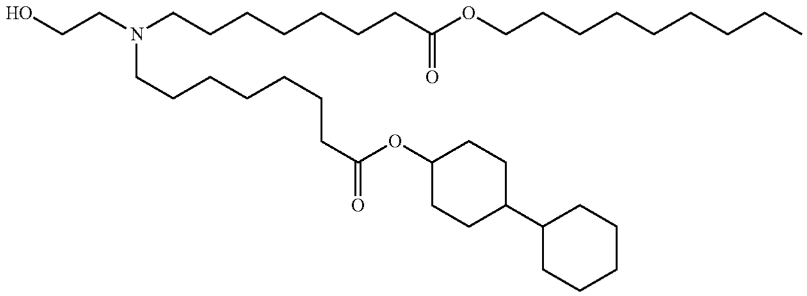
,
(Compound 81)
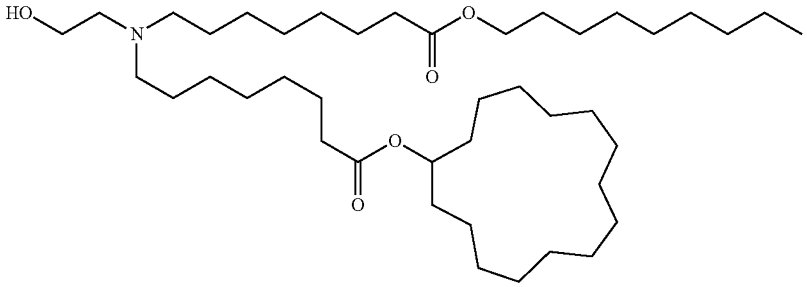
,
(Compound 82)
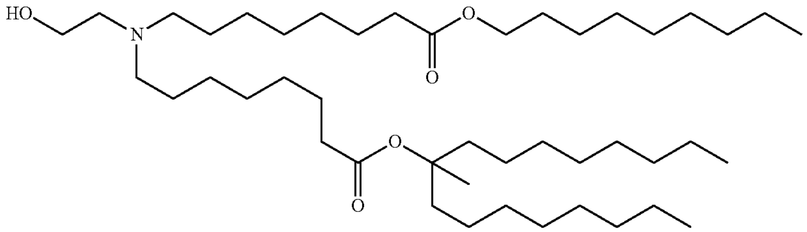
,
(Compound 83)
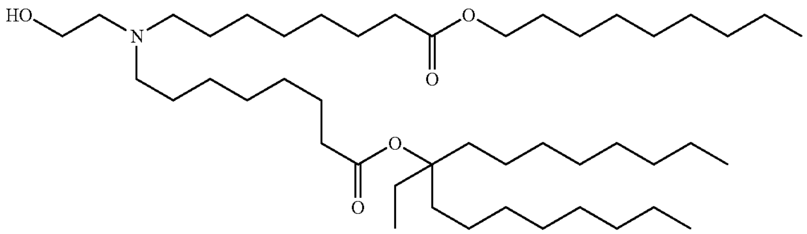
, -continued
(Compound 84)
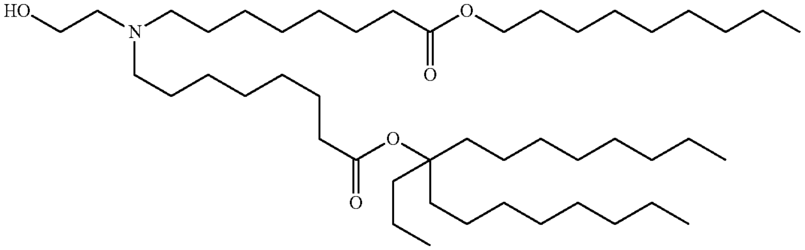
,
(Compound 85)
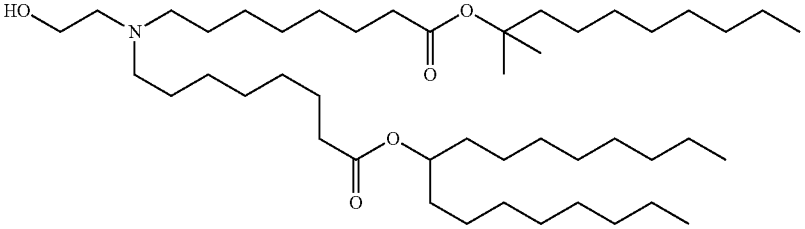
,
(Compound 86)
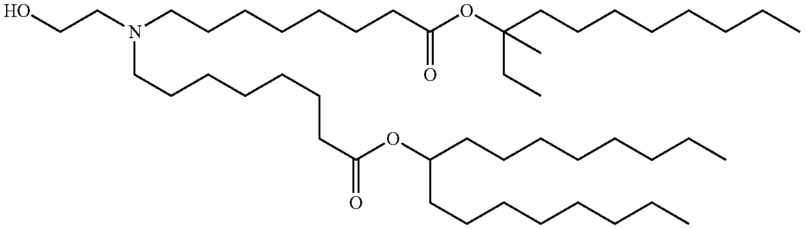
,
(Compound 87)
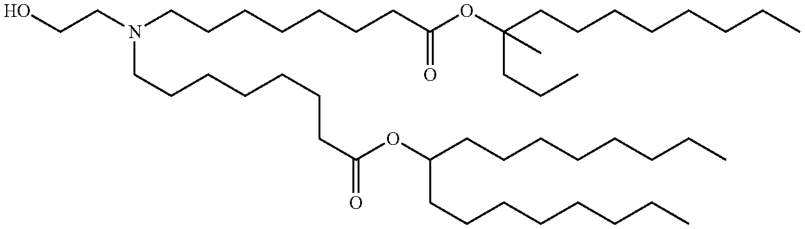
,
(Compound 88)
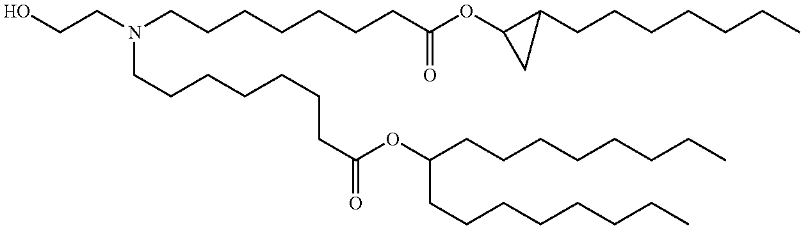
,
(Compound 89)
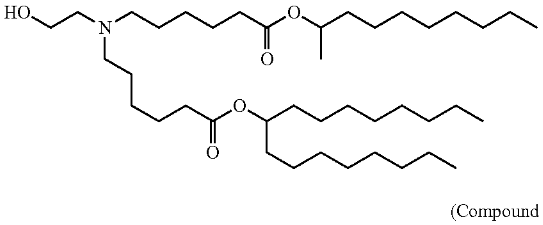
,
(Compound 90)
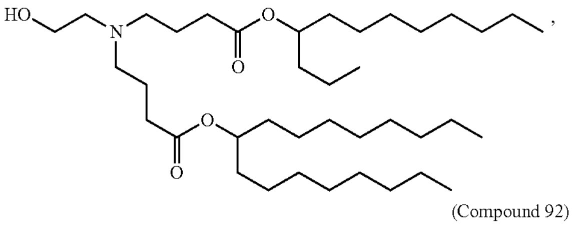
,
(Compound 91)
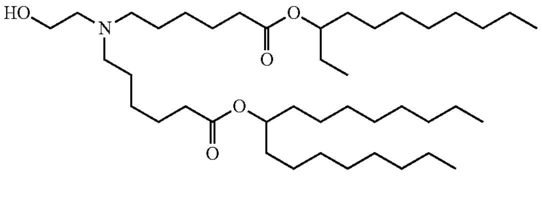
,
(Compound 92)
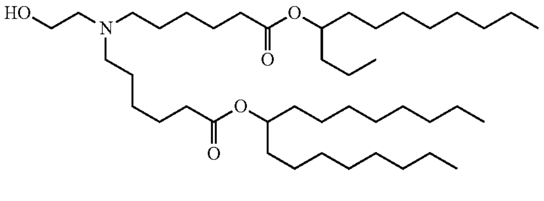
, -continued
(Compound 93)
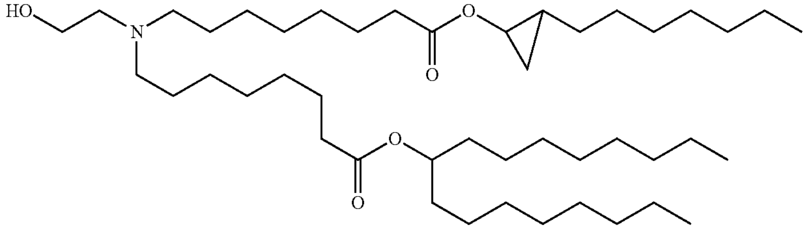
,
(Compound 94)
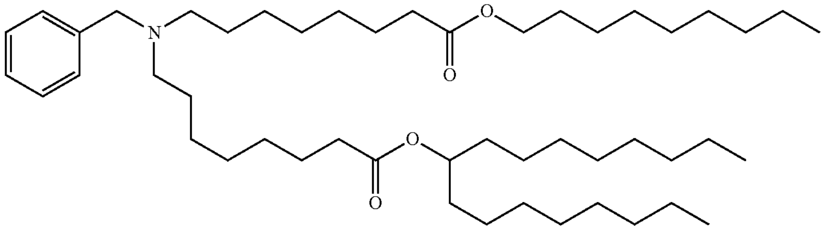
,
(Compound 95)
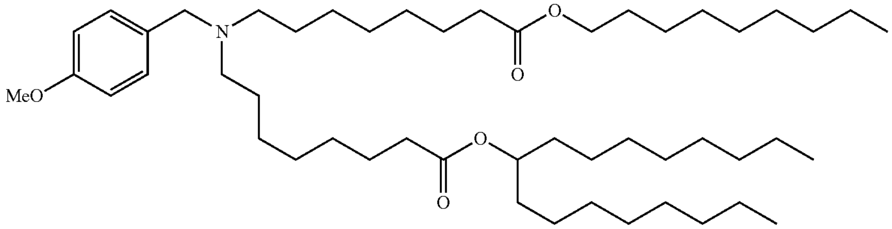
,
(Compound 96)
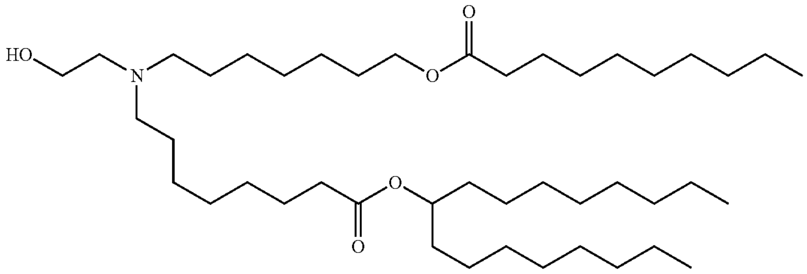
,
(Compound 97)
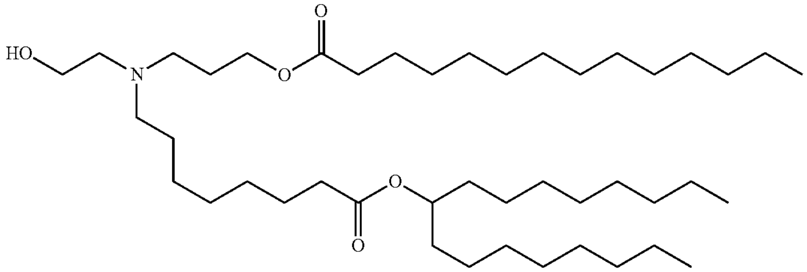
,
(Compound 98)
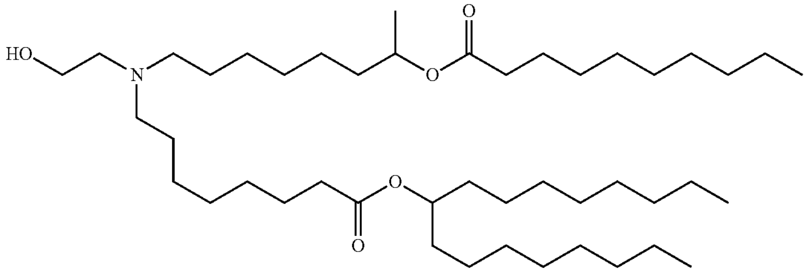
, -continued
(Compound 99)
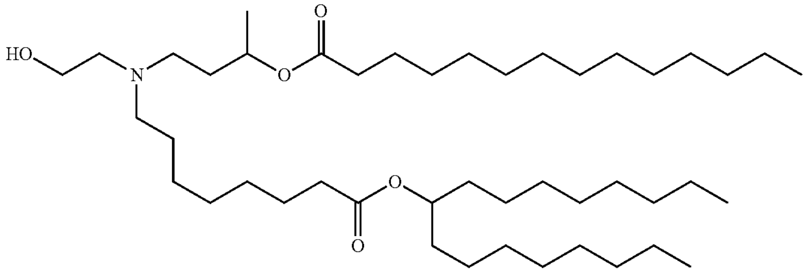
,
(Compound 100)
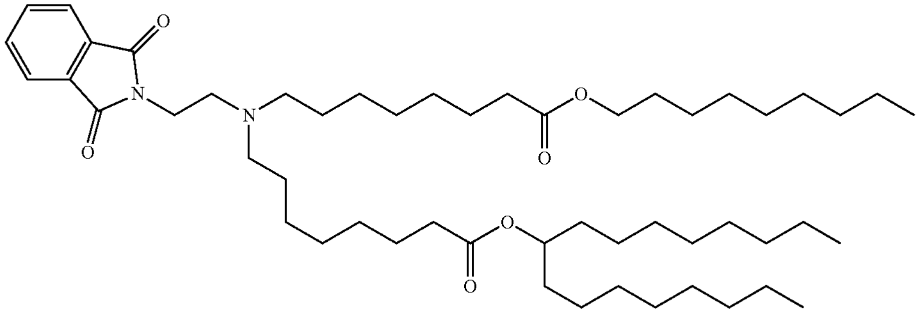
,
(Compound 101)
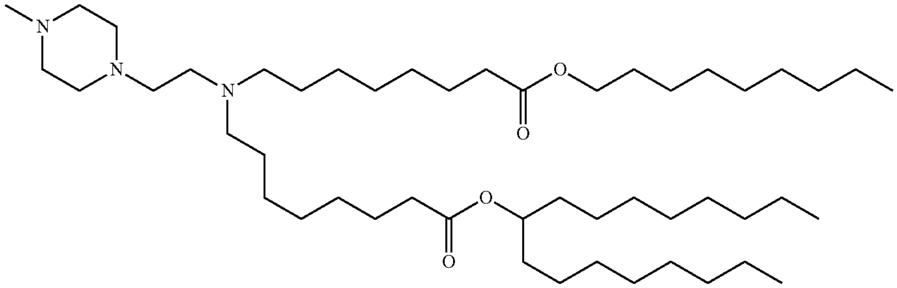
,
(Compound 102)
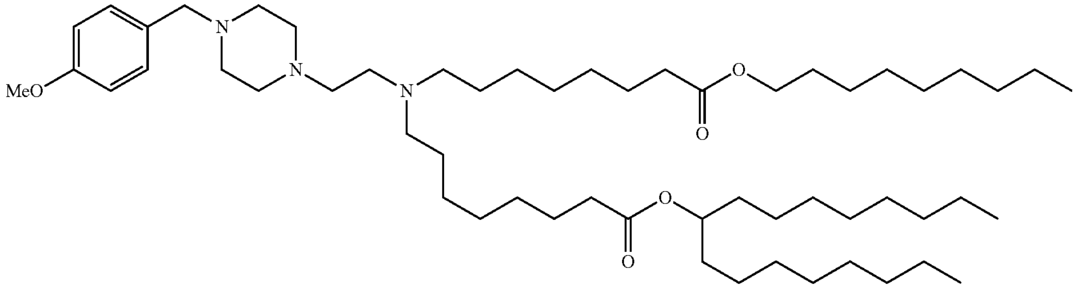
,
(Compound 103)
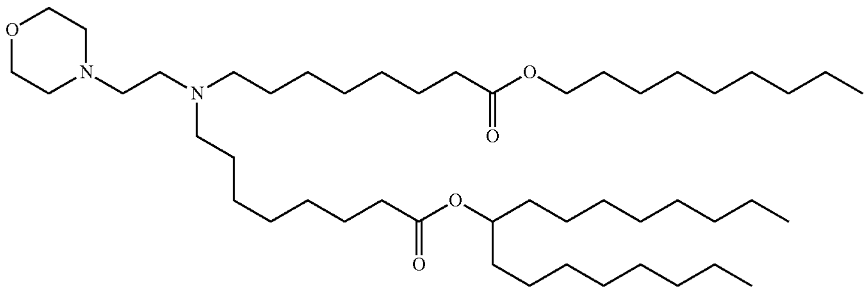
, -continued
(Compound 104)
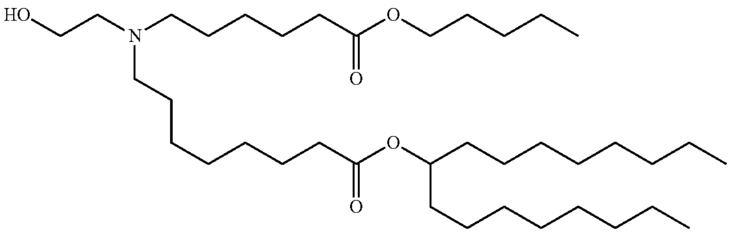
,
(Compound 105)
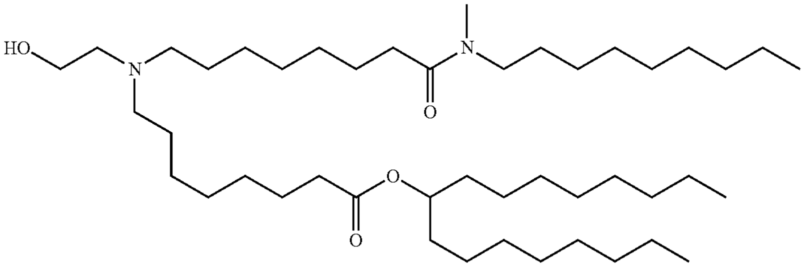
,
(Compound 106)
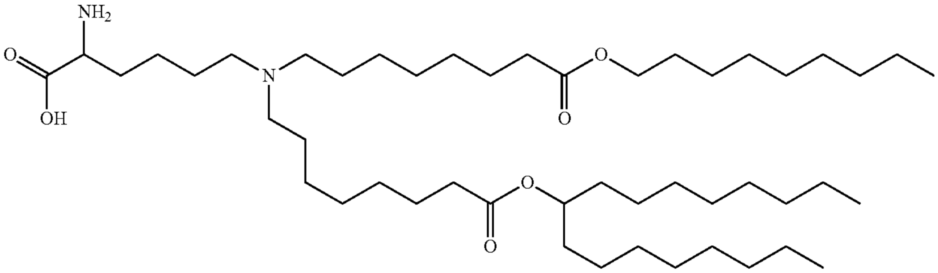
,
(Compound 107)
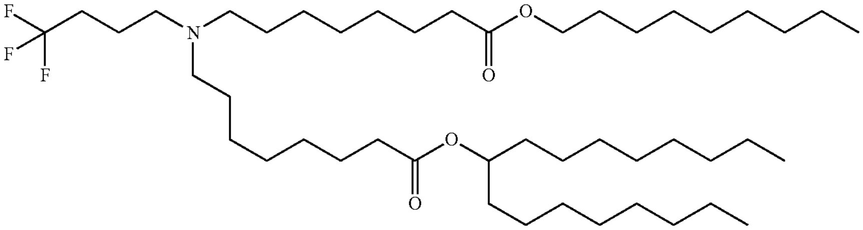
,
(Compound 108)
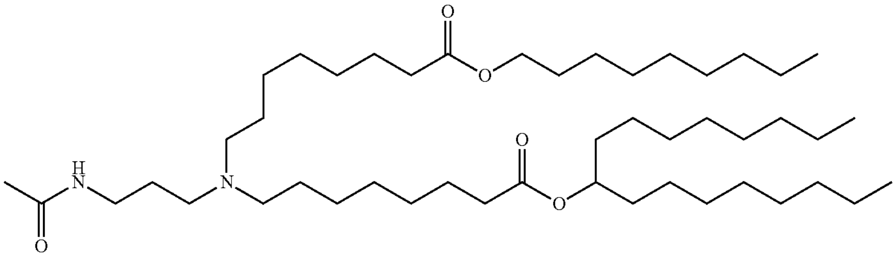
,
(Compound 109)
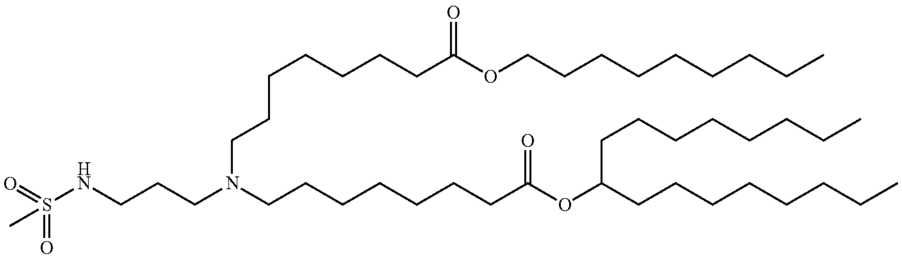
, -continued
(Compound 110)
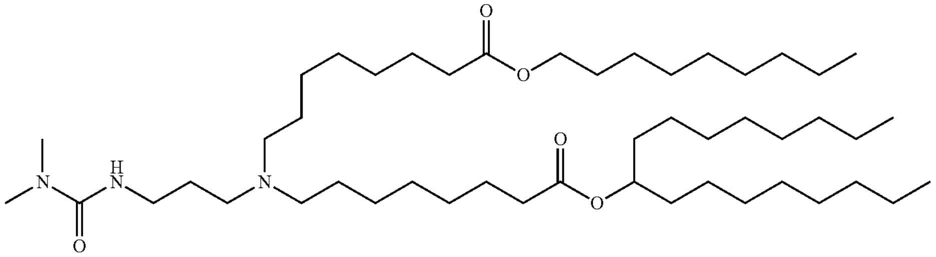
,
(Compound 111)
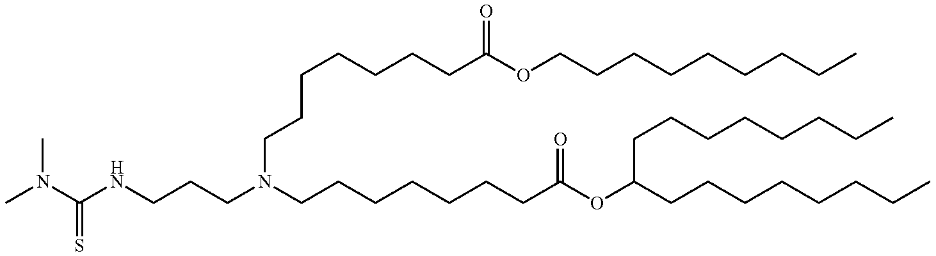
,
(Compound 112)
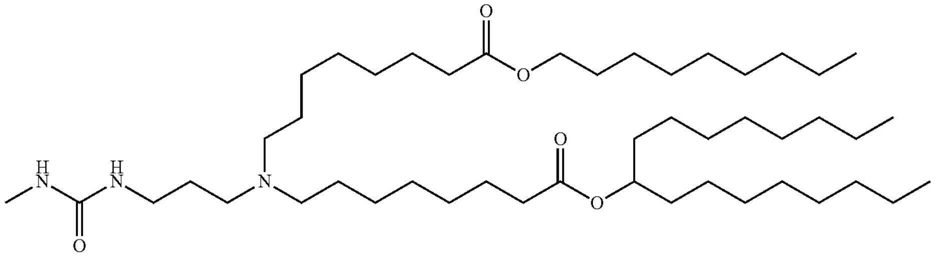
,
(Compound 113)
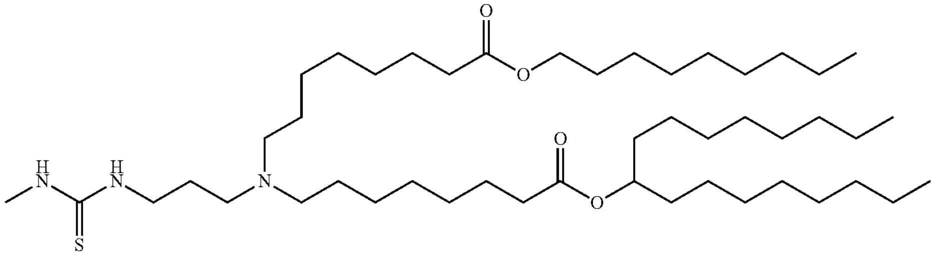
,
(Compound 114)
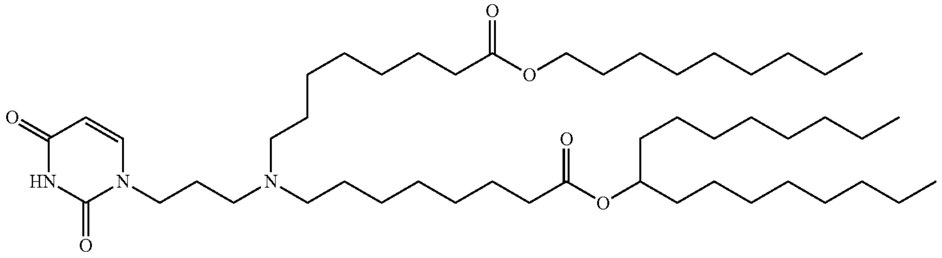
,
(Compound 115)
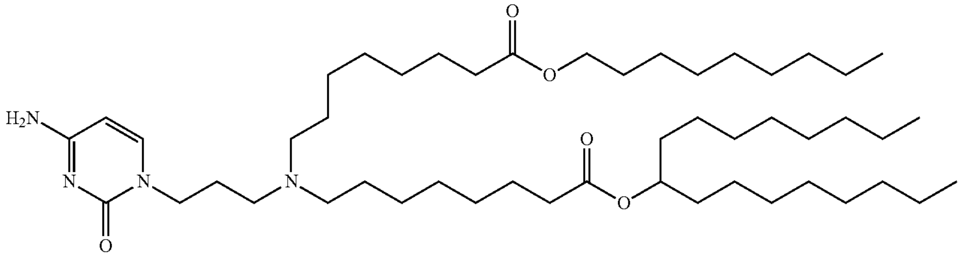
, -continued
(Compound 116)
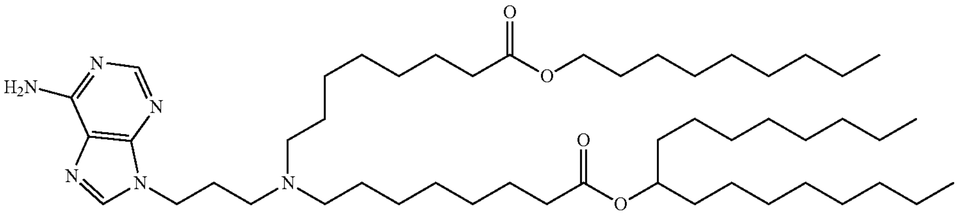
,
(Compound 117)
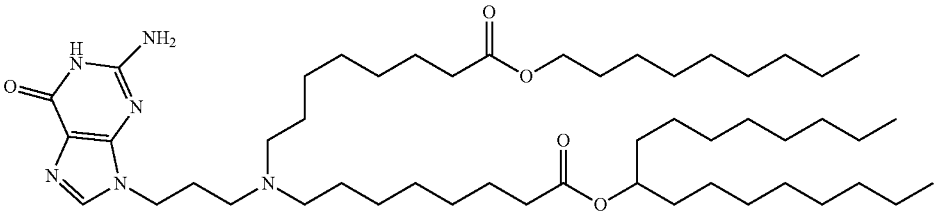
,
(Compound 118)
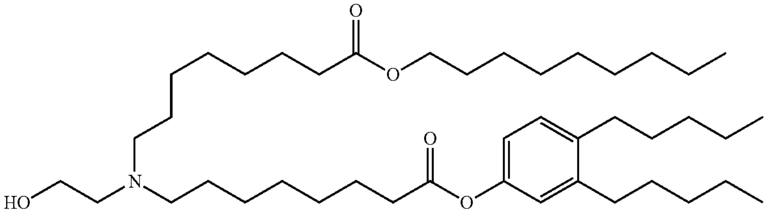
,
(Compound 119)
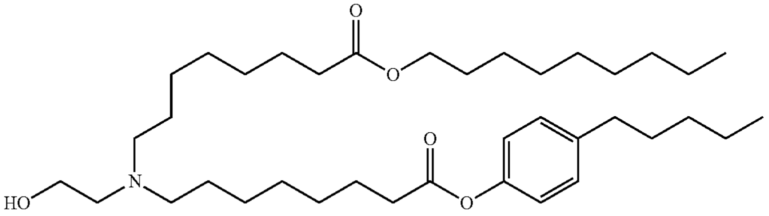
,
(Compound 120)
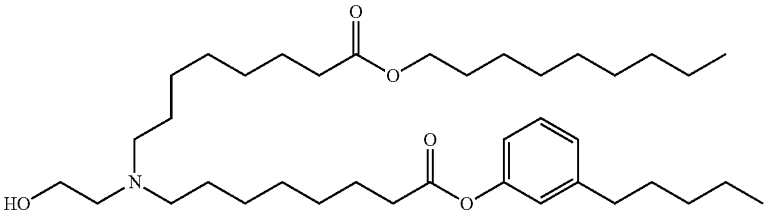
,
(Compound 121)
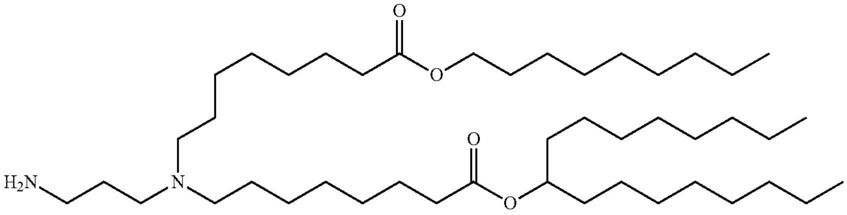
,
(Compound 122)
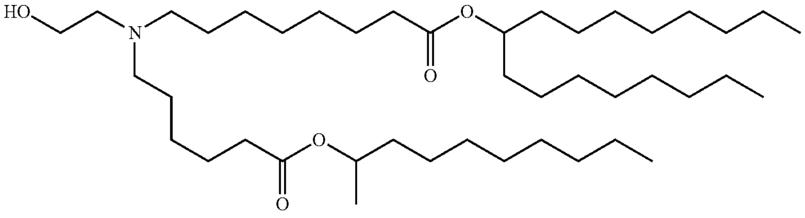
, -continued
(Compound 123)
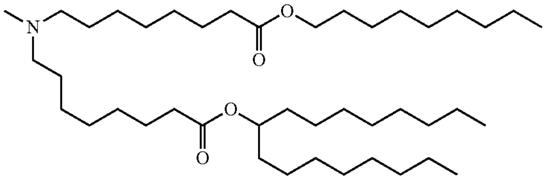
,
(Compound 124)
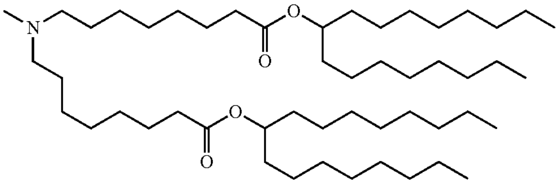
,
(Compound 125)
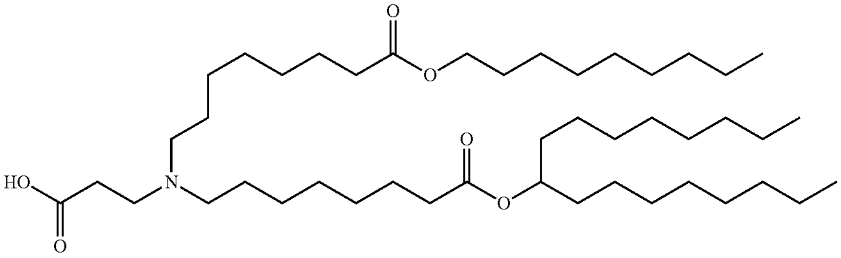
,
(Compound 126)
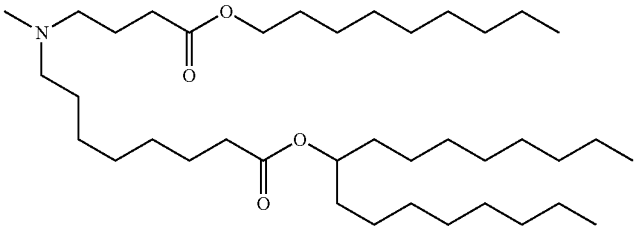
,
(Compound 127)
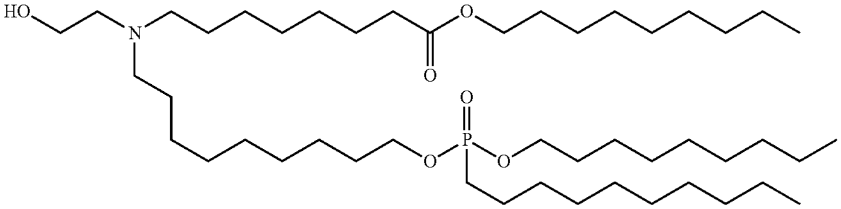
,
(Compound 128)
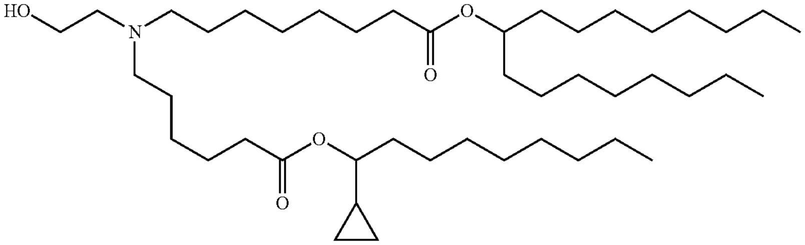
,
(Compound 129)
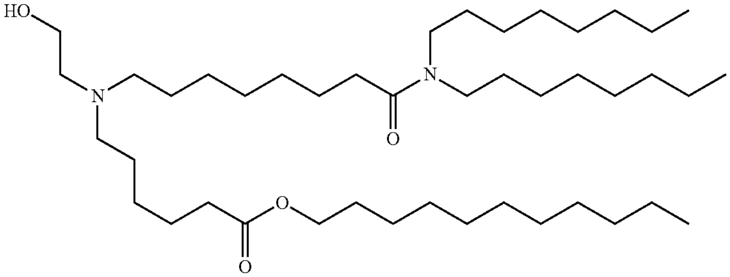
, -continued
(Compound 130)
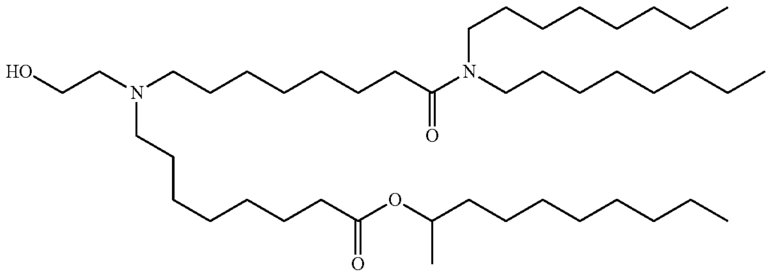
,
(Compound 131)
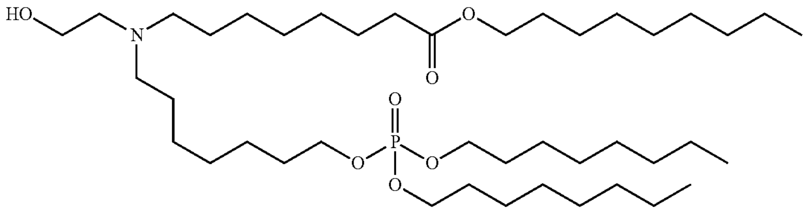
,
(Compound 132)
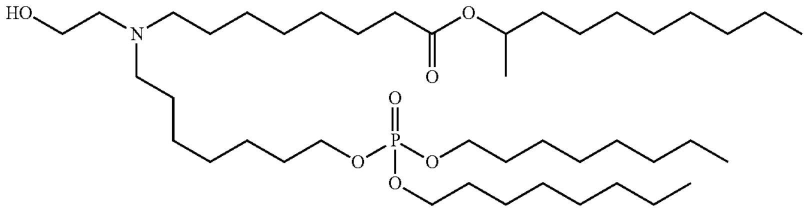
,
(Compound 133)
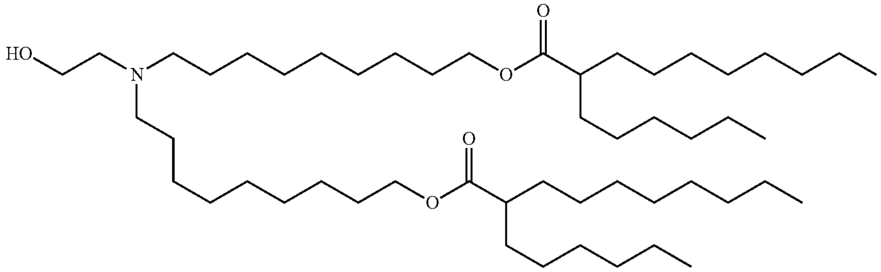
,
(Compound 134)
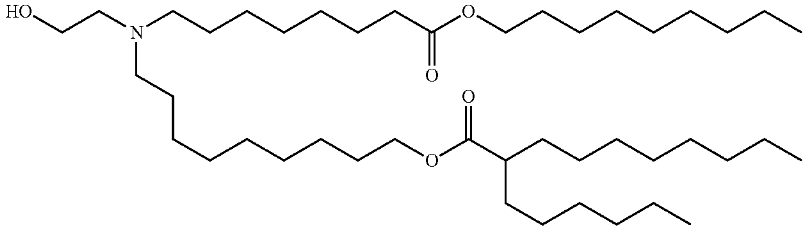
,
(Compound 135)
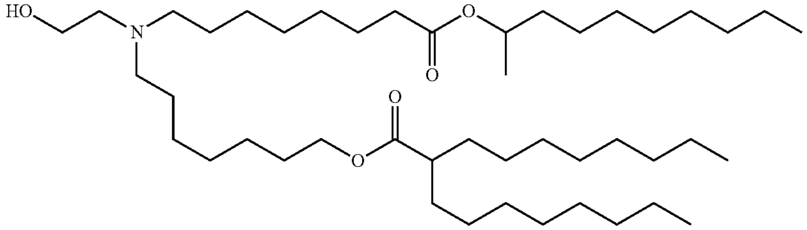
,
(Compound 136)
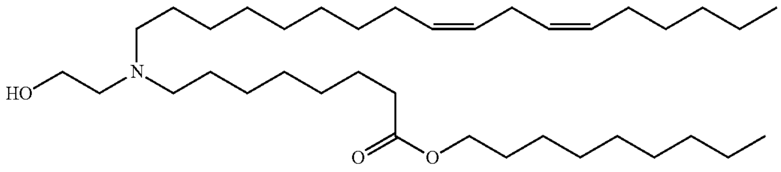
, -continued
(Compound 137)
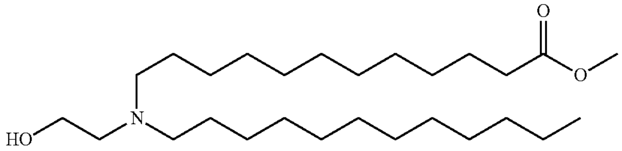
,
(Compound 138)
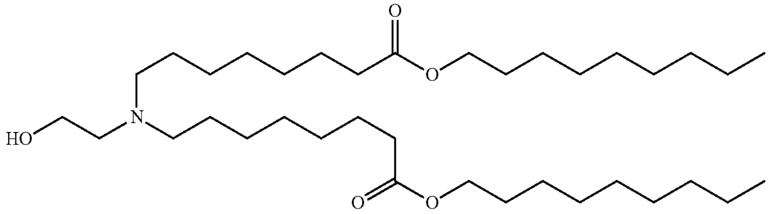
,
(Compound 139)
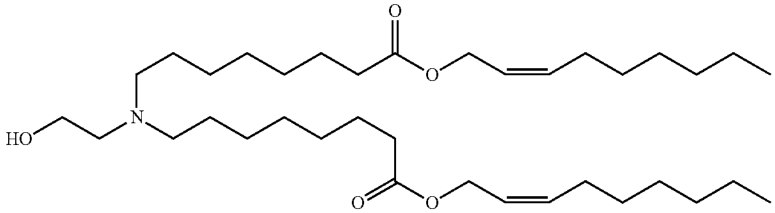
,
(Compound 140)
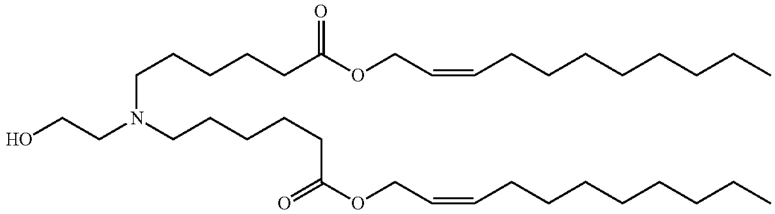
,
(Compound 141)
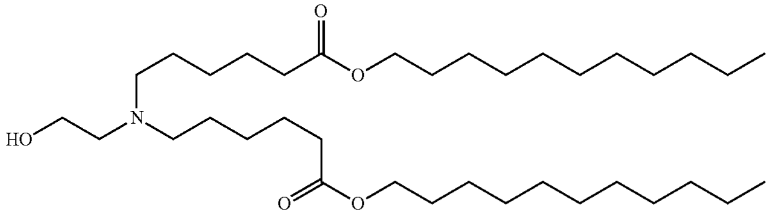
,
(Compound 142)
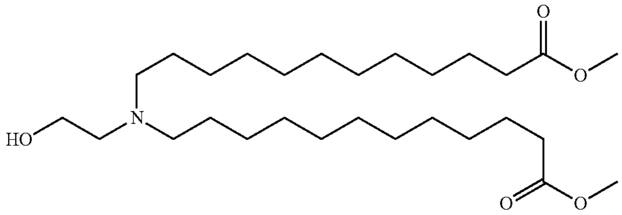
,
(Compound 143)
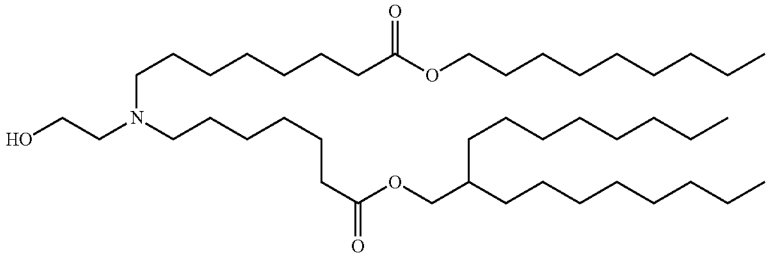
, -continued
(Compound 144)
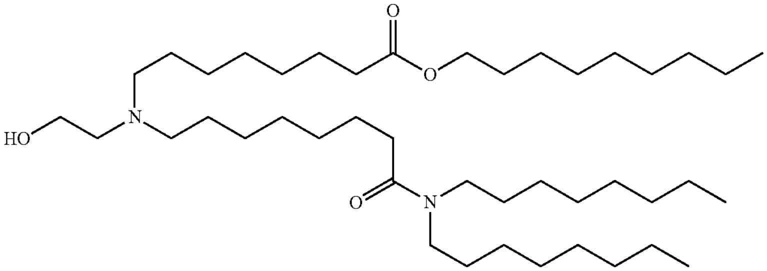
,
(Compound 145)
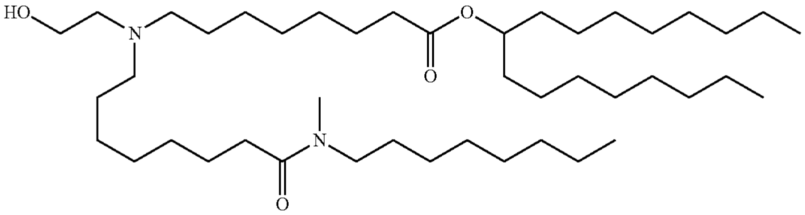
,
(Compound 146)
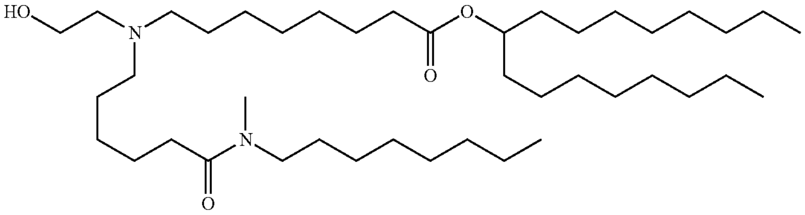
,
(Compound 147)
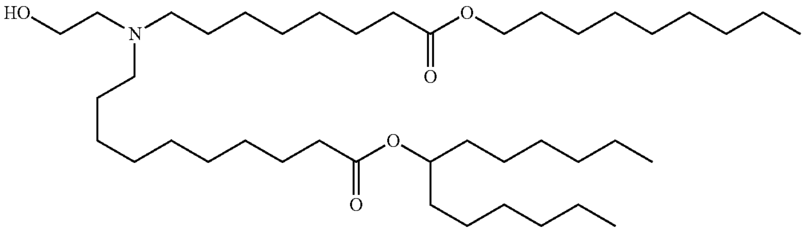
,
(Compound 148)
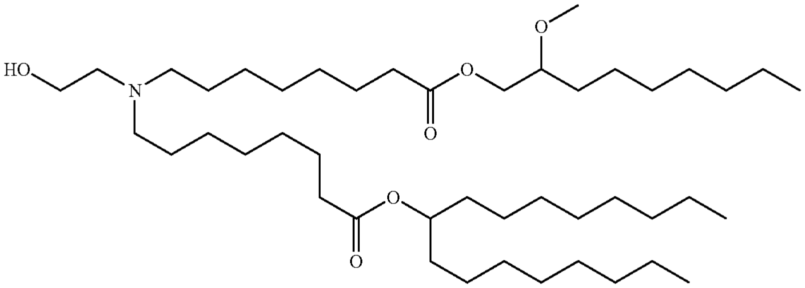
,
(Compound 149)
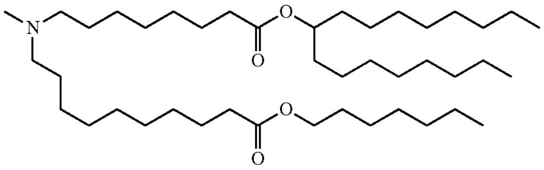
,
(Compound 150)
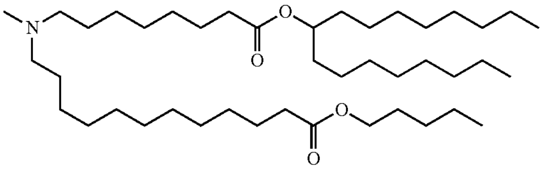
, -continued
(Compound 151)
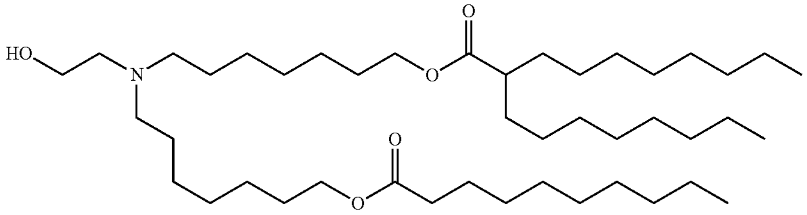
,
(Compound 152)
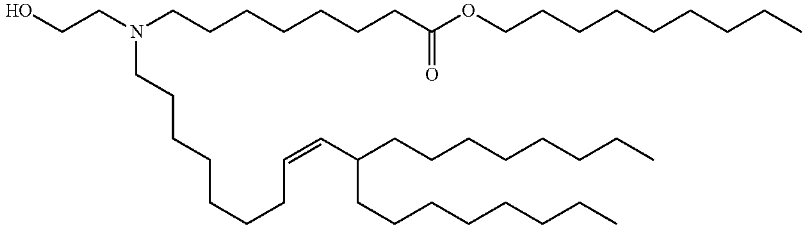
,
(Compound 153)
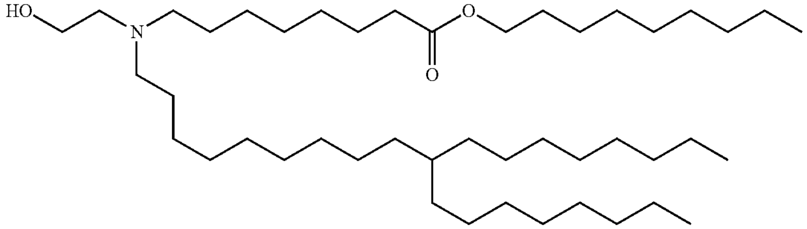
,
(Compound 154)
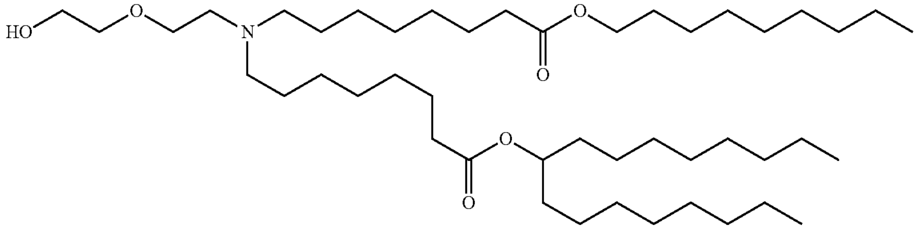
,
(Compound 155)
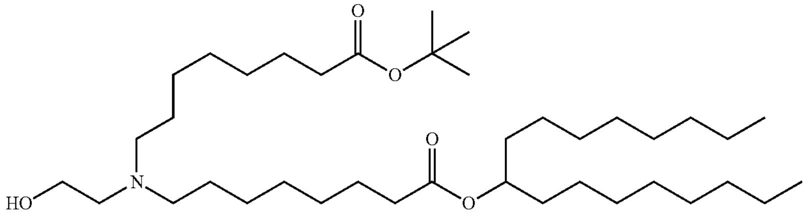
,
(Compound 156)
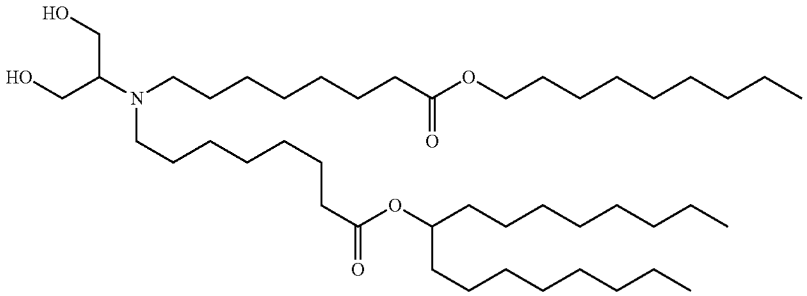
, -continued
(Compound 157)
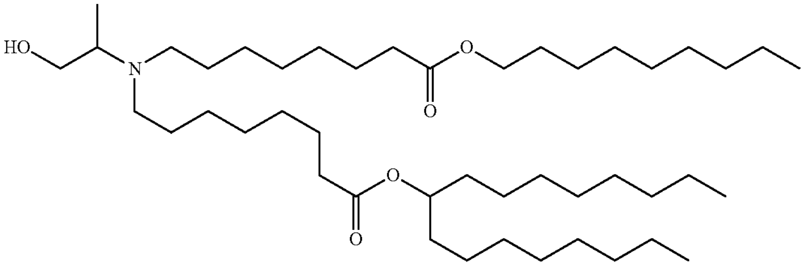
,
(Compound 158)
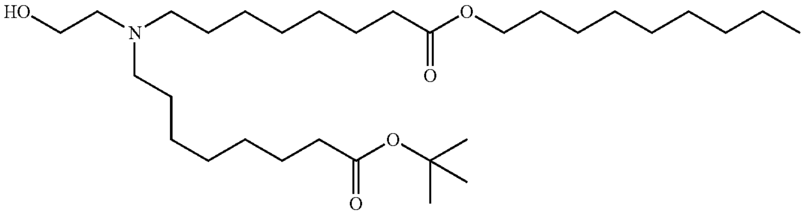
,
(Compound 159)
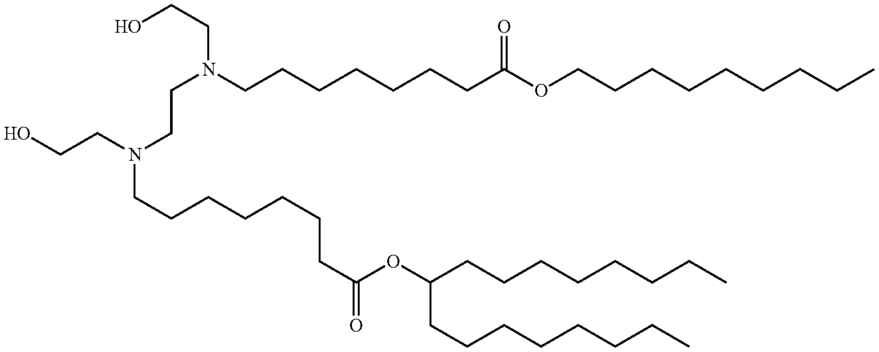
,
(Compound 160)
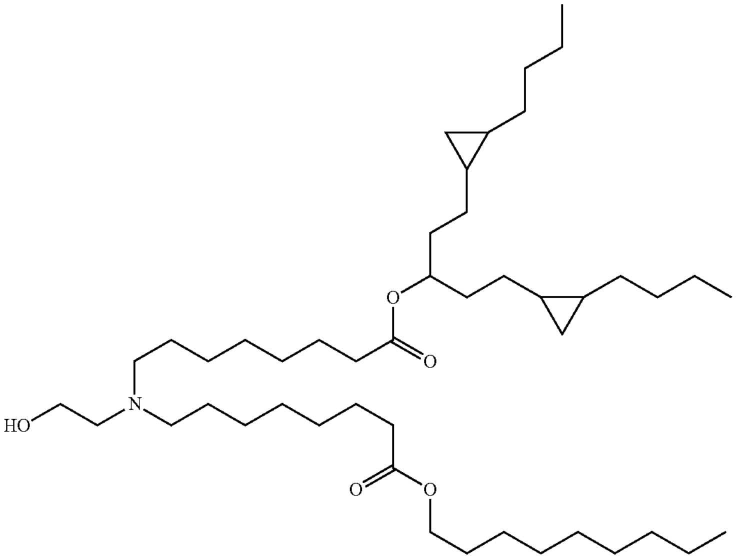
,
(Compound 161)
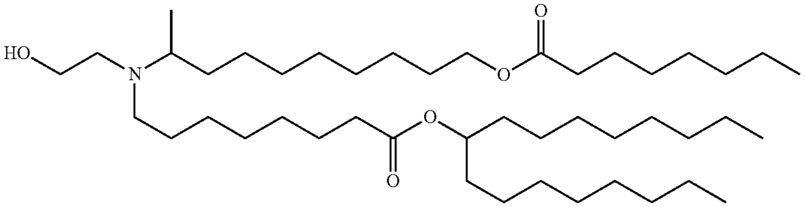
, -continued
(Compound 162)
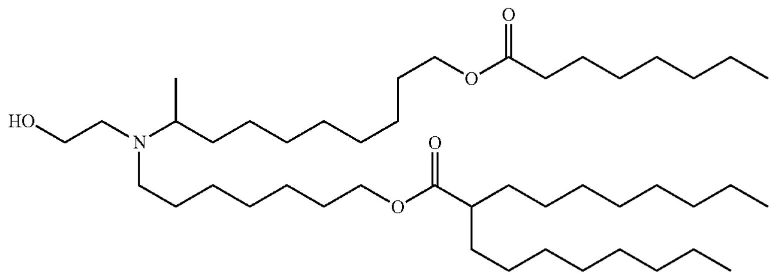
,
(Compound 163)
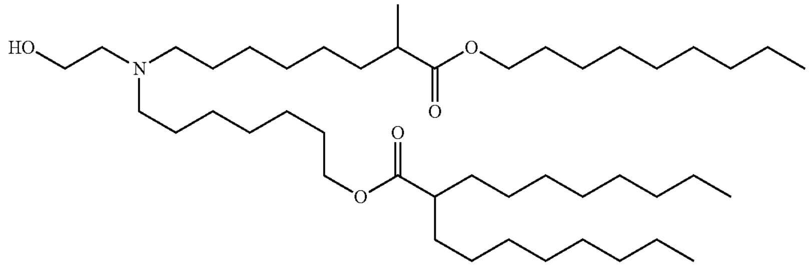
,
(Compound 164)
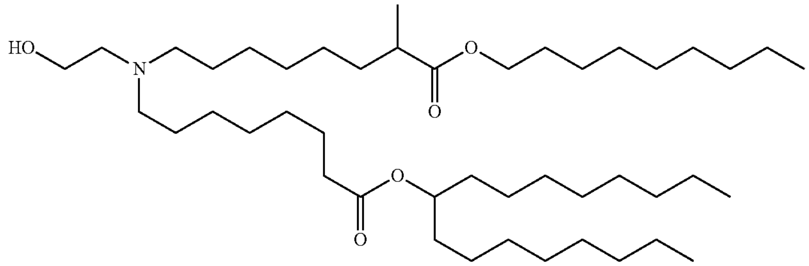
,
(Compound 165)
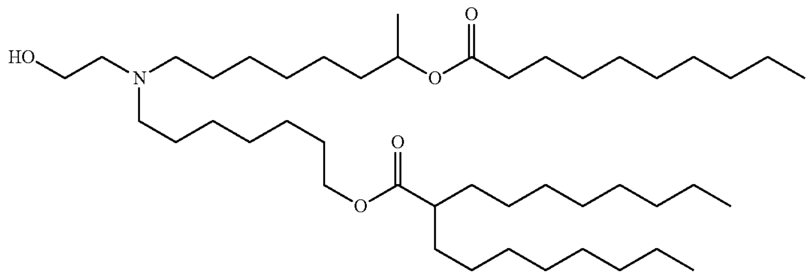
,
(Compound 166)
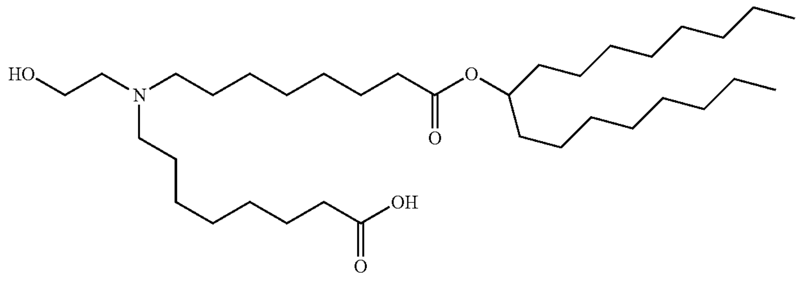
, -continued
(Compound 167)
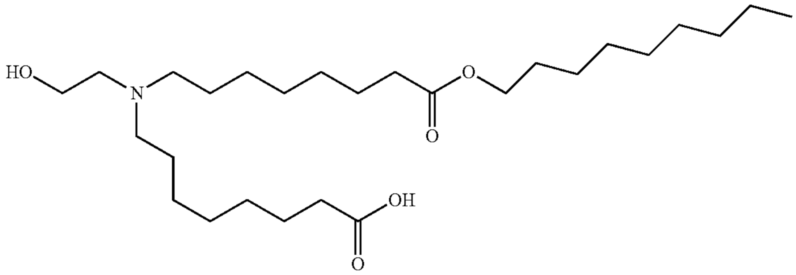
,
(Compound 168)
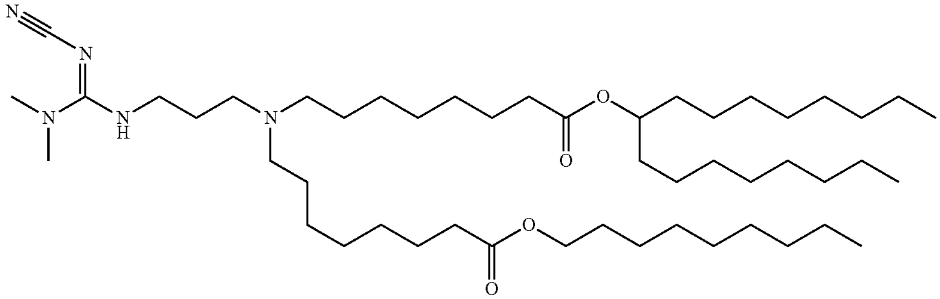
,
(Compound 169)
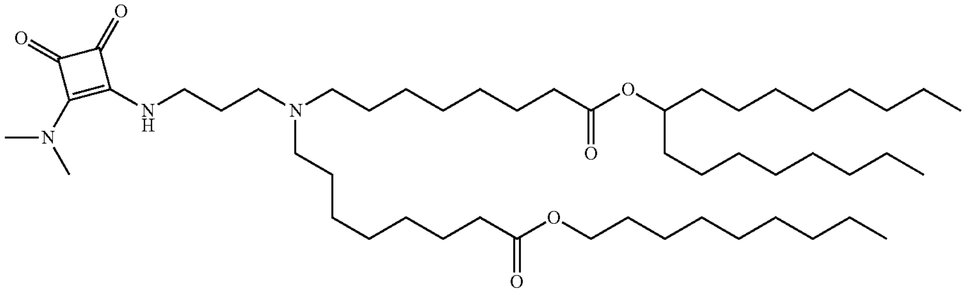
,
(Compound 170)
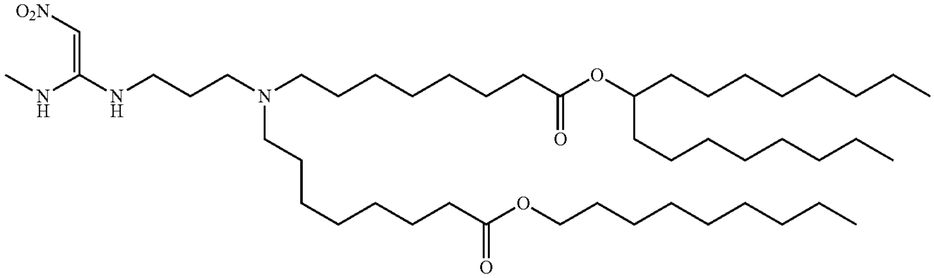
,
(Compound 171)
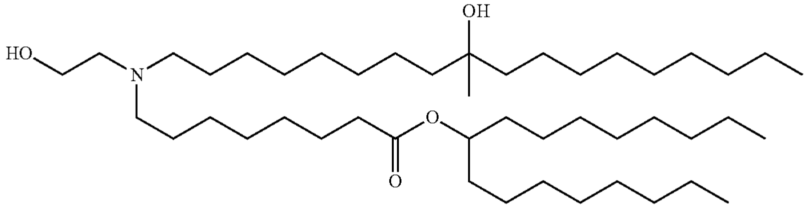
,
(Compound 172)
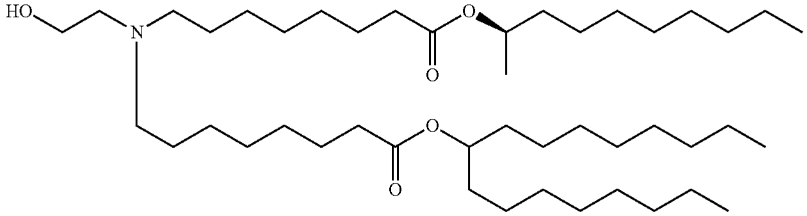
, -continued
(Compound 173)
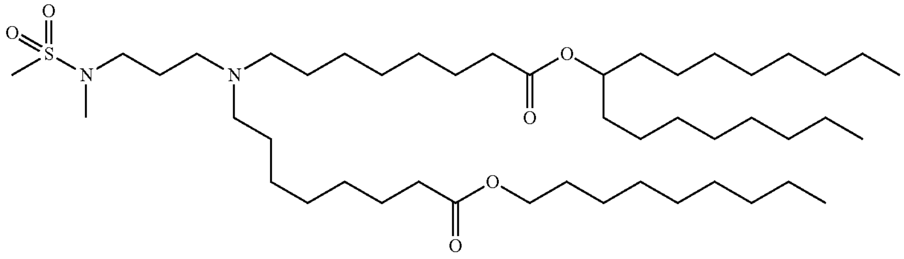
,
(Compound 174)
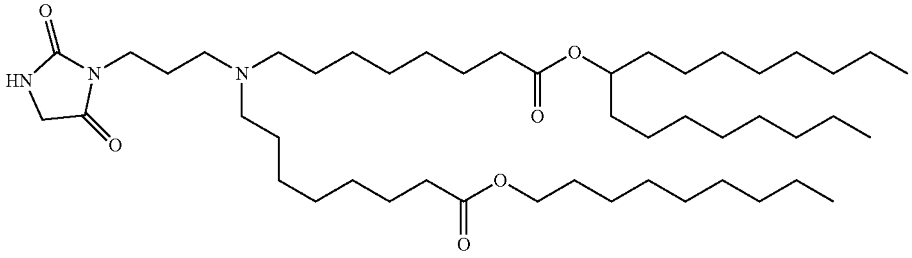
,
(Compound 175)
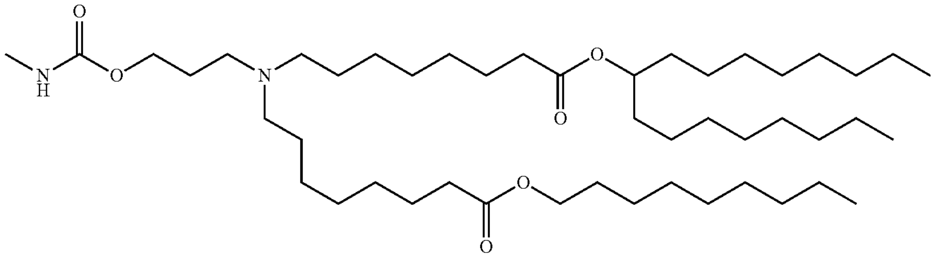
,
(Compound 176)
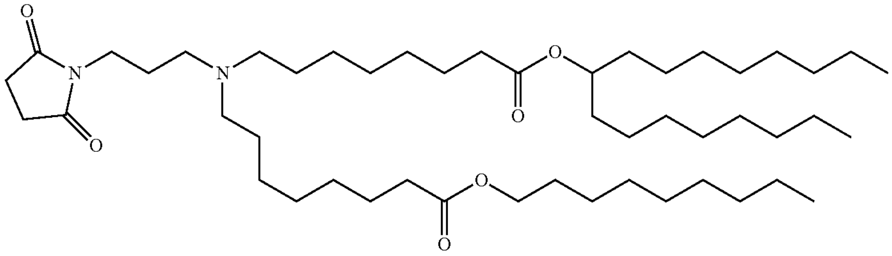
,
(Compound 177)
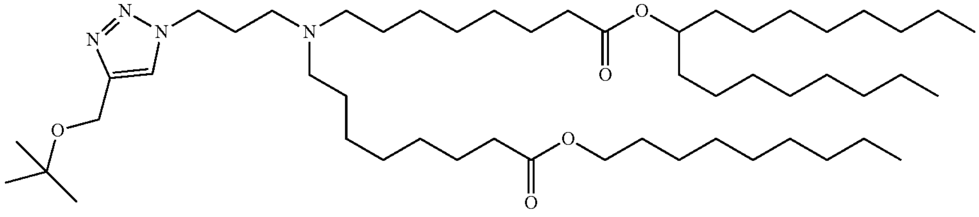
,
(Compound 178)
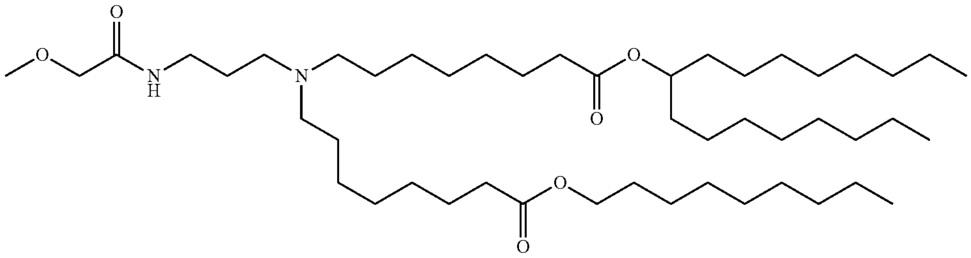
, -continued
(Compound 179)
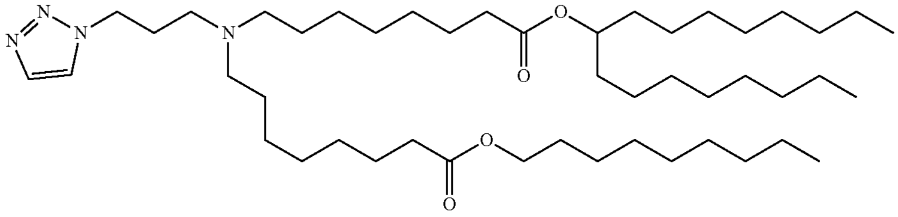
,
(Compound 180)
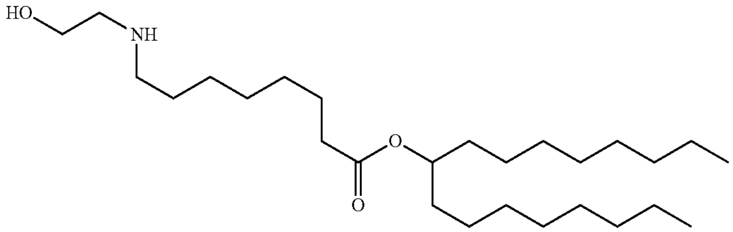
,
(Compound 181)
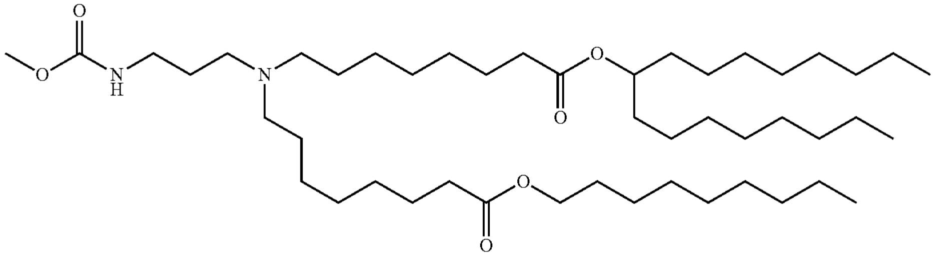
,
(Compound 182)
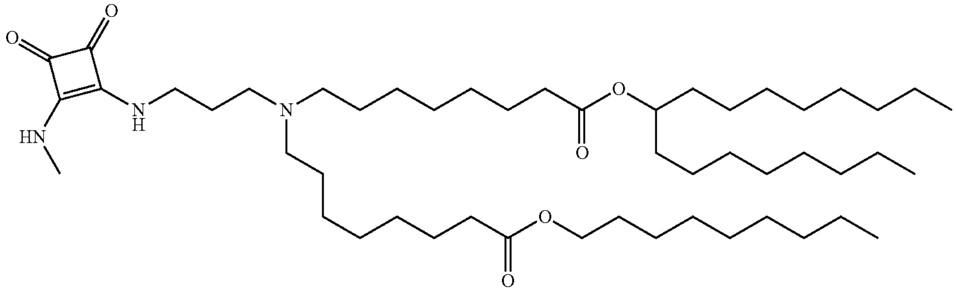
,
(Compound 183)
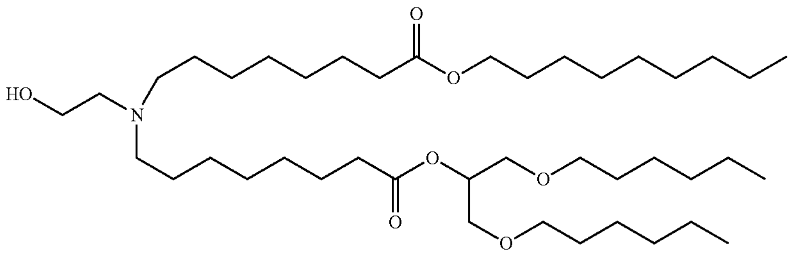
,
(Compound 184)
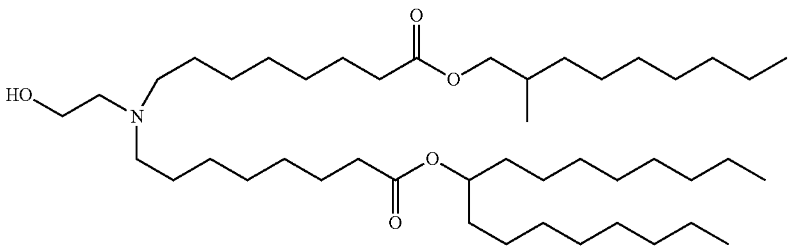
, -continued
(Compound 185)
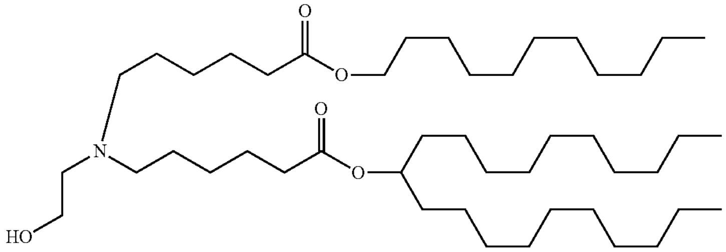
,
(Compound 186)
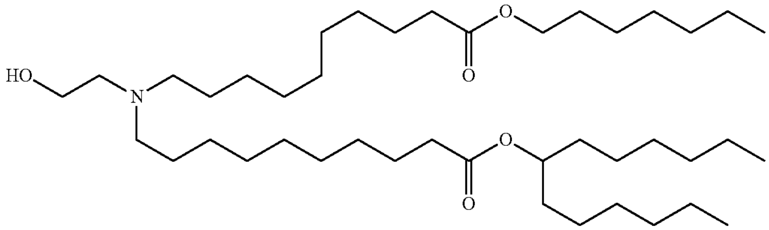
,
(Compound 187)
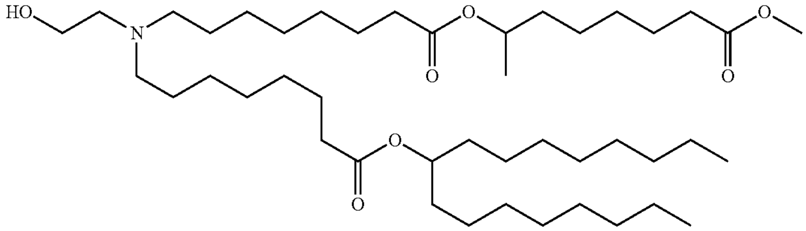
,
(Compound 188)
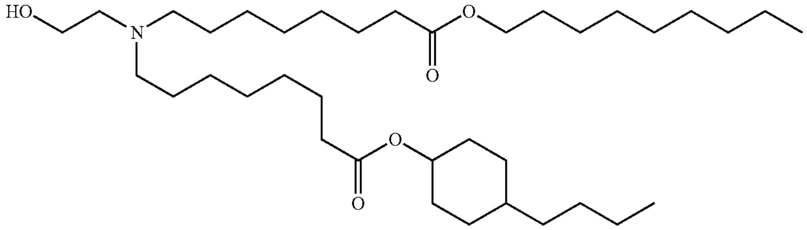
,
(Compound 189)
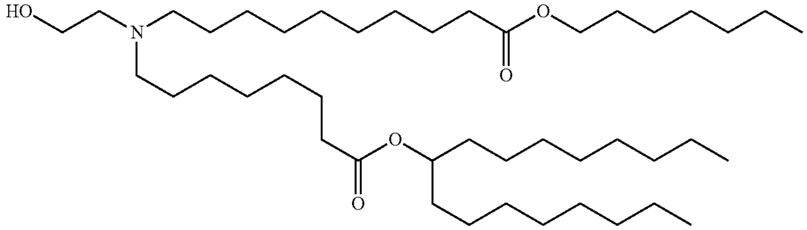
,
(Compound 190)
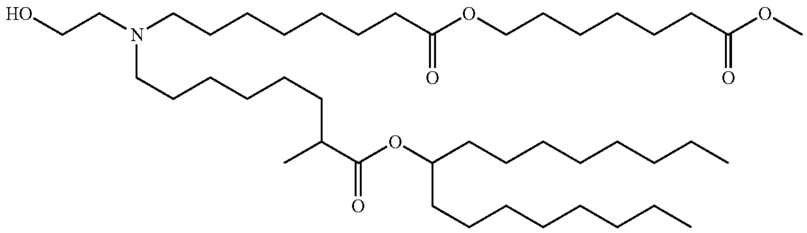
, -continued
(Compound 191)
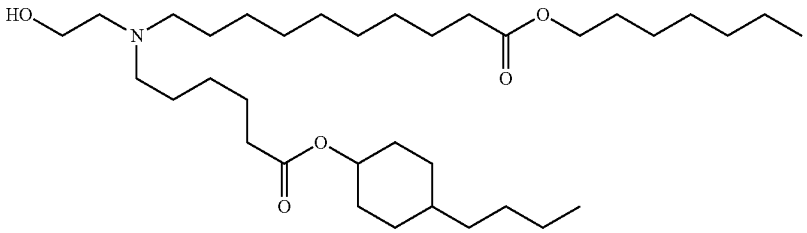
,
(Compound 192)
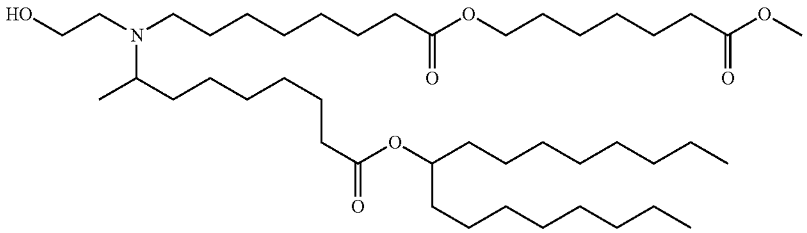
,
(Compound 193)
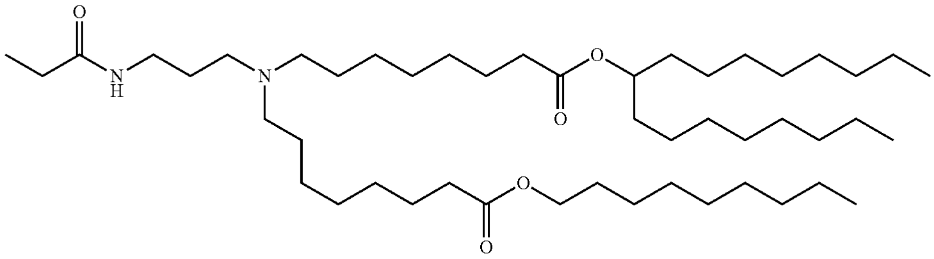
,
(Compound 194)
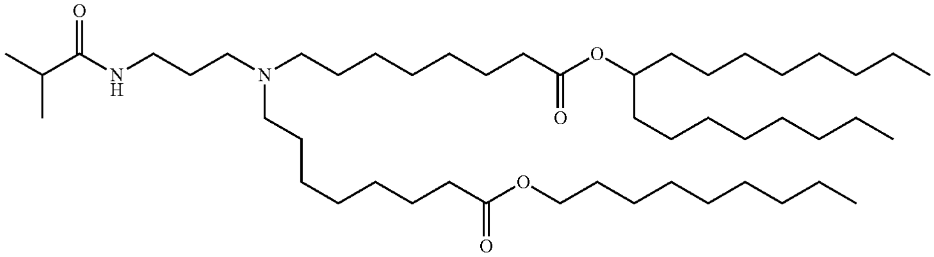
,
(Compound 195)
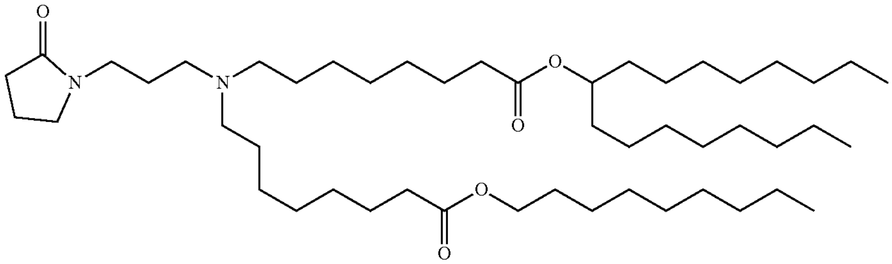
,
(Compound 196)
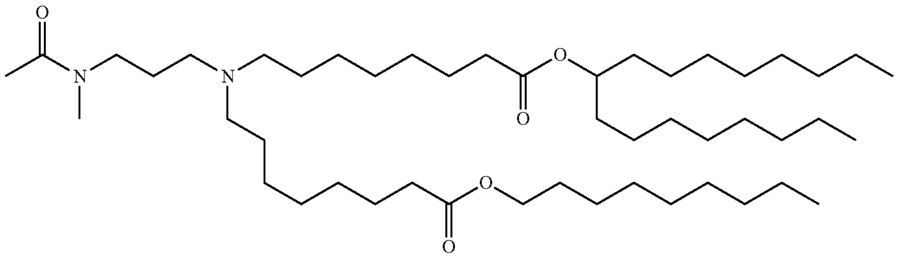
, -continued
(Compound 197)
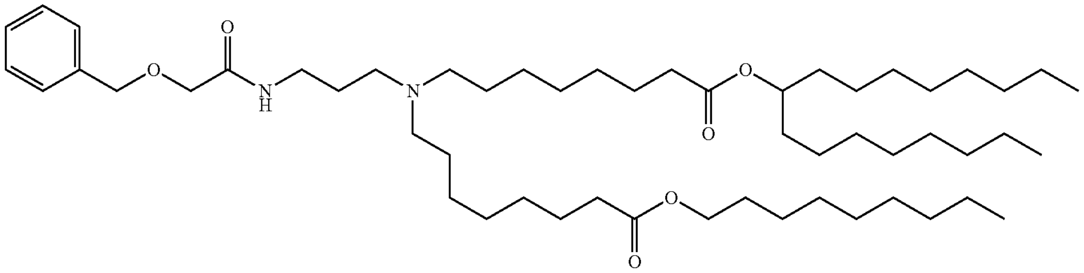
,
(Compound 198)
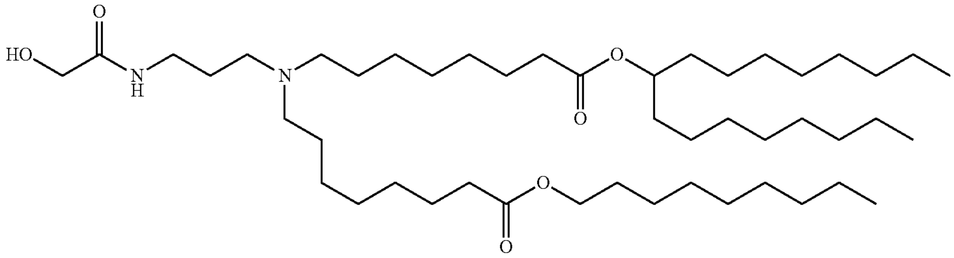
,
(Compound 199)
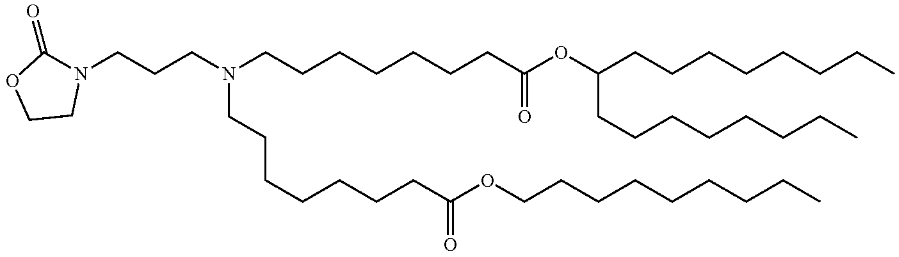
,
(Compound 200)
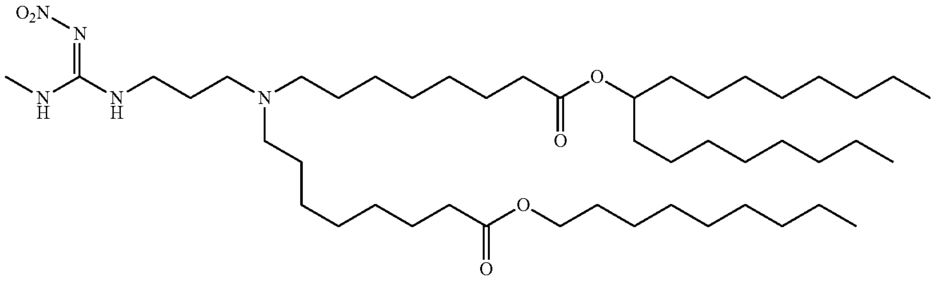
,
(Compound 201)
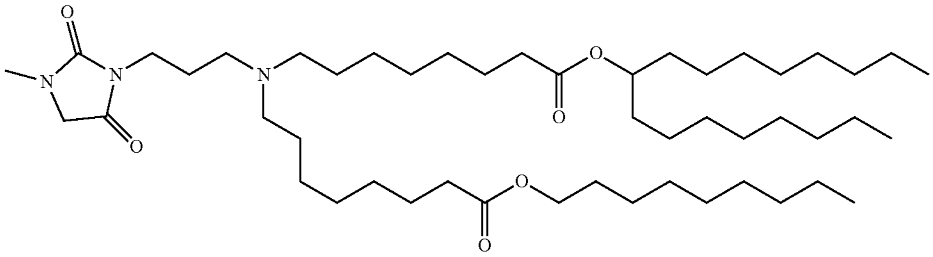
,
(Compound 202)
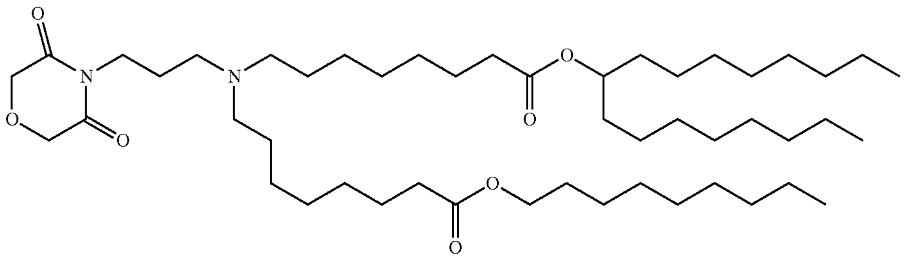
, -continued
(Compound 203)
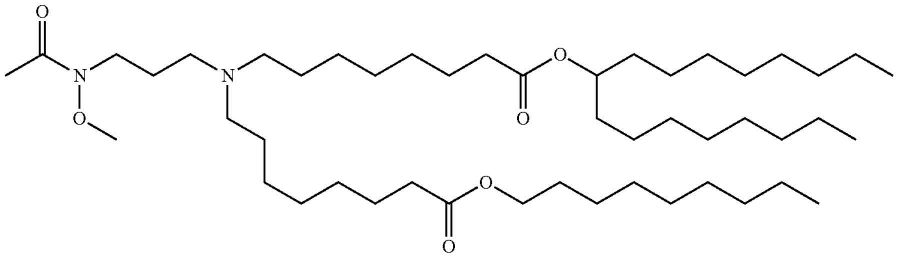
,
(Compound 204)
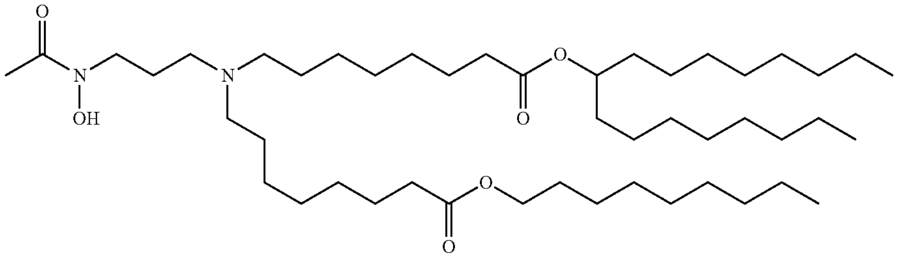
,
(Compound 205)
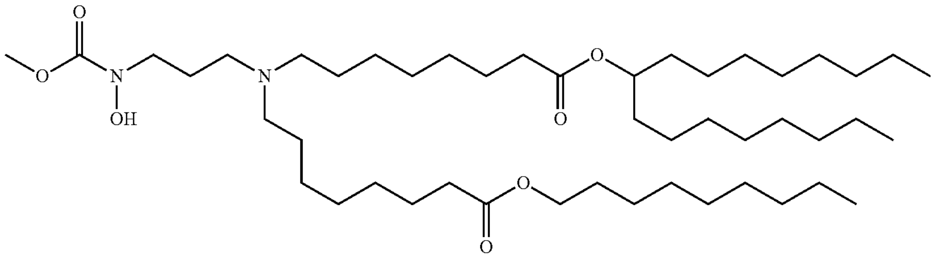
,
(Compound 206)
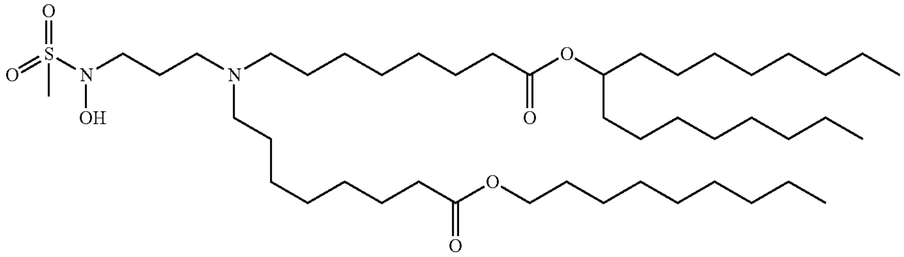
,
(Compound 207)
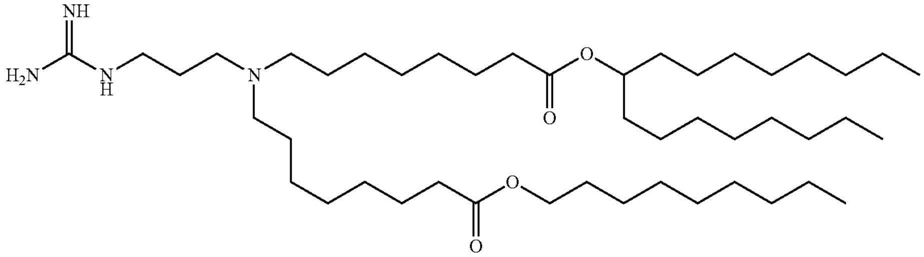
,
(Compound 208)
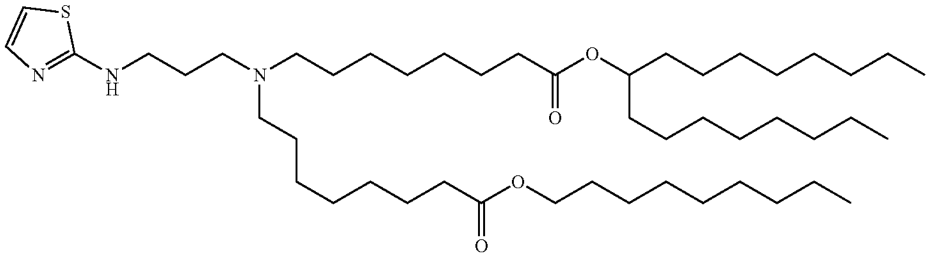
, -continued
(Compound 209)
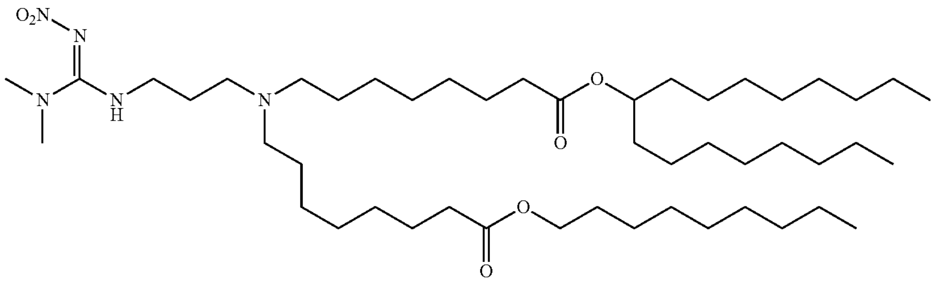
,
(Compound 210)
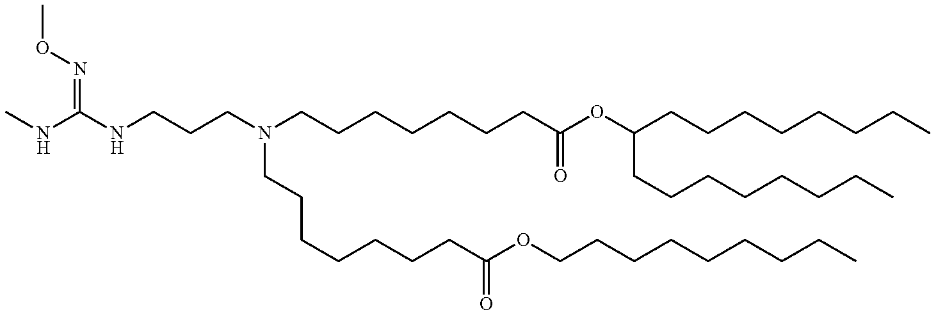
,
(Compound 211)
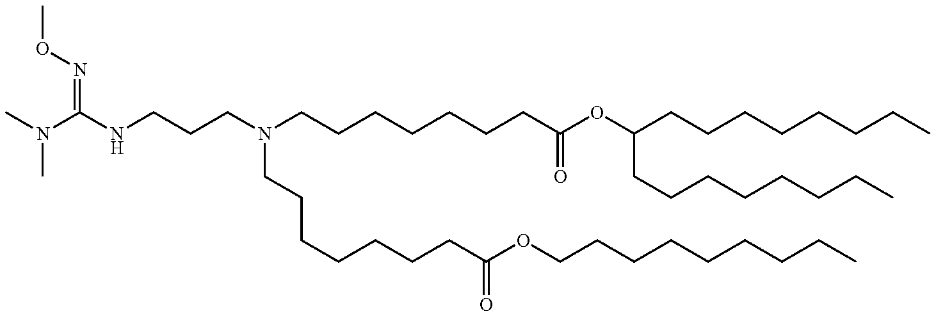
,
(Compound 212)
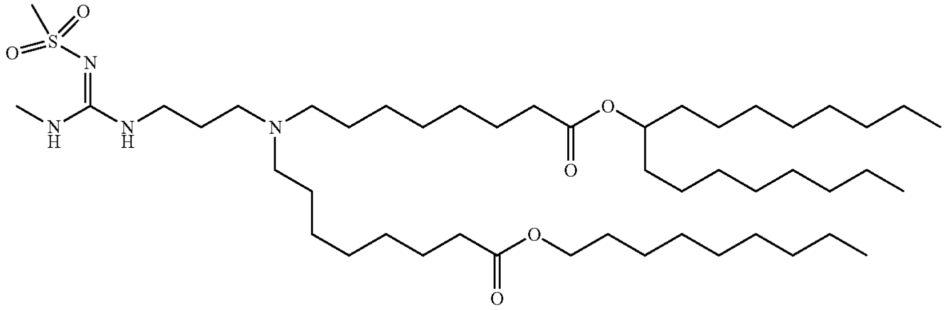
,
(Compound 213)
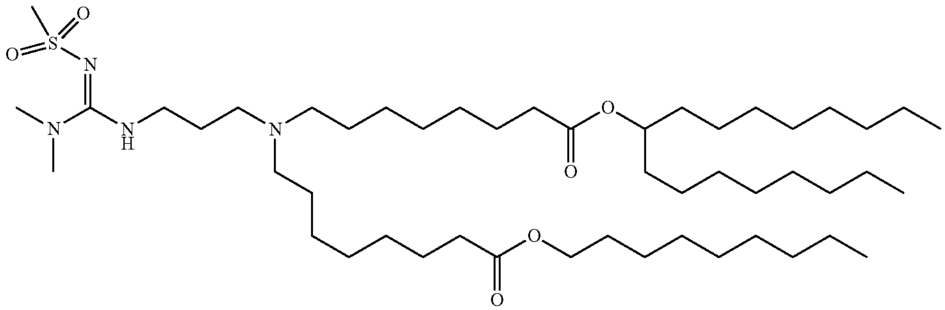
, -continued
(Compound 214)
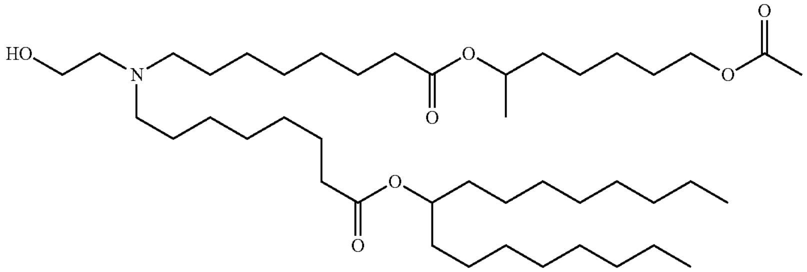
,
(Compound 215)
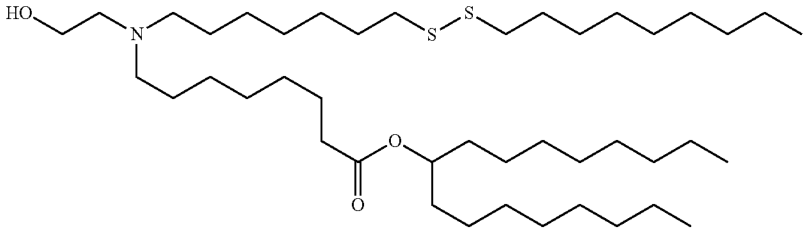
,
(Compound 216)
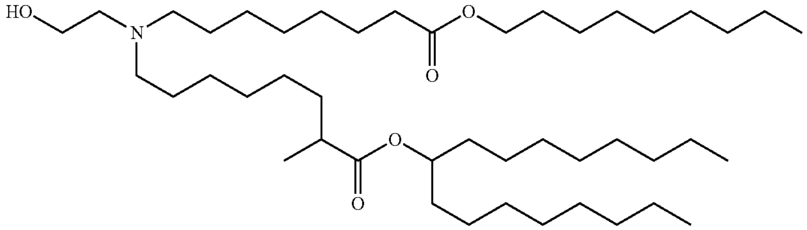
,
(Compound 217)
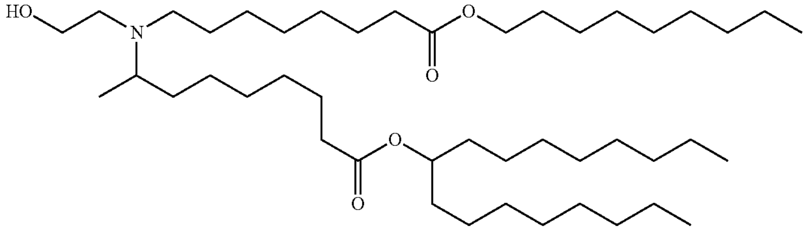
,
(Compound 218)
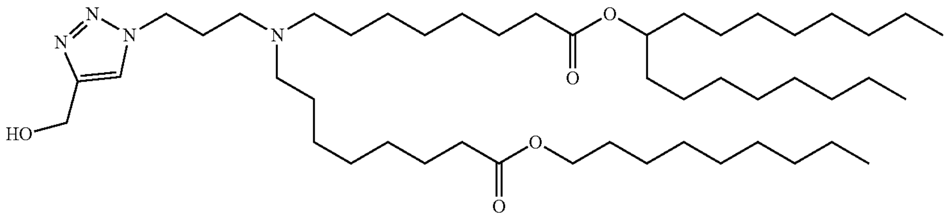
,
(Compound 219)
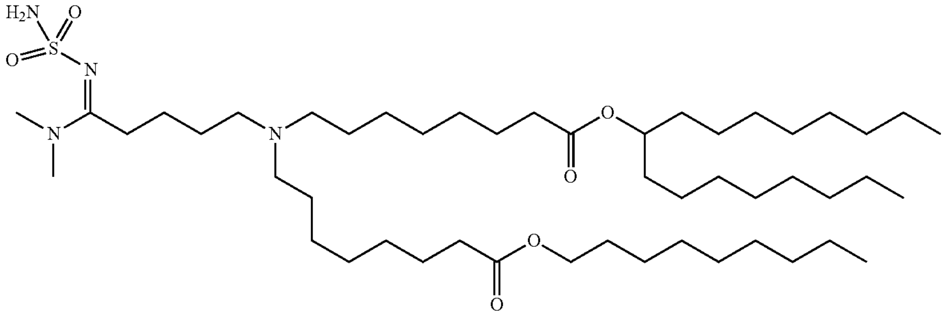
, -continued
(Compound 220)
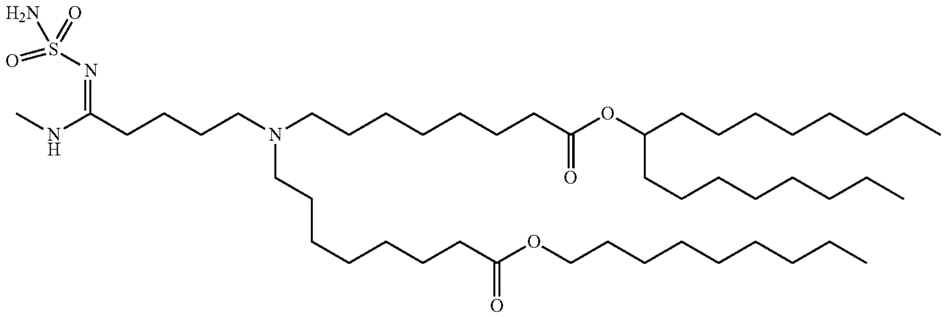
,
(Compound 221)
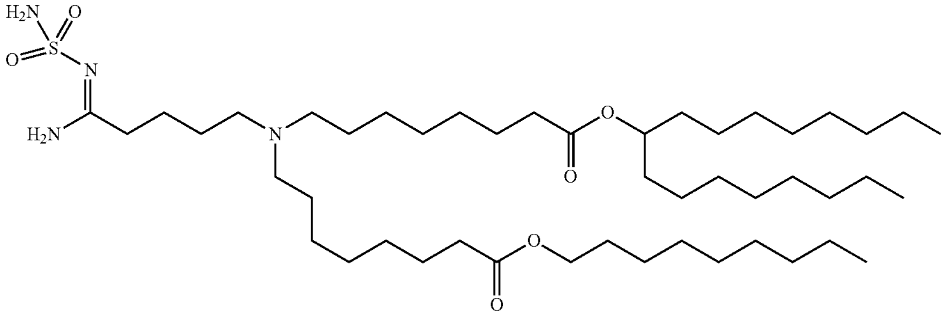
,
(Compound 222)
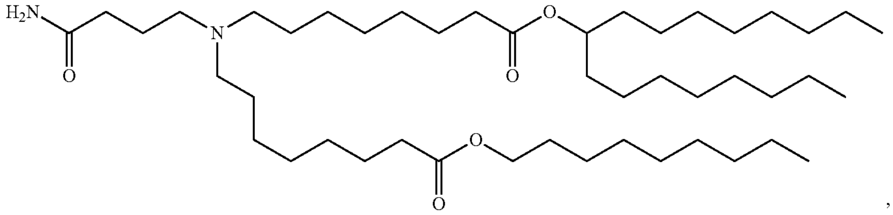
,
(Compound 223)
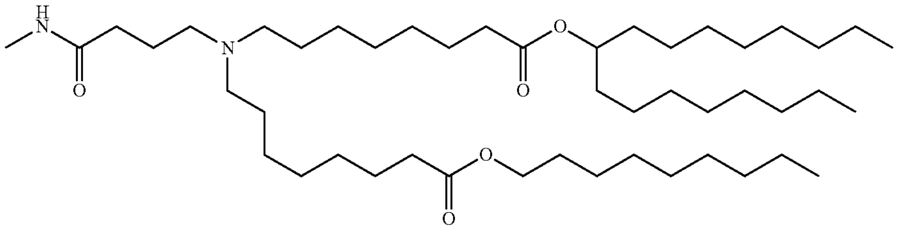
,
(Compound 224)
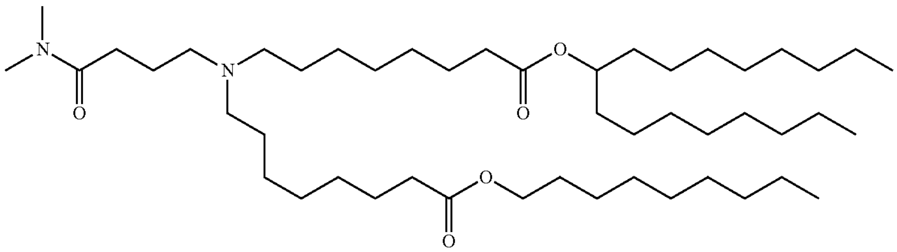
,
(Compound 225)
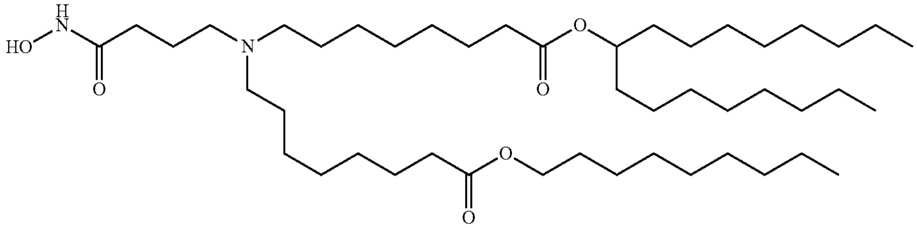
, -continued
(Compound 226)
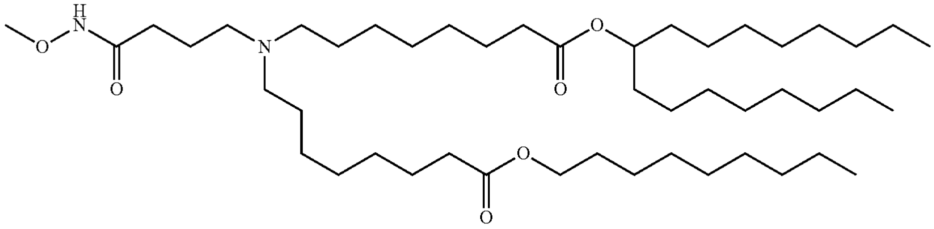
,
(Compound 227)
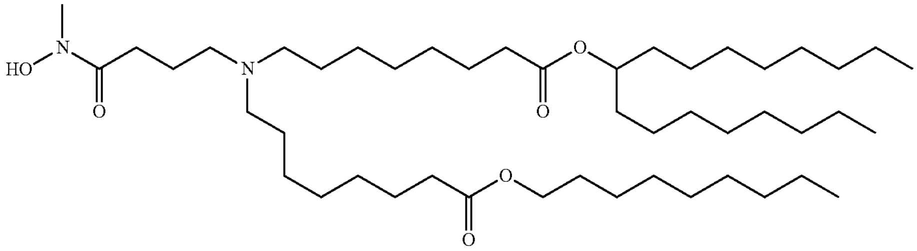
,
(Compound 228)
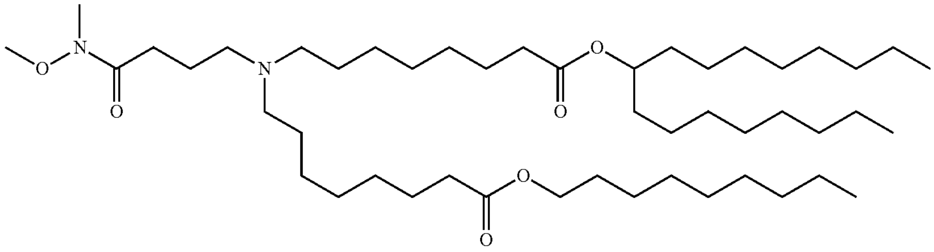
,
(Compound 229)
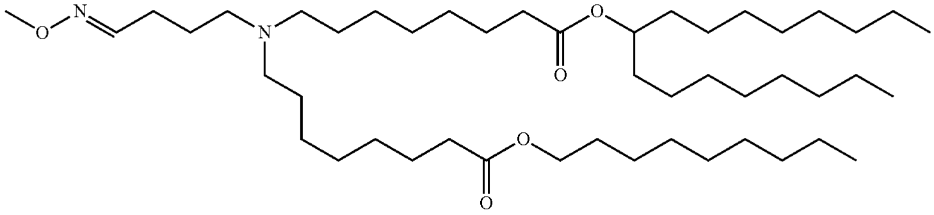
,
(Compound 230)
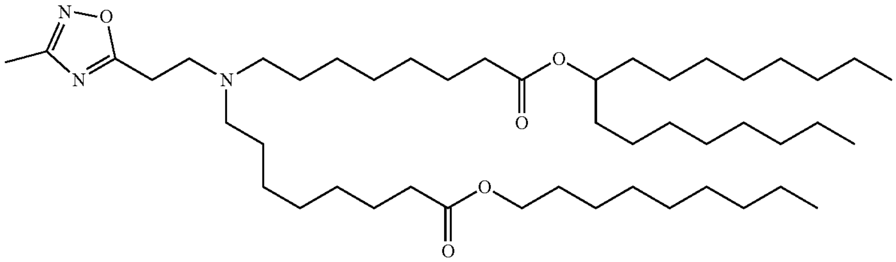
,
(Compound 231)
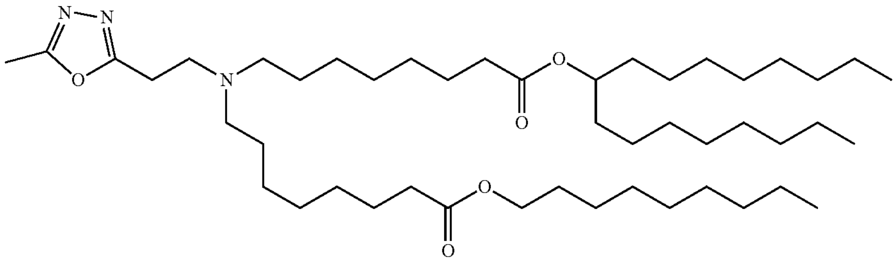
, -continued (Compouund 232)

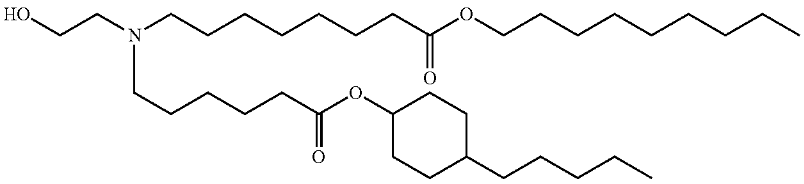

, and

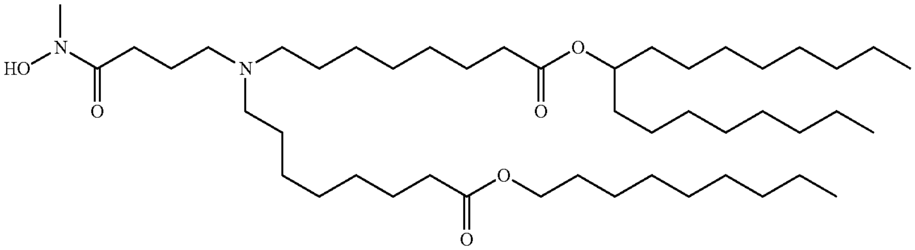

, salts and isomers thereof.

In some embodiments, a nanoparticle comprises the following compound:

(Compound 233)

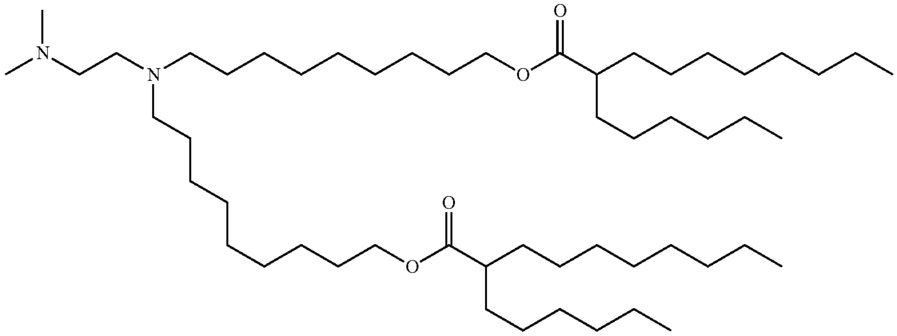

or salts and isomers thereof.

In some embodiments, the disclosure features a nanoparticle composition including a lipid component comprising a compound as described herein (e.g., a compound according to Formula (I), (IA), (II), (IIa), (IIb), (IIc), (IId) or (IIe)).

Kits for accomplishing these methods are also provided in other aspects of the invention. The kit includes a container housing a lipid nanoparticle formulation, a container housing a vaccine formulation, and instructions for adding a personalized mRNA cancer vaccine to the vaccine formulation to produce a personalized mRNA cancer vaccine formulation, mixing the personalized mRNA cancer vaccine formulation with the lipid nanoparticle formulation within 24 hours of administration to a subject. In some embodiments the kit includes a mRNA having an open reading frame encoding 2-100 cancer antigens.

The articles include pharmaceutical or diagnostic grade compounds of the invention in one or more containers. The article may include instructions or labels promoting or describing the use of the compounds of the invention.

As used herein, "promoted" includes all methods of doing business including methods of education, hospital and other clinical instruction, pharmaceutical industry activity including pharmaceutical sales, and any advertising or other promotional activity including written, oral and electronic communication of any form, associated with compositions of the invention in connection with treatment of cancer.

"Instructions" can define a component of promotion, and typically involve written instructions on or associated with packaging of compositions of the invention. Instructions also can include any oral or electronic instructions provided in any manner.

Thus the agents described herein may, in some embodiments, be assembled into pharmaceutical or diagnostic or research kits to facilitate their use in therapeutic, diagnostic or research applications. A kit may include one or more containers housing the components of the invention and instructions for use. Specifically, such kits may include one or more agents described herein, along with instructions describing the intended therapeutic application and the proper administration of these agents. In certain embodiments agents in a kit may be in a pharmaceutical formulation and dosage suitable for a particular application and for a method of administration of the agents.

The kit may be designed to facilitate use of the methods described herein by physicians and can take many forms. Each of the compositions of the kit, where applicable, may be provided in liquid form (e.g., in solution), or in solid form, (e.g., a dry powder). In certain cases, some of the compositions may be constitutable or otherwise processable (e.g., to an active form), for example, by the addition of a suitable solvent or other species (for example, water or a cell culture medium), which may or may not be provided with the kit. As used herein, “instructions” can define a component of instruction and/or promotion, and typically involve written instructions on or associated with packaging of the invention. Instructions also can include any oral or electronic instructions provided in any manner such that a user will clearly recognize that the instructions are to be associated with the kit, for example, audiovisual (e.g., videotape, DVD, etc.), Internet, and/or web-based communications, etc. The written instructions may be in a form prescribed by a governmental agency regulating the manufacture, use or sale of pharmaceuticals or biological products, which instructions can also reflects approval by the agency of manufacture, use or sale for human administration.

The kit may contain any one or more of the components described herein in one or more containers. As an example, in one embodiment, the kit may include instructions for mixing one or more components of the kit and/or isolating and mixing a sample and applying to a subject. The kit may include a container housing agents described herein. The agents may be prepared sterilely, packaged in syringe and shipped refrigerated. Alternatively it may be housed in a vial or other container for storage. A second container may have other agents prepared sterilely. Alternatively the kit may include the active agents premixed and shipped in a syringe, vial, tube, or other container.

The kit may have a variety of forms, such as a blister pouch, a shrink wrapped pouch, a vacuum scalable pouch, a scalable thermoformed tray, or a similar pouch or tray form, with the accessories loosely packed within the pouch, one or more tubes, containers, a box or a bag. The kit may be sterilized after the accessories are added, thereby allowing the individual accessories in the container to be otherwise unwrapped. The kits can be sterilized using any appropriate sterilization techniques, such as radiation sterilization, heat sterilization, or other sterilization methods known in the art. The kit may also include other components, depending on the specific application, for example, containers, cell media, salts, buffers, reagents, syringes, needles, a fabric, such as gauze, for applying or removing a disinfecting agent, disposable gloves, a support for the agents prior to administration etc.

The compositions of the kit may be provided as any suitable form, for example, as liquid solutions or as dried powders. When the composition provided is a dry powder, the powder may be reconstituted by the addition of a suitable solvent, which may also be provided. In embodiments where liquid forms of the composition are sued, the liquid form may be concentrated or ready to use. The solvent will depend on the compound and the mode of use or administration. Suitable solvents for drug compositions are well known and are available in the literature. The solvent will depend on the compound and the mode of use or administration.

The kits, in one set of embodiments, may comprise a carrier means being compartmentalized to receive in close confinement one or more container means such as vials, tubes, and the like, each of the container means comprising one of the separate elements to be used in the method. For example, one of the containers may comprise a positive control for an assay. Additionally, the kit may include containers for other components, for example, buffers useful in the assay.

The present invention also encompasses a finished packaged and labeled pharmaceutical product. This article of manufacture includes the appropriate unit dosage form in an appropriate vessel or container such as a glass vial or other container that is hermetically sealed. In the case of dosage forms suitable for parenteral administration the active ingredient is sterile and suitable for administration as a particulate free solution. In other words, the invention encompasses both parenteral solutions and lyophilized powders, each being sterile, and the latter being suitable for reconstitution prior to injection. Alternatively, the unit dosage form may be a solid suitable for oral, transdermal, topical or mucosal delivery.

In a preferred embodiment, the unit dosage form is suitable for intravenous, intramuscular or subcutaneous delivery. Thus, the invention encompasses solutions, preferably sterile, suitable for each delivery route.

In another preferred embodiment, compositions of the invention are stored in containers with biocompatible detergents, including but not limited to, lecithin, taurocholic acid, and cholesterol; or with other proteins, including but not limited to, gamma globulins and serum albumins. More preferably, compositions of the invention are stored with human serum albumins for human uses, and stored with bovine serum albumins for veterinary uses.

As with any pharmaceutical product, the packaging material and container are designed to protect the stability of the product during storage and shipment. Further, the products of the invention include instructions for use or other informational material that advise the physician, technician or patient on how to appropriately prevent or treat the disease or disorder in question. In other words, the article of manufacture includes instruction means indicating or suggesting a dosing regimen including, but not limited to, actual doses, monitoring procedures (such as methods for monitoring mean absolute lymphocyte counts, tumor cell counts, and tumor size) and other monitoring information.

More specifically, the invention provides an article of manufacture comprising packaging material, such as a box, bottle, tube, vial, container, sprayer, insufflator, intravenous (i.v.) bag, envelope and the like; and at least one unit dosage form of a pharmaceutical agent contained within said packaging material. The invention also provides an article of manufacture comprising packaging material, such as a box, bottle, tube, vial, container, sprayer, insufflator, intravenous (i.v.) bag, envelope and the like; and at least one unit dosage form of each pharmaceutical agent contained within said packaging material. The invention further provides an article of manufacture comprising packaging material, such as a box, bottle, tube, vial, container, sprayer, insufflator, intravenous (i.v.) bag, envelope and the like; and at least one unit dosage form of each pharmaceutical agent contained within said packaging material. The invention further provides an article of manufacture comprising a needle or syringe, preferably packaged in sterile form, for injection of the formulation, and/or a packaged alcohol pad.

Relative amounts of the active ingredient, the pharmaceutically acceptable excipient, and/or any additional ingredients in a vaccine composition may vary, depending upon the identity, size, and/or condition of the subject being treated and further depending upon the route by which the composition is to be administered. For example, the composition may comprise between 0.1% and 99% (w/w) of the active ingredient. By way of example, the composition may comprise between 0.1% and 100%, e.g., between 0.5 and 50%, between 1-30%, between 5-80%, at least 80% (w/w) active ingredient.

In some embodiments, the RNA (e.g., mRNA) vaccine compositions may be administered at dosage levels sufficient to deliver 0.0001 mg/kg to 100 mg/kg, 0.001 mg/kg to 0.05 mg/kg. 0.005 mg/kg to 0.05 mg/kg, 0.001 mg/kg to 0.005 mg/kg. 0.05 mg/kg to 0.5 mg/kg, 0.01 mg/kg to 50 mg/kg, 0.1 mg/kg to 40 mg/kg, 0.5 mg/kg to 30 mg/kg. 0.01 mg/kg to 10 mg/kg, 0.1 mg/kg to 10 mg/kg, or 1 mg/kg to 25 mg/kg, of subject body weight per day, one or more times a day, per week, per month, etc. to obtain the desired therapeutic, diagnostic, prophylactic, or imaging effect (see e.g., the range of unit doses described in International Publication No WO2013078199, herein incorporated by reference in its entirety). The desired dosage may be delivered three times a day, two times a day, once a day, every other day, every third day, every week, every two weeks, every three weeks, every four weeks, every 2 months, every three months, every 6 months, etc. In certain embodiments, the desired dosage may be delivered using multiple administrations (e.g., two, three, four, five, six, seven, eight, nine, ten, eleven, twelve, thirteen, fourteen, or more administrations). When multiple administrations are employed, split dosing regimens such as those described herein may be used. In some embodiments, the RNA vaccine compositions may be administered at dosage levels sufficient to deliver 0.0005 mg/kg to 0.01 mg/kg. e.g., about 0.0005 mg/kg to about 0.0075 mg/kg, e.g., about 0.0005 mg/kg, about 0.001 mg/kg, about 0.002 mg/kg, about 0.003 mg/kg, about 0.004 mg/kg or about 0.005 mg/kg. In some embodiments, the RNA vaccine compositions may be administered once or twice (or more) at dosage levels sufficient to deliver 0.025 mg/kg to 0.250 mg/kg, 0.025 mg/kg to 0.500 mg/kg, 0.025 mg/kg to 0.750 mg/kg, or 0.025 mg/kg to 1.0 mg/kg.

In some embodiments, the RNA vaccine compositions may be administered twice (e.g., Day 0 and Day 7, Day 0 and Day 14, Day 0 and Day 21, Day 0 and Day 28, Day 0 and Day 60, Day 0 and Day 90, Day 0 and Day 120, Day 0 and Day 150, Day 0 and Day 180, Day 0 and 3 months later, Day 0 and 6 months later, Day 0 and 9 months later, Day 0 and 12 months later, Day 0 and 18 months later, Day 0 and 2 years later, Day 0 and 5 years later, or Day 0 and 10 years later) at a total dose of or at dosage levels sufficient to deliver a total dose of 0.0100 mg, 0.025 mg, 0.050 mg, 0.075 mg, 0.100 mg, 0.125 mg, 0.150 mg, 0.175 mg, 0.200 mg, 0.225 mg, 0.250 mg, 0.275 mg, 0.300 mg, 0.325 mg, 0.350 mg, 0.375 mg, 0.400 mg, 0.425 mg, 0.450 mg, 0.475 mg, 0.500 mg, 0.525 mg, 0.550 mg, 0.575 mg, 0.600 mg, 0.625 mg, 0.650 mg, 0.675 mg, 0.700 mg, 0.725 mg, 0.750 mg, 0.775 mg, 0.800 mg, 0.825 mg. 0.850 mg, 0.875 mg, 0.900 mg, 0.925 mg, 0.950 mg, 0.975 mg, or 1.0 mg. Higher and lower dosages and frequency of administration are encompassed by the present disclosure. For example, a the RNA vaccine composition may be administered three or four times.

In some embodiments, the RNA vaccine compositions may be administered twice (e.g., Day 0 and Day 7, Day 0 and Day 14, Day 0 and Day 21, Day 0 and Day 28, Day 0 and Day 60, Day 0 and Day 90, Day 0 and Day 120, Day 0 and Day 150, Day 0 and Day 180, Day 0 and 3 months later, Day 0 and 6 months later, Day 0 and 9 months later, Day 0 and 12 months later, Day 0 and 18 months later, Day 0 and 2 years later, Day 0 and 5 years later, or Day 0 and 10 years later) at a total dose of or at dosage levels sufficient to deliver a total dose of 0.010 mg, 0.025 mg, 0.100 mg or 0.400 mg.

In some embodiments the RNA vaccine for use in a method of vaccinating a subject is administered the subject a single dosage of between 10 μg/kg and 400 μg/kg of the nucleic acid vaccine in an effective amount to vaccinate the subject. In some embodiments the RNA vaccine for use in a method of vaccinating a subject is administered the subject a single dosage of between 10 μg and 400 μg of the nucleic acid vaccine in an effective amount to vaccinate the subject.

In some embodiments, the RNA vaccine composition may comprise the polynucleotide described herein, formulated in a lipid nanoparticle comprising MC3, Cholesterol, DSPC and PEG2000-DMG, the buffer trisodium citrate, sucrose and water for injection. As a non-limiting example, the composition comprises: 2.0 mg/mL of drug substance (e.g., polynucleotides encoding cancer antigens), 21.8 mg/mL of MC3, 10.1 mg/mL of cholesterol, 5.4 mg/mL of DSPC. 2.7 mg/mL of PEG2000-DMG, 5.16 mg/mL of trisodium citrate, 71 mg/mL of sucrose and 1.0 mL of water for injection.

In some embodiments, a nanoparticle (e.g., a lipid nanoparticle) has a mean diameter of 10-500 nm, 20-400 nm, 30-300 nm, 40-200 nm. In some embodiments, a nanoparticle (e.g., a lipid nanoparticle) has a mean diameter of 50-150 nm, 50-200 nm, 80-100 nm or 80-200 nm.

Flagellin is an approximately 500 amino acid monomeric protein that polymerizes to form the flagella associated with bacterial motion. Flagellin is expressed by a variety of flagellated bacteria (*Salmonella typhimurium* for example) as well as non-flagellated bacteria (such as *Escherichia coli*). Sensing of flagellin by cells of the innate immune system (dendritic cells, macrophages, etc.) is mediated by the Toll-like receptor 5 (TLR5) as well as by Nod-like receptors (NLRs) Ipaf and Naip5. TLRs and NLRs have been identified as playing a role in the activation of innate immune response and adaptive immune response. As such, flagellin provides an adjuvant effect in a vaccine.

The nucleotide and amino acid sequences encoding known flagellin polypeptides are publicly available in the NCBI GenBank database. The flagellin sequences from S. *Typhimurium*, H. *Pylori*, V. Cholera, *S. marcesens, S. flexneri, T. pallidum, L. pneumophila, B. burgdorferei, C. difficile, R. meliloti, A. tumefaciens, R. lupini*, B. clarridgeiae, P. *Mirabilis*, B. subtilus, *L. monocytogenes, P. aeruginosa*, and *E. coli*, among others are known.

A flagellin polypeptide, as used herein, refers to a full length flagellin protein, immunogenic fragments thereof, and peptides having at least 50% sequence identity to a flagellin protein or immunogenic fragments thereof. Exemplary flagellin proteins include flagellin from *Salmonella typhi* (UniPro Entry number: Q56086), *Salmonella typhimurium* (A0A0C9DG09), *Salmonella enteritidis* (A0A0C9BAB7), and *Salmonella choleraesuis* (Q6V2X8), and proteins having an amino acid sequence identified by any one of SEQ ID NO: 420-422 (Table 66). In some embodiments, the flagellin polypeptide has at least 60%, 70%, 75%, 80%, 90%, 95%, 97%, 98%, or 99% sequence identity to a flagellin protein or immunogenic fragments thereof.

In some embodiments, the flagellin polypeptide is an immunogenic fragment. An immunogenic fragment is a portion of a flagellin protein that provokes an immune response. In some embodiments, the immune response is a TLR5 immune response. An example of an immunogenic fragment is a flagellin protein in which all or a portion of a hinge region has been deleted or replaced with other amino acids. For example, an antigenic polypeptide may be inserted in the hinge region. Hinge regions are the hypervariable regions of a flagellin. Hinge regions of a flagellin are also referred to as "D3 domain or region." "propeller domain or region," "hypervariable domain or region" and "variable domain or region." "At least a portion of a hinge region," as used herein, refers to any part of the hinge region of the flagellin, or the entirety of the hinge region. In other embodiments an immunogenic fragment of flagellin is a 20, 25, 30, 35, or 40 amino acid C-terminal fragment of flagellin.

The flagellin monomer is formed by domains DO through D3. DO and D1, which form the stem, are composed of tandem long alpha helices and are highly conserved among different bacteria. The D1 domain includes several stretches of amino acids that are useful for TLR5 activation. The entire D1 domain or one or more of the active regions within the domain are immunogenic fragments of flagellin. Examples of immunogenic regions within the D1 domain include residues 88-114 and residues 411-431 in *Salmonella typhimurium* FliC flagellin. Within the 13 amino acids in the 88-100 region, at least 6 substitutions are permitted between *Salmonella* flagellin and other flagellins that still preserve TLR5 activation. Thus, immunogenic fragments of flagellin include flagellin like sequences that activate TLR5 and contain a 13 amino acid motif that is 53% or more identical to the *Salmonella* sequence in 88-100 of FliC (LQRVRELAVQSAN; SEQ ID NO: 428).

In some embodiments, the RNA (e.g., mRNA) vaccine includes an RNA that encodes a fusion protein of flagellin and one or more antigenic polypeptides. A "fusion protein" as used herein, refers to a linking of two components of the construct. In some embodiments, a carboxy-terminus of the antigenic polypeptide is fused or linked to an amino terminus of the flagellin polypeptide. In other embodiments, an amino-terminus of the antigenic polypeptide is fused or linked to a carboxy-terminus of the flagellin polypeptide. The fusion protein may include, for example, one, two, three, four, five, six or more flagellin polypeptides linked to one, two, three, four, five, six or more antigenic polypeptides. When two or more flagellin polypeptides and/or two or more antigenic polypeptides are linked such a construct may be referred to as a "multimer."

Each of the components of a fusion protein may be directly linked to one another or they may be connected through a linker. For instance, the linker may be an amino acid linker. The amino acid linker encoded for by the RNA (e.g., mRNA) vaccine to link the components of the fusion protein may include, for instance, at least one member selected from the group consisting of a lysine residue, a glutamic acid residue, a serine residue and an arginine residue. In some embodiments the linker is 1-30, 1-25, 1-25, 5-10, 5, 15, or 5-20 amino acids in length.

In other embodiments the RNA (e.g., mRNA) vaccine includes at least two separate RNA polynucleotides, one encoding one or more antigenic polypeptides and the other encoding the flagellin polypeptide. The at least two RNA polynucleotides may be co-formulated in a carrier such as a lipid nanoparticle.

Liposomes, Lipoplexes, and Lipid Nanoparticles

The RNA vaccines of the invention can be formulated using one or more liposomes, lipoplexes, or lipid nanoparticles. In one embodiment, pharmaceutical compositions of RNA vaccines include liposomes. Liposomes are artificially-prepared vesicles which may primarily be composed of a lipid bilayer and may be used as a delivery vehicle for the administration of nutrients and pharmaceutical formulations. Liposomes can be of different sizes such as, but not limited to, a multilamellar vesicle (MLV) which may be hundreds of nanometers in diameter and may contain a series of concentric bilayers separated by narrow aqueous compartments, a small unicellular vesicle (SUV) which may be smaller than 50 nm in diameter, and a large unilamellar vesicle (LUV) which may be between 50 and 500 nm in diameter. Liposome design may include, but is not limited to, opsonins or ligands in order to improve the attachment of liposomes to unhealthy tissue or to activate events such as, but not limited to, endocytosis. Liposomes may contain a low or a high pH in order to improve the delivery of the pharmaceutical formulations.

The formation of liposomes may depend on the physicochemical characteristics such as, but not limited to, the pharmaceutical formulation entrapped and the liposomal ingredients, the nature of the medium in which the lipid vesicles are dispersed, the effective concentration of the entrapped substance and its potential toxicity, any additional processes involved during the application and/or delivery of the vesicles, the optimization size, polydispersity and the shelf-life of the vesicles for the intended application, and the batch-to-batch reproducibility and possibility of large-scale production of safe and efficient liposomal products.

As a non-limiting example, liposomes such as synthetic membrane vesicles may be prepared by the methods, apparatus and devices described in US Patent Publication No. US20130177638, US20130177637, US20130177636, US20130177635, US20130177634, US20130177633, US20130183375, US20130183373 and US20130183372, the contents of each of which are herein incorporated by reference in its entirety.

In one embodiment, pharmaceutical compositions described herein may include, without limitation, liposomes such as those formed from 1,2-dioleyloxy-N,N-dimethylaminopropane (DODMA) liposomes, DiLa2 liposomes from Marina Biotech (Bothell, W A), 1,2-dilinoleyloxy-3-dimethylaminopropane (DLin-DMA), 2,2-dilinoleyl-4-(2-dimethylamino-ethyl)-[1,3]-dioxolane (DLin-KC2-DMA), and MC3 (US20100324120; herein incorporated by reference in its entirety) and liposomes which may deliver small molecule drugs such as, but not limited to, DOXIL® from Janssen Biotech, Inc. (Horsham, P A).

In one embodiment, pharmaceutical compositions described herein may include, without limitation, liposomes such as those formed from the synthesis of stabilized plasmid-lipid particles (SPLP) or stabilized nucleic acid lipid particle (SNALP) that have been previously described and shown to be suitable for oligonucleotide delivery in vitro and in vivo (see Wheeler et al. *Gene Therapy.* 1999 6:271-281; Zhang et al. *Gene Therapy.* 1999 6:1438-1447; Jeffs et al. *Pharm Res.* 2005 22:362-372; Morrissey et al., *Nat Biotechnol.* 2005 2:1002-1007; Zimmermann et al., *Nature.* 2006 441:111-114; Heyes et al. *J Contr Rel.* 2005 107:276-287; Semple et al. *Nature Biotech.* 2010 28:172-176; Judge et al. *J Clin Invest.* 2009 119:661-673; deFougerolles *Hum Gene Ther.* 2008 19:125-132; U.S. Patent Publication No US20130122104; all of which are incorporated herein in their entireties). The original manufacture method by Wheeler et al. was a detergent dialysis method, which was later improved by Jeffs et al. and is referred to as the spontaneous vesicle formation method. The liposome formulations are composed of 3 to 4 lipid components in addition to the polynucleotide. As an example a liposome can contain, but is not limited to, 55% cholesterol, 20% disteroylphosphatidyl choline (DSPC), 10% PEG-S-DSG, and 15% 1,2-dioleyloxy-N,N-dimethylaminopropane (DODMA), as described by Jeffs et al. As another example, certain liposome formulations may contain, but are not limited to, 48% cholesterol, 20% DSPC, 2% PEG-c-DMA, and 30% cationic lipid, where the cationic lipid can be 1,2-distearloxy-N,N-dimethylaminopropane (DSDMA), DODMA, DLin-DMA, or 1,2-dilinolenyloxy-3-dimethylaminopropane (DLenDMA), as described by Heyes et al.

In some embodiments, liposome formulations may comprise from about 25.0% cholesterol to about 40.0% cholesterol, from about 30.0% cholesterol to about 45.0% cholesterol, from about 35.0% cholesterol to about 50.0% cholesterol and/or from about 48.5% cholesterol to about 60% cholesterol. In a preferred embodiment, formulations may comprise a percentage of cholesterol selected from the group consisting of 28.5%, 31.5%. 33.5%, 36.5%, 37.0%, 38.5%, 39.0% and 43.5%. In some embodiments, formulations may comprise from about 5.0% to about 10.0% DSPC and/or from about 7.0% to about 15.0% DSPC.

In one embodiment, pharmaceutical compositions may include liposomes which may be formed to deliver polynucleotides which may encode at least one immunogen (antigen) or any other polypeptide of interest. The RNA vaccine may be encapsulated by the liposome and/or it may be contained in an aqueous core which may then be encapsulated by the liposome (see International Pub. Nos. WO2012031046, WO2012031043, WO2012030901 and WO2012006378 and US Patent Publication No. US20130189351, US20130195969 and US20130202684; the contents of each of which are herein incorporated by reference in their entirety).

In another embodiment, liposomes may be formulated for targeted delivery. As a non-limiting example, the liposome may be formulated for targeted delivery to the liver. The liposome used for targeted delivery may include, but is not limited to, the liposomes described in and methods of making liposomes described in US Patent Publication No.

US20130195967, the contents of which are herein incorporated by reference in its entirety.

In another embodiment, the polynucleotide which may encode an immunogen (antigen) may be formulated in a cationic oil-in-water emulsion where the emulsion particle comprises an oil core and a cationic lipid which can interact with the polynucleotide anchoring the molecule to the emulsion particle (see International Pub. No. WO2012006380;

herein incorporated by reference in its entirety).

In one embodiment, the RNA vaccines may be formulated in a water-in-oil emulsion comprising a continuous hydrophobic phase in which the hydrophilic phase is dispersed. As a non-limiting example, the emulsion may be made by the methods described in International Publication No. WO201087791, the contents of which are herein incorporated by reference in its entirety.

In another embodiment, the lipid formulation may include at least cationic lipid, a lipid which may enhance transfection and a least one lipid which contains a hydrophilic head group linked to a lipid moiety (International Pub. No. WO2011076807 and U.S. Pub. No. 20110200582; the contents of each of which is herein incorporated by reference in their entirety). In another embodiment, the polynucleotides encoding an immunogen may be formulated in a lipid vesicle which may have crosslinks between functionalized lipid bilayers (scc U.S. Pub. No. 20120177724, the contents of which is herein incorporated by reference in its entirety).

In one embodiment, the polynucleotides may be formulated in a liposome as described in International Patent Publication No. WO2013086526, the contents of which is herein incorporated by reference in its entirety. The RNA vaccines may be encapsulated in a liposome using reverse pH gradients and/or optimized internal buffer compositions as described in International Patent Publication No. WO2013086526, the contents of which is herein incorporated by reference in its entirety.

In one embodiment, the RNA vaccine pharmaceutical compositions may be formulated in liposomes such as, but not limited to, DiLa2 liposomes (Marina Biotech, Bothell, W A), SMARTICLES® (Marina Biotech, Bothell, W A), neutral DOPC (1,2-dioleoyl-sn-glycero-3-phosphocholine) based liposomes (e.g., siRNA delivery for ovarian cancer (Landen et al. *Cancer Biology & Therapy* 2006 5 (12)1708-1713); herein incorporated by reference in its entirety) and hyaluronan-coated liposomes (Quiet Therapeutics, Israel).

In one embodiment, the cationic lipid may be a low molecular weight cationic lipid such as those described in U.S. patent application No. 20130090372, the contents of which are herein incorporated by reference in its entirety.

In one embodiment, the RNA vaccines may be formulated in a lipid vesicle which may have crosslinks between functionalized lipid bilayers.

In one embodiment, the RNA vaccines may be formulated in a liposome comprising a cationic lipid. The liposome may have a molar ratio of nitrogen atoms in the cationic lipid to the phosphates in the RNA (N:P ratio) of between 1:1 and 20:1 as described in International Publication No. WO2013006825, herein incorporated by reference in its entirety. In another embodiment, the liposome may have a N:P ratio of greater than 20:1 or less than 1:1.

In one embodiment, the RNA vaccines may be formulated in a lipid-polycation complex. The formation of the lipid-polycation complex may be accomplished by methods known in the art and/or as described in U.S. Pub. No. 20120178702, herein incorporated by reference in its entirety. As a non-limiting example, the polycation may include a cationic peptide or a polypeptide such as, but not limited to, polylysine, polyornithine and/or polyarginine and the cationic peptides described in International Pub. No. WO2012013326 or US Patent Pub. No. US20130142818; each of which is herein incorporated by reference in its entirety. In another embodiment, the RNA vaccines may be formulated in a lipid-polycation complex which may further include a non-cationic lipid such as, but not limited to, cholesterol or dioleoyl phosphatidylethanolamine (DOPE).

In one embodiment, the RNA vaccines may be formulated in an aminoalcohol lipidoid. Aminoalcohol lipidoids which may be used in the present invention may be prepared by the methods described in U.S. Pat. No. 8,450,298, herein incorporated by reference in its entirety.

The liposome formulation may be influenced by, but not limited to, the selection of the cationic lipid component, the degree of cationic lipid saturation, the nature of the PEGylation, ratio of all components and biophysical parameters such as size. In one example by Semple et al. (Semple et al. *Nature Biotech.* 2010 28:172-176; herein incorporated by reference in its entirety), the liposome formulation was composed of 57.1% cationic lipid, 7.1% dipalmitoylphosphatidylcholine, 34.3% cholesterol, and 1.4% PEG-c-DMA. As another example, changing the composition of the cationic lipid could more effectively deliver siRNA to various antigen presenting cells (Basha et al. *Mol Ther.* 2011 19:2186-2200; herein incorporated by reference in its entirety). In some embodiments, liposome formulations may comprise from about 35 to about 45% cationic lipid, from about 40% to about 50% cationic lipid, from about 50% to about 60% cationic lipid and/or from about 55% to about 65% cationic lipid. In some embodiments, the ratio of lipid to mRNA in liposomes may be from about 5:1 to about 20:1, from about 10:1 to about 25:1, from about 15:1 to about 30:1 and/or at least 30:1.

In some embodiments, the ratio of PEG in the lipid nanoparticle (LNP) formulations may be increased or decreased and/or the carbon chain length of the PEG lipid may be modified from $C_{14}$ to C18 to alter the pharmacokinetics and/or biodistribution of the LNP formulations. As a non-limiting example, LNP formulations may contain from about 0.5% to about 3.0%, from about 1.0% to about 3.5%, from about 1.5% to about 4.0%, from about 2.0% to about 4.5%, from about 2.5% to about 5.0% and/or from about 3.0% to about 6.0% of the lipid molar ratio of PEG-c-DOMG (R-3-[(ω-methoxy-poly(ethyleneglycol)2000) carbamoyl)]-1,2-dimyristyloxypropyl-3-amine) (also referred to herein as PEG-DOMG) as compared to the cationic lipid, DSPC and cholesterol. In another embodiment the PEG-c-DOMG may be replaced with a PEG lipid such as, but not limited to, PEG-DSG (1,2-Distearoyl-sn-glycerol, methoxypolyethylene glycol), PEG-DMG (1,2-Dimyristoyl-sn-glycerol) and/or PEG-DPG (1,2-Dipalmitoyl-sn-glycerol, methoxypolyethylene glycol). The cationic lipid may be selected from any lipid known in the art such as, but not limited to, DLin-MC3-DMA, DLin-DMA, C12-200 and DLin-KC2-DMA.

In one embodiment, the RNA vaccines may be formulated in a lipid nanoparticle such as those described in International Publication No. WO2012170930, the contents of which is herein incorporated by reference in its entirety.

In one embodiment, the RNA vaccine formulation comprising the polynucleotide is a nanoparticle which may comprise at least one lipid. The lipid may be selected from, but is not limited to, DLin-DMA, DLin-K-DMA, 98N12-5, $C_{12-200}$, DLin-MC3-DMA, DLin-KC2-DMA, DODMA, PLGA, PEG, PEG-DMG, PEGylated lipids and amino alcohol lipids.

In another aspect, the lipid may be a cationic lipid such as, but not limited to, DLin-DMA, DLin-D-DMA, DLin-MC3-DMA, DLin-KC2-DMA, DODMA and amino alcohol lipids.

The amino alcohol cationic lipid may be the lipids described in and/or made by the methods described in US Patent Publication No. US20130150625, herein incorporated by reference in its entirety. As a non-limiting example, the cationic lipid may be 2-amino-3-[(9Z,12Z)-oc tadeca-9,12-dien-1-yloxy]-2-{[(9Z,2Z)-octadeca-9,12-dien-1-yloxy] methyl} propan-1-ol (Compound 1 in US20130150625); 2-amino-3-[(9Z)-octadec-9-en-1-yloxy]-2-{[(9Z)-oc tadec-9-en-1-yloxy]methyl} propan-1-ol (Compound 2 in US20130150625); 2-amino-3-[(9Z,12Z)-octadeca-9,12-dien-1-yloxy]-2-[(octyloxy)methyl]propan-1-ol (Compound 3 in US20130150625); and 2-(dimethylamino)-3-[(9Z,12Z)-octadeca-9,12-dien-1-yloxy]-2-≡5 [(9Z,12Z)-octadeca-9,12-dien-1-yloxy]methyl} propan-1-ol (Compound 4 in US20130150625); or any pharmaceutically acceptable salt or stereoisomer thereof.

Lipid nanoparticle formulations typically comprise a lipid, in particular, an ionizable cationic lipid, for example, 2,2-dilinoleyl-4-dimethylaminoethyl-[1,3]-dioxolane (DLin-KC2-DMA), dilinoleyl-methyl-4-dimethylaminobutyrate (DLin-MC3-DMA), or di((Z)-non-2-en-1-yl) 9-((4-(dimethylamino) butanoyl)oxy) heptadecanedioate (L319), and further comprise a neutral lipid, a sterol and a molecule capable of reducing particle aggregation, for example a PEG or PEG-modified lipid.

In one embodiment, the lipid nanoparticle formulation consists essentially of (i) at least one lipid selected from the group consisting of 2,2-dilinoleyl-4-dimethylaminoethyl-[1,3]-dioxolane (DLin-KC2-DMA), dilinoleyl-methyl-4-dimethylaminobutyrate (DLin-MC3-DMA), and di((Z)-non-2-en-1-yl) 9-((4-(dimethylamino) butanoyl)oxy) heptadecanedioate (L319); (ii) a neutral lipid selected from DSPC, DPPC, POPC, DOPE and SM; (iii) a sterol, e.g., cholesterol; and (iv) a PEG-lipid, e.g., PEG-DMG or PEG-cDMA, in a molar ratio of about 20-60% cationic lipid: 5-25% neutral lipid: 25-55% sterol; 0.5-15% PEG-lipid. In one embodiment, the formulation includes from about 25% to about 75% on a molar basis of a cationic lipid selected from 2,2-dilinoleyl-4-dimethylaminoethyl-[1,3]-di oxolane (DLin-KC2-DMA), dilinoleyl-methyl-4-dimethylaminobutyrate (DLin-MC3-DMA), and di((Z)-non-2-en-1-yl) 9-((4-(dimethylamino) butanoyl)oxy) heptadecanedioate (L319), e.g., from about 35 to about 65%, from about 45 to about 65%, about 60%, about 57.5%, about 50% or about 40% on a molar basis.

In one embodiment, the formulation includes from about 0.5% to about 15% on a molar basis of the neutral lipid e.g., from about 3 to about 12%, from about 5 to about 10% or about 15%, about 10%, or about 7.5% on a molar basis. Exemplary neutral lipids include, but are not limited to, DSPC, POPC, DPPC, DOPE and SM. In one embodiment, the formulation includes from about 5% to about 50% on a molar basis of the sterol (e.g., about 15 to about 45%, about 20 to about 40%, about 40%, about 38.5%, about 35%, or about 31% on a molar basis. An exemplary sterol is cholesterol. In one embodiment, the formulation includes from about 0.5% to about 20% on a molar basis of the PEG or PEG-modified lipid (e.g., about 0.5 to about 10%, about 0.5 to about 5%, about 1.5%, about 0.5%, about 1.5%, about 3.5%, or about 5% on a molar basis. In one embodiment, the PEG or PEG modified lipid comprises a PEG molecule of an average molecular weight of 2,000 Da. In other embodiments, the PEG or PEG modified lipid comprises a PEG molecule of an average molecular weight of less than 2,000, for example around 1,500 Da, around 1,000 Da, or around 500 Da. Exemplary PEG-modified lipids include, but are not limited to, PEG-distearoyl glycerol (PEG-DMG) (also referred herein as PEG-$C_{14}$ or C14-PEG), PEG-CDMA (further discussed in Reyes et al. *J. Controlled Release,* 107, 276-287 (2005) the contents of which are herein incorporated by reference in its entirety)

In one embodiment, the formulations of the inventions include 25-75% of a cationic lipid selected from 2,2-dilinoleyl-4-dimethylaminoethyl-[1,3]-dioxolane (DLin-KC2-DMA), dilinoleyl-methyl-4-dimethylaminobutyrate (DLin-MC3-DMA), and di((Z)-non-2-en-1-yl) 9-((4-(dimethylamino) butanoyl)oxy) heptadecanedioate (L319), 0.5-15% of the neutral lipid, 5-50% of the sterol, and 0.5-20% of the PEG or PEG-modified lipid on a molar basis.

In one embodiment, the formulations of the inventions include 35-65% of a cationic lipid selected from 2,2-dilinoleyl-4-dimethylaminoethyl-[1,3]-dioxolane (DLin-KC2-DMA), dilinoleyl-methyl-4-dimethylaminobutyrate (DLin-MC3-DMA), and di((Z)-non-2-en-1-yl) 9-((4-(dimethylamino) butanoyl)oxy) heptadecanedioate (L319), 3-12% of the neutral lipid, 15-45% of the sterol, and 0.5-10% of the PEG or PEG-modified lipid on a molar basis. In one embodiment, the formulations of the inventions include 45-65% of a cationic lipid selected from 2,2-dilinoleyl-4-dimethylaminoethyl-[1,3]-dioxolane (DLin-KC2-DMA), dilinoleyl-methyl-4-dimethylaminobutyrate (DLin-MC3-DMA), and di((Z)-non-2-en-1-yl) 9-((4-(dimethylamino) butanoyl)oxy) heptadecanedioate (L319), 5-10% of the neutral lipid, 25-40% of the sterol, and 0.5-10% of the PEG or PEG-modified lipid on a molar basis.

In one embodiment, the formulations of the inventions include about 60% of a cationic lipid selected from 2,2-dilinoleyl-4-dimethylaminoethyl-[1.3]-dioxolane (DLin-KC2-DMA), dilinoleyl-methyl-4-dimethylaminobutyrate (DLin-MC3-DMA), and di((Z)-non-2-en-1-yl) 9-((4-(dimethylamino) butanoyl)oxy) heptadecanedioate (L319), about 7.5% of the neutral lipid, about 31% of the sterol, and about 1.5% of the PEG or PEG-modified lipid on a molar basis.

In one embodiment, the formulations of the inventions include about 50% of a cationic lipid selected from 2,2-dilinoleyl-4-dimethylaminoethyl-[1,3]-dioxolane (DLin-KC2-DMA), dilinoleyl-methyl-4-dimethylaminobutyrate (DLin-MC3-DMA), and di((Z)-non-2-en-1-yl) 9-((4-(dimethylamino) butanoyl)oxy) heptadecanedioate (L319), about 10% of the neutral lipid, about 38.5% of the sterol, and about 1.5% of the PEG or PEG-modified lipid on a molar basis.

In one embodiment, the formulations of the inventions include about 50% of a cationic lipid selected from 2,2-dilinoleyl-4-dimethylaminoethyl-[1,3]-dioxolane (DLin-KC2-DMA), dilinoleyl-methyl-4-dimethylaminobutyrate (DLin-MC3-DMA), and di((Z)-non-2-en-1-yl) 9-((4-(dimethylamino) butanoyl)oxy) heptadecanedioate (L319), about 10% of the neutral lipid, about 35% of the sterol, about 4.5% or about 5% of the PEG or PEG-modified lipid, and about 0.5% of the targeting lipid on a molar basis.

In one embodiment, the formulations of the inventions include about 40% of a cationic lipid selected from 2,2-dilinoleyl-4-dimethylaminoethyl-[1,3]-dioxolane (DLin-KC2-DMA), dilinoleyl-methyl-4-dimethylaminobutyrate (DLin-MC3-DMA), and di((Z)-non-2-en-1-yl) 9-((4-(dimethylamino) butanoyl)oxy) heptadecanedioate (L319), about 15% of the neutral lipid, about 40% of the sterol, and about 5% of the PEG or PEG-modified lipid on a molar basis.

In one embodiment, the formulations of the inventions include about 57.2% of a cationic lipid selected from 2,2-dilinoleyl-4-dimethylaminoethyl-[1,3]-dioxolane (DLin-KC2-DMA), dilinoleyl-methyl-4-dimethylaminobutyrate (DLin-MC3-DMA), and di((Z)-non-2-en-1-yl) 9-((4-(dimethylamino) butanoyl)oxy) heptadecanedioate (L319), about 7.1% of the neutral lipid, about 34.3% of the sterol, and about 1.4% of the PEG or PEG-modified lipid on a molar basis.

In one embodiment, the formulations of the inventions include about 57.5% of a cationic lipid selected from the PEG lipid is PEG-CDMA (PEG-CDMA is further discussed in Reyes et al. (*J. Controlled Release,* 107, 276-287 (2005), the contents of which are herein incorporated by reference in its entirety), about 7.5% of the neutral lipid, about 31.5% of the sterol, and about 3.5% of the PEG or PEG-modified lipid on a molar basis.

In preferred embodiments, lipid nanoparticle formulation consists essentially of a lipid mixture in molar ratios of about 20-70% cationic lipid: 5-45% neutral lipid: 20-55% cholesterol: 0.5-15% PEG-modified lipid; more preferably in a molar ratio of about 20-60% cationic lipid: 5-25% neutral lipid: 25-55% cholesterol: 0.5-15% PEG-modified lipid. In particular embodiments, the molar lipid ratio is approximately 50/10/38.5/1.5 (mol % cationic lipid/neutral lipid, e.g., DSPC/Chol/PEG-modified lipid, e.g., PEG-DMG, PEG-DSG or PEG-DPG), 57.2/7.1134.3/1.4 (mol % cationic lipid/neutral lipid, e.g., DPPC/Chol/PEG-modified lipid, e.g., PEG-cDMA), 40/15/40/5 (mol % cationic lipid/neutral lipid, e.g., DSPC/Chol/PEG-modified lipid, e.g., PEG-DMG), 50/10/35/4.5/0.5 (mol % cationic lipid/neutral lipid, e.g., DSPC/Chol/PEG-modified lipid, e.g., PEG-DSG), 50/10/35/5 (cationic lipid/neutral lipid, e.g., DSPC/Chol/PEG-modified lipid, e.g., PEG-DMG), 40/10/40/10 (mol % cationic lipid/neutral lipid, e.g., DSPC/Chol/PEG-modified lipid, e.g., PEG-DMG or PEG-cDMA), 35/15/40/10 (mol % cationic lipid/neutral lipid, e.g., DSPC/Chol/PEG-modified lipid, e.g., PEG-DMG or PEG-cDMA) or 52/13/30/5 (mol % cationic lipid/neutral lipid, e.g., DSPC/Chol/PEG-modified lipid, e.g., PEG-DMG or PEG-cDMA).

Exemplary lipid nanoparticle compositions and methods of making same are described, for example, in Semple et al. (2010) *Nat. Biotechnol.* 28:172-176; Jayarama et al. (2012), *Angew. Chem. Int. Ed.,* 51:8529-8533; and Maier et al. (2013) Molecular Therapy 21, 1570-1578 (the contents of each of which are incorporated herein by reference in their entirety).

In one embodiment, the lipid nanoparticle formulations described herein may comprise a cationic lipid, a PEG lipid and a structural lipid and optionally comprise a non-cationic lipid. As a non-limiting example, the lipid nanoparticle may comprise about 40-60% of cationic lipid, about 5-15% of a non-cationic lipid, about 1-2% of a PEG lipid and about 30-50% of a structural lipid. As another non-limiting example, the lipid nanoparticle may comprise about 50% cationic lipid, about 10% non-cationic lipid, about 1.5% PEG lipid and about 38.5% structural lipid. As yet another non-limiting example, the lipid nanoparticle may comprise about 55% cationic lipid, about 10% non-cationic lipid, about 2.5% PEG lipid and about 32.5% structural lipid. In one embodiment, the cationic lipid may be any cationic lipid described herein such as, but not limited to, DLin-KC2-DMA, DLin-MC3-DMA and L319. In one embodiment, the lipid nanoparticle formulations described herein may be 4 component lipid nanoparticles. The lipid nanoparticle may comprise a cationic lipid, a non-cationic lipid, a PEG lipid and a structural lipid. As a non-limiting example, the lipid nanoparticle may comprise about 40-60% of cationic lipid, about 5-15% of a non-cationic lipid, about 1-2% of a PEG lipid and about 30-50% of a structural lipid. As another non-limiting example, the lipid nanoparticle may comprise about 50% cationic lipid, about 10% non-cationic lipid, about 1.5% PEG lipid and about 38.5% structural lipid. As yet another non-limiting example, the lipid nanoparticle may comprise about 55% cationic lipid, about 10% non-cationic lipid, about 2.5% PEG lipid and about 32.5% structural lipid. In one embodiment, the cationic lipid may be any cationic lipid described herein such as, but not limited to, DLin-KC2-DMA, DLin-MC3-DMA and L319.

In one embodiment, the lipid nanoparticle formulations described herein may comprise a cationic lipid, a non-cationic lipid, a PEG lipid and a structural lipid. As a non-limiting example, the lipid nanoparticle comprise about 50% of the cationic lipid DLin-KC2-DMA, about 10% of the non-cationic lipid DSPC, about 1.5% of the PEG lipid PEG-DOMG and about 38.5% of the structural lipid cholesterol. As a non-limiting example, the lipid nanoparticle comprise about 50% of the cationic lipid DLin-MC3-DMA, about 10% of the non-cationic lipid DSPC, about 1.5% of the PEG lipid PEG-DOMG and about 38.5% of the structural lipid cholesterol. As a non-limiting example, the lipid nanoparticle comprise about 50% of the cationic lipid DLin-MC3-DMA, about 10% of the non-cationic lipid DSPC, about 1.5% of the PEG lipid PEG-DMG and about 38.5% of the structural lipid cholesterol. As yet another non-limiting example, the lipid nanoparticle comprise about 55% of the cationic lipid L319, about 10% of the non-cationic lipid DSPC, about 2.5% of the PEG lipid PEG-DMG and about 32.5% of the structural lipid cholesterol.

In one embodiment, the cationic lipid may be selected from, but not limited to, a cationic lipid described in International Publication Nos. WO2012040184, WO2011153120, WO2011149733, WO2011090965, WO2011043913, WO2011022460, WO2012061259, WO2012054365, WO2012044638, WO2010080724, WO201021865, WO2008103276, WO2013086373 and WO2013086354, U.S. Pat. Nos. 7,893,302, 7,404,969, 8,283,333, and 8,466,122 and US Patent Publication No. US20100036115, US20120202871, US20130064894, US20130129785, US20130150625, US20130178541 and US20130225836; the contents of each of which are herein incorporated by reference in their entirety. In another embodiment, the cationic lipid may be selected from, but not limited to, formula A described in International Publication Nos. WO2012040184, WO2011153120, WO2011149733, WO2011090965, WO2011043913, WO2011022460, WO2012061259, WO2012054365, WO2012044638 and WO2013116126 or US Patent Publication No. US20130178541 and US20130225836; the contents of each of which is herein incorporated by reference in their entirety. In yet another embodiment, the cationic lipid may be selected from, but not limited to, formula CLI-CLXXIX of International Publication No. WO2008103276, formula CLI-CLXXIX of U.S. Pat. No. 7,893,302, formula CLI-CLXXXXII of U.S. Pat. No. 7,404,969 and formula I-VI of US Patent Publication No. US20100036115, formula I of US Patent Publication No US20130123338; each of which is herein incorporated by reference in their entirety. As a non-limiting example, the cationic lipid may be selected from (20Z,23Z)—N,N-dimethylnonacosa-20,23-dien-10-amine, (17Z,20Z)—N,N-dimemylhexacosa-17,20-dien-9-amine, (1Z,19Z)—N5N-dimethylpentacosa-1 6, 19-dien-8-amine, (13Z,16Z)—N,N-dimethyldocosa-13,16-dien-5-amine, (12Z,15Z)—N,N-dimethylhenicosa-12,15-dien-4-amine. (14Z,17Z)—N,N-dimethyltricosa-14,17-dien-6-amine, (15Z,18Z)—N,N-dimethyltetracosa-15,18-dien-7-amine, (18Z,21Z)—N,N-dimethylheptacosa-18,21-dien-10-amine, (15Z,18Z)—N,N-dimethyltetracosa-15,18-dien-5-amine, (14Z,17Z)—N, N-dimethyltricosa-14,17-dien-4-amine, (19Z,22Z)—N,N-dimcihyloctacosa-19,22-dien-9-amine, (18Z,21 Z)—N,N-dimethylheptacosa-18,21-dien-8-amine, (17Z,20Z)—N,N-dimethylhexacosa-17,20-dien-7-amine. (16Z,19Z)—N,N-dimethylpentacosa-16,19-dien-6-amine, (22Z,25Z)—N,N-dimethylhentriaconta-22,25-dien-10-amine, (21 Z,24Z)—N,N-dimethyltriaconta-21,24-dien-9-amine, (18Z)—N,N-dimetylheptacos-18-en-10-amine, (17Z)—N, N-dimethylhexacos-17-en-9-amine, (19Z,22Z)—N,N-dimethyloctacosa-19,22-dien-7-amine, N,N-dimethylheptacosan-10-amine, (20Z,23Z)—N-ethyl-N-methylnonacosa-20,23-dien-10-amine, 1-[(11Z,14Z)-1-n onylicosa-11,14-dien-1-yl]pyrrolidine, (20Z)—N,N-dimethylheptacos-20-en-1 O-amine, (15Z)—N,N-dimethyl eptacos-15-en-1 O-amine, (14Z)—N,N-dimethylnonacos-14-en-10-amine, (17Z)—N,N-dimethylnonacos-17-en-10-amine, (24Z)—N,N-dimethyltritriacont-24-cn-10-amine, (20Z)—N,N-dimethylnonacos-20-en-1 O-amine, (22Z)—N, N-dimethylhentriacont-22-en-10-amine, (16Z)—N,N-dimethylpentacos-16-en-8-amine, (12Z,15Z)—N,N-dimethyl-2-nonylhenicosa-12,15-dien-1-amine, (13Z,16Z)—N,N-dimethyl-3-no nyldocosa-13,16-dien-1-amine, N,N-dimethyl-1-[(1S,2R)-2-octylcyclopropyl]cptadecan-8-amine, 1-[(1S,2R)-2-hexylcyclopropyl]-N,N-dimethylnonadecan-10-amine, N,N-dimethyl-1-[(1S,2R)-2-octylcyclopropyl]nonadecan-10-amine, N,N-dimethyl-21-[(1S,2R)-2-octylcyclopropyl]henicosan-10-amine, N,N-dimethyl-1-[(1S,2S)-2-{[(1R,2R)-2-pentylcycl opropyl methyl}cyclopropy l]nonadecan-10-amine, N,N-dimethyl-1-[(1S,2R)-2-octylcyclopropyl]hexadecan-8-amine, N,N-dimethyl-[(1R,2S)-2-un decylcyclopropyl|tetradecan-5-amine, N,N-dimethyl-3-{7-[(1S,2R)-2-octylcyclopropyl] heptyl} dodecan-1-amine, 1-[(1R,2S)-2-hepty lcyclopropyl]-N,N-dimethyloctadecan-9-amine, 1-[(1S,2R)-2-decylcyclopropyl]-N,N-dimethylpentadecan-6-amine, N,N-dimethyl-1-[(1S,2R)-2-octylcyclopropyl]pentadecan-8-amine, R—N,N-dimethyl-1-[(9Z,12Z)-octadeca-9,12-dien-1-yloxy]-3-(octyloxy) propan-2-amine, S—N,N-dimethyl-1-[(9Z,12Z)-octadeca-9,12-dien-1-yloxy]-3-(octyloxy) propan-2-amine, 1-{2-[(9Z,12Z)-oc tadeca-9,12-dien-1-yloxy]-1-[(octyloxy)methyl]ethyl}pyrrolidine, (2S)—N,N-dimethyl-1-[(9Z,12Z)-octadeca-9,12-dien-1-yloxy]-3-[(5Z)-oct-5-en-1-yloxy]propan-2-amine, 1-{2-[(9Z,12Z)-octadeca-9,12-dien-1-yloxy]-1-[(octyloxy) methyl]ethyl}azetidine, (2S)-1-(h exyloxy)-N,N-dimethyl-3-[(9Z,12Z)-octadeca-9,12-dien-1-yloxy]propan-2-amine, (2S)-1-(h eptyloxy)-N,N-dimethyl-3-[(9Z,12Z)-octadeca-9,12-dien-1-yloxy]propan-2-amine, N,N-dimethyl-1-(nonyloxy)-3-[(9Z,12Z)-octadeca-9,12-dien-1-yloxy]propan-2-amine, N,N-dimethyl-1-[(9Z)-octadec-9-en-1-yloxy]-3-(octyloxy) propan-2-amine; (2S)—N,N-dimethyl-1-[(6Z,9Z,12Z)-octadeca-6,9, 12-trien-1-yloxy]-3-(octyloxy) propan-2-amine, (2S)-1-[(11Z,14Z)-icosa-11,14-dien-1-yloxy]-N,N-dimethyl-3-(pentyloxy) propan-2-amine, (2S)-1-(h exyloxy)-3-[(11Z,14Z)-icosa-11,14-dien-1-yloxy]-N,N-dimethylpropan-2-amine, 1-[(11Z,14Z)-icosa-11,14-dien-1-yloxy]-N,N-dimethyl-3-(octyloxy) propan-2-amine, 1-[(13Z,16Z)-docosa-13,16-dien-1-yloxy]-N,N-dimethyl-3-(octyloxy) propan-2-amine, (2S)-1-[(13Z,16Z)-docosa-13,16-dien-1-yloxy]-3-(hexyloxy)-N,N-dimethylpropan-2-amine, (2S)-1-[(13Z)-docos-13-en-1-yloxy]-3-(hexyloxy)-N,N-dimethylpropan-2-amine, 1-[(13Z)-docos-13-en-1-yloxy]-N,N-dimethyl-3-(octyloxy) propan-2-amine, 1-[(9Z)-hexadec-9-en-1-yloxy]-N. N-dimethyl-3-(octyloxy) propan-2-amine, (2R)—N,N-dimethyl-H (1-metoylo ctyl) oxy]-3-[(9Z,12Z)-octadeca-9,12-dien-1-yloxy]propan-2-amine, (2R)-1-[(3,7-dimethyloctyl)oxy]-N, N-dimethyl-3-[(9Z,12Z)-octadeca-9,12-dien-1-yloxy]propan-2-amine, N,N-dimethyl-1-(octyloxy)-3-({8-[(1S,2S)-2-{[(1R,2R)-2-pentylcycl opropyl methyl}cyclopropyl]octyl} oxy) propan-2-amine, N,N-dimethyl-1-{[8-(2-oclylcyclopropyl)octyl] oxy}-3-(octyloxy)propan-2-amine and (11E,20Z,23Z)—N,N-dimethylnonacosa-11,20,2-trien-10-amine or a pharmaceutically acceptable salt or stereoisomer thereof.

In one embodiment, the lipid may be a cleavable lipid such as those described in International Publication No. WO2012170889, herein incorporated by reference in its entirety.

In another embodiment, the lipid may be a cationic lipid such as, but not limited to, Formula (I) of U.S. Patent Application No. US20130064894, the contents of which are herein incorporated by reference in its entirety.

In one embodiment, the cationic lipid may be synthesized by methods known in the art and/or as described in International Publication Nos. WO2012040184, WO2011153120, WO2011149733, WO2011090965, WO2011043913, WO2011022460, WO2012061259, WO2012054365, WO2012044638, WO2010080724, WO201021865, WO2013086373 and WO2013086354; the contents of each of which are herein incorporated by reference in their entirety.

In another embodiment, the cationic lipid may be a trialkyl cationic lipid. Non-limiting examples of trialkyl cationic lipids and methods of making and using the trialkyl cationic lipids are described in International Patent Publication No. WO2013126803, the contents of which are herein incorporated by reference in its entirety.

In one embodiment, the LNP formulations of the RNA vaccines may contain PEG-c-DOMG at 3% lipid molar ratio. In another embodiment, the LNP formulations RRNA vaccines may contain PEG-c-DOMG at 1.5% lipid molar ratio.

In one embodiment, the pharmaceutical compositions of the RNA vaccines may include at least one of the PEGylated lipids described in International Publication No. WO2012099755, the contents of which is herein incorporated by reference in its entirety.

In one embodiment, the LNP formulation may contain PEG-DMG 2000 (1,2-dimyristoyl-sn-glycero-3-phophoethanolamine-N-[methoxy (polyethylene glycol)-2000). In one embodiment, the LNP formulation may contain PEG-DMG 2000, a cationic lipid known in the art and at least one other component. In another embodiment, the LNP formulation may contain PEG-DMG 2000, a cationic lipid known in the art, DSPC and cholesterol. As a non-limiting example, the LNP formulation may contain PEG-DMG 2000*, DLin-DMA, DSPC and cholesterol. As another non-limiting example the LNP formulation may contain PEG-DMG* 2000, DLin-DMA, *DSPC and cholesterol in a molar ratio of* 2:40:10:48 (see e.g., Geall et al., Nonviral delivery of self-amplifying RNA vaccines, *PNAS* 2012; PMID: 22908294; herein incorporated by reference in its entirety).

In one embodiment, the LNP formulation may be formulated by the methods described in International Publication Nos. WO2011127255 or WO2008103276, the contents of each of which is herein incorporated by reference in their entirety. As a non-limiting example, the RNA vaccines described herein may be encapsulated in LNP formulations as described in WO2011127255 and/or WO2008103276; each of which is herein incorporated by reference in their entirety.

In one embodiment, the RNA vaccines described herein may be formulated in a nanoparticle to be delivered by a parenteral route as described in U.S. Pub. No. US20120207845; the contents of which are herein incorporated by reference in its entirety.

In one embodiment, the RNA vaccines may be formulated in a lipid nanoparticle made by the methods described in US Patent Publication No US20130156845 or International Publication No WO2013093648 or WO2012024526, each of which is herein incorporated by reference in its entirety.

The lipid nanoparticles described herein may be made in a sterile environment by the system and/or methods described in US Patent Publication No. US20130164400, herein incorporated by reference in its entirety.

In one embodiment, the LNP formulation may be formulated in a nanoparticle such as a nucleic acid-lipid particle described in U.S. Pat. No. 8,492,359, the contents of which are herein incorporated by reference in its entirety. As a non-limiting example, the lipid particle may comprise one or more active agents or therapeutic agents; one or more cationic lipids comprising from about 50 mol % to about 85 mol % of the total lipid present in the particle; one or more non-cationic lipids comprising from about 13 mol % to about 49.5 mol % of the total lipid present in the particle; and one or more conjugated lipids that inhibit aggregation of particles comprising from about 0.5 mol % to about 2 mol % of the total lipid present in the particle. The nucleic acid in the nanoparticle may be the polynucleotides described herein and/or are known in the art.

In one embodiment, the LNP formulation may be formulated by the methods described in International Publication Nos. WO2011127255 or WO2008103276, the contents of each of which are herein incorporated by reference in their entirety. As a non-limiting example, modified RNA described herein may be encapsulated in LNP formulations as described in WO2011127255 and/or WO2008103276; the contents of each of which are herein incorporated by reference in their entirety.

In one embodiment, LNP formulations described herein may comprise a polycationic composition. As a non-limiting example, the polycationic composition may be selected from formula 1-60 of US Patent Publication No. US20050222064; the content of which is herein incorporated by reference in its entirety. In another embodiment, the LNP formulations comprising a polycationic composition may be used for the delivery of the modified RNA described herein in vivo and/or in vitro.

In one embodiment, the LNP formulations described herein may additionally comprise a permeability enhancer molecule. Non-limiting permeability enhancer molecules are described in US Patent Publication No. US20050222064; the content of which is herein incorporated by reference in its entirety.

In one embodiment, the RNA vaccine pharmaceutical compositions may be formulated in liposomes such as, but not limited to, DiLa2 liposomes (Marina Biotech, Bothell, W A), SMARTICLES® (Marina Biotech, Bothell, W A), neutral DOPC (1,2-dioleoyl-sn-glycero-3-phosphocholine) based liposomes (e.g., siRNA delivery for ovarian cancer (Landen et al. *Cancer Biology & Therapy* 2006 5 (12) 1708-1713); herein incorporated by reference in its entirety) and hyaluronan-coated liposomes (Quiet Therapeutics, Israel).

In one embodiment, the RNA vaccines may be formulated in a lyophilized gel-phase liposomal composition as described in US Publication No. US2012060293, herein incorporated by reference in its entirety.

The nanoparticle formulations may comprise a phosphate conjugate. The phosphate conjugate may increase in vivo circulation times and/or increase the targeted delivery of the nanoparticle. Phosphate conjugates for use with the present invention may be made by the methods described in International Application No. WO2013033438 or US Patent Publication No. US20130196948, the contents of each of which are herein incorporated by reference in its entirety. As a non-limiting example, the phosphate conjugates may include a compound of any one of the formulas described in International Application No. WO2013033438, herein incorporated by reference in its entirety.

The nanoparticle formulation may comprise a polymer conjugate. The polymer conjugate may be a water soluble conjugate. The polymer conjugate may have a structure as described in U.S. patent application No. 20130059360, the contents of which are herein incorporated by reference in its entirety. In one aspect, polymer conjugates with the polynucleotides of the present invention may be made using the methods and/or segmented polymeric reagents described in U.S. patent application No. 20130072709, herein incorporated by reference in its entirety. In another aspect, the polymer conjugate may have pendant side groups comprising ring moieties such as, but not limited to, the polymer conjugates described in US Patent Publication No. US20130196948, the contents of which is herein incorporated by reference in its entirety.

The nanoparticle formulations may comprise a conjugate to enhance the delivery of nanoparticles of the present invention in a subject. Further, the conjugate may inhibit phagocytic clearance of the nanoparticles in a subject. In one aspect, the conjugate may be a "self" peptide designed from the human membrane protein CD47 (e.g., the "self" particles described by Rodriguez et al (Science 2013 339, 971-975), herein incorporated by reference in its entirety). As shown by Rodriguez et al. the self peptides delayed macrophage-mediated clearance of nanoparticles which enhanced delivery of the nanoparticles. In another aspect, the conjugate may be the membrane protein CD47 (e.g., see Rodriguez et al. Science 2013 339, 971-975, herein incorporated by reference in its entirety). Rodriguez et al. showed that, similarly to "self" peptides, CD47 can increase the circulating particle ratio in a subject as compared to scrambled peptides and PEG coated nanoparticles.

In one embodiment, the RNA vaccines of the present invention are formulated in nanoparticles which comprise a conjugate to enhance the delivery of the nanoparticles of the present invention in a subject. The conjugate may be the CD47 membrane or the conjugate may be derived from the CD47 membrane protein, such as the "self" peptide described previously. In another aspect the nanoparticle may comprise PEG and a conjugate of CD47 or a derivative thereof. In yet another aspect, the nanoparticle may comprise both the "self" peptide described above and the membrane protein CD47.

In another aspect, a "self" peptide and/or CD47 protein may be conjugated to a virus-like particle or pseudovirion, as described herein for delivery of the RNA vaccines of the present invention.

In another embodiment, RNA vaccine pharmaceutical compositions comprising the polynucleotides of the present invention and a conjugate which may have a degradable linkage. Non-limiting examples of conjugates include an aromatic moiety comprising an ionizable hydrogen atom, a spacer moiety, and a water-soluble polymer. As a non-limiting example, pharmaceutical compositions comprising a conjugate with a degradable linkage and methods for delivering such pharmaceutical compositions are described in US Patent Publication No. US20130184443, the contents of which are herein incorporated by reference in its entirety.

The nanoparticle formulations may be a carbohydrate nanoparticle comprising a carbohydrate carrier and a RNA vaccine. As a non-limiting example, the carbohydrate carrier may include, but is not limited to, an anhydride-modified phytoglycogen or glycogen-type material, phtoglycogen octenyl succinate, phytoglycogen beta-dextrin, anhydride-modified phytoglycogen beta-dextrin. (See e.g., International Publication No. WO2012109121; the contents of which are herein incorporated by reference in its entirety).

Nanoparticle formulations of the present invention may be coated with a surfactant or polymer in order to improve the delivery of the particle. In one embodiment, the nanoparticle may be coated with a hydrophilic coating such as, but not limited to, PEG coatings and/or coatings that have a neutral surface charge. The hydrophilic coatings may help to deliver nanoparticles with larger payloads such as, but not limited to, RNA vaccines within the central nervous system. As a non-limiting example nanoparticles comprising a hydrophilic coating and methods of making such nanoparticles are described in US Patent Publication No. US20130183244, the contents of which are herein incorporated by reference in its entirety.

In one embodiment, the lipid nanoparticles of the present invention may be hydrophilic polymer particles. Non-limiting examples of hydrophilic polymer particles and methods of making hydrophilic polymer particles are described in US Patent Publication No. US20130210991, the contents of which are herein incorporated by reference in its entirety.

In another embodiment, the lipid nanoparticles of the present invention may be hydrophobic polymer particles.

Lipid nanoparticle formulations may be improved by replacing the cationic lipid with a biodegradable cationic lipid which is known as a rapidly eliminated lipid nanoparticle (rcLNP). Ionizable cationic lipids, such as, but not limited to, DLinDMA, DLin-KC2-DMA, and DLin-MC3-DMA, have been shown to accumulate in plasma and tissues over time and may be a potential source of toxicity. The rapid metabolism of the rapidly eliminated lipids can improve the tolerability and therapeutic index of the lipid nanoparticles by an order of magnitude from a 1 mg/kg dose to a 10 mg/kg dose in rat. Inclusion of an enzymatically degraded ester linkage can improve the degradation and metabolism profile of the cationic component, while still maintaining the activity of the reLNP formulation. The ester linkage can be internally located within the lipid chain or it may be terminally located at the terminal end of the lipid chain. The internal ester linkage may replace any carbon in the lipid chain.

In one embodiment, the internal ester linkage may be located on either side of the saturated carbon.

In one embodiment, an immune response may be elicited by delivering a lipid nanoparticle which may include a nanospecies, a polymer and an immunogen. (U.S.

Publication No. 20120189700 and International Publication No. WO2012099805; each of which is herein incorporated by reference in their entirety). The polymer may encapsulate the nanospecies or partially encapsulate the nanospecies. The immunogen may be a recombinant protein, a modified RNA and/or a polynucleotide described herein. In one embodiment, the lipid nanoparticle may be formulated for use in a vaccine such as, but not limited to, against a pathogen.

Lipid nanoparticles may be engineered to alter the surface properties of particles so the lipid nanoparticles may penetrate the mucosal barrier. Mucus is located on mucosal tissue such as, but not limited to, oral (e.g., the buccal and esophageal membranes and tonsil tissue), ophthalmic, gastrointestinal (e.g., stomach, small intestine, large intestine, colon, rectum), nasal, respiratory (e.g., nasal, pharyngeal, tracheal and bronchial membranes), genital (e.g., vaginal, cervical and urethral membranes). Nanoparticles larger than 10-200 nm which are preferred for higher drug encapsulation efficiency and the ability to provide the sustained delivery of a wide array of drugs have been thought to be too large to rapidly diffuse through mucosal barriers. Mucus is continuously secreted, shed, discarded or digested and recycled so most of the trapped particles may be removed from the mucosal tissue within seconds or within a few hours. Large polymeric nanoparticles (200 nm-500 nm in diameter) which have been coated densely with a low molecular weight polyethylene glycol (PEG) diffused through mucus only 4 to 6-fold lower than the same particles diffusing in water (Lai et al. *PNAS* 2007 104 (5): 1482-487; Lai et al. *Adv Drug Deliv Rev.* 2009 61 (2): 158-171; each of which is herein incorporated by reference in their entirety). The transport of nanoparticles may be determined using rates of permeation and/or fluorescent microscopy techniques including, but not limited to, fluorescence recovery after photobleaching (FRAP) and high resolution multiple particle tracking (MPT). As a non-limiting example, compositions which can penetrate a mucosal barrier may be made as described in U.S. Pat. No. 8,241,670 or International Patent Publication No. WO2013110028, the contents of each of which are herein incorporated by reference in its entirety.

The lipid nanoparticle engineered to penetrate mucus may comprise a polymeric material (i.e. a polymeric core) and/or a polymer-vitamin conjugate and/or a tri-block co-polymer. The polymeric material may include, but is not limited to, polyamines, polyethers, polyamides, polyesters, polycarbamates, polyureas, polycarbonates, poly(styrenes), polyimides, polysulfones, polyurethanes, polyacetylenes, polyethylenes, polyethyencimines, polyisocyanates, polyacrylates, polymethacrylates, polyacrylonitriles, and polyarylates. The polymeric material may be biodegradable and/or biocompatible. Non-limiting examples of biocompatible polymers are described in International Patent Publication No. WO2013116804, the contents of which are herein incorporated by reference in its entirety. The polymeric material may additionally be irradiated. As a non-limiting example, the polymeric material may be gamma irradiated (See e.g., International App. No.

WO201282165, herein incorporated by reference in its entirety). Non-limiting examples of specific polymers include poly(caprolactone) (PCL), ethylene vinyl acetate polymer (EVA), poly(lactic acid) (PLA), poly(L-lactic acid) (PLLA), poly(glycolic acid) (PGA), poly(lactic acid-co-glycolic acid) (PLGA), poly(L-lactic acid-co-glycolic acid) (PLLGA), poly(D,L-lactide) (PDLA), poly(L-lactide) (PLLA), poly(D,L-lactide-co-caprolactone), poly(D,L-lactide-co-caprolactone-co-glycolide), poly(D,L-lactide-co-PEO-co-D,L-lactide), poly(D,L-lactide-co-PPO-co-D,L-lactide), polyalkyl cyanoacralate, polyurethane, poly-L-lysine (PLL), hydroxypropyl methacrylate (HPMA), polyethyleneglycol, poly-L-glutamic acid, poly(hydroxy acids), polyanhydrides, polyorthoesters, poly(ester amides), polyamides, poly(ester ethers), polycarbonates, polyalkylenes such as polyethylene and polypropylene, polyalkylene glycols such as poly(ethylene glycol) (PEG), polyalkylene oxides (PEO), polyalkylene terephthalates such as poly(ethylene terephthalate), polyvinyl alcohols (PVA), polyvinyl ethers, polyvinyl esters such as poly(vinyl acetate), polyvinyl halides such as poly(vinyl chloride) (PVC), polyvinylpyrrolidone, polysiloxanes, polystyrene (PS), polyurethanes, derivatized celluloses such as alkyl celluloses, hydroxyalkyl celluloses, cellulose ethers, cellulose esters, nitro celluloses, hydroxypropylcellulose, carboxymethylcellulose, polymers of acrylic acids, such as poly(methyl(meth) acrylate) (PMMA), poly(ethyl(meth) acrylate), poly(butyl(meth) acrylate), poly(isobutyl(meth) acrylate), poly(hexyl(meth) acrylate), poly(isodecyl(meth) acrylate), poly(lauryl(meth) acrylate), poly(phenyl(meth) acrylate), poly(methyl acrylate), poly(isopropyl acrylate), poly(isobutyl acrylate), poly(octadecyl acrylate) and copolymers and mixtures thereof, polydioxanone and its copolymers, polyhydroxyalkanoates, polypropylene fumarate, polyoxymethylene, poloxamers, poly(ortho) esters, poly(butyric acid), poly(valeric acid), poly(lactide-co-caprolactone), PEG-PLGA-PEG and trimethylene carbonate, polyvinylpyrrolidone. The lipid nanoparticle may be coated or associated with a co-polymer such as, but not limited to, a block co-polymer (such as a branched polyether-polyamide block copolymer described in International Publication No. WO2013012476, herein incorporated by reference in its entirety), and (poly(ethylene glycol))-(poly(propylene oxide))-(poly(ethylene glycol)) triblock copolymer (see e.g., US Publication 20120121718 and US Publication 20100003337 and U.S. Pat. No. 8,263,665; each of which is herein incorporated by reference in their entirety). The co-polymer may be a polymer that is generally regarded as safe (GRAS) and the formation of the lipid nanoparticle may be in such a way that no new chemical entities are created. For example, the lipid nanoparticle may comprise poloxamers coating PLGA nanoparticles without forming new chemical entities which are still able to rapidly penetrate human mucus (Yang et al. *Angew. Chem. Int. Ed.* 2011 50:2597-2600; the contents of which are herein incorporated by reference in its entirety). A non-limiting scalable method to produce nanoparticles which can penetrate human mucus is described by Xu et al. (*See e.g., J Control Release* 2013, 170 (2): 279-86; the contents of which are herein incorporated by reference in its entirety).

The vitamin of the polymer-vitamin conjugate may be vitamin E. The vitamin portion of the conjugate may be substituted with other suitable components such as, but not limited to, vitamin A, vitamin E, other vitamins, cholesterol, a hydrophobic moiety, or a hydrophobic component of other surfactants (e.g., sterol chains, fatty acids, hydrocarbon chains and alkylene oxide chains).

The lipid nanoparticle engineered to penetrate mucus may include surface altering agents such as, but not limited to, polynucleotides, anionic proteins (e.g., bovine serum albumin), surfactants (e.g., cationic surfactants such as for example dimethyldioctadecyl-ammonium bromide), sugars or sugar derivatives (e.g., cyclodextrin), nucleic acids, polymers (e.g., heparin, polyethylene glycol and poloxamer), mucolytic agents (e.g., N-acetylcysteine, mugwort, bromelain, papain, clerodendrum, acetylcysteine, bromhexine, carbocisteine, eprazinone, mesna, ambroxol, sobrerol, domiodol, letosteine, stepronin, tiopronin, gelsolin, thymosin B4 dornase alfa, neltenexine, erdosteine) and various DNases including rhDNasc. The surface altering agent may be embedded or enmeshed in the particle's surface or disposed (e.g., by coating, adsorption, covalent linkage, or other process) on the surface of the lipid nanoparticle. (se e e.g., US Publication 20100215580 and US Publication 20080166414 and US20130164343; the contents of each of which is herein incorporated by reference in their entirety).

In one embodiment, the mucus penetrating lipid nanoparticles may comprise at least one polynucleotide described herein. The polynucleotide may be encapsulated in the lipid nanoparticle and/or disposed on the surface of the particle. The polynucleotide may be covalently coupled to the lipid nanoparticle. Formulations of mucus penetrating lipid nanoparticles may comprise a plurality of nanoparticles. Further, the formulations may contain particles which may interact with the mucus and alter the structural and/or adhesive properties of the surrounding mucus to decrease mucoadhesion which may increase the delivery of the mucus penetrating lipid nanoparticles to the mucosal tissue.

In another embodiment, the mucus penetrating lipid nanoparticles may be a hypotonic formulation comprising a mucosal penetration enhancing coating. The formulation may be hypotonic for the epithelium to which it is being delivered. Non-limiting examples of hypotonic formulations may be found in International Patent Publication No.

WO2013110028, the contents of which are herein incorporated by reference in its entirety.

In one embodiment, in order to enhance the delivery through the mucosal barrier the RNA vaccine formulation may comprise or be a hypotonic solution. Hypotonic solutions were found to increase the rate at which mucoinert particles such as, but not limited to, mucus-penetrating particles, were able to reach the vaginal epithelial surface (See e.g., Ensign et al. *Biomaterials* 2013 34 (28): 6922-9; the contents of which is herein incorporated by reference in its entirety).

In one embodiment, the RNA vaccine is formulated as a lipoplex, such as, without limitation, the ATUPLEX™ system, the DACC system, the DBTC system and other siRNA-lipoplex technology from Silence Therapeutics (London, United Kingdom), STEMFECT™ from STEMGENT® (Cambridge, M A), and polyethylenimine (PEI) or protamine-based targeted and non-targeted delivery of nucleic acids (Aleku et al. Cancer Res. 2008 68:9788-9798; Strumberg et al. Int J Clin Pharmacol Ther 2012 50:76-78; Santel et al., Gene Ther 2006 13:1222-1234; Santel et al., Gene Ther 2006 13:1360-1370; Gutbier et al., Pulm Pharmacol. Ther. 2010 23:334-344; Kaufmann et al. Microvasc Res 2010 80:286-293Weide et al. J Immunother. 2009 32:498-507; Weide et al. J Immunother. 2008 31:180-188; Pascolo Expert Opin. Biol. Ther. 4:1285-1294; Fotin-Mleczek et al., 2011 J. Immunother. 34:1-15; Song et al., Nature Biotechnol. 2005, 23:709-717; Peer et al., Proc Natl Acad Sci USA. 2007 6; 104:4095-4100; deFougerolles Hum Gene Ther. 2008 19:125-132; all of which are incorporated herein by reference in its entirety).

In one embodiment such formulations may also be constructed or compositions altered such that they passively or actively are directed to different cell types in vivo, including but not limited to hepatocytes, immune cells, tumor cells, endothelial cells, antigen presenting cells, and leukocytes (Akinc et al. *Mol Ther.* 2010 18:1357-1364; Song et al., *Nat Biotechnol.* 2005 23:709-717; Judge et al., *J Clin Invest.* 2009 119:661-673; Kaufmann et al., *Microvasc Res* 2010 80:286-293; Santel et al., *Gene Ther* 2006 13:1222-1234; Santel et al., *Gene Ther* 2006 13:1360-1370; Gutbier et al., *Pulm Pharmacol. Ther.* 2010 23:334-344; Basha et al., *Mol. Ther.* 2011 19:2186-2200; Fenske and Cullis, *Expert Opin Drug Deliv.* 2008 5:25-44; Peer et al., *Science.* 2008 319:627-630; Peer and Lieberman, *Gene Ther.* 2011 18:1127-1133; all of which are incorporated herein by reference in its entirety). One example of passive targeting of formulations to liver cells includes the DLin-DMA, DLin-KC2-DMA and DLin-MC3-DMA-based lipid nanoparticle formulations which have been shown to bind to apolipoprotein E and promote binding and uptake of these formulations into hepatocytes in vivo (Akinc et al. *Mol Ther.* 2010 18:1357-1364; herein incorporated by reference in its entirety). Formulations can also be selectively targeted through expression of different ligands on their surface as exemplified by, but not limited by, folate, transferrin, N-acetylgalactosamine (GalNAc), and antibody targeted approaches (Kolhatkar et al., Curr Drug Discov Technol. 2011 8:197-206; Musacchio and Torchilin, *Front Biosci.* 2011 16:1388-1412; Yu et al., *Mol Membr Biol.* 2010 27:286-298; Patil et al., *Crit Rev Ther Drug Carrier Syst.* 2008 25:1-61; Benoit et al., *Biomacromolecules.* 2011 12:2708-2714; Zhao et al., *Expert Opin Drug Deliv.* 2008 5:309-319; Akinc et al., *Mol Ther.* 2010 18:1357-1364; Srinivasan et al., *Methods Mol Biol.* 2012 820:105-116; Ben-Aric et al., *Methods Mol Biol.* 2012 757:497-507; Peer 2010 J Co ntrol Release. 20:63-68; Peer et al., *Proc Natl Acad Sci U S A.* 2007 104:4095-4100; Kim et al., *Methods Mol Biol.* 2011 721:339-353; Subramanya ct al., *Mol Ther.* 2010 18:2028-2037; Song et al., *Nat Biotechnol.* 2005 23:709-717; Peer et al., *Science.* 2008 319:627-630; Peer and Lieberman, *Gene Ther.* 2011 18:1127-1133; all of which are incorporated herein by reference in its entirety).

In one embodiment, the RNA vaccine is formulated as a solid lipid nanoparticle. A solid lipid nanoparticle (SLN) may be spherical with an average diameter between 10 to 1000 nm. SLN possess a solid lipid core matrix that can solubilize lipophilic molecules and may be stabilized with surfactants and/or emulsifiers. In a further embodiment, the lipid nanoparticle may be a self-assembly lipid-polymer nanoparticle (see Zhang et al., ACS Nano, 2008, 2 (8), pp 1696-1702; the contents of which are herein incorporated by reference in its entirety). As a non-limiting example, the SLN may be the SLN described in International Patent Publication No. WO2013105101, the contents of which are herein incorporated by reference in its entirety. As another non-limiting example, the SLN may be made by the methods or processes described in International Patent Publication No. WO2013105101, the contents of which are herein incorporated by reference in its entirety.

Liposomes, lipoplexes, or lipid nanoparticles may be used to improve the efficacy of polynucleotides directed protein production as these formulations may be able to increase cell transfection by the RNA vaccine; and/or increase the translation of encoded protein. One such example involves the use of lipid encapsulation to enable the effective systemic delivery of polyplex plasmid DNA (Heyes et al., *Mol Ther.* 2007 15:713-720; herein incorporated by reference in its entirety). The liposomes, lipoplexes, or lipid nanoparticles may also be used to increase the stability of the polynucleotide.

In one embodiment, the RNA vaccines of the present invention can be formulated for controlled release and/or targeted delivery. As used herein, "controlled release" refers to a pharmaceutical composition or compound release profile that conforms to a particular pattern of release to effect a therapeutic outcome. In one embodiment, the RRNA vaccines may be encapsulated into a delivery agent described herein and/or known in the art for controlled release and/or targeted delivery. As used herein, the term "encapsulate" means to enclose, surround or encase. As it relates to the formulation of the compounds of the invention, encapsulation may be substantial, complete or partial. The term "substantially encapsulated" means that at least greater than 50, 60, 70, 80, 85, 90, 95, 96, 97, 98, 99, 99.9, 99.9 or greater than 99.999% of the pharmaceutical composition or compound of the invention may be enclosed, surrounded or encased within the delivery agent. "Partially encapsulation" means that less than 10, 10, 20, 30, 40 50 or less of the pharmaceutical composition or compound of the invention may be enclosed, surrounded or encased within the delivery agent. Advantageously, encapsulation may be determined by measuring the escape or the activity of the pharmaceutical composition or compound of the invention using fluorescence and/or electron micrograph. For example, at least 1, 5, 10, 20, 30, 40, 50, 60, 70, 80, 85, 90, 95, 96, 97, 98, 99, 99.9, 99.99 or greater than 99.99% of the pharmaceutical composition or compound of the invention are encapsulated in the delivery agent.

In one embodiment, the controlled release formulation may include, but is not limited to, tri-block co-polymers. As a non-limiting example, the formulation may include two different types of tri-block co-polymers (International Pub. No. WO2012131104 and WO2012131106; the contents of each of which is herein incorporated by reference in its entirety).

In another embodiment, the RNA vaccines may be encapsulated into a lipid nanoparticle or a rapidly eliminated lipid nanoparticle and the lipid nanoparticles or a rapidly eliminated lipid nanoparticle may then be encapsulated into a polymer, hydrogel and/or surgical sealant described herein and/or known in the art. As a non-limiting example, the polymer, hydrogel or surgical sealant may be PLGA, ethylene vinyl acetate (EVAc), poloxamer, GELSITE® (Nanotherapeutics, Inc. Alachua, F L), HYLENEX® (Halozyme Therapeutics, San Diego CA), surgical sealants such as fibrinogen polymers (Ethicon Inc. Cornelia, G A), TISSELL® (Baxter International, Inc Deerfield, IL), PEG-based sealants, and COSEAL® (Baxter International, Inc Deerfield, IL).

In another embodiment, the lipid nanoparticle may be encapsulated into any polymer known in the art which may form a gel when injected into a subject. As another non-limiting example, the lipid nanoparticle may be encapsulated into a polymer matrix which may be biodegradable.

In one embodiment, the RNA vaccine formulation for controlled release and/or targeted delivery may also include at least one controlled release coating. Controlled release coatings include, but are not limited to, OPADRY®, polyvinylpyrrolidone/vinyl acetate copolymer, polyvinylpyrrolidone, hydroxypropyl methylcellulose, hydroxypropyl cellulose, hydroxyethyl cellulose, EUDRAGIT RL®, EUDRAGIT RS® and cellulose derivatives such as ethylcellulose aqueous dispersions (AQUACOAT® and SURELEASE®).

In one embodiment, the RNA vaccine controlled release and/or targeted delivery formulation may comprise at least one degradable polyester which may contain polycationic side chains. Degradable polyesters include, but are not limited to, poly(serine ester), poly(L-lactide-co-L-lysine), poly(4-hydroxy-L-proline ester), and combinations thereof. In another embodiment, the degradable polyesters may include a PEG conjugation to form a PEGylated polymer.

In one embodiment, the RNA vaccine controlled release and/or targeted delivery formulation comprising at least one polynucleotide may comprise at least one PEG and/or PEG related polymer derivatives as described in U.S. Pat. No. 8,404,222, herein incorporated by reference in its entirety.

In another embodiment, the RNA vaccine controlled release delivery formulation comprising at least one polynucleotide may be the controlled release polymer system described in US20130130348, herein incorporated by reference in its entirety.

In one embodiment, the RNA vaccines of the present invention may be encapsulated in a therapeutic nanoparticle, referred to herein as "therapeutic nanoparticle RRNA vaccines." Therapeutic nanoparticles may be formulated by methods described herein and known in the art such as, but not limited to, International Pub Nos. WO2010005740, WO2010030763, WO2010005721, WO2010005723, WO2012054923, US Pub. Nos. US20110262491, US20100104645, US20100087337, US20100068285, US20110274759, US20100068286, US20120288541, US20130123351 and US20130230567 and U.S. Pat. Nos. 8,206,747, 8,293,276, 8,318,208 and 8,318,211; the contents of each of which are herein incorporated by reference in their entirety. In another embodiment, therapeutic polymer nanoparticles may be identified by the methods described in US Pub No. US20120140790, the contents of which is herein incorporated by reference in its entirety.

In one embodiment, the therapeutic nanoparticle RNA vaccine may be formulated for sustained release. As used herein, "sustained release" refers to a pharmaceutical composition or compound that conforms to a release rate over a specific period of time. The period of time may include, but is not limited to, hours, days, weeks, months and years. As a non-limiting example, the sustained release nanoparticle may comprise a polymer and a therapeutic agent such as, but not limited to, the polynucleotides of the present invention (see International Pub No. 2010 075072 and US Pub No. US20100216804, US20110217377 and US20120201859, each of which is herein incorporated by reference in their entirety). In another non-limiting example, the sustained release formulation may comprise agents which permit persistent bioavailability such as, but not limited to, crystals, macromolecular gels and/or particulate suspensions (see US Patent Publication No US20130150295, the contents of which is herein incorporated by reference in its entirety).

In one embodiment, the therapeutic nanoparticle RNA vaccines may be formulated to be target specific. As a non-limiting example, the therapeutic nanoparticles may include a corticosteroid (see International Pub. No. WO2011084518; herein incorporated by reference in its entirety). As a non-limiting example, the therapeutic nanoparticles may be formulated in nanoparticles described in International Pub No. WO2008121949, WO2010005726, WO2010005725, WO2011084521 and US Pub No. US20100069426, US20120004293 and US20100104655, each of which is herein incorporated by reference in their entirety.

In one embodiment, the nanoparticles of the present invention may comprise a polymeric matrix. As a non-limiting example, the nanoparticle may comprise two or more polymers such as, but not limited to, polyethylenes, polycarbonates, polyanhydrides, polyhydroxyacids, polypropylfumerates, polycaprolactones, polyamides, polyacetals, polyethers, polyesters, poly(orthoesters), polycyanoacrylates, polyvinyl alcohols, polyurethanes, polyphosphazenes, polyacrylates, polymethacrylates, polycyanoacrylates, polyureas, polystyrenes, polyamines, polylysine, poly(ethylene imine), poly(serine ester), poly(L-lactide-co-L-lysine), poly(4-hydroxy-L-proline ester) or combinations thereof.

In one embodiment, the therapeutic nanoparticle comprises a diblock copolymer. In one embodiment, the diblock copolymer may include PEG in combination with a polymer such as, but not limited to, polyethylenes, polycarbonates, polyanhydrides, polyhydroxyacids, polypropylfumerates, polycaprolactones, polyamides, polyacetals, polyethers, polyesters, poly(orthoesters), polycyanoacrylates, polyvinyl alcohols, polyurethanes, polyphosphazenes, polyacrylates, polymethacrylates, polycyanoacrylates, polyureas, polystyrenes, polyamines, polylysine, poly(ethylene imine), poly (serine ester), poly(L-lactide-co-L-lysine), poly(4-hydroxy-L-proline ester) or combinations thereof. In another embodiment, the diblock copolymer may comprise the diblock copolymers described in European Patent Publication No. the contents of which are herein incorporated by reference in its entirety. In yet another embodiment, the diblock copolymer may be a high-X diblock copolymer such as those described in International Patent Publication No. WO2013120052, the contents of which are herein incorporated by reference in its entirety.

As a non-limiting example the therapeutic nanoparticle comprises a PLGA-PEG block copolymer (see US Pub. No. US20120004293 and U.S. Pat. No. 8,236,330, each of which is herein incorporated by reference in their entirety). In another non-limiting example, the therapeutic nanoparticle is a stealth nanoparticle comprising a diblock copolymer of PEG and PLA or PEG and PLGA (see U.S. Pat. No. 8,246,968 and International Publication No. WO2012166923, the contents of each of which are herein incorporated by reference in its entirety). In yet another non-limiting example, the therapeutic nanoparticle is a stealth nanoparticle or a target-specific stealth nanoparticle as described in US Patent Publication No. US20130172406, the contents of which are herein incorporated by reference in its entirety.

In one embodiment, the therapeutic nanoparticle may comprise a multiblock copolymer (See e.g., U.S. Pat. Nos. 8,263,665 and 8,287,910 and US Patent Pub. No. US20130195987; the contents of each of which are herein incorporated by reference in its entirety).

In yet another non-limiting example, the lipid nanoparticle comprises the block copolymer PEG-PLGA-PEG (see e.g., the thermosensitive hydrogel (PEG-PLGA-PEG) was used as a TGF-beta1 gene delivery vehicle in Lee et al. Thermosensitive Hydrogel as a Tgf-β1 Gene Delivery Vehicle Enhances Diabetic Wound Healing. *Pharmaceutical Research,* 2003 20 (12): 1995-2000; as a controlled gene delivery system in Li e t al. Controlled Gene Delivery System Based on Thermosensitive Biodegradable Hydrogel. *Pharmaceutical Rescarch* 2003 20 (6): 884-888; and Chang et al., Non-ionic amphiphilic biodegradable PEG-PLGA-PEG copolymer enhances gene delivery efficiency in rat skeletal muscle. *J Controlled Release.* 2007 118:245-253; each of which is herein incorporated by reference in its entirety). The RNA vaccines of the present invention may be formulated in lipid nanoparticles comprising the PEG-PLGA-PEG block copolymer.

In one embodiment, the therapeutic nanoparticle may comprise a multiblock copolymer (Sec e.g., U.S. Pat. Nos. 8,263,665 and 8,287,910 and US Patent Pub. No. US20130195987; the contents of each of which are herein incorporated by reference in its entirety).

In one embodiment, the block copolymers described herein may be included in a polyion complex comprising a non-polymeric micelle and the block copolymer. (See e.g., U.S. Pub. No. 20120076836; herein incorporated by reference in its entirety).

In one embodiment, the therapeutic nanoparticle may comprise at least one acrylic polymer. Acrylic polymers include but are not limited to, acrylic acid, methacrylic acid, acrylic acid and methacrylic acid copolymers, methyl methacrylate copolymers, ethoxyethyl methacrylates, cyanoethyl methacrylate, amino alkyl methacrylate copolymer, poly (acrylic acid), poly(methacrylic acid), polycyanoacrylates and combinations thereof.

In one embodiment, the therapeutic nanoparticles may comprise at least one poly(vinyl ester) polymer. The poly (vinyl ester) polymer may be a copolymer such as a random copolymer. As a non-limiting example, the random copolymer may have a structure such as those described in International Application No. WO2013032829 or US Patent Publication No US20130121954, the contents of which are herein incorporated by reference in its entirety. In one aspect, the poly(vinyl ester) polymers may be conjugated to the polynucleotides described herein. In another aspect, the poly(vinyl ester) polymer which may be used in the present invention may be those described in, herein incorporated by reference in its entirety.

In one embodiment, the therapeutic nanoparticle may comprise at least one diblock copolymer. The diblock copolymer may be, but it not limited to, a poly(lactic) acid-poly (ethylene)glycol copolymer (see e.g., International Patent Publication No.

WO2013044219; herein incorporated by reference in its entirety). As a non-limiting example, the therapeutic nanoparticle may be used to treat cancer (see International publication No. WO2013044219; herein incorporated by reference in its entirety).

In one embodiment, the therapeutic nanoparticles may comprise at least one cationic polymer described herein and/or known in the art.

In one embodiment, the therapeutic nanoparticles may comprise at least one amine-containing polymer such as, but not limited to polylysine, polyethylene imine, poly(amidoamine) dendrimers, poly(beta-amino esters) (See e.g., U.S. Pat. No. 8,287,849; herein incorporated by reference in its entirety) and combinations thereof.

In another embodiment, the nanoparticles described herein may comprise an amine cationic lipid such as those described in International Patent Application No. WO2013059496, the contents of which are herein incorporated by reference in its entirety. In one aspect the cationic lipids may have an amino-amine or an amino-amide moiety.

In one embodiment, the therapeutic nanoparticles may comprise at least one degradable polyester which may contain polycationic side chains. Degradable polyesters include, but are not limited to, poly(serine ester), poly(L-lactide-co-L-lysine), poly(4-hydroxy-L-proline ester), and combinations thereof. In another embodiment, the degradable polyesters may include a PEG conjugation to form a PEGylated polymer.

In another embodiment, the therapeutic nanoparticle may include a conjugation of at least one targeting ligand. The targeting ligand may be any ligand known in the art such as, but not limited to, a monoclonal antibody. (Kirpotin et al, *Cancer Res.* 2006 66:6732-6740; herein incorporated by reference in its entirety).

In one embodiment, the therapeutic nanoparticle may be formulated in an aqueous solution which may be used to target cancer (see International Pub No. WO2011084513 and US Pub No. US20110294717, each of which is herein incorporated by reference in their entirety).

In one embodiment, the therapeutic nanoparticle RNA vaccines, e.g., therapeutic nanoparticles comprising at least one RNA vaccine may be formulated using the methods described by Podobinski et al in U.S. Pat. No. 8,404,799, the contents of which are herein incorporated by reference in its entirety.

In one embodiment, the RNA vaccines may be encapsulated in, linked to and/or associated with synthetic nanocarriers. Synthetic nanocarriers include, but are not limited to, those described in International Pub. Nos. WO2010005740, WO2010030763, WO201213501, WO2012149252, WO2012149255, WO2012149259, WO2012149265, WO2012149268, WO2012149282, WO2012149301, WO2012149393, WO2012149405, WO2012149411, WO2012149454 and WO2013019669, and US Pub. Nos. US20110262491, US20100104645, US20100087337 and US20120244222, each of which is herein incorporated by reference in their entirety. The synthetic nanocarriers may be formulated using methods known in the art and/or described herein. As a non-limiting example, the synthetic nanocarriers may be formulated by the methods described in International Pub Nos. WO2010005740, WO2010030763 and WO201213501 and US Pub. Nos. US20110262491, US20100104645, US20100087337 and US2012024422, each of which is herein incorporated by reference in their entirety. In another embodiment, the synthetic nanocarrier formulations may be lyophilized by methods described in International Pub. No. WO2011072218 and U.S. Pat. No. 8,211,473; the content of each of which is herein incorporated by reference in their entirety. In yet another embodiment, formulations of the present invention, including, but not limited to, synthetic nanocarriers, may be lyophilized or reconstituted by the methods described in US Patent Publication No. US20130230568, the contents of which are herein incorporated by reference in its entirety.

In one embodiment, the synthetic nanocarriers may contain reactive groups to release the polynucleotides described herein (see International Pub. No. WO20120952552 and US Pub No. US20120171229, each of which is herein incorporated by reference in their entirety). In one embodiment, the synthetic nanocarriers may contain an immunostimulatory agent to enhance the immune response from delivery of the synthetic nanocarrier. As a non-limiting example, the synthetic nanocarrier may comprise a Th1 immunostimulatory agent which may enhance a Th1-based response of the immune system (see International Pub No. WO2010123569 and US Pub. No. US20110223201, each of which is herein incorporated by reference in its entirety).

In one embodiment, the synthetic nanocarriers may be formulated for targeted release. In one embodiment, the synthetic nanocarrier is formulated to release the polynucleotides at a specified pH and/or after a desired time interval. As a non-limiting example, the synthetic nanoparticle may be formulated to release the RNA vaccines after 24 hours and/or at a pH of 4.5 (scc International Pub. Nos. WO2010138193 and WO2010138194 and US Pub Nos. US20110020388 and US20110027217, each of which is herein incorporated by reference in their entireties).

In one embodiment, the synthetic nanocarriers may be formulated for controlled and/or sustained release of the polynucleotides described herein. As a non-limiting example, the synthetic nanocarriers for sustained release may be formulated by methods known in the art, described herein and/or as described in International Pub No. WO2010138192 and US Pub No. 2010 0303850, each of which is herein incorporated by reference in their entirety.

In one embodiment, the RNA vaccine may be formulated for controlled and/or sustained release wherein the formulation comprises at least one polymer that is a crystalline side chain (CYSC) polymer. CYSC polymers are described in U.S. Pat. No. 8,399,007, herein incorporated by reference in its entirety.

In one embodiment, the synthetic nanocarrier may be formulated for use as a vaccine. In one embodiment, the synthetic nanocarrier may encapsulate at least one polynucleotide which encode at least one antigen. As a non-limiting example, the synthetic nanocarrier may include at least one antigen and an excipient for a vaccine dosage form (see International Pub No. WO2011150264 and US Pub No. US20110293723, each of which is herein incorporated by reference in their entirety). As another non-limiting example, a vaccine dosage form may include at least two synthetic nanocarriers with the same or different antigens and an excipient (see International Pub No. WO2011150249 and US Pub No. US20110293701, each of which is herein incorporated by reference in their entirety). The vaccine dosage form may be selected by methods described herein, known in the art and/or described in International Pub No. WO2011150258 and US Pub No. US20120027806, each of which is herein incorporated by reference in their entirety).

In one embodiment, the synthetic nanocarrier may comprise at least one polynucleotide which encodes at least one adjuvant. As non-limiting example, the adjuvant may comprise dimethyldioctadecylammonium-bromide, dimethyldioctadecylammonium-chloride, dimethyldioctadecylammonium-phosphate or dimethyldioctadecylammonium-acetate (DDA) and an apolar fraction or part of said apolar fraction of a total lipid extract of a *mycobacterium* (See e.g., U.S. Pat. No. 8,241,610; herein incorporated by reference in its entirety). In another embodiment, the synthetic nanocarrier may comprise at least one polynucleotide and an adjuvant. As a non-limiting example, the synthetic nanocarrier comprising and adjuvant may be formulated by the methods described in International Pub No. WO2011150240 and US Pub No. US20110293700, each of which is herein incorporated by reference in its entirety.

In one embodiment, the synthetic nanocarrier may encapsulate at least one polynucleotide which encodes a peptide, fragment or region from a virus. As a non-limiting example, the synthetic nanocarrier may include, but is not limited to, the nanocarriers described in International Pub No. WO2012024621, WO201202629, WO2012024632 and US Pub No. US20120064110, US20120058153 and US20120058154, each of which is herein incorporated by reference in their entirety.

In one embodiment, the synthetic nanocarrier may be coupled to a polynucleotide which may be able to trigger a humoral and/or cytotoxic T lymphocyte (CTL) response (See e.g., International Publication No. WO2013019669, herein incorporated by reference in its entirety).

In one embodiment, the RNA vaccine may be encapsulated in, linked to and/or associated with zwitterionic lipids. Non-limiting examples of zwitterionic lipids and methods of using zwitterionic lipids are described in US Patent Publication No. US20130216607, the contents of which are herein incorporated by reference in its entirety. In one aspect, the zwitterionic lipids may be used in the liposomes and lipid nanoparticles described herein.

In one embodiment, the RNA vaccine may be formulated in colloid nanocarriers as described in US Patent Publication No. US20130197100, the contents of which are herein incorporated by reference in its entirety.

In one embodiment, the nanoparticle may be optimized for oral administration. The nanoparticle may comprise at least one cationic biopolymer such as, but not limited to, chitosan or a derivative thereof. As a non-limiting example, the nanoparticle may be formulated by the methods described in U.S. Pub. No. 20120282343; herein incorporated by reference in its entirety.

In some embodiments, LNPs comprise the lipid KL52 (an amino-lipid disclosed in U.S. Application Publication No. 2012/0295832 expressly incorporated herein by reference in its entirety). Activity and/or safety (as measured by examining one or more of ALT/AST, white blood cell count and cytokine induction) of LNP administration may be improved by incorporation of such lipids. LNPs comprising KL52 may be administered intravenously and/or in one or more doses. In some embodiments, administration of LNPs comprising KL52 results in equal or improved mRNA and/or protein expression as compared to LNPs comprising MC3.

In some embodiments, RNA vaccine may be delivered using smaller LNPs. Such particles may comprise a diameter from below 0.1 um u p to 100 nm such as, but not limited to, less than 0.1 um, less than 1.0 um, less than 5 μm, less than 10 μm, less than 15 μm, less than 20 μm, less than 25 μm, less than 30 μm, less than 35 μm, less than 40 μm, less than 50 μm, less than 55 μm, less than 60 μm, less than 65 μm, less than 70 μm, less than 75 μm, less than 80 μm, less than 85 μm, less than 90 μm, less than 95 μm, less than 100 μm, less than 125 μm, less than 150 μm, less than 175 μm, less than 200 μm, less than 225 μm, less than 250 μm, less than 275 μm, less than 300 μm, less than 325 μm, less than 350 μm, less than 375 μm, less than 400 μm, less than 425 μm, less than 450 μm, less than 475 μm, less than 500 μm, less than 525 μm, less than 550 μm, less than 575 μm, less than 600 μm, less than 625 μm, less than 650 μm, less than 675 μm, less than 700 μm, less than 725 μm, less than 750 μm, less than 775 μm, less than 800 μm, less than 825 μm, less than 850 μm, less than 875 μm, less than 900 μm, less than 925 μm, less than 950 μm, less than 975 μm. In another embodiment, RNA vaccines may be delivered using smaller LNPs which may comprise a diameter from about 1 nm to about 100 nm, from about 1 nm to about 10 nm, about 1 nm to about 20 nm, from about 1 nm to about 30 nm, from about 1 nm to about 40 nm, from about 1 nm to about 50 nm, from about 1 nm to about 60 nm, from about 1 nm to about 70 nm, from about 1 nm to about 80 nm, from about 1 nm to about 90 nm, from about 5 nm to about from 100 nm, from about 5 nm to about 10 nm, about 5 nm to about 20 nm, from about 5 nm to about 30 nm, from about 5 nm to about 40 nm, from about 5 nm to about 50 nm, from about 5 nm to about 60 nm, from about 5 nm to about 70 nm, from about 5 nm to about 80 nm, from about 5 nm to about 90 nm, about 10 to about 50 nM, from about 20 to about 50 nm, from about 30 to about 50 nm, from about 40 to about 50 nm, from about 20 to about 60 nm, from about 30 to about 60 nm, from about 40 to about 60 nm, from about 20 to about 70 nm, from about 30 to about 70 nm, from about 40 to about 70 nm, from about 50 to about 70 nm, from about 60 to about 70 nm, from about 20 to about 80 nm, from about 30 to about 80 nm, from about 40 to about 80 nm, from about 50 to about 80 nm, from about 60 to about 80 nm, from about 20 to about 90 nm, from about 30 to about 90 nm, from about 40 to about 90 nm, from about 50 to about 90 nm, from about 60 to about 90 nm and/or from about 70 to about 90 nm.

In some embodiments, such LNPs are synthesized using methods comprising microfluidic mixers. Exemplary microfluidic mixers may include, but are not limited to a slit interdigital micromixer including, but not limited to those manufactured by Microinnova (Allerheiligen bei Wildon, Austria) and/or a staggered herringbone micromixer (SHM) (Zhigaltsev, I. V. et al., *Bottom-up design and synthesis of limit size lipid nanoparticle systems with aqueous and triglyceride cores using millisecond microfluidic mixing have been published* (*Langmuir.* 2012. 28:3633-40; Belliveau, N. M. et al., Microfluidic synthesis of highly potent limit-size lipid nanoparticles for in vivo delivery of siRNA. *Molecular Therapy-Nucleic Acids.* 2012. 1: e37; Chen, D. et al., Rapid discovery of potent siRNA-containing lipid nanoparticles enabled by controlled microfluidic formulation. *J Am Chem* Soc. 2012. 134 (16): 6948-51; each of which is herein incorporated by reference in its entirety). In some embodiments, methods of LNP generation comprising SHM, further comprise the mixing of at least two input streams wherein mixing occurs by microstructure-induced chaotic advection (MICA). According to this method, fluid streams flow through channels present in a herringbone pattern causing rotational flow and folding the fluids around each other. This method may also comprise a surface for fluid mixing wherein the surface changes orientations during fluid cycling. Methods of generating LNPs using SHM include those disclosed in U.S. Application Publication Nos. 2004/0262223 and 2012/0276209, each of which is expressly incorporated herein by reference in their entirety.

In one embodiment, the RNA vaccine of the present invention may be formulated in lipid nanoparticles created using a micromixer such as, but not limited to, a Slit Interdigital Microstructured Mixer (SIMM-V2) or a Standard Slit Interdigital Micro Mixer (SSIMM) or Caterpillar (CPMM) or Impinging-jet (IJMM) from the Institut für Mikrotechnik Mainz GmbH, Mainz Germany).

In one embodiment, the RNA vaccines of the present invention may be formulated in lipid nanoparticles created using microfluidic technology (see Whitesides, George M. The Origins and the Future of Microfluidics. *Nature,* 2006 442:368-373; and Abraham et al. Chaotic Mixer for Microchannels. Science, 2002 295:647-651; each of which is herein incorporated by reference in its entirety). As a non-limiting example, controlled microfluidic formulation includes a passive method for mixing streams of steady pressure-driven flows in micro channels at a low Reynolds number (See e.g., Abraham et al. *Chaotic Mixer for Microchannels. Science,* 2002 295:647-651; which is herein incorporated by reference in its entirety).

In one embodiment, the RNA vaccines of the present invention may be formulated in lipid nanoparticles created using a micromixer chip such as, but not limited to, those from Harvard Apparatus (Holliston, M A) or Dolomite Microfluidics (Royston, UK). A micromixer chip can be used for rapid mixing of two or more fluid streams with a split and recombine mechanism.

In one embodiment, the RNA vaccines of the invention may be formulated for delivery using the drug encapsulating microspheres described in International Patent Publication No. WO2013063468 or U.S. Pat. No. 8,440,614, each of which is herein incorporated by reference in its entirety. The microspheres may comprise a compound of the formula (I), (II), (III), (IV), (V) or (VI) as described in International Patent Publication No. WO2013063468, the contents of which are herein incorporated by reference in its entirety. In another aspect, the amino acid, peptide, polypeptide, lipids (APPL) are useful in delivering the RNA vaccines of the invention to cells (see International Patent Publication No. WO2013063468, the contents of which is herein incorporated by reference in its entirety).

In one embodiment, the RNA vaccines of the invention may be formulated in lipid nanoparticles having a diameter from about 10 to about 100 nm such as, but not limited to, about 10 to about 20 nm, about 10 to about 30 nm, about 10 to about 40 nm, about 10 to about 50 nm, about 10 to about 60 nm, about 10 to about 70 nm, about 10 to about 80 nm, about 10 to about 90 nm, about 20 to about 30 nm, about 20 to about 40 nm, about 20 to about 50 nm, about 20 to about 60 nm, about 20 to about 70 nm, about 20 to about 80 nm, about 20 to about 90 nm, about 20 to about 100 nm, about 30 to about 40 nm, about 30 to about 50 nm, about 30 to about 60 nm, about 30 to about 70 nm, about 30 to about 80 nm, about 30 to about 90 nm, about 30 to about 100 nm, about 40 to about 50 nm, about 40 to about 60 nm, about 40 to about 70 nm, about 40 to about 80 nm, about 40 to about 90 nm, about 40 to about 100 nm, about 50 to about 60 nm, about 50 to about 70 nm about 50 to about 80 nm, about 50 to about 90 nm, about 50 to about 100 nm, about 60 to about 70 nm, about 60 to about 80 nm, about 60 to about 90 nm, about 60 to about 100 nm, about 70 to about 80 nm, about 70 to about 90 nm, about 70 to about 100 nm, about 80 to about 90 nm, about 80 to about 100 nm and/or about 90 to about 100 nm.

In one embodiment, the lipid nanoparticles may have a diameter from about 10 to 500 nm.

In one embodiment, the lipid nanoparticle may have a diameter greater than 100 nm, greater than 150 nm, greater than 200 nm, greater than 250 nm, greater than 300 nm, greater than 350 nm, greater than 400 nm, greater than 450 nm, greater than 500 nm, greater than 550 nm, greater than 600 nm, greater than 650 nm, greater than 700 nm, greater than 750 nm, greater than 800 nm, greater than 850 nm, greater than 900 nm, greater than 950 nm or greater than 1000 nm.

In one aspect, the lipid nanoparticle may be a limit size lipid nanoparticle described in International Patent Publication No. WO2013059922, the contents of which are herein incorporated by reference in its entirety. The limit size lipid nanoparticle may comprise a lipid bilayer surrounding an aqueous core or a hydrophobic core; where the lipid bilayer may comprise a phospholipid such as, but not limited to, diacylphosphatidylcholine, a diacylphosphatidylethanolamine, a ceramide, a sphingomyelin, a dihydrosphingomyelin, a cephalin, a cerebroside, a $C_8$-C20 fatty acid diacylphophatidylcholine, and 1-palmitoyl-2-oleoyl phosphatidylcholine (POPC). In another aspect the limit size lipid nanoparticle may comprise a polyethylene glycol-lipid such as, but not limited to, DLPE-PEG, DMPE-PEG, DPPC-PEG and DSPE-PEG.

In some embodiments, a cationic lipid is an ionizable cationic lipid and the non-cationic lipid is a neutral lipid, and the sterol is a cholesterol. In some embodiments, a cationic lipid is selected from the group consisting of 2,2-dilinoleyl-4-dimethylaminoethyl-[1,3]-dioxolane (DLin-KC2-DMA), dilinoleyl-methyl-4-dimethylaminobutyrate (DLin-MC3-DMA), di((Z)-non-2-en-1-yl) 9-((4-(dimethylamino) butanoyl)oxy) heptadecanedioate (L319), (12Z,15Z)—N,N-dimethyl-2-nonylhenicosa-12,15-dien-1-amine (L608), and N,N-dimethyl-1-[(1S,2R)-2-octylcyclopropyl]heptadecan-8-amine (L530).

In some embodiments, the lipid is (L608)

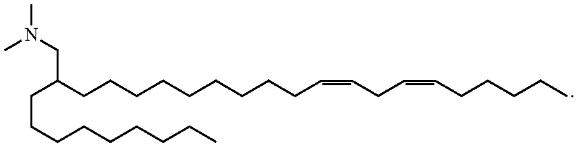

.

In some embodiments, the lipid is (L530)

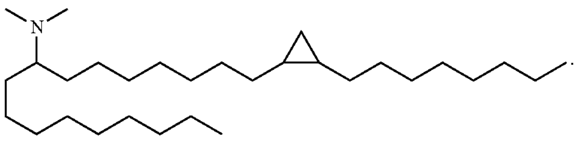

.

In one embodiment, the RNA vaccines may be delivered, localized and/or concentrated in a specific location using the delivery methods described in International Patent Publication No. WO2013063530, the contents of which are herein incorporated by reference in its entirety. As a non-limiting example, a subject may be administered an empty polymeric particle prior to, simultaneously with or after delivering the RNA vaccines to the subject. The empty polymeric particle undergoes a change in volume once in contact with the subject and becomes lodged, embedded, immobilized or entrapped at a specific location in the subject.

In one embodiment, the RNA vaccines may be formulated in an active substance release system (See e.g., US Patent Publication No. US20130102545, the contents of which is herein incorporated by reference in its entirety). The active substance release system may comprise 1) at least one nanoparticle bonded to an oligonucleotide inhibitor strand which is hybridized with a catalytically active nucleic acid and 2) a compound bonded to at least one substrate molecule bonded to a therapeutically active substance (e.g., polynucleotides described herein), where the therapeutically active substance is released by the cleavage of the substrate molecule by the catalytically active nucleic acid.

In one embodiment, the RNA vaccines may be formulated in a nanoparticle comprising an inner core comprising a non-cellular material and an outer surface comprising a cellular membrane. The cellular membrane may be derived from a cell or a membrane derived from a virus. As a non-limiting example, the nanoparticle may be made by the methods described in International Patent Publication No. WO2013052167, herein incorporated by reference in its entirety. As another non-limiting example, the nanoparticle described in International Patent Publication No. WO2013052167, herein incorporated by reference in its entirety, may be used to deliver the RNA vaccines described herein.

In one embodiment, the RNA vaccines may be formulated in porous nanoparticle-supported lipid bilayers (protocells). Protocells are described in International Patent Publication No. WO2013056132, the contents of which are herein incorporated by reference in its entirety.

In one embodiment, the RNA vaccines described herein may be formulated in polymeric nanoparticles as described in or made by the methods described in U.S. Pat. Nos. 8,420,123 and 8,518,963 and European Patent No. EP2073848B1, the contents of each of which are herein incorporated by reference in their entirety. As a non-limiting example, the polymeric nanoparticle may have a high glass transition temperature such as the nanoparticles described in or nanoparticles made by the methods described in U.S. Pat. No. 8,518,963, the contents of which are herein incorporated by reference in its entirety. As another non-limiting example, the polymer nanoparticle for oral and parenteral formulations may be made by the methods described in European Patent No. EP2073848B1, the contents of which are herein incorporated by reference in its entirety.

In another embodiment, the RNA vaccines described herein may be formulated in nanoparticles used in imaging. The nanoparticles may be liposome nanoparticles such as those described in US Patent Publication No US20130129636, herein incorporated by reference in its entirety. As a non-limiting example, the liposome may comprise gadolinium (III)2-{4,7-bis-carboxymethyl-10-[(N,N-distearylamidomethyl-N'-amido-methyl]-1,4,7,10-tetra-azacyclododec-1-yl}-acetic acid and a neutral, fully saturated phospholipid component (see e.g., US Patent Publication No US20130129636, the contents of which is herein incorporated by reference in its entirety).

In one embodiment, the nanoparticles which may be used in the present invention are formed by the methods described in U.S. Patent Application No. US20130130348, the contents of which is herein incorporated by reference in its entirety.

The nanoparticles of the present invention may further include nutrients such as, but not limited to, those which deficiencies can lead to health hazards from anemia to neural tube defects (see e.g., the nanoparticles described in International Patent Publication No WO2013072929, the contents of which is herein incorporated by reference in its entirety). As a non-limiting example, the nutrient may be iron in the form of ferrous, ferric salts or elemental iron, iodine, folic acid, vitamins or micronutrients.

In one embodiment, the RNA vaccines of the present invention may be formulated in a swellable nanoparticle. The swellable nanoparticle may be, but is not limited to, those described in U.S. Pat. No. 8,440,231, the contents of which is herein incorporated by reference in its entirety. As a non-limiting embodiment, the swellable nanoparticle may be used for delivery of the RNA vaccines of the present invention to the pulmonary system (see e.g., U.S. Pat. No. 8,440,231, the contents of which is herein incorporated by reference in its entirety).

The RNA vaccines of the present invention may be formulated in polyanhydride nanoparticles such as, but not limited to, those described in U.S. Pat. No. 8,449,916, the contents of which is herein incorporated by reference in its entirety.

The nanoparticles and microparticles of the present invention may be geometrically engineered to modulate macrophage and/or the immune response. In one aspect, the geometrically engineered particles may have varied shapes, sizes and/or surface charges in order to incorporated the polynucleotides of the present invention for targeted delivery such as, but not limited to, pulmonary delivery (see e.g., International Publication No WO2013082111, the contents of which is herein incorporated by reference in its entirety). Other physical features the geometrically engineering particles may have include, but are not limited to, fenestrations, angled arms, asymmetry and surface roughness, charge which can alter the interactions with cells and tissues. As a non-limiting example, nanoparticles of the present invention may be made by the methods described in International Publication No WO2013082111, the contents of which is herein incorporated by reference in its entirety.

In one embodiment, the nanoparticles of the present invention may be water soluble nanoparticles such as, but not limited to, those described in International Publication No. WO2013090601, the contents of which is herein incorporated by reference in its entirety. The nanoparticles may be inorganic nanoparticles which have a compact and zwitterionic ligand in order to exhibit good water solubility. The nanoparticles may also have small hydrodynamic diameters (HD), stability with respect to time, pH, and salinity and a low level of non-specific protein binding.

In one embodiment the nanoparticles of the present invention may be developed by the methods described in US Patent Publication No. US20130172406, the contents of which are herein incorporated by reference in its entirety.

In one embodiment, the nanoparticles of the present invention are stealth nanoparticles or target-specific stealth nanoparticles such as, but not limited to, those described in US Patent Publication No. US20130172406; the contents of which is herein incorporated by reference in its entirety. The nanoparticles of the present invention may be made by the methods described in US Patent Publication No. US20130172406, the contents of which are herein incorporated by reference in its entirety.

In another embodiment, the stealth or target-specific stealth nanoparticles may comprise a polymeric matrix. The polymeric matrix may comprise two or more polymers such as, but not limited to, polyethylenes, polycarbonates, polyanhydrides, polyhydroxyacids, polypropylfumerates, polycaprolactones, polyamides, polyacetals, polyethers, polyesters, poly(orthoesters), polycyanoacrylates, polyvinyl alcohols, polyurethanes, polyphosphazenes, polyacrylates, polymethacrylates, polycyanoacrylates, polyureas, polystyrenes, polyamines, polyesters, polyanhydrides, polyethers, polyurethanes, polymethacrylates, polyacrylates, polycyanoacrylates or combinations thereof.

In one embodiment, the nanoparticle may be a nanoparticle-nucleic acid hybrid structure having a high density nucleic acid layer. As a non-limiting example, the nanoparticle-nucleic acid hybrid structure may made by the methods described in US Patent Publication No. US20130171646, the contents of which are herein incorporated by reference in its entirety. The nanoparticle may comprise a nucleic acid such as, but not limited to, polynucleotides described herein and/or known in the art.

At least one of the nanoparticles of the present invention may be embedded in in the core a nanostructure or coated with a low density porous 3-D structure or coating which is capable of carrying or associating with at least one payload within or on the surface of the nanostructure. Non-limiting examples of the nanostructures comprising at least one nanoparticle are described in International Patent Publication No. WO2013123523, the contents of which are herein incorporated by reference in its entirety.

In some embodiments the RNA vaccine may be associated with a cationic or polycationic compounds, including protamine, nucleoline, spermine or spermidine, or other cationic peptides or proteins, such as poly-L-lysine (PLL), polyarginine, basic polypeptides, cell penetrating peptides (CPPs), including HIV-binding peptides, HIV-1 Tat (HIV), Tat-derived peptides, Penetratin, VP22 derived or analog peptides, Pestivirus Erns, HSV, VP22 (Herpes simplex), MAP, KALA or protein transduction domains (PTDs), PpT620, proline-rich peptides, arginine-rich peptides, lysine-rich peptides, MPG-peptide(s), Pep-1, L-oligomers, Calcitonin peptide(s), Antennapedia-derived peptides (particularly from *Drosophila* antennapedia), pAntp, plsl, FGF, Lactoferrin, Transportan, Buforin-2, Bac715-24, SynB. SynB (1), pVEC, hCT-derived peptides, SAP, histones, cationic polysaccharides, for example chitosan, polybrene, cationic polymers, e.g. polyethyleneimine (PEI), cationic lipids, e.g. DOTMA: [1-(2,3-sioleyloxy) propyl)]-N,N,N-trimethylammonium chloride, DMRIE, di-C14-amidine, DOTIM, SAINT, DC-Chol, BGTC, CTAP, DOPC, DODAP, DOPE: Diolcyl phosphatidylethanol-amine, DOSPA, DODAB, DOIC, DMEPC, DOGS:

Dioctadecylamidoglicylspermin, DIMRI: Dimyristooxypropyl dimethyl hydroxyethyl ammonium bromide, DOTAP: dioleoyloxy-3-(trimethylammonio) propane, DC-6-14:0,0-ditetradecanoyl-N-. alpha.-trimethylammonioacetyl) diethanolamine chloride, CLIP 1: rac-[(2, 3-dioctadecyloxypropyl) (2-hydroxyethyl)]-dimethylammonium chloride, CLIP6: rac-[2 (2,3-dihexadecyloxypropyloxymethyloxy)ethyl]-trimethylammonium, CLIP9: rac-[2 (2,3-dihexadecyloxypropyloxysuccinyloxy)ethyl]-trimethylammonium, oligofectamine, or cationic or polycationic polymers, e.g. modified polyaminoacids, such as beta-aminoacid-polymers or reversed polyamides, etc., modified polyethylenes, such as PVP (poly(N-ethyl-4-vinylpyridinium bromide)), etc., modified acrylates, such as pDMAEMA (poly(dimethylaminoethyl methylacrylate)), etc., modified amidoamines such as pAMAM (poly(amidoamine)), etc., modified polybetaminoester (PBAE), such as diamine end modified 1,4 butanediol diacrylate-co-5-amino-1-pentanol polymers, etc., dendrimers, such as polypropylamine dendrimers or pAMAM based dendrimers, etc., polyimine(s), such as PEI: poly(ethyleneimine), poly(propyleneimine), etc., polyallylamine, sugar backbone based polymers, such as cyclodextrin based polymers, dextran based polymers, chitosan, etc., silan backbone based polymers, such as PMOXA-PDMS copolymers, etc., blockpolymers consisting of a combination of one or more cationic blocks (e.g., selected from a cationic polymer as mentioned above) and of one or more hydrophilic or hydrophobic blocks (e.g., polyethyleneglycole); etc.

In other embodiments the RNA vaccine is not associated with a cationic or polycationic compounds.

Modes of Vaccine Administration

Cancer RNA vaccines may be administered by any route which results in a therapeutically effective outcome. These include, but are not limited, to intradermal, intramuscular, and/or subcutaneous administration. The present disclosure provides methods comprising administering RNA vaccines to a subject in need thereof. The exact amount required will vary from subject to subject, depending on the species, age, and general condition of the subject, the severity of the disease, the particular composition, its mode of administration, its mode of activity, and the like. Cancer RNA vaccines compositions are typically formulated in dosage unit form for case of administration and uniformity of dosage.

It will be understood, however, that the total daily usage of cancer RNA vaccines compositions may be decided by the attending physician within the scope of sound medical judgment. The specific therapeutically effective, prophylactically effective, or appropriate imaging dose level for any particular patient will depend upon a variety of factors including the disorder being treated and the severity of the disorder; the activity of the specific compound employed; the specific composition employed; the age, body weight, general health, sex and diet of the patient; the time of administration, route of administration, and rate of excretion of the specific compound employed; the duration of the treatment; drugs used in combination or coincidental with the specific compound employed; and like factors well known in the medical arts.

In some embodiments, cancer RNA vaccines compositions may be administered at dosage levels sufficient to deliver 0.0001 mg/kg to 100 mg/kg. 0.001 mg/kg to 0.05 mg/kg, 0.005 mg/kg to 0.05 mg/kg, 0.001 mg/kg to 0.005 mg/kg, 0.05 mg/kg to 0.5 mg/kg, 0.01 mg/kg to 50 mg/kg. 0.1 mg/kg to 40 mg/kg. 0.5 mg/kg to 30 mg/kg, 0.01 mg/kg to 10 mg/kg, 0.1 mg/kg to 10 mg/kg, or 1 mg/kg to 25 mg/kg, of subject body weight per day, one or more times a day, per week, per month, etc. to obtain the desired therapeutic, diagnostic, prophylactic, or imaging effect (see e.g., the range of unit doses described in International Publication No WO2013078199, herein incorporated by reference in its entirety). The desired dosage may be delivered three times a day, two times a day, once a day, every other day, every third day, every week, every two weeks, every three weeks, every four weeks, every 2 months, every three months, every 6 months, etc., In certain embodiments, the desired dosage may be delivered using multiple administrations (e.g., two, three, four, five, six, seven, eight, nine, ten, eleven, twelve, thirteen, fourteen, or more administrations). When multiple administrations are employed, split dosing regimens such as those described herein may be used. In exemplary embodiments, cancer RNA vaccines compositions may be administered at dosage levels sufficient to deliver 0.0005 mg/kg to 0.01 mg/kg, e.g., about 0.0005 mg/kg to about 0.0075 mg/kg, e.g., about 0.0005 mg/kg, about 0.001 mg/kg, about 0.002 mg/kg, about 0.003 mg/kg, about 0.004 mg/kg or about 0.005 mg/kg.

A RNA vaccine pharmaceutical composition described herein can be formulated into a dosage form described herein, such as an intranasal, intratracheal, or injectable (e.g., intravenous, intraocular, intravitreal, intramuscular, intradermal, intracardiac, intraperitoneal, and subcutaneous).

This invention is not limited in its application to the details of construction and the arrangement of components set forth in the following description or illustrated in the drawings. The invention is capable of other embodiments and of being practiced or of being carried out in various ways. Also, the phraseology and terminology used herein is for the purpose of description and should not be regarded as limiting. The use of "including," "comprising," or "having," "containing," "involving," and variations thereof herein, is meant to encompass the items listed thereafter and equivalents thereof as well as additional items.

EXAMPLES

Example 1. Manufacture of Polynucleotides

According to the present disclosure, the manufacture of polynucleotides and or parts or regions thereof may be accomplished utilizing the methods taught in International Application WO2014/152027 entitled "Manufacturing Methods for Production of RNA Transcripts", the contents of which is incorporated herein by reference in its entirety.

Purification methods may include those taught in International Application

WO2014/152030 and WO2014/152031, each of which is incorporated herein by reference in its entirety.

Detection and characterization methods of the polynucleotides may be performed as taught in WO2014/144039, which is incorporated herein by reference in its entirety.

Characterization of the polynucleotides of the disclosure may be accomplished using a procedure selected from the group consisting of polynucleotide mapping, reverse transcriptase sequencing, charge distribution analysis, and detection of RNA impurities, wherein characterizing comprises determining the RNA transcript sequence, determining the purity of the RNA transcript, or determining the charge heterogeneity of the RNA transcript. Such methods are taught in, for example, WO2014/144711 and WO2014/144767, the contents of each of which is incorporated herein by reference in its entirety.

Example 2 Chimeric Polynucleotide Synthesis

Introduction

According to the present disclosure, two regions or parts of a chimeric polynucleotide may be joined or ligated using triphosphate chemistry.

According to this method, a first region or part of 100 nucleotides or less is chemically synthesized with a 5' monophosphate and terminal 3'desOH or blocked OH. If the region is longer than 80 nucleotides, it may be synthesized as two strands for ligation.

If the first region or part is synthesized as a non-positionally modified region or part using in vitro transcription (IVT), conversion 5'monophosphate with subsequent capping of the 3' terminus may follow.

Monophosphate protecting groups may be selected from any of those known in the art The second region or part of the chimeric polynucleotide may be synthesized using either chemical synthesis or IVT methods. IVT methods may include an RNA polymerase that can utilize a primer with a modified cap. Alternatively, a cap of up to 130 nucleotides may be chemically synthesized and coupled to the IVT region or part.

The entire chimeric polynucleotide need not be manufactured with a phosphate-sugar backbone. If one of the regions or parts encodes a polypeptide, then it is preferable that such region or part comprise a phosphate-sugar backbone.

Ligation is then performed using any known click chemistry, orthoclick chemistry, solulink, or other bioconjugate chemistries known to those in the art.

Synthetic Route

The chimeric polynucleotide is made using a series of starting segments. Such segments include:

(a) Capped and protected 5' segment comprising a normal 3'OH (SEG. 1)
(b) 5' triphosphate segment which may include the coding region of a polypeptide and comprising a normal 3'OH (SEG. 2)
(c) 5' monophosphate segment for 3' end of the chimeric polynucleotide (e.g., the tail) comprising cordycepin or no 3'OH (SEG. 3)

After synthesis (chemical or IVT), segment 3 (SEG. 3) is treated with cordycepin and then with pyrophosphatase to create 5'monophosphate.

Segment 2 (SEG. 2) is then ligated to SEG. 3 using RNA ligase. The ligated polynucleotide is then purified and treated with pyrophosphatase to cleave the diphosphate. The treated SEG.2-SEG. 3 construct is then purified and SEG. 1 is ligated to the 5' terminus. A further purification step of the chimeric polynucleotide may be performed.

Where the chimeric polynucleotide encodes a polypeptide, the ligated or joined segments may be represented as: 5'UTR (SEG. 1), open reading frame or ORF (SEG. 2) and 3'UTR+PolyA (SEG. 3).

The yields of each step may be as much as 90-95%.

Example 3: PCR for cDNA Production

PCR procedures for the preparation of cDNA are performed using 2× KAPA HIFI™ HotStart ReadyMix by Kapa Biosystems (Woburn, M A). This system includes 2× KAPA ReadyMix 12.5 μl; Forward Primer (10 μM) 0.75 μl; Reverse Primer (10 μM) 0.75 μl; Template cDNA-100 ng; and $dH_2O$ diluted to 25.0 μl. The reaction conditions are at 95° C. for 5 min. and 25 cycles of 98° C. for 20 se c, then 58° C. for 15 se c, then 72° C. for 45 se c, then 72° C. for 5 min. then 4° C. to termination.

The reaction is cleaned up using Invitrogen's PURELINK™ PCR Micro Kit (Carlsbad, C A) per manufacturer's instructions (up to 5 ug). Larger reactions will require a cleanup using a product with a larger capacity. Following the cleanup, the cDNA is quantified using the NANODROP™ and analyzed by agarose gel electrophoresis to confirm the cDNA is the expected size. The cDNA is then submitted for sequencing analysis before proceeding to the in vitro transcription reaction.

Example 4. In vitro Transcription (IVT)

The in vitro transcription reaction generates polynucleotides containing uniformly modified polynucleotides. Such uniformly modified polynucleotides may comprise a region or part of the polynucleotides of the disclosure. The input nucleotide triphosphate (NTP) mix is made in-house using natural and un-natural NTPs.

A typical in vitro transcription reaction includes the following:

| | | |
|---|---|---|
| 1 | Template cDNA | 1.0 μg |
| 2 | 10x transcription buffer (400 mM Tris-HCl pH 8.0, 190 mM $MgCl_2$, 50 mM DTT, 10 mM Spermidine) | 2.0 μl |
| 3 | Custom NTPs (25 mM each) | 7.2 μl |
| 4 | RNase Inhibitor | 20 U |
| 5 | T7 RNA polymerase | 3000 U |
| 6 | $dH_20$ | Up to 20.0 μl. and |
| 7 | Incubation at 37° C. for 3 hr-5 hrs. | |

The crude IVT mix may be stored at 4° C. overnight for cleanup the next day. 1 U of RNase-free DNase is then used to digest the original template. After 15 minutes of incubation at 37° C., the mRNA is purified using Ambion's MEGACLEAR™ Kit (Austin, TX) following the manufacturer's instructions. This kit can purify up to 500 μg of RNA. Following the cleanup, the RNA is quantified using the NanoDrop and analyzed by agarose gel electrophoresis to confirm the RNA is the proper size and that no degradation of the RNA has occurred.

Example 5. In vivo Immunogenicity Assay with mRNA Cancer Vaccines

An MC38 immunogenicity study using mRNA vaccines in mice was performed. mRNA antigens: three MC38 neoepitopes Adpgk, Dpagt1, Reps1 having formats: 25me r, TMG, secreted CD40L-TMG fusion protein) were generated. The positive control was a benchmark comparison to 25-mer peptide immunization+anti-CD40+poly(I: C) (Yadav et al, Nature 2015). Mice were immunized on days 0, 7, and 14. A readout was measured on Days 3, 10, and 17; followed by MC38 challenge on day 21 and sacrifice on day 35. Characterization of the epitope-specific T cell population was made by frequency of antigen-specific T cell population by dextramers staining. A cytokine profile was generated: Intracellular cytokine staining (IFNγ, TNFα, IL-2) and ELISPOT (upon MC38 mutant peptide stimulation). The following memory and T cell differentiation markers: CD44, CD62L, IL7R, KLRG1, CD122 and exhaustion markers: PD1, Lag3, Tim3, 2B4 were used.

Figure 2:
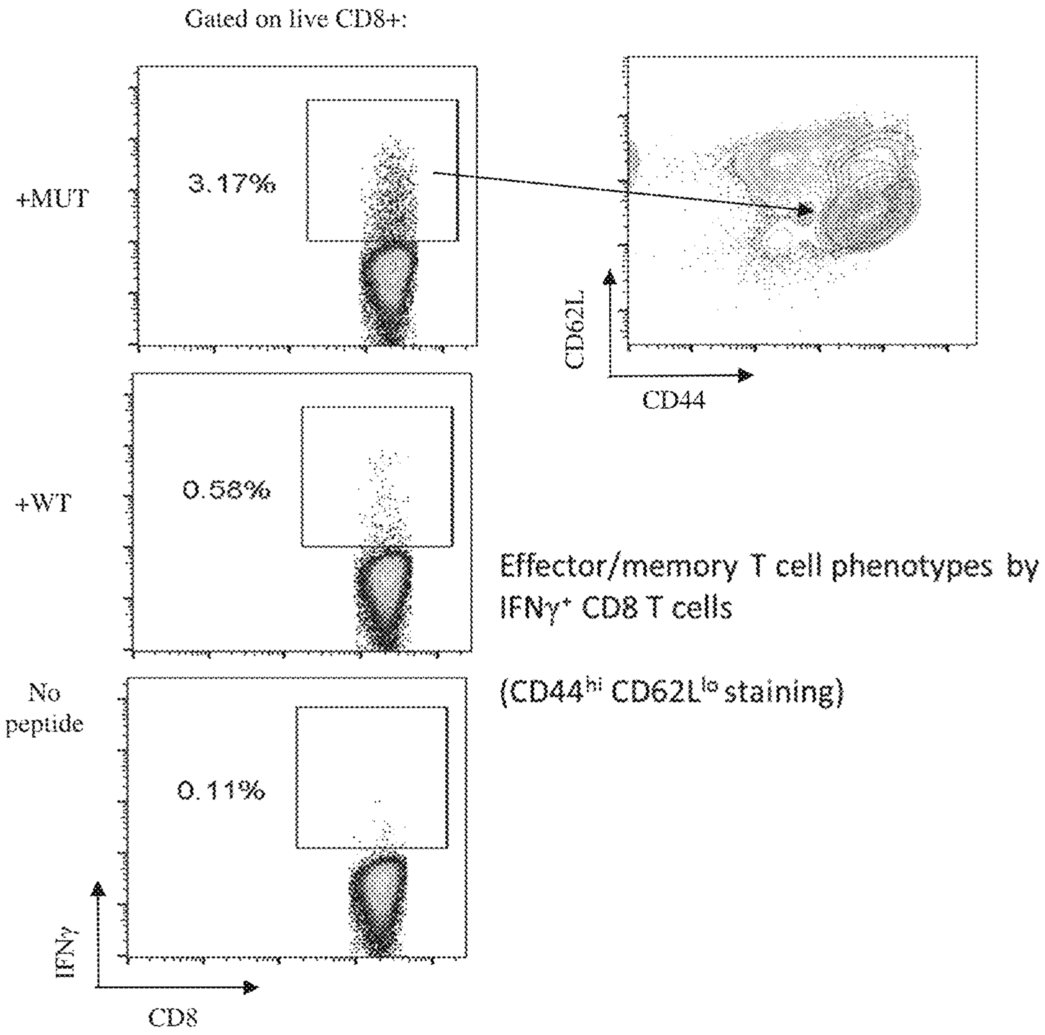
FIG. 2 shows the results of an assay to demonstrate a mRNA vaccine induced antigen specific effector/memory CD8 T cell response.
Figure 3:
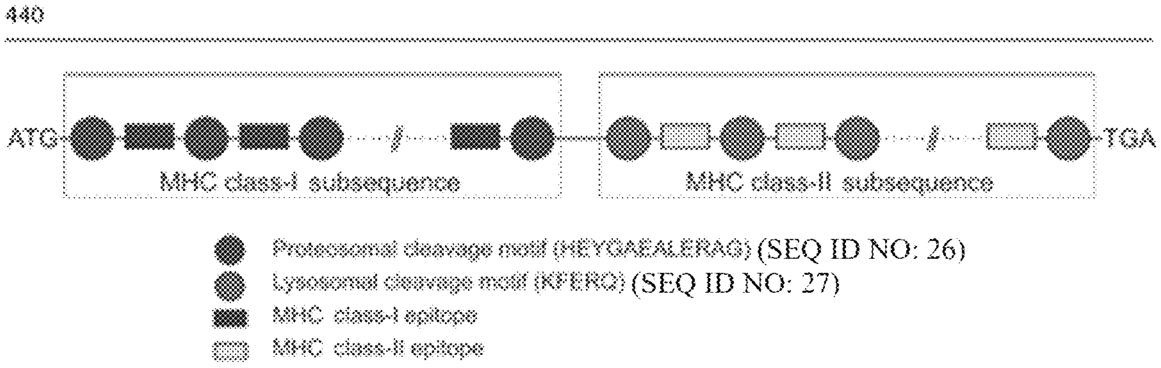
FIG. 3 is a schematic depicting a multi-factorial consideration of antigen design of mRNA-based neoepitopes.

The results showing that mRNA vaccine induced an antigen specific CD8 response are shown in FIG. 1. Results showing that mRNA vaccines induced antigen specific effector/memory CD8 T cells are shown in FIG. 2.

Some of the considerations for antigen designs include MHC classes, Expression localization, Polypeptide format and configuration, and Potency enhancing motifs. A multifactorial consideration of antigen design of mRNA-based neoepitopes is shown in FI GS. 3 (schematic) and 4 (table).

Example 6. Method Development of FACS-Based MHC-Presentation

Objective: Validation of FACS-based assay of mRNA encoded epitopes in MCF7 (HLA*201). The mRNA used was a combination a concatamer of four different epitopes: mut.gp100 (T209M)+mut.tyrpsoinase (N271D)+mut.CDK4 (R24C)+mut.MART1 (A27L) TMG.G25 (½)^3.nPEST seq: control mRNA of tandem minigene of three repeats of mut.gp100 (T209M). Protein production was detected using an Anti-mut.MART1 (A27L)

TCRmer-PE and Anti-HLA antibodies.

The method involved: MCF7 transfected with 250 ng mRNA using LF2000; Peptide-pulsed control preparation: MCF7 were left un-pulsed or pulsed with synthetic peptide s in serum-free RPMI for 3 h at 37C; and FACS analysis with anti-HLA and TCRmer (specific for mutant MART1-HLA*201 complex) at ~20h.

Figure 5:
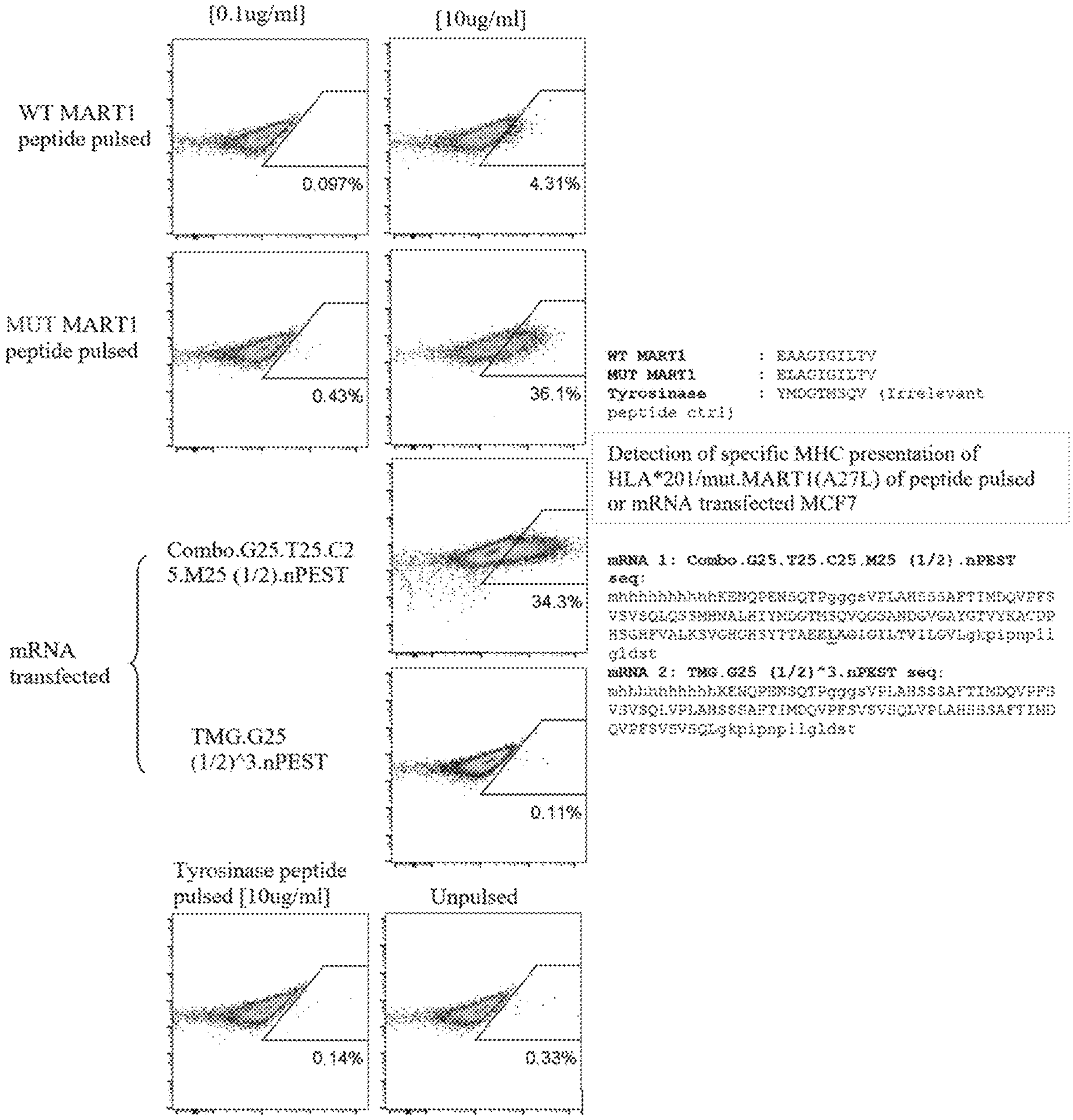
FIG. 5 depicts the results of a validation of FACS-based assay of mRNA encoded epitopes in MCF7 (HLA*201). Specific MHC1/mut.MARTIpeptide presentation by anti-mut.MARTITCRmer was detected on MCF7 cells. The sequences, from top to bottom, correspond to SEQ ID NOs: 15-19.
Figure 6A:
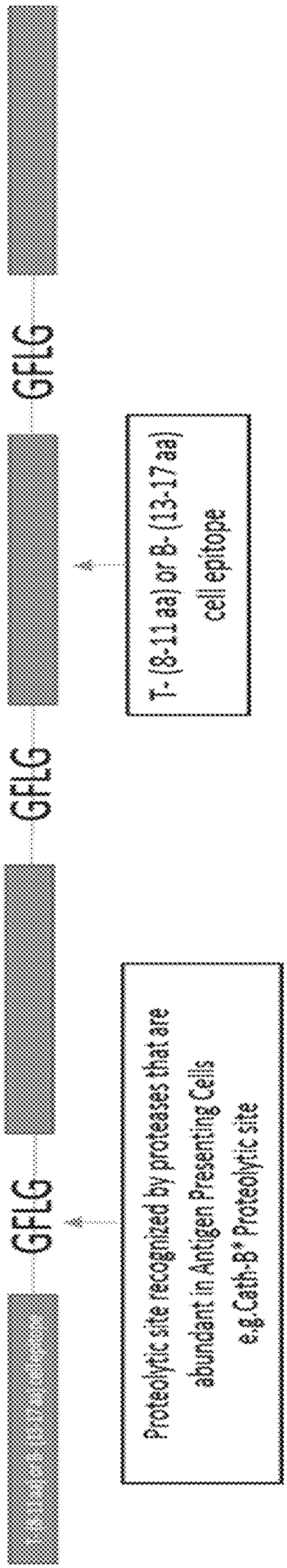
FIGS. 6A and 6B are schematics of an exemplary peptide epitopes. The polypeptide of FIG. 6A includes two or more epitopes. The epitopes can be of the same sequence or different sequence and can be all T-cell epitopes, all B-cell epitopes or a combination of both. The schematic of FIG. 6B shows the peptide epitope with various end units for enhancing MHC processing of the peptides.
Figure 6B:
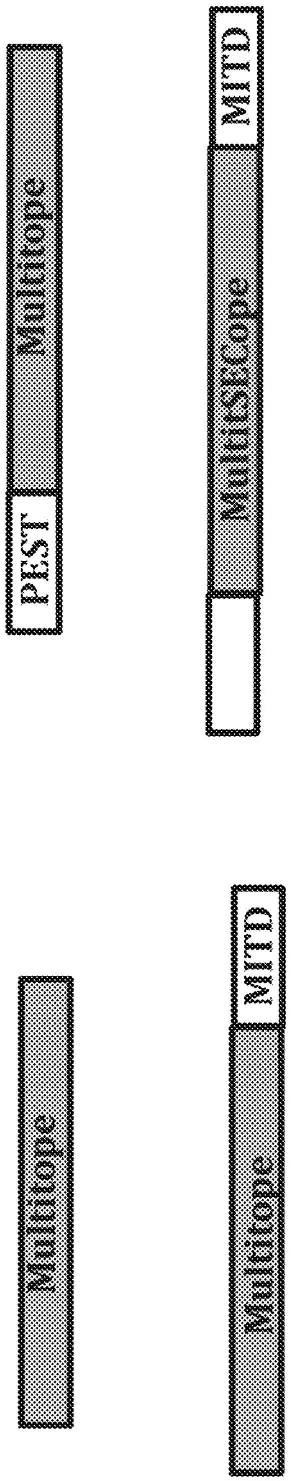

The data is shown in FIG. 5. Specific MHC1/mut.MARTIpeptide presentation by anti-mut.MARTITCRmer was detected on MCF7 cells.

Example 7. T Cell Response Elicited with mRNA Encoding Concatamers of 20 Epitopes mRNA concatamers induced both class I and class II T cell responses. CA60 encodes 20 epitopes derived from the mutanome of a patient. It includes 5 murine class II epitopes, murine class I epitopes, a murine positive control (SIINFEKL (SEQ ID NO: 22), derived from ovalbumin), and 4 human (HLA-A2) epitopes (not shown). Mice were immunized with 10 μg mRNA twice (prime+boost at day 14) and spleen cells were analyzed at day 21 by flow cytometry.

Figure 7:
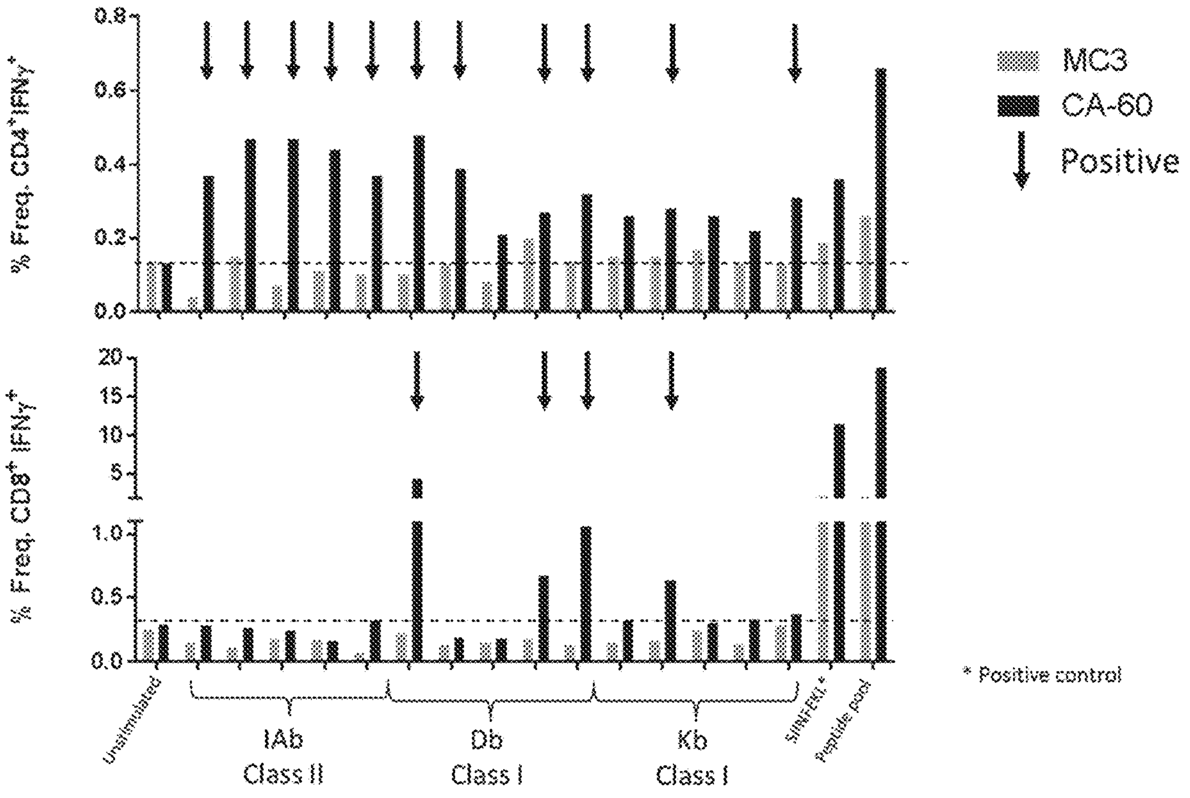
FIG. 7 depicts exemplary T cell response elicited with mRNA encoding concatamers of 20 epitopes. mRNA concatamers induced both class I and class II T cell responses.

The data are shown in FIG. 7. Four out of ten Class I epitopes and five out of five class II epitopes were immunogenic. The epitopes showed responses two-fold over the unstimulated control. Some Class I predicted epitopes showed some level of cross presentation.

Example 8. Epitopes are Immunogenic Irrespective of Position within mRNA Concatamer The epitopes were immunogenic irrespective of their position within the mRNA. CA80 and CA81 encode the same 20 epitopes known to elicit T cell responses. They include 5 class II epitopes, 10 murine class I epitopes, a murine positive control (SIINFEKL (SEQ ID NO: 22), derived from ovalbumin), and 4 human (HLA-A2) epitopes (not shown). CA80 and CA81 differ only in the relative positions of the different epitopes. Mice were immunized with 10 ug mRNA twice (prime+boost at day 14) and spleen cells were analyzed at day 21 by flow cytometry.

Figure 8A:
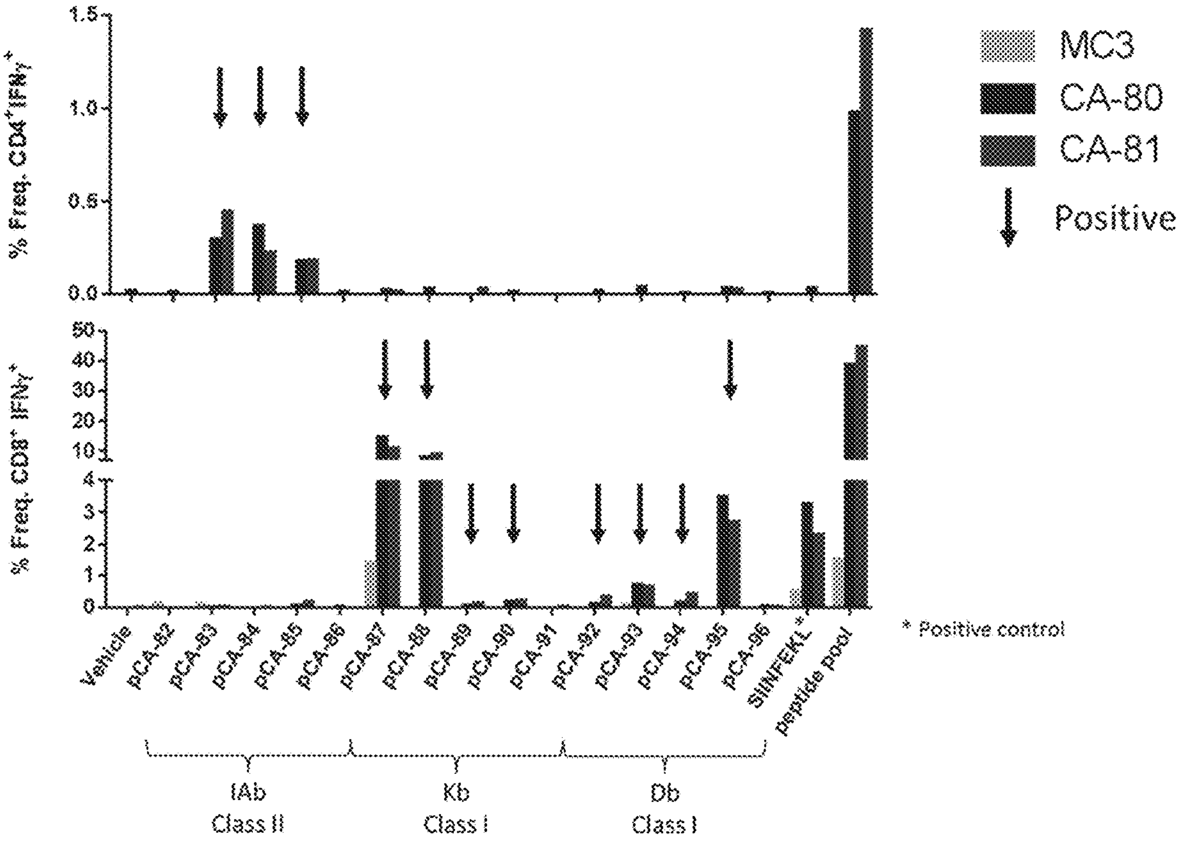
FIG. 8A depicts exemplary T cell response elicited with mRNA encoding concatamers with epitopes in differing positions. CA80 and CA81 encode the same 20 epitopes known to elicit T cell responses. They include 5 class II epitopes, 10 murine class I epitopes, a murine positive control (SIINFEKL (SEQ ID NO: 22), derived from ovalbumin), and 4 human (HLA-A2) epitopes (not shown). CA80 and CA81 differ only in the relative positions of the different epitopes.
Figure 8B:
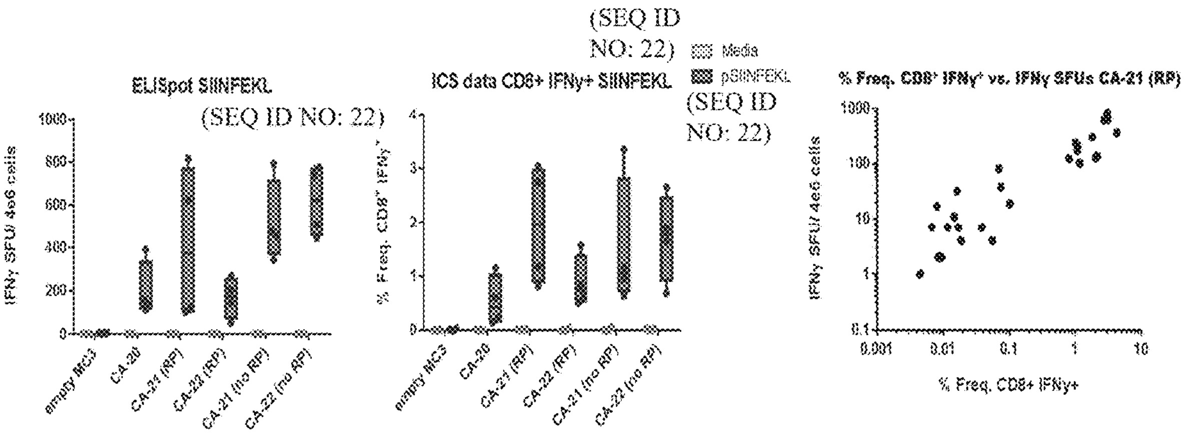
FIG. 8B depicts exemplary correlation between interferon-gamma spot forming units (SFUs) and CD8+ IFN-γ+ responses.

The data are shown in FIG. 8A. Eight out of 10 class I epitopes and three out of five class II epitopes were immunogenic. The epitopes showed responses eight-fold over the unstimulated control. The same level of immunogenicity was observed irrespective of the position within the mRNA. FIG. 8B shows that there is a strong correlation (R squared=0.78) between percent frequency of CD8+ IFNγ+ cells and interferon-gamma spot forming units (SFUs) in ELISpot assays.

Figure 9A:
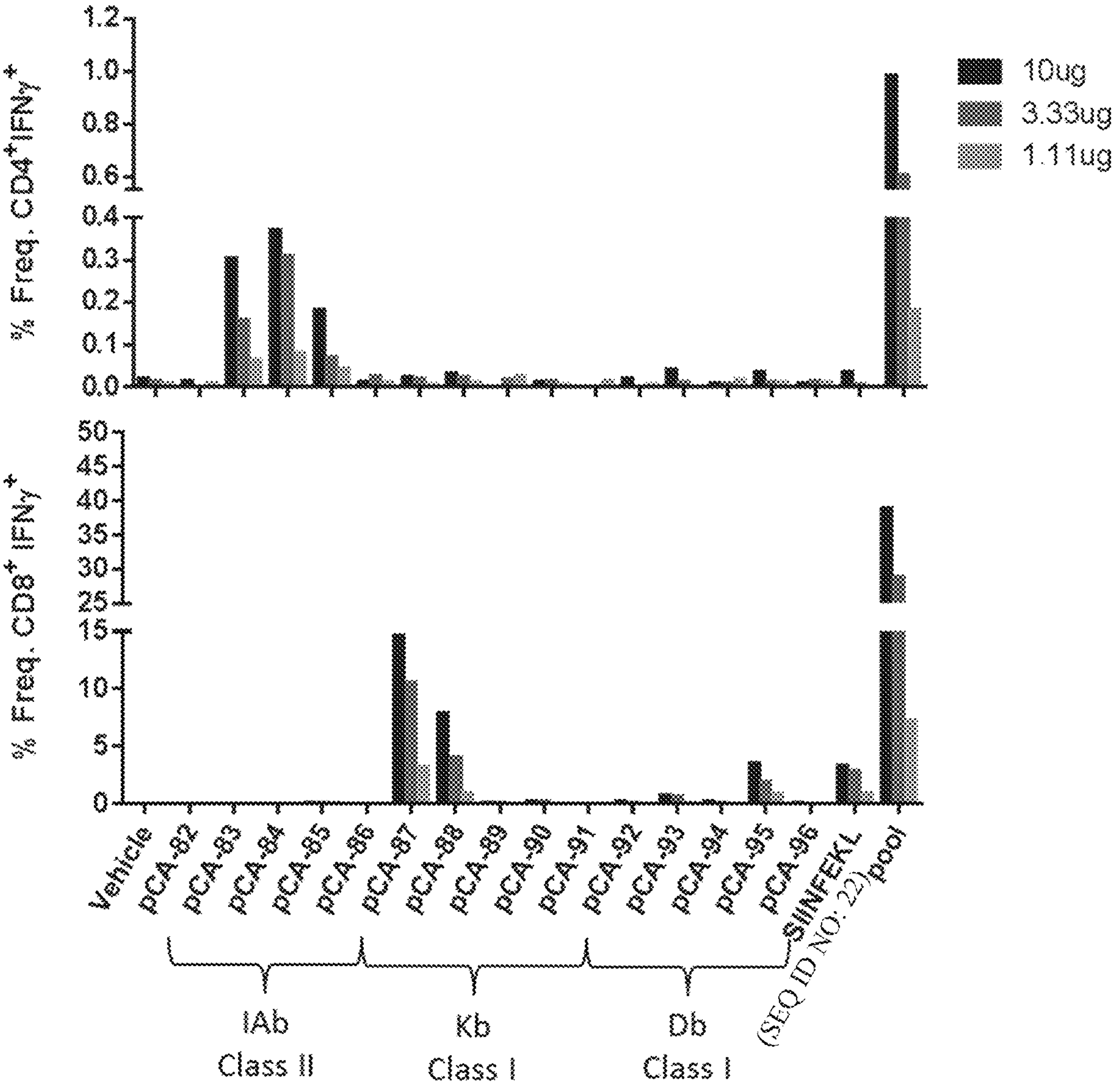

A dose response was observed for vaccination with CA-80. As shown in FIGS. 9A and 9B, a loss of "hits" was observed as the amount of vaccine administered decreased.

Figure 10:
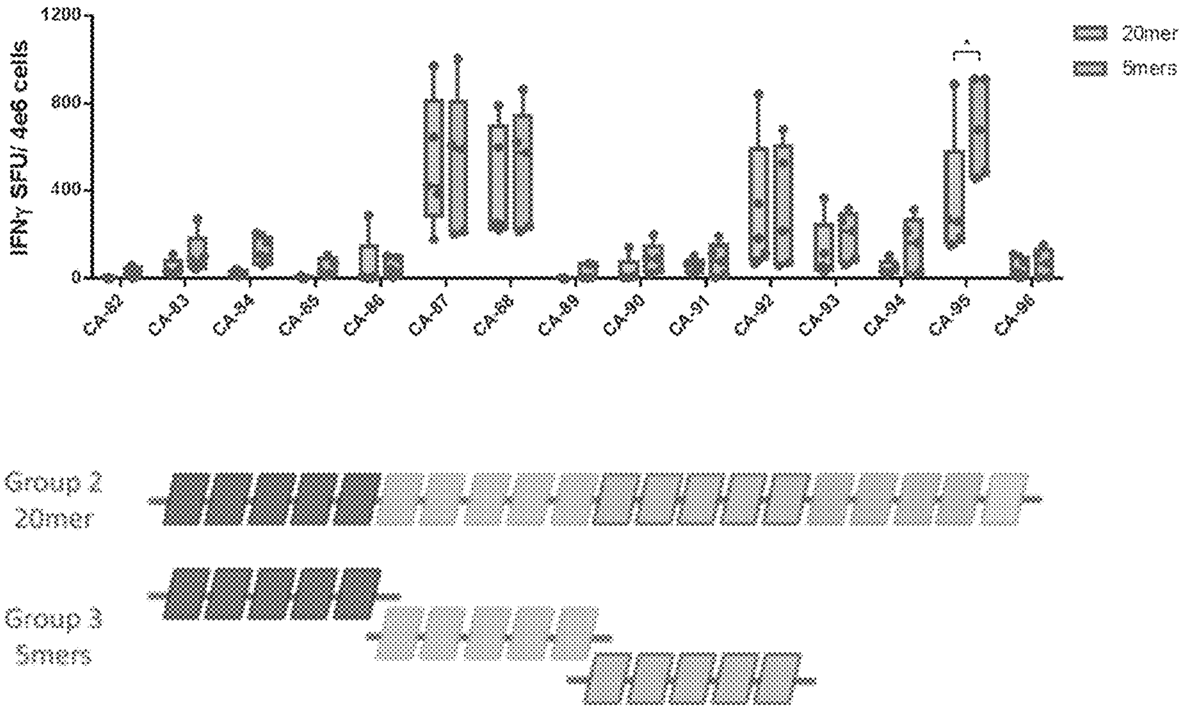
FIG. 10 depicts an exemplary comparison of T-cell responses to known epitopes when immunizing with 20mer vs 5mers. T cell responses to known epitopes were comparable when vaccinating as a 20mer or (3) 3mers. A trend toward slightly higher T-cell responses was observed when immunizing with 5mers.

T-cell responses to known epitopes were compared when immunizing using a 20mer vs. 5mers. As shown in FIG. 10, T cell responses to known epitopes were comparable when vaccinating as a 20me r or (3) 3mers. A trend toward slightly higher T-cell responses was observed when immunizing with 5mers.

Figure 11:
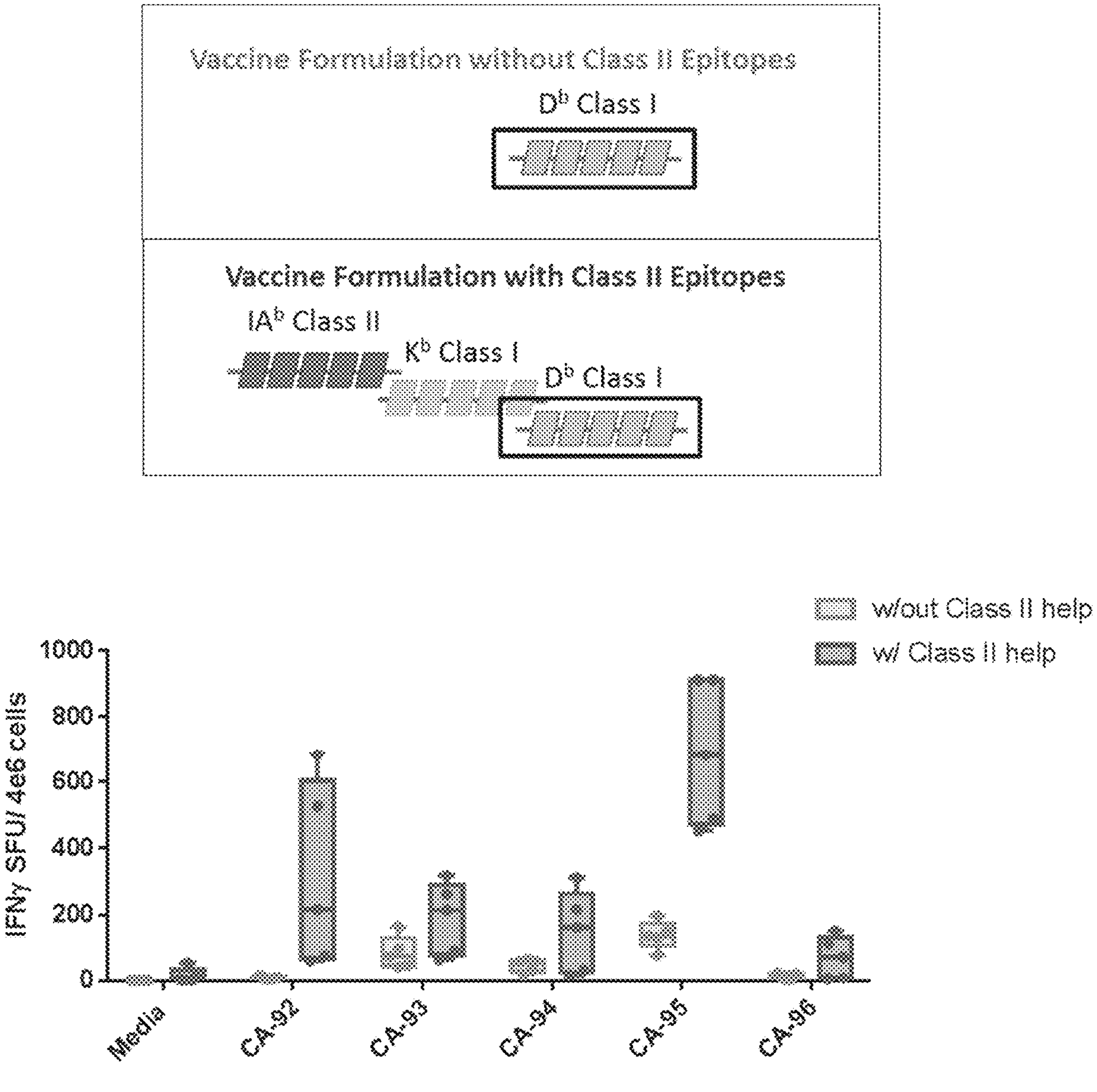
FIG. 11 depicts an exemplary comparison of T-cell responses to Class I epitopes alone or in the presence of Class II help. T-cell responses to 5 known Class I epitopes were compared when the epitopes were administered alone as a 5mer (w/out Class II help) or with 5 known Class II epitopes (w/Class II help). This group also included an additional 5mer of known Class I epitopes. T-cell responses to known Class I epitopes were higher in the presence of 5mer containing known Class II epitopes.
Figure 12:
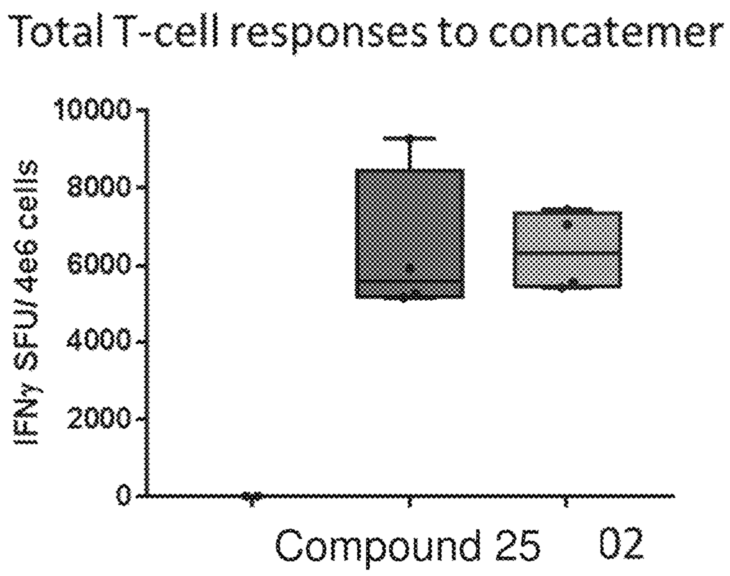
FIG. 12 depicts exemplary T-cell responses observed with vaccination with concatameric vaccines formulated with MC3 or Compound 25. CA-81 (containing 15 known mouse epitopes) was formulated in MC3 and Compound 25. T-cell responses were measured against each epitope in the vaccine and responses were compared between the two formulations.

T-cell responses were compared when immunizing with Class I epitopes alone or in the presence of Class II help. As shown in FIG. 11, T-cell responses to 5 known Class I epitopes were compared when the epitopes were administered alone as a 5me r (w/out Class II help) or with 5 known Class II epitopes (w/Class II help). This group also included an additional 5me r of known Class I epitopes. T-cell responses to known Class I epitopes were higher in the presence of 5me r containing known Class II epitopes. Thus, Class II/Th epitopes enhance Class I/Tc responses T-cell responses were observed with vaccination with concatameric vaccines formulated with MC3 or Compound 25. CA-81 (containing 15 known mouse epitopes) was formulated in MC3 and Compound 25. As shown in FIG. 12, T-cell responses were measured against each epitope in the vaccine and responses were compared between the two formulations. Compound 25 formulated material produced similar T-cell responses to MC3 formulated material

Example 9. Phase I, Open-Label Study to Assess Safety, Tolerability, and Immunogenicity of mRNA Vaccine in Patients with Solid Tumors A phase I, open-label study to assess the safety, tolerability, and immunogenicity of mRNA 1 alone in patients with resected solid tumors, and in combination with pembrolizumab (a humanized anti-PD-1 antibody) in patients with unresectable solid tumors is performed.

Objectives: Primary: safety & tolerability of mRNA-1 in patients with resected solid tumors (Part A) & mRNA-1+pembrolizumab in patients with unresectable solid tumors (Part B)

Secondary: Part A: RFS in patients with resected solid tumors treated.

Part B: ORR, DOR, PFS & OS in patients with unresectable solid tumors (pembro label) Exploratory Study Objectives: Immunogenicity Methodology: Two-part, open-label, 3+3 dose-escalation: fixed dose of either 0.1 mg, 0.2 mg or 0.4 mg of mRNA-1 administered via intramuscular (IM) injections once during 21-day cycles for a maximum of 4 doses over 4 cycles.

Figure 13:
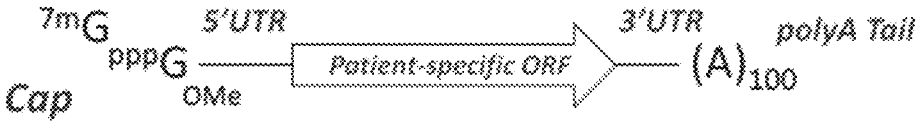
FIG. 13 is a schematic of an exemplary mRNA component of mRNA-1.

A schematic of the mRNA component of mRNA-1 is shown in FIG. 13. mRNA-1 contains a canonical dinucleotide mammalian cap 1 structure at the 5' end comprised of a 7-methyl guanosine linked in a 5'-5' triphosphate configuration to the penultimate nucleotide that is methylated at the 2' position of the ribose sugar (Kozak, 1991; Fechter and Brownlee, 2005). The cap structure is required for initiation of translation. Following the cap structure is the 48-nt 5' untranslated region (5' UTR) that has been optimized to facilitate initiation of translation. The 5' UTR ends at the AUG methionine start codon encoding the first amino acid of the protein coding region, or open reading frame (ORF), of mRNA-1 which will be uniquely defined for each patient. The ORF of mRNA-1 ends with the three mammalian stop codons linked in a row (5'-UGA-UAA-UAG-3') that start a common, pre-specified 3' UTR nucleotide sequence that has been optimized to promote mRNA stabilization. mRNA-1 ends with an approximately 100-nt adenosine homopolymer, the polyA tail, which is required for mRNA stabilization and protein translation. Both the cap structure at the 5' end and the poly A tail at 3' end are required for mRNA-1 to be translated by the cellular translational machinery. RNA lacking either 5' cap or 3' polyA tail cannot be translated and therefore will not produce protein. Any degradant of mRNA-1 lacking either the cap 1 structure on 5' end or the polyA tail on 3' end would not produce any protein.

An example of the general molecular sequence of mRNA-1 is provided in FIG. 14, in which the patient specific coding region is depicted by reference as (N). The nucleosides in mRNA-1 are chemically identical to naturally-occurring mammalian mRNA nucleosides, with the exception that the uridine nucleoside normally present in mammalian mRNA is fully replaced with N1-methyl-pseudouridine, a naturally-occurring pyrimidine base present in mammalian tRNAs (Rozenski, Crain et al. 1999; Kariko, Buckstein et al. 2005). This nucleoside is included in mRNA-1 in place of the normal uridine base to minimize the indiscriminate recognition of mRNA-1 by pathogen-associated molecular pattern (PAMP) receptors (e.g., Toll-like receptors (TLR), Desmet and Ishii, 2012).

Example 10. Phase I, Open-Label Study to Assess Safety, Tolerability, and Immunogenicity of mRNA Vaccine in Patients with Solid Tumors A phase I, open-label study to assess the safety, tolerability, and immunogenicity of mRNA 2 alone in patients with resected solid tumors, and in combination with pembrolizumab (a humanized anti-PD-1 antibody) in patients with unresectable solid tumors is performed.

Objectives: Primary: safety, tolerability, and recommended Phase 2 dose of mRNA-4157 monotherapy in patients with resected solid tumors (Part A) & mRNA-4157+ pembrolizumab in patients with unresectable solid tumors (Part B)

Methodology: Two-part, open-label, 3+3 dose-escalation: fixed dose of either 0.1 mg. 0.2 mg or 0.4 mg of mRNA-4157 administered via intramuscular (IM) injections once during 21-day cycles for a maximum of 9 doses over 9 cycles (i.e., 6 months dosing).

Example 11. Recurrent Splice Site and Silent Mutation "Hotspots" in p53

Figure 17:
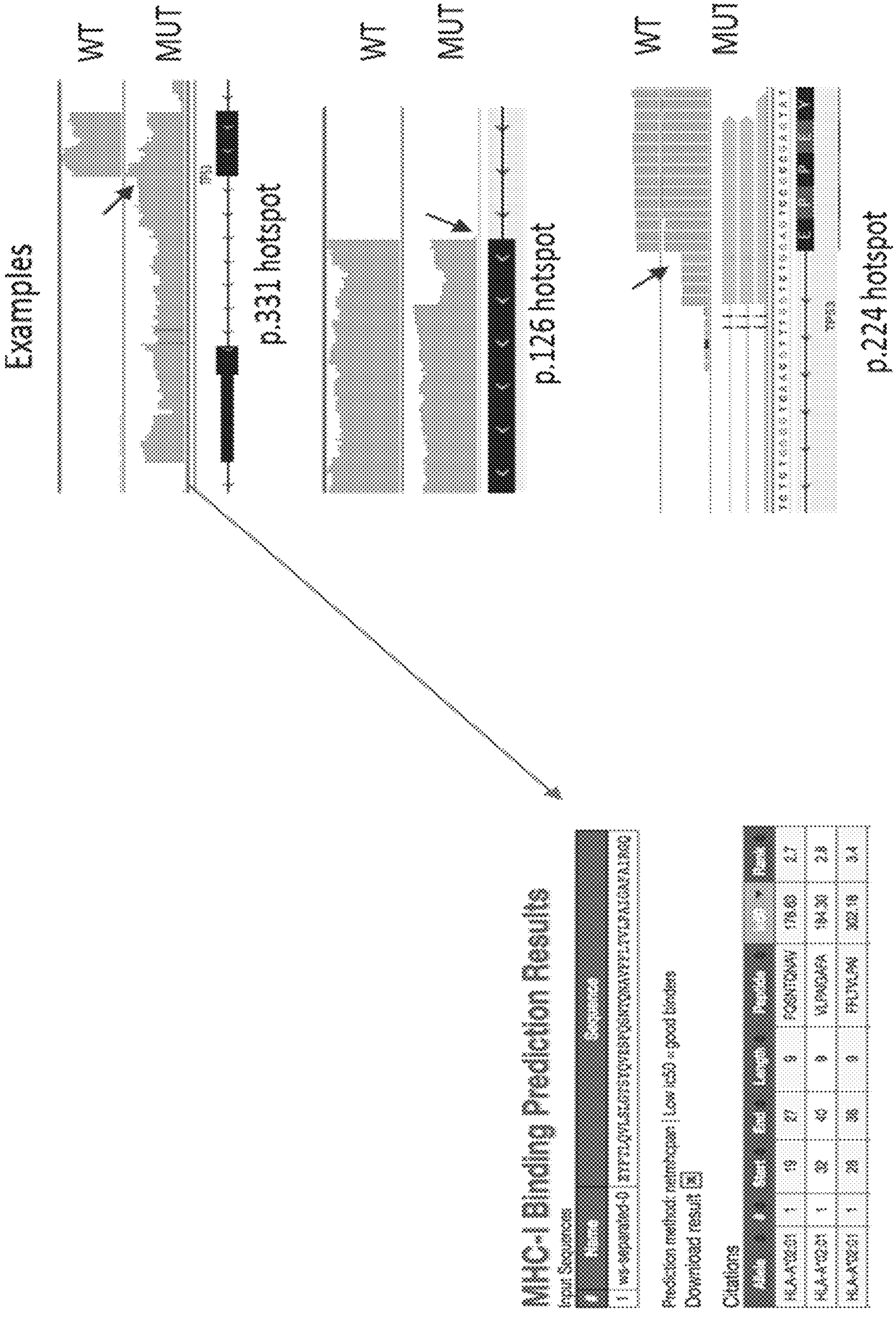
FIG. 17 is a schematic depicting hotspot splice site and silent mutations leading to production of retained introns and cryptic splicing. Several mutation sites were confirmed by RNA-seq to produce retained introns or cryptic splicing. Two representative mutation-derived peptides had multiple HLA-A2 binding epitopes with no matches elsewhere in the coding genome. From top to bottom, left to right the sequences correspond to SEQ ID NOs: 5, 23, 24, and 25.

The p53 gene (official symbol TP53) is mutated more frequently than any other gene in human cancers. Large cohort studies have shown that, for most p53 mutations, the genomic position is unique to one or only a few patients and the mutation cannot be used as recurrent neoantigens for therapeutic vaccines designed for a specific population of patients. A small subset of p53 loci do, however, exhibit a "hotspot" pattern, in which several positions in the gene are mutated with relatively high frequency. Strikingly, a large portion of these recurrently mutated regions occur near exon-intron boundaries, disrupting the canonical nucleotide sequence motifs recognized by the mRNA splicing machinery, as shown in FIG. 16. Mutation of a splicing motif can alter the final mRNA sequence even if no change to the local amino acid sequence is predicted (i.e. for synonymous or intronic mutations). Therefore, these mutations are often annotated as "noncoding" by common annotation tools and neglected for further analysis, even though they may alter mRNA splicing in unpredictable ways and exert severe functional impact on the translated protein. If an alternatively spliced isoform produces an in-frame sequence change (i.e., no PTC is produced), it can escape depletion by NMD and be readily expressed, processed, and presented on the cell surface by the HLA system. Further, mutation-derived alternative splicing is usually "cryptic", i.e., not expressed in normal tissues, and therefore may be recognized by T-cells as non-self neoantigens. As shown in FIG. 17, which depicts hotspot splice site and silent mutations leading to production of retained introns and cryptic splicing, several mutation sites were confirmed by RNA-seq to produce retained introns or cryptic splicing. Two representative mutation-derived peptides had multiple HLA-A2 binding epitopes with no matches elsewhere in the coding genome.

Recurrent mutations in p53 that were identified included:

(1) mutations at the canonical 5' splice site neighboring codon p.T125, inducing a retained intron having peptide sequence TAKSVTCTVSCPEGLASMRLQCLAVSPCISFVWNFGIPLHPLASCQCFFIVYPLNV (SEQ ID NO: 1) that contains epitopes AVSPCISFVW (SEQ ID NO: 2) (HLA-B*57:01, HLA-B*58:01), HPLASCQCFF (SEQ ID NO: 3) (HLA-B*35:01, HLA-B*53:01), FVWNFGIPL (SEQ ID NO: 4) (HLA-A*02:01, HLA-A*02:06, HLA-B*35:01);

(2) mutations at the canonical 5' splice site neighboring codon p.331, inducing a retained intron having peptide sequence EYFTLQVLSLGTSYQVESFQSNTQNAVFFLTVLPAIGAFAIRGQ (SEQ ID NO: 5) that contains epitopes LQVLSLGTSY (SEQ ID NO: 6) (HLA-B*15:01), FQSNTQNAVF (SEQ I DNO: 7) (HLA-B*15:01);

(3) mutations at the canonical 3' splice site neighboring codon p.126, inducing a cryptic alternative exonic 3' splice site producing the novel spanning peptide sequence AKSVTCTMFCQLAK (SEQ ID NO: 8) that contains epitopes CTMFCQLAK (SEQ ID NO: 9) (HLA-A*11:01), KSVTCTMF (SEQ ID NO: 10) (HLA-B*58:01); and (4) mutations at the canonical 5' splice site neighboring codon p.224, inducing a cryptic alternative intronic 5' splice site producing the novel spanning peptide sequence VPYEPPEVWLALTVPPSTAWAA (SEQ ID NO: 11) that contains epitopes VPYEPPEVW (SEQ ID NO: 12) (HLA-B*53:01, HLA-B*51:01), LTVPPSTAW (SEQ ID NO: 13) (HLA-B*58:01, HLA-B*57:01), wherein the transcript codon positions refer to the canonical full-length p53 transcript ENST00000269305 (SEQ ID NO: 14) from the Ensembl v83 human genome annotation.

EQUIVALENTS

Those skilled in the art will recognize, or be able to ascertain using no more than routine experimentation, many equivalents to the specific embodiments of the disclosure described herein. Such equivalents are intended to be encompassed by the following claims.

All references, including patent documents, disclosed herein are incorporated by reference in their entirety.

What is claimed is:

1. A personalized cancer vaccine for treating a cancer in a subject, comprising:

a messenger ribonucleic acid (mRNA) having an open reading frame (ORF) encoding 5-100 peptide epitopes arranged in a head to tail formation, and a lipid nanoparticle, wherein the lipid nanoparticle comprises 5-25 mol % non-cationic lipid, 25-55 mol % sterol, 0.5-15 mol % polyethylene glycol (PEG)-modified lipid, and 20-60 mol % of a compound of Formula (I):

(I)

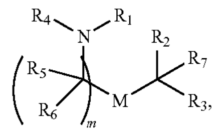

or a salt thereof, wherein:

$R_1$ is selected from the group consisting of $C_{5-30}$ alkyl, $C_{5-20}$ alkenyl, and —R"M'R';

$R_2$ and $R_3$ are independently selected from the group consisting of $C_{1-14}$ alkyl and $C_{2-14}$ alkenyl;

$R_4$ is $—(CH_2)_nQ$, wherein Q is —OR, and n is selected from 1, 2, 3, 4, and 5;

each $R_5$ is H;

each $R_6$ is H;

M and M' are independently selected from —C(O)O— and —OC(O)—;

$R_7$ is H;

R is H;

R' is selected from the group consisting of $C_{1-18}$ alkyl and $C_{2-18}$ alkenyl;

R" is selected from the group consisting of $C_{3-14}$ alkyl and $C_{3-14}$ alkenyl; and m is selected from 5, 6, 7, 8, 9, 10, 11, 12, and 13, wherein:

(i) at least one of the peptide epitopes is a major histocompatibility complex (MHC) class I epitope and at least one of the peptide epitopes is an MHC class II epitope, and (ii) the mRNA comprises N1-methylpseudouridine.

2. The personalized cancer vaccine of claim 1, wherein at least two of the peptide epitopes are linked directly to one another without a linker.

3. The personalized cancer vaccine of claim 2, wherein a first peptide epitope is linked at its N-terminus directly to a C-terminus of a second peptide epitope without a linker, and wherein a junction formed by 2-10 amino acids of the N-terminus of the first peptide epitope linked to 2-10 amino acids of the C-terminus of the second peptide epitope does not form an immunogenic peptide.

4. The personalized cancer vaccine of claim 1, wherein the compound of Formula (I) comprises a structure of Formula (IA):

(IA)

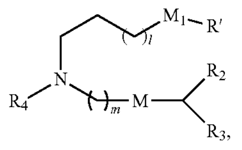

or a salt thereof, wherein 1 is selected from 1, 2, 3, 4, and 5; m is selected from 5, 6, 7, 8, and 9; and $M_1$ is M'.

5. The personalized cancer vaccine of claim 1, wherein the compound of Formula (I) comprises a structure of Formula (II):

(II)

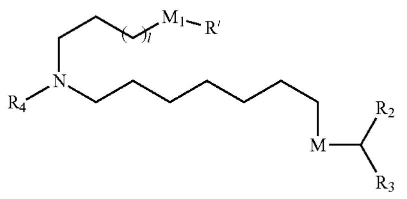

or a salt thereof, wherein 1 is selected from 1, 2, 3, 4, and 5; and $M_1$ is M'.

6. The personalized cancer vaccine of claim 1, wherein the compound of Formula (I) comprises a structure of Formula (IIa), (IIb), (IIc), or (IIe):

(IIa)

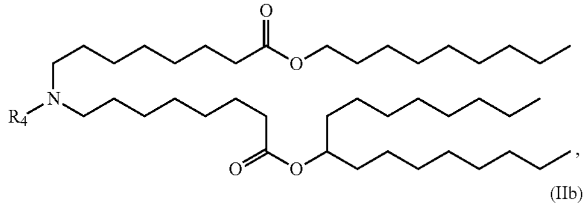

(IIb)

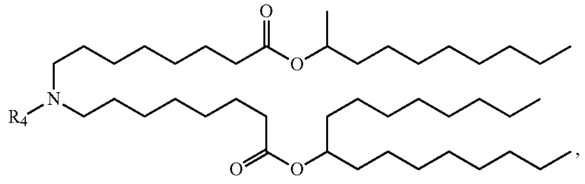

-continued (IIc)

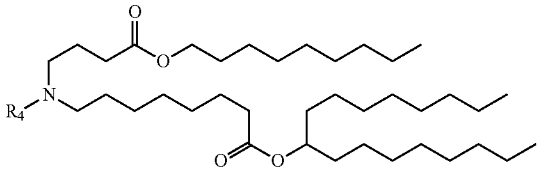

, or (IIe)

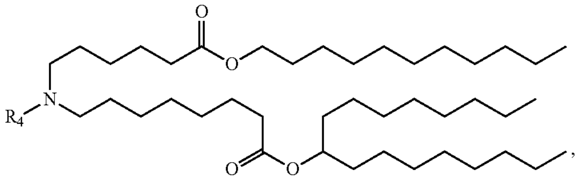

, or a salt thereof.

7. The personalized cancer vaccine of claim 1, wherein the non-cationic lipid is selected from the group consisting of disteroylphosphatidyl choline (DSPC), 1-palmitoyl-2-oleoyl phosphatidylcholine (POPC), dipalmitoylphosphatidylcholine (DPPC), dioleoyl phosphatidylethanolamine (DOPE) and sphingomyelin (SM).

8. The personalized cancer vaccine of claim 1, wherein the PEG-modified lipid is selected from the group consisting of PEG-c-DOMG (R-3-[(ω-methoxy-poly(ethyleneglycol) 2000) carbamoyl)]-1,2-dimyristyloxypropyl-3-amine), PEG-DSG (1,2-distearoyl-sn-glycerol, methoxypolyethylene glycol), PEG-DMG (polyethylene glycol-1,2-dimyristoyl-sn-glycerol), PEG-DPG (1,2-dipalmitoyl-sn-glycerol, methoxypolyethylene glycol), and PEG-CDMA (poly(ethyleneglycol)-carbamoyl-1,2-dimyristyloxypropylamine).

9. The personalized cancer vaccine of claim 1, wherein the sterol is cholesterol.

10. The personalized cancer vaccine of claim 1, wherein the compound of Formula (I) is (Compound 25)

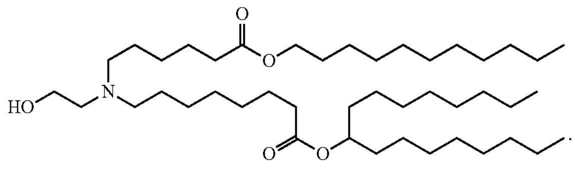

.

11. The personalized cancer vaccine of claim 1, wherein the mRNA further comprises a 5' untranslated region (5'-UTR), a 3' untranslated region (3'-UTR), a 5' cap, and a poly-A tail.

12. The personalized cancer vaccine of claim 1, wherein the mRNA further comprises at least one chemical modification selected from the group consisting of pseudouridine, N1-ethylpseudouridine, 2-thiouridine, 4'-thiouridine, 5-methylcytosine, 2-thio-1-methy 1-1-deaza-pseudouridine, 2-thio-1-methyl-pseudouridine, 2-thio-5-aza-uridine, 2-thio-dihydropseudouridine, 2-thio-dihydrouridine, 2-thio-pseudouridine, 4-methoxy-2-thio-pseudouridine, 4-methoxy-pseudouridine, 4-thio-1-methyl-pseudouridine, 4-thio-pseudouridine, 5-aza-uridine, dihydropseudouridine, 5-methyluridine, 5-methoxyuridine and 2'-O-methyl uridine.

13. The personalized cancer vaccine of claim 1, wherein the mRNA is fully modified with N1-methylpseudouridine.

14. A personalized cancer vaccine for treating a cancer in a subject, comprising:

a messenger ribonucleic acid (mRNA) having an open reading frame (ORF) encoding 5-50 peptide epitopes arranged in a head to tail formation, and a lipid nanoparticle, wherein the lipid nanoparticle comprises 5-25 mol % non-cationic lipid, 25-55 mol % sterol, 0.5-15 mol % PEG-modified lipid, and 20-60 mol % compound of Formula (I):

(I)

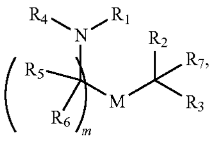

or a salt thereof, wherein:

$R_1$ is selected from the group consisting of $C_{5-30}$ alkyl, $C_{5-20}$ alkenyl, and —R"M'R';

$R_2$ and $R_3$ are independently selected from the group consisting of $C_{1-14}$ alkyl and $C_{2-14}$ alkenyl;

$R_4$ is —$(CH_2)_n$Q, wherein Q is —OR, and n is selected from 1, 2, 3, 4, and 5;

each $R_5$ is H;

each $R_6$ is H;

M and M' are independently selected from —C(O)O— and —OC(O)—;

$R_7$ is H;

R is H;

R' is selected from the group consisting of $C_{1-18}$ alkyl and $C_{2-18}$ alkenyl;

R" is selected from the group consisting of $C_{3-14}$ alkyl and $C_{3-14}$ alkenyl; and m is selected from 5, 6, 7, 8, 9, 10, 11, 12, and 13, wherein:

(i) at least one of the peptide epitopes is an MHC class I epitope and at least one of the peptide epitopes is an MHC class II epitope, and (ii) the mRNA comprises N1-methylpseudouridine.

15. The personalized cancer vaccine of claim 14, wherein at least two of the peptide epitopes are linked directly to one another without a linker.

16. The personalized cancer vaccine of claim 15, wherein a first peptide epitope is linked at its N-terminus directly to a C-terminus of a second peptide epitope without a linker, and wherein a junction is formed between 2-10 amino acids of the N-terminus of the first peptide epitope linked to 2-10 amino acids of the C-terminus of the second peptide epitope does not form an immunogenic peptide.

17. The personalized cancer vaccine of claim 14, wherein the compound of Formula (I) comprises a structure of Formula (IA):

(IA)

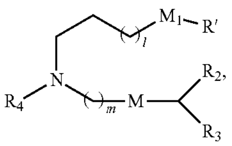

or a salt thereof, wherein 1 is selected from 1, 2, 3, 4, and 5; m is selected from 5, 6, 7, 8, and 9; and $M_1$ is M'.

18. The personalized cancer vaccine of claim 14, wherein the compound of Formula (I) comprises a structure of Formula (II):

(II)

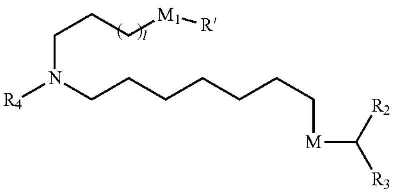

or a salt thereof, wherein 1 is selected from 1, 2, 3, 4, and 5; and $M_1$ is M'.

19. The personalized cancer vaccine of claim 14, wherein the compound of Formula (I) comprises a structure of Formula (IIa), (IIb), (IIc), or (IIe):

(IIa)

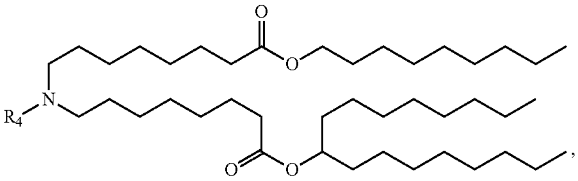

-continued (IIb)

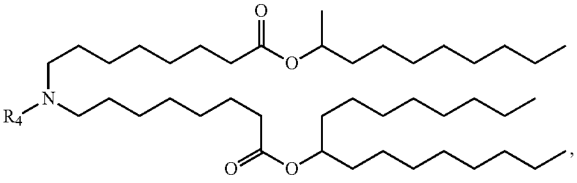

(IIc)

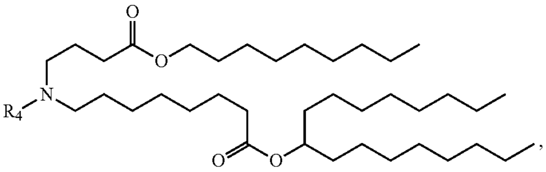

or (IId)

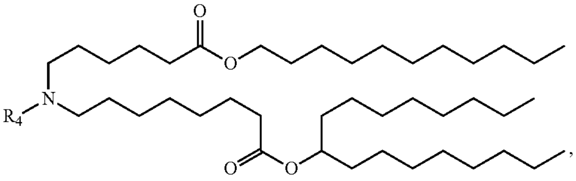

or a salt thereof.

20. The personalized cancer vaccine of claim 14, wherein the non-cationic lipid is selected from the group consisting of DSPC, POPC, DPPC, DOPE and SM.

21. The personalized cancer vaccine of claim 20, wherein the PEG-modified lipid is selected from the group consisting of PEG-c-DOMG, PEG-DSG, PEG-DMG, PEG-DPG, and PEG-cDMA.

22. The personalized cancer vaccine of claim 21, wherein the sterol is cholesterol.

23. The personalized cancer vaccine of claim 22, wherein the compound of Formula (I) is (Compound 25)

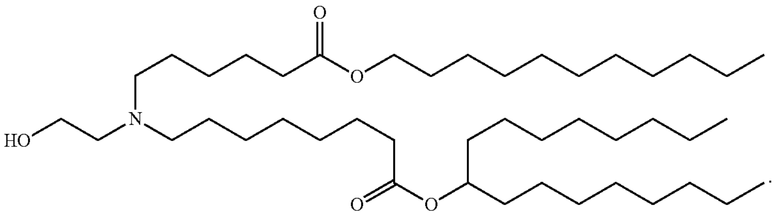

24. The personalized cancer vaccine of claim 23, wherein the mRNA further comprises a 5' untranslated region (5'-UTR), a 3' untranslated region (3'-UTR), a 5' cap, and a poly-A tail.

25. The personalized cancer vaccine of claim 24, wherein the mRNA further comprises at least one chemical modification selected from the group consisting of pseudouridine, N1-ethylpseudouridine, 2-thiouridine, 4'-thiouridine, 5-methylcytosine, 2-thio-1-methyl-1-deaza-pseudouridine, 2-thio-1-methyl-pseudouridine, 2-thio-5-aza-uridine, 2-thio-dihydropseudouridine, 2-thio-dihydrouridine, 2-thio-pseudouridine, 4-methoxy-2-thio-pseudouridine, 4-methoxy-pseudouridine, 4-thio-1-methyl-pseudouridine, 4-thio-pseudouridine, 5-aza-uridine, dihydropseudouridine, 5-methyluridine, 5-methoxyuridine and 2'-O-methyl uridine.

26. The personalized cancer vaccine of claim 24, wherein the mRNA is fully modified with N1-methylpseudouridine.

27. A personalized cancer vaccine for treating a cancer in a subject, comprising:

a messenger ribonucleic acid (mRNA) having an open reading frame (ORF) encoding 5-50 cancer antigen peptide epitopes arranged in a head to tail formation, and a lipid nanoparticle, wherein the lipid nanoparticle comprises (i) 5-25 mol % non-cationic lipid selected from the group consisting of DSPC, POPC, DPPC, DOPE and SM, (ii) 25-55 mol % cholesterol, (iii) 0.5-15 mol % PEG-modified lipid selected from the group consisting of PEG-c-DOMG, PEG-DSG, PEG-DMG, PEG-DPG, and PEG-cDMA, and (iv) 20-60 mol % of Compound 25

(Compound 25)

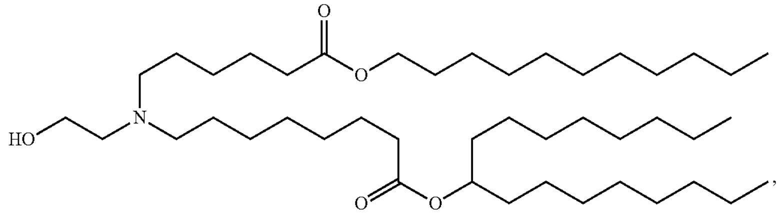

wherein:

(i) at least one of the peptide epitopes is an MHC class I epitope and at least one of the peptide epitopes is an MHC class II epitope, (ii) at least two of the peptide epitopes are linked directly to one another without a linker, (iii) the mRNA further comprises a 5' untranslated region (5'-UTR), a 3' untranslated region (3'-UTR), a 5' cap, and a poly-A tail, and (iv) the mRNA comprises N1-methylpseudouridine.

28. The personalized cancer vaccine of claim 27, wherein the ORF encodes 40 or fewer peptide epitopes.

29. The personalized cancer vaccine of claim 27, wherein the lipid nanoparticle comprises about 5 to 15 mol % of the non-cationic lipid, about 30 to 50 mol % of cholesterol, about 1 to 2 mol % of the PEG-modified lipid and about 40 to 60 mol % of Compound 25.

30. The personalized cancer vaccine of claim 27, wherein the non-cationic lipid is DSPC or DOPE.

31. The personalized cancer vaccine of claim 27, wherein the PEG-modified lipid is PEG-DSG or PEG-DMG.

32. The personalized cancer vaccine of claim 27, wherein each peptide epitope is 9-29 amino acids in length.

33. The personalized cancer vaccine of claim 27, wherein the ORF encodes 25-35 peptide epitopes.

34. The personalized cancer vaccine of claim 27, wherein at least 30% of the peptide epitopes are MHC class I epitopes.

35. The personalized cancer vaccine of claim 27, wherein at least 50% of the peptide epitopes are MHC class I epitopes.

36. The personalized cancer vaccine of claim 27, wherein the ratio of the MHC class I epitopes to the MHC class II epitopes is at least 3:1.

* * * * *